(12) United States Patent
Regev et al.

(10) Patent No.: US 11,897,953 B2
(45) Date of Patent: Feb. 13, 2024

(54) COMPOSITIONS AND METHODS TARGETING COMPLEMENT COMPONENT 3 FOR INHIBITING TUMOR GROWTH

(71) Applicants: The Broad Institute, Inc., Cambridge, MA (US); Massachusetts Institute of Technology, Cambridge, MA (US); The Brigham and Women's Hospital, Inc., Boston, MA (US)

(72) Inventors: Aviv Regev, Cambridge, MA (US); Ana Carrizosa Anderson, Boston, MA (US); Ayshwarya Subramanian, Cambridge, MA (US); Orit Rozenblatt-Rosen, Cambridge, MA (US)

(73) Assignees: The Broad Institute, Inc., Cambridge, MA (US); Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 716 days.

(21) Appl. No.: 16/622,636

(22) PCT Filed: Jun. 14, 2018

(86) PCT No.: PCT/US2018/037662
§ 371 (c)(1),
(2) Date: Dec. 13, 2019

(87) PCT Pub. No.: WO2018/232195
PCT Pub. Date: Dec. 20, 2018

(65) Prior Publication Data
US 2020/0102386 A1    Apr. 2, 2020

Related U.S. Application Data

(60) Provisional application No. 62/519,788, filed on Jun. 14, 2017.

(51) Int. Cl.
*A61K 35/17*    (2015.01)
*C07K 14/725*   (2006.01)
*C07K 16/28*    (2006.01)
*C12N 5/0783*   (2010.01)
*A61P 35/00*    (2006.01)

(52) U.S. Cl.
CPC .............. *C07K 16/28* (2013.01); *A61K 35/17* (2013.01); *A61P 35/00* (2018.01); *C07K 14/7051* (2013.01); *C12N 5/0636* (2013.01)

(58) Field of Classification Search
None
See application file for complete search history.

(56) References Cited

U.S. PATENT DOCUMENTS

| | | |
|---|---|---|
| 5,641,870 A | 6/1997 | Rinderknecht et al. |
| 5,686,281 A | 11/1997 | Roberts |
| 5,843,728 A | 12/1998 | Seed et al. |
| 5,851,828 A | 12/1998 | Seed et al. |
| 5,858,358 A | 1/1999 | June et al. |
| 5,869,326 A | 2/1999 | Hofmann |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 5,989,431 A | 11/1999 | Evans et al. |
| 6,004,811 A | 12/1999 | Seed et al. |
| 6,040,177 A | 3/2000 | Riddell et al. |
| 6,284,240 B1 | 9/2001 | Seed et al. |
| 6,352,694 B1 | 3/2002 | Seed et al. |
| 6,392,013 B1 | 5/2002 | Seed et al. |
| 6,410,014 B1 | 6/2002 | Seed |
| 6,479,626 B1 | 11/2002 | Kim et al. |
| 6,489,458 B2 | 12/2002 | Hackett et al. |
| 6,534,055 B1 | 3/2003 | June et al. |
| 6,534,261 B1 | 3/2003 | Cox et al. |
| 6,548,256 B2 | 4/2003 | Lienau et al. |
| 6,607,882 B1 | 8/2003 | Cox et al. |
| 6,746,838 B1 | 6/2004 | Choo et al. |
| 6,753,162 B1 | 6/2004 | Seed et al. |
| 6,794,136 B1 | 9/2004 | Eisenberg et al. |
| 6,797,514 B2 | 9/2004 | Berenson et al. |
| 6,824,978 B1 | 11/2004 | Cox et al. |
| 6,866,997 B1 | 3/2005 | Choo et al. |
| 6,867,041 B2 | 3/2005 | Berenson et al. |
| 6,887,466 B2 | 5/2005 | June et al. |
| 6,903,185 B2 | 6/2005 | Kim et al. |
| 6,905,680 B2 | 6/2005 | June et al. |
| 6,905,681 B1 | 6/2005 | June et al. |
| 6,905,874 B2 | 6/2005 | Berenson et al. |
| 6,933,113 B2 | 8/2005 | Case et al. |
| 6,979,539 B2 | 12/2005 | Cox et al. |

(Continued)

FOREIGN PATENT DOCUMENTS

| | | |
|---|---|---|
| EP | 0 404 097 A2 | 12/1990 |
| EP | 2 771 468 B1 | 2/2015 |

(Continued)

OTHER PUBLICATIONS

Yaskanin & Waxman, Cellular Immunol 163:139-147 (Year: 1995).*

(Continued)

*Primary Examiner* — Jessica H Roark
(74) *Attorney, Agent, or Firm* — F. Brent Nix, Esq.; Johnson, Marcou, Isaacs & Nix, LLC

(57) ABSTRACT

This invention relates generally to compositions and methods for modulating complement component 3 (C3) activity or expression to treat, control or otherwise influence tumors and tissues, including cells and cell types of the tumors and tissues, and malignant, microenvironmental, or immunologic states of the tumor cells and tissues. The invention also relates to methods of diagnosing, prognosing and/or staging of tumors, tissues and cells.

3 Claims, 42 Drawing Sheets

Specification includes a Sequence Listing.

(56) References Cited

U.S. PATENT DOCUMENTS

| | | |
|---|---|---|
| 7,013,219 B2 | 3/2006 | Case et al. |
| 7,030,215 B2 | 4/2006 | Liu et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,175,843 B2 | 2/2007 | June et al. |
| 7,220,719 B2 | 5/2007 | Case et al. |
| 7,232,566 B2 | 6/2007 | June et al. |
| 7,241,573 B2 | 7/2007 | Choo et al. |
| 7,241,574 B2 | 7/2007 | Choo et al. |
| 7,446,190 B2 | 11/2008 | Sadelain et al. |
| 7,572,631 B2 | 8/2009 | Berenson et al. |
| 7,585,849 B2 | 9/2009 | Liu et al. |
| 7,595,376 B2 | 9/2009 | Kim et al. |
| 7,741,465 B1 | 6/2010 | Eshhar et al. |
| 7,985,739 B2 | 7/2011 | Kay et al. |
| 8,021,867 B2 | 9/2011 | Smith et al. |
| 8,034,334 B2 | 10/2011 | Dudley et al. |
| 8,088,379 B2 | 1/2012 | Robbins et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,637,307 B2 | 1/2014 | June et al. |
| 8,697,359 B1 | 4/2014 | Zhang |
| 8,697,854 B2 | 4/2014 | Schendel et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,906,682 B2 | 12/2014 | June et al. |
| 8,911,993 B2 | 12/2014 | June et al. |
| 8,916,381 B1 | 12/2014 | June et al. |
| 8,932,814 B2 | 1/2015 | Cong et al. |
| 8,945,839 B2 | 2/2015 | Zhang |
| 8,975,071 B1 | 3/2015 | June et al. |
| 8,993,233 B2 | 3/2015 | Zhang et al. |
| 8,999,641 B2 | 4/2015 | Zhang et al. |
| 9,101,584 B2 | 8/2015 | June et al. |
| 9,102,760 B2 | 8/2015 | June et al. |
| 9,102,761 B2 | 8/2015 | June et al. |
| 9,181,527 B2 | 11/2015 | Sentman |
| 9,233,125 B2 | 1/2016 | Davila et al. |
| 2004/0171156 A1 | 9/2004 | Hartley et al. |
| 2004/0224402 A1 | 11/2004 | Bonyhadi et al. |
| 2010/0104509 A1 | 4/2010 | King et al. |
| 2010/0255011 A1 | 10/2010 | Lieber et al. |
| 2011/0265198 A1 | 10/2011 | Gregory et al. |
| 2012/0017290 A1 | 1/2012 | Cui et al. |
| 2012/0244133 A1 | 9/2012 | Rosenberg et al. |
| 2013/0071414 A1 | 3/2013 | Dotti et al. |
| 2013/0236946 A1 | 9/2013 | Gouble |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0184139 A1 | 7/2015 | Zhang et al. |
| 2015/0368342 A1 | 12/2015 | Wu et al. |
| 2015/0368360 A1 | 12/2015 | Liang et al. |
| 2016/0046724 A1 | 2/2016 | Brogdon et al. |
| 2016/0129109 A1 | 5/2016 | Davila et al. |
| 2016/0166613 A1 | 6/2016 | Spencer et al. |
| 2016/0175359 A1 | 6/2016 | Spencer et al. |
| 2016/0208243 A1 | 7/2016 | Zhang et al. |
| 2017/0211142 A1 | 7/2017 | Smargon et al. |
| 2017/0246298 A1* | 8/2017 | Francois ............... A61K 47/10 |
| 2017/0283504 A1 | 10/2017 | Wiltzius et al. |
| 2017/0306335 A1 | 10/2017 | Zhang et al. |
| 2017/0349894 A1 | 12/2017 | Dahlman et al. |
| 2017/0349914 A1 | 12/2017 | Cox et al. |
| 2018/0010134 A1 | 1/2018 | Sharp et al. |
| 2018/0085444 A1 | 3/2018 | Morgan et al. |
| 2019/0256900 A1 | 8/2019 | Zhang et al. |
| 2020/0023007 A1* | 1/2020 | Regev ............... C07K 14/70596 |

FOREIGN PATENT DOCUMENTS

| | | |
|---|---|---|
| EP | 2 784 162 B1 | 4/2015 |
| EP | 2 764 103 B1 | 8/2015 |
| EP | 3 00 9511 A2 | 4/2016 |
| NO | 2014/011987 A1 | 1/2014 |
| WO | 92/15322 A1 | 9/1992 |
| WO | 93/11161 A1 | 6/1993 |
| WO | 97/49450 A1 | 12/1997 |
| WO | 98/52609 A1 | 11/1998 |
| WO | 03/020763 A2 | 3/2003 |
| WO | 03/057171 A2 | 7/2003 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2011/146862 A1 | 11/2011 |
| WO | 2012/058460 A2 | 5/2012 |
| WO | 2012/079000 A1 | 6/2012 |
| WO | 2013/039889 A1 | 3/2013 |
| WO | 2013/040371 A2 | 3/2013 |
| WO | 2013/044225 A1 | 3/2013 |
| WO | 2013/154760 A1 | 10/2013 |
| WO | 2013/166321 A1 | 11/2013 |
| WO | 2013/176915 A1 | 11/2013 |
| WO | 2014/018423 A2 | 1/2014 |
| WO | 2014/018863 A1 | 1/2014 |
| WO | 2014/059173 A2 | 4/2014 |
| WO | 2014/083173 A1 | 6/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/133567 A1 | 9/2014 |
| WO | 2014/133568 A1 | 9/2014 |
| WO | 2014/134165 A1 | 9/2014 |
| WO | 2014/172606 A1 | 10/2014 |
| WO | 2014/184744 A1 | 11/2014 |
| WO | 2014/191128 A1 | 12/2014 |
| WO | 2014/204723 A1 | 12/2014 |
| WO | 2014/204724 A1 | 12/2014 |

(56) References Cited

FOREIGN PATENT DOCUMENTS

| | | |
|---|---|---|
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2014/210353 A2 | 12/2014 |
| WO | 2015/057834 A1 | 4/2015 |
| WO | 2015/057852 A1 | 4/2015 |
| WO | 2015/058052 A1 | 4/2015 |
| WO | 2015/070083 A1 | 5/2015 |
| WO | 2015/089351 A1 | 6/2015 |
| WO | 2015/089354 A1 | 6/2015 |
| WO | 2015/089364 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2015/120096 A2 | 8/2015 |
| WO | 2015/142675 A2 | 9/2015 |
| WO | 2015/158671 A1 | 10/2015 |
| WO | 2015/187528 A1 | 12/2015 |
| WO | 2016/000304 A1 | 1/2016 |
| WO | 2016/011210 A2 | 1/2016 |
| WO | 2016/014789 A2 | 1/2016 |
| WO | 2016/028682 A1 | 2/2016 |
| WO | 2016/040476 A1 | 3/2016 |
| WO | 2016/049024 A2 | 3/2016 |
| WO | 2016/049258 A2 | 3/2016 |
| WO | 2016/070061 A1 | 5/2016 |
| WO | 2016/094867 A1 | 6/2016 |
| WO | 2016/094874 A1 | 6/2016 |
| WO | 2016/094880 A1 | 6/2016 |
| WO | 2016/106244 A1 | 6/2016 |
| WO | 2016/108926 A1 | 7/2016 |
| WO | 2016/094872 A9 | 8/2016 |
| WO | 2016/161516 A1 | 10/2016 |
| WO | 2016/168584 A1 | 10/2016 |
| WO | 2016/191756 A1 | 12/2016 |
| WO | 2016/196388 A1 | 12/2016 |
| WO | 2016/205749 A1 | 12/2016 |
| WO | 2016/205764 A1 | 12/2016 |
| WO | 2017/011804 A1 | 1/2017 |
| WO | WO 2017/004153 A1 | 1/2017 |
| WO | 2017/070395 A1 | 4/2017 |
| WO | 2017/070605 A1 | 4/2017 |
| WO | WO 2017/087784 A1 | 5/2017 |
| WO | WO-2017087784 A1 * | 5/2017 ........... A61K 31/555 |
| WO | 2017/132291 A1 | 8/2017 |
| WO | 2017/164936 A1 | 9/2017 |
| WO | 2017/189308 A1 | 11/2017 |
| WO | 2017189281 A1 | 11/2017 |
| WO | 2017/211900 A1 | 12/2017 |
| WO | 2017/219027 A1 | 12/2017 |
| WO | 2018/028647 A1 | 2/2018 |
| WO | 2018/035250 A1 | 2/2018 |
| WO | 2018/170333 A1 | 9/2018 |
| WO | 2018/232195 A1 | 12/2018 |
| WO | 2019/018423 A1 | 1/2019 |

OTHER PUBLICATIONS

Suresh et al., J. Immunol. 170:788-794 (Year: 2003).*
Downs-Canner et al., Ann Surg Oncol 23:655-662 (Year: 2016).*
Ren et al., Clin Cancer Res 23(9):2255-66 (Year: 2016).*
The Broad Institute, Inc., "International Preliminary Report on Patentability received in PCT Application No. PCT/US2018/037662", dated Dec. 26, 2019, 6 pages.
Liszewski, et al., "Intracellular Complement Activation Sustains T Cell Homeostasis and Mediates Effector Differentiation", Immunity, vol. 39, Dec. 12, 2013, 1143-1157.
Puram, et al., "Single-Cell Transcriptomic Analysis of Primary and Metastatic Tumor Ecosystems in Head and Neck Cancer", Cell, vol. 171, No. 7, Dec. 14, 2017, 1611-1624.
Tirosh, et al., "Dissecting The Multicellular Ecosystem of Metastatic Melanoma by Single-Cell RNA-Seq", Science, vol. 352, No. 6282, Apr. 8, 2016, 189-196.
Tirosh, et al., "Single-Cell RNA-seq Supports a Developmental Hierarchy in Human Oligodendroglioma", Nature, vol. 539, No. 7628, Nov. 10, 2016, 309-313.
Venteicher, et al., "Decoupling Genetics, Lineages, and Microenvironment in IDH-Mutant Gliomas by Single-Cell RNA-Seq", Science, vol. 355, No. 6332, Mar. 31, 2017, 29 pages.
The Broad Institute, Inc., Communication pursuant to Rule 164(1) EPC for EP 18818420.4, dated Feb. 10, 2021, 18 pages.
Ajona, et al., "A Combined PD-1/C5a Blockade Synergistically Protects Against Lung Cancer Growth and Metastasis", Cancer Discovery, vol. 7, No. 7, Mar. 2017, pp. 694-703.
Liszweski, et al., "Intracellular Complement Activation Sustains T cell Homeostasis and Mediates Effector Differentiation", Immunity, vol. 39, No. 6, Dec. 2013, pp. 1143-1157.
Markiewski, et al., "Modulation of the Antitumor Immune Response by Complement", Nature Immunology, vol. 9, No. 11, Sep. 28, 2008, pp. 1225-1235.
Nabizadeh, et al., "The Complement C3a Receptor Contributes to Melanoma Tumorigenesis by Inhibiting Neutrophil and CD4+ T cell Responses", The Journal of Immunology, vol. 196, No. 11, Jun. 2016, pp. 4783-4792.
Wang, et al., "Autocrine Complement Inhibits IL 10-Dependent T-Cell-Mediated Antitumor Immunity to Promote Tumor Progression", Cancer Discovery, vol. 6, No. 9, Jun. 2016, pp. 1022-1035.
Roozendaal, et al., "Complement Receptors CD21 and CD35 in Humoral Immunity", Immunological Reviews, 2007, pp. 157-166.
The Broad Institute, Inc., "Notification of Transmittal of the International Search Report and the Written Opinion of the International Searching Authority, or the Declaration for PCT/US2018/037662", dated Sep. 11, 2018, 9 pages.

* cited by examiner

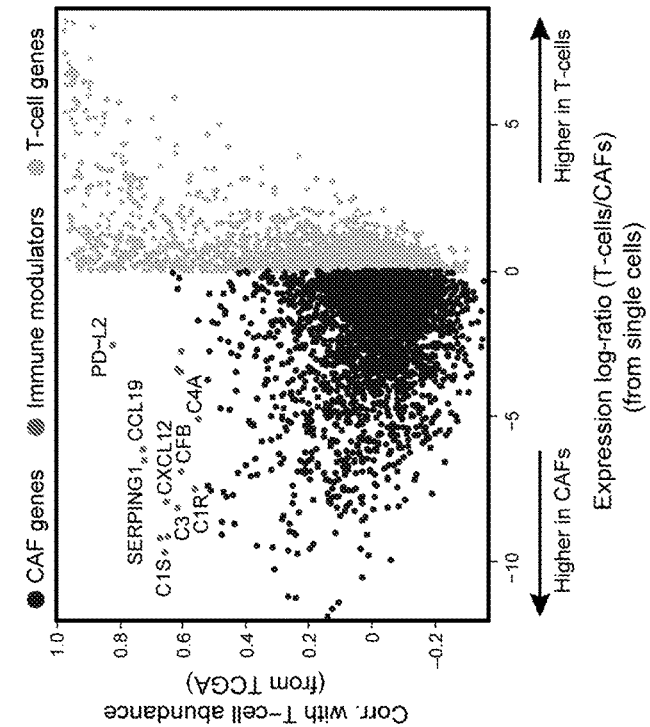
FIG. 1A
FIG. 1B
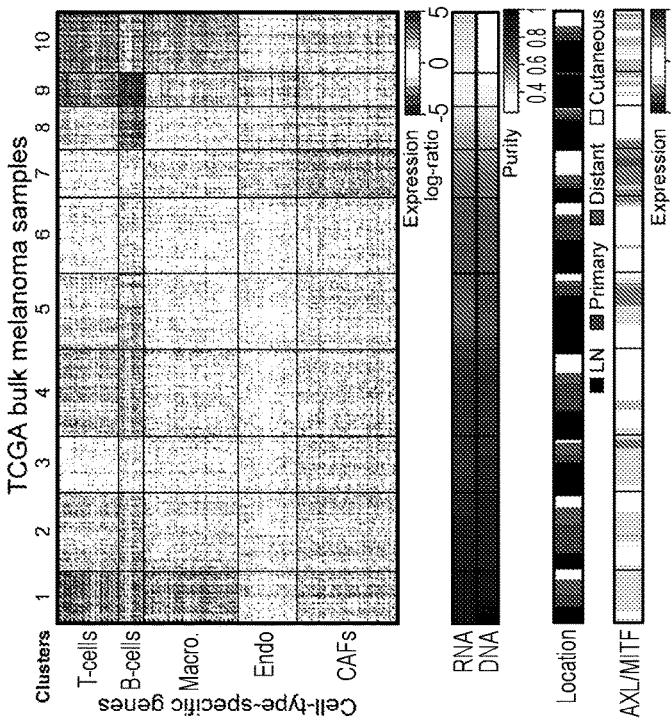
FIG. 1C
FIG. 1D

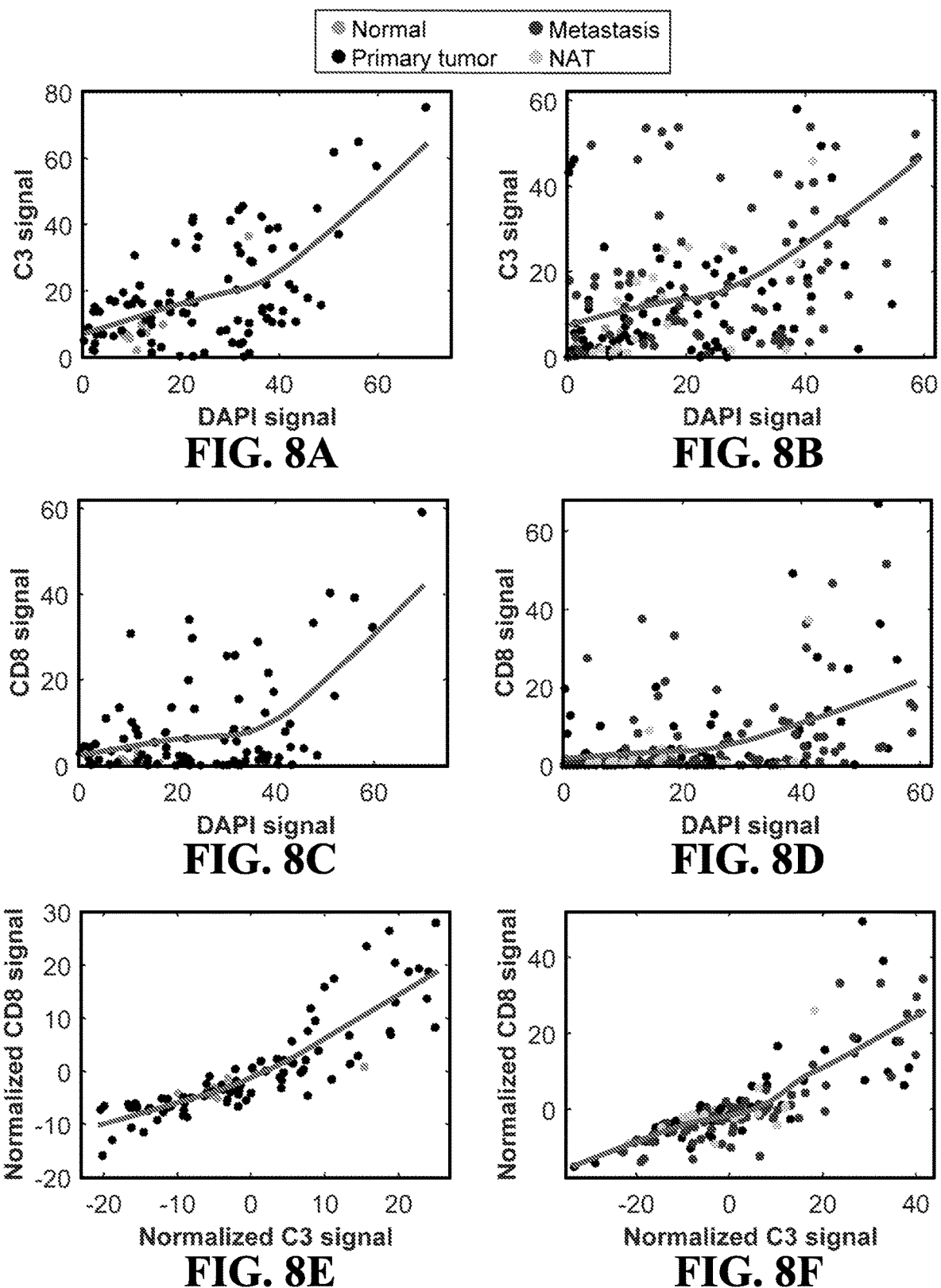

```
SEQUENCE LISTING

<160> NUMBER OF SEQ ID NOS: 4

<210> SEQ ID NO 1
<211> LENGTH: 288
<212> TYPE: PRT
<213> ORGANISM: Artificial Sequence
<220> FEATURE:
<223> OTHER INFORMATION: Synthetic

<400> SEQUENCE: 1

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Arg Ala Ala Gln Pro
    130                 135                 140
```

Ser Asp Ala Ser Pro Ala Gln Val Asp Leu Arg Thr Leu Gly Tyr
145                 150                 155                 160

Ser Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
                195                 200                 205

Lys Tyr Gln Asp Met Ile Ala Ala Leu Pro Glu Ala Thr His Glu Ala
            210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
                260                 265                 270

Glu Ala Val His Ala Trp Arg Asn Ala Leu Thr Gly Ala Pro Leu Asn
                275                 280                 285

<210> SEQ ID NO 2
<211> LENGTH: 183
<212> TYPE: PRT
<213> ORGANISM: Artificial Sequence
<220> FEATURE:
<223> OTHER INFORMATION: Synthetic

<400> SEQUENCE: 2

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
    50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180

<210> SEQ ID NO 3
<211> LENGTH: 107
<212> TYPE: PRT
<213> ORGANISM: Homo sapiens

```
<400> SEQUENCE: 3

Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
            35              40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85              90                  95

Ala Pro Pro Arg Asp Phe Ala Ala Tyr Arg Ser
            100             105

<210> SEQ ID NO 4
<211> LENGTH: 9
<212> TYPE: PRT
<213> ORGANISM: Homo sapiens

<400> SEQUENCE: 4

Ile Glu Val Met Tyr Pro Pro Pro Tyr
1               5
```

COMPOSITIONS AND METHODS TARGETING COMPLEMENT COMPONENT 3 FOR INHIBITING TUMOR GROWTH

CROSS-REFERENCE TO RELATED APPLICATIONS

This application is a U.S. National Stage of International Application No. PCT/US2018/037662, filed, Jun. 14, 2018, which claims the benefit of U.S. Provisional Application No. 62/519,788, filed Jun. 14, 2017. The entire contents of the above-identified application are hereby fully incorporated herein by reference.

STATEMENT REGARDING FEDERALLY SPONSORED RESEARCH

This invention was made with government support under Grant Nos. CA180922 and CA187975 awarded by the National Institutes of Health. The government has certain rights in the invention.

TECHNICAL FIELD

The present invention generally relates to methods and compositions for the treatment of cancer by targeting complement component 3 (C3).

BACKGROUND

Tumors are complex ecosystems defined by spatiotemporal interactions between heterogeneous cell types, including malignant, immune and stromal cells (1). Each tumor's cellular composition, as well as the interplay between these components, may exert critical roles in cancer development (2). However, the specific components, their salient biological functions, and the means by which they collectively define tumor behavior remain incompletely characterized.

Tumor cellular diversity poses both challenges and opportunities for cancer therapy. This is most clearly demonstrated by the remarkable but varied clinical efficacy achieved in malignant melanoma with targeted therapies and immunotherapies. First, immune checkpoint inhibitors produce substantial clinical responses in some patients with metastatic melanomas (3-7); however, the genomic and molecular determinants of response to these agents remain poorly understood. Although tumor neoantigens and PD-L1 expression clearly contribute (8-10), it is likely that other factors from subsets of malignant cells, the microenvironment, and tumor-infiltrating lymphocytes (TILs) also play essential roles (11). Second, melanomas that harbor the BRAFV600E mutation are commonly treated with RAF/MEK-inhibition prior to or following immune checkpoint inhibition. Although this regimen improves survival, virtually all patients eventually develop resistance to these drugs (12,13). Unfortunately, no targeted therapy currently exists for patients whose tumors lack BRAF mutations-including NRAS mutant tumors, those with inactivating NF1 mutations, or rarer events (e.g., RAF fusions). Collectively, these factors highlight the need for a deeper understanding of melanoma composition and its impact on clinical course.

The next wave of therapeutic advances in cancer will likely be accelerated by emerging technologies that systematically assess the malignant, microenvironmental, and immunologic states most likely to inform treatment response and resistance. An ideal approach would assess salient cellular heterogeneity by quantifying variation in oncogenic signaling pathways, drug-resistant tumor cell subsets, and the spectrum of immune, stromal and other cell states that may inform immunotherapy response. Toward this end, emerging single-cell genomic approaches enable detailed evaluation of genetic and transcriptional features present in 100s-1000s of individual cells per tumor (14-16). In principle, this approach may provide a comprehensive means to identify all major cellular components simultaneously, determine their individual genomic and molecular states (15), and ascertain which of these features may predict or explain clinical responses to anticancer agents.

Intra-tumoral heterogeneity contributes to therapy failure and disease progression in cancer. Tumor cells vary in proliferation, stemness, invasion, apoptosis, chemoresistance and metabolism (72). Various factors may contribute to this heterogeneity. On the one hand, in the genetic model of cancer, distinct tumor subclones are generated by branched genetic evolution of cancer cells; on the other hand, it is also becoming increasingly clear that certain cancers display diversity due to features of normal tissue organization. From this perspective, non-genetic determinants, related to developmental pathways and epigenetic programs, such as those associated with the self-renewal of tissue stem cells and their differentiation into specialized cell types, contribute to tumor functional heterogeneity (73,74). In particular, in a hierarchical developmental model of cancer, cancer stem cells (CSC) have the unique capacity to self-renew and to generate non-tumorigenic differentiated cancer cells. This model is still controversial, but—if correct—has important practical implications for patient management (75,76). Pioneering studies in leukemias have indeed demonstrated that targeting stem cell programs or triggering cellular differentiation can override genetic alterations and yield clinical benefit (72,77).

Relating the genetic and non-genetic models of cancer heterogeneity, especially in solid human tumors, has been limited due to technical challenges. Analysis of human tumor genomes has shed light on the genetic model, but is typically performed in bulk and does not inform us on the concomitant functional states of cancer cells. Conversely, various markers have been used to isolate candidate CSCs across different human malignancies, and to demonstrate their capacity to propagate tumors in mouse xenograft experiments (72,78-80). For example, in the field of human gliomas, candidate CSCs have been isolated in high-grade (WHO grades III-IV) lesions, using either combinations of cell surface markers such as CD133, SSEA-1, A2B5, CD44 and α-6 integrin or by in vitro selection and expansion of gliomaspheres in serum-free conditions (75,76,78,80-83). However, these functional approaches have generated controversy, as they require in vitro or in vivo selection in animal models with results dependent on xenogeneic environments that are very different from the native human tumor milieu. In addition, these methods do not interrogate the relative contribution of genetic mutations to the observed phenotypes (which can limit reproducibility) and do not allow an unbiased analysis of cellular states in situ in human patients (72). It also remains largely unknown if candidate CSC-like cells described in human high-grade tumors are aberrantly generated during glioma progression by dedifferentiation of mature glial cells or if gliomas contain CSC-like cells early in their development—as grade II lesions—a question central for our understanding of the initial steps of gliomagenesis (84). Thus, it is critical to cancer biology to develop a framework that allows the unbiased analysis of cellular programs at the single-cell level and across different genetic clones in human tumors, in situ, and at each stage of clinical progression, especially early in their development.

Furthermore, there is a need to identify gene expression profiles representative of malignant, microenvironmental, or immunologic states of tumors and tissues, and of cells and cell types which they comprise. Identification of gene expression profiles associated with cell types and immunological states can provide for novel therapeutic targets, as well as methods of identifying, designing and selecting appropriate treatment regimens.

Citation or identification of any document in this application is not an admission that such document is available as prior art to the present invention.

SUMMARY

The invention relates to gene expression signatures and networks of tumors and tissues, as well as multicellular ecosystems of tumors and tissues and the cells and cell type which they comprise. Tumors are multicellular assemblies that encompass many distinct genotypic and phenotypic states. The invention provides for the characterization of components, functions and interactions of tumors and tissues and the cells which they comprise. Single-cell RNA-seq was applied to thousands of malignant and non-malignant cells derived from melanomas, gliomas, head and neck cancer, brain metastases of breast cancer, and tumors in The Cancer Genome Atlas (TCGA) to examine tumor ecosystems. Components of the complement system were found to be correlated to immune cell abundance across different cancer types, however the function of complement in cancer was not elucidated (see e.g., International patent applications PCT/US2016/40015, filed Jun. 29, 2016 and PCT/US2017/014995, filed Jan. 25, 2017; Tirosh et al., Dissecting the multicellular ecosystem of metastatic melanoma by single-cell RNA-seq, Science. 2016 Apr. 8; 352(6282):189-96); Tirosh et al., Single-cell RNA-seq supports a developmental hierarchy in human oligodendroglioma, *Nature*. (2016), vol. 539, pp. 309-313; and Venteicher et al., Decoupling genetics, lineages, and microenvironment in IDH-mutant gliomas by single-cell RNA-seq, Science. (2017), Mar 31; 355(6332)), herein incorporated by reference in its entirety. The present application is based on the discovery of a role for C3 in a tumor control phenotype in vivo. The present invention also provides novel compositions and therapeutic strategies based on modulation of C3 function in the treatment of cancer.

The invention provides signature genes, gene products, and expression profiles of signature genes, gene networks, and gene products of tumors and component cells. The cancer may include, without limitation, liquid tumors such as leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). Lymphoproliferative disorders are also considered to be proliferative diseases. In one embodiment, the patient is suffering from melanoma. The signature genes, gene products, and expression profiles are useful to identify components of tumors and tissues and states of such components, such as, without limitation, neoplastic cells, malignant cells, stem cells, immune cells, and malignant, microenvironmental, or immunologic states of such component cells.

In one aspect, the present invention provides for an isolated T cell modified to decrease the function, activity and/or expression of complement receptor. The T cell may be a CD8+ T cell, CD4+ T cell, or CD4+ Treg. The complement receptor may be CR1/2 (CD35/CD21). The T cell may express an endogenous T cell receptor (TCR) or chimeric antigen receptor (CAR). The T cell may be a tumor infiltrating lymphocyte (TIL).

In another aspect, the present invention provides for a pharmaceutical composition comprising one or more modified T cells according to any embodiment herein. In certain embodiments, the present invention provides for a method of treating cancer in a subject in need thereof, comprising administering the pharmaceutical composition to the subject. Thus, the present invention provides for obtaining TILs from a subject or for generating a T cell that expresses an endogenous TCR or expresses a CAR and transferring the cells to a subject in need thereof.

In another aspect, the present invention provides for a method of increasing tumor-infiltrating lymphocytes (TILs) in a tumor comprising administering an agent that decreases the activity and/or expression of C3 or a complement receptor.

In another aspect, the present invention provides for a method of treating or enhancing treatment of cancer comprising administering an agent to a subject in need thereof that decreases the activity and/or expression of C3 or a complement receptor.

In certain embodiments, administering of the agent increases an immune response. In certain embodiments, the complement receptor is CR1/2 (CD35/CD21). In certain embodiments, the agent comprises a small molecule, peptide, therapeutic antibody, antibody fragment or antibody-like protein scaffold. In certain embodiments, the agent comprises a CRISPR system, TALE, TALEN, or Zinc Finger protein. In certain embodiments, the agent is an isolated natural product capable of inhibiting C3. In certain embodiments, the agent comprises a metalloproteinase inhibitor, whereby C3 is not cleaved. In certain embodiments, the agent comprises a serine protease inhibitor, whereby C3 is not cleaved. In certain embodiments, administering of the agent decreases lymphangiogenesis. In certain embodiments, administering of the agent decreases PDPN expression in cancer associated fibroblasts (CAFs).

In certain embodiments, the agent is administered in combination with an immunotherapy. The agent may further enhance an immune response. The immunotherapy may be immune checkpoint blockade or adoptive cell therapy. The immune checkpoint blockade may comprise anti-TIM3, anti-CTLA4, anti-PD-L1, anti-PD1, anti-TIGIT, anti-LAG3, or combinations thereof. The adoptive cell therapy may comprise CAR T therapy.

In certain embodiments, the cancer comprises a cancer of the blood, kidney, skin, bone, bladder, colon, brain, breast, head and neck, endometrium, lung, testes, ovary, pancreas or prostate.

In certain embodiments, the method further comprises monitoring efficacy of the treatment comprising detecting PDPN expression in CAFs. In certain embodiments, PDPN expression is decreased if the treatment is effective. Detecting PDPN may be by immunohistochemistry.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

Color versions of figures described herein are available in Tirosh et al., Dissecting the multicellular ecosystem of metastatic melanoma by single-cell RNA-seq (Science. 2016 Apr. 8; 352(6282):189-96); Tirosh et al., Single-cell RNA-seq supports a developmental hierarchy in human oligodendroglioma (*Nature*. (2016), vol. 539, pp. 309-313); and Venteicher et al., Decoupling genetics, lineages, and microenvironment in IDH-mutant gliomas by single-cell RNA-seq (Science. (2017), Mar 31; 355(6332), herein incorporated by reference in its entirety.

FIG. 1A-1G shows deconvolution of bulk melanoma profiles by specific signatures of non-cancer cell types revealing cell-cell interactions. Panel (A) Bulk tumors segregate to distinct clusters based on their inferred cell type composition. Top panel: heat map showing the relative expression of gene sets defined from single-cell RNA-seq as specific to each of five cell types from the tumor microenvironment (y-axis) across 495 melanoma TCGA bulk-RNA signatures (x-axis). Each column is one tumor and tumors are partitioned into 10 distinct patterns identified by K-means clustering (vertical lines and cluster numbers at the top). Lower panels show from top to bottom tumor purity, specimen location (from TCGA), and AXL/MITF scores. Tumor purity as estimated by the expression of cell-type specific gene-sets ("RNA") was strongly correlated with that estimated by ABSOLUTE mutation analysis ("DNA", R=0.8, bottom panel, both smoothed with a moving average of 40 tumors). Tumor classification, and in particular tumors with high abundance of CAFs, is strongly correlated with an increased ratio of AXL program/MITF-program expression (bottom). (B) Inferred cell-to-cell interactions between CAFs and T cells. Scatter plot compares for each gene (circle) the correlation of its expression with inferred T cell abundance across bulk tumors (y-axis, from TCGA transcriptomes) to how specific its expression is to CAFs vs. T cells (x-axis, based on single-cell transcriptomes). Genes that are highly specific to CAFs in a single cell analysis of tumors (red), but also associated with high T cell abundance in bulk tumors (black border) are key candidates for CAF/T cell interactions. This analysis identified known (CXCL12, CCL19) genes linked to immune cell chemotaxis and putative immune modulators, including multiple complement factors (CIR, CIS. C3. C4A. CFB and CINH [SERPING1]). (C) Correlation between quantitative immunofluorescence signal (% Area) of C3 and CD8 levels across 308 core biopsies of melanoma tissue microarrays. Shown are 90 included samples with 80 tumor specimens (black dots) showing a correlation (R=0.86) between C3/C8 signal and 10 normal control specimens (grey dots). See FIG. 8A-F for normalization and additional specimens. (D) Correlation coefficient (y-axis) between the average expression of CAF-derived complement factors shown in (B) and that of T cell markers (CD3/D/E/G, CD8A/B) across 26 TCGA cancer types with >100 samples (x-axis, left panel) and across 36 GTEx tissue types with >100 samples (x axis, right panel). Bars are colored based on correlation ranges as indicated at the bottom. Panel (E) shows correlations between the inferred frequencies of distinct cell types across TCGA samples. Panel (F) depicts correlated abundance of CD3+ cells and alpha-SMA+ TAFs by IHC. Panel (G) provides Kaplan Meier plots for progression free survival of patients included in the melanoma TCGA study, demonstrating that stratification by the frequency of TAFs (left) or MITF-levels (right) are associated with significant survival outcomes only in the context of low-immune melanomas.

FIG. 8A-8F depicts TMA analysis of complement factor 3 association with CD8+ T-cell infiltration, and control staining. Two TMAs (CC38-01 and ME208, shown in A, C, E and B, D, F, respectively) were used to evaluate the association between complement factor 3 (C3) and CD8 across a large number of tissues obtained by core biopsies of normal skin, primary tumors, metastatic lesions and NATs (normal skin with adjacent tumor). In both TMAs with a total of 308 core biopsies, Applicants observed high correlation between C3 and CD8 (R>0.8, shown in FIG. 1C for one TMA). To verify that this correlation is not due to technical effects in which some tissues stain more than others irrespective of the stains examined (e.g., due to variability in cellularity or tissue quality), Applicants normalized the values (% area, Methods) for both C3 and CD8 by those of DAPI staining. Indeed, Applicants found a non-random yet non-linear association between DAPI stains and either C3 (A, B), or CD8 (C, D), which were removed by subtracting a LOWESS regression, shown as red curves in panels A-D. The normalized C3 and CD8 values were not correlated with DAPI levels, yet maintained a high correlation with one another (E, F). R=0.86 and 0.74 for primary and normal skin in panel E (TMA CC38-01), and R=0.78, 0.86, 0.63 and 0.31 for primary melanomas, metastasis, NATs and normal skin in panel F (TMA ME208), respectively.

DETAILED DESCRIPTION OF THE EXAMPLE EMBODIMENTS

General Definitions

Figure 1G:
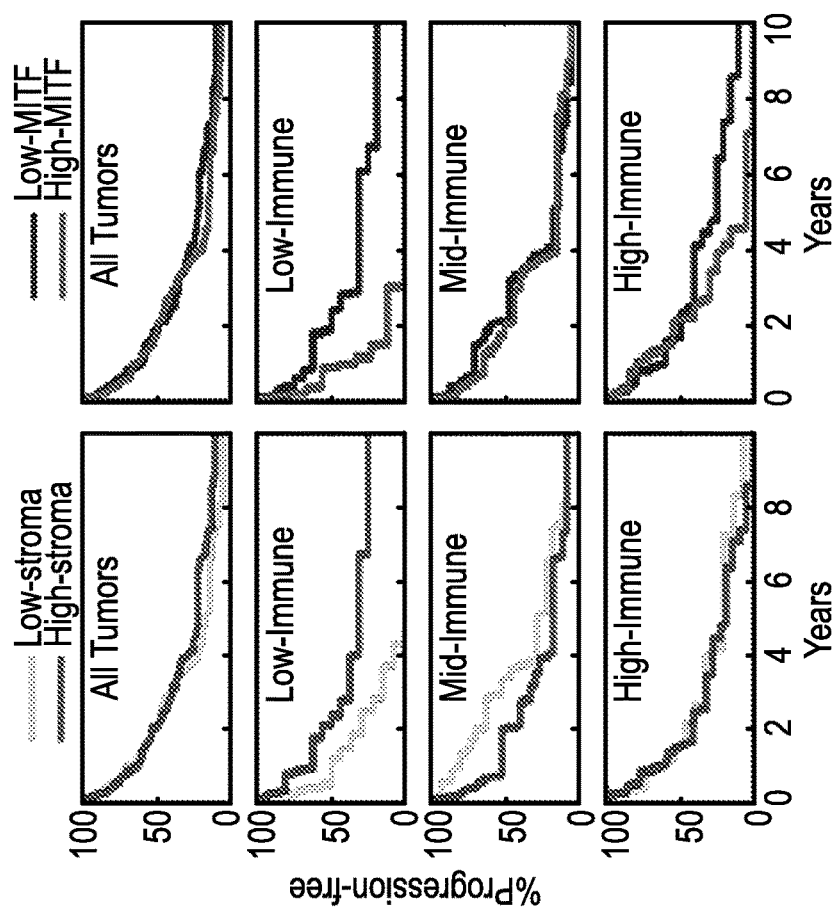
Figure 1E:
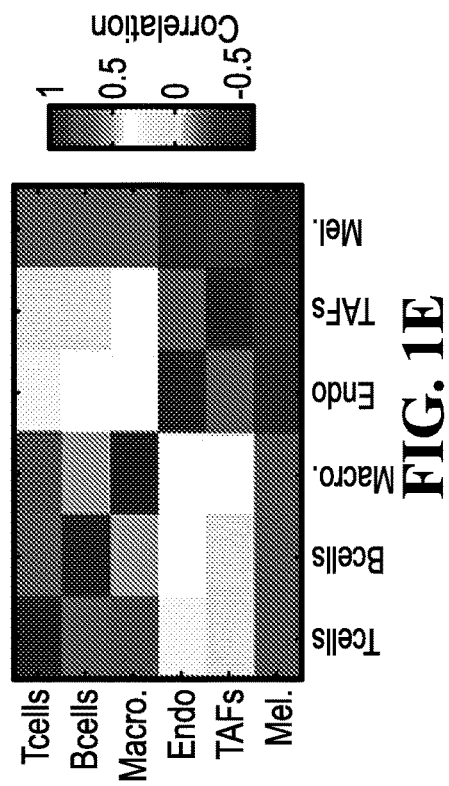
Figure 1F:
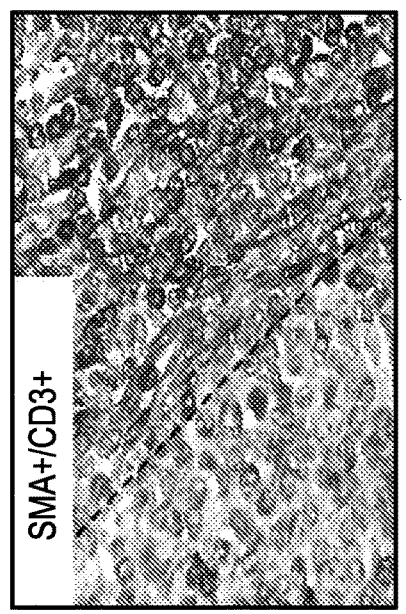

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboaotry Manual (1988) (Harlow and Lane, eds.): Antibodies A Laboaotry Manual, $2^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew el al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Reference is made to International Patent Application Serial No. PCT/US16/40015, filed Jun. 29, 2016 and International publication number WO2017004153 A1, published Jan. 5, 2017. Reference is also made to Tirosh et al., Dissecting the multicellular ecosystem of metastatic melanoma by single-cell RNA-seq (Science. 2016 Apr. 8; 352 (6282):189-96); Tirosh et al., Single-cell RNA-seq supports a developmental hierarchy in human oligodendroglioma (Nature. (2016), vol. 539, pp. 309-313); and Venteicher et al., Decoupling genetics, lineages, and microenvironment in IDH-mutant gliomas by single-cell RNA-seq (Science. (2017), Mar 31; 355(6332), herein incorporated by reference in its entirety.

Publications, published patent documents, and patent applications cited in this application may be considered indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

Overview

The invention relates to gene expression signatures and networks of tumors and tissues, as well as multicellular ecosystems of tumors and tissues and the cells and cell type which they comprise. The invention provides methods of characterizing components, functions and interactions of tumors and tissues and the cells which they comprise.

The invention provides signature genes, gene products, and expression profiles of signature genes, gene networks, and gene products of tumors and component cells, and including especially melanoma tumors, gliomas, head and neck cancer, brain metastases of breast cancer, and tumors in The Cancer Genome Atlas (TCGA) and tissues. This invention further relates generally to compositions and methods for identifying genes and gene networks that respond to, modulate, control or otherwise influence tumors and tissues, including cells and cell types of the tumors and tissues, and malignant, microenvironmental, or immunologic states of the tumor cells and tissues. The invention also relates to methods of diagnosing, prognosing and/or staging of tumors, tissues and cells, and provides compositions and methods of modulating expression of genes and gene networks of tumors, tissues and cells, as well as methods of identifying, designing and selecting appropriate treatment regimens.

The invention further relates to controlling an immune response by modulating the activity of a component of the complement system. Cancer is but a single exemplary condition that can be controlled by an immune reaction. The present invention describes for the first time how complement expression in the microenvironment can control the abundance of immune cells at a site of disease or condition requiring a shift in balance of an immune response. Since correlation analysis cannot determine causality, Applicants further determined an in vivo role for cell-to-cell interactions in the control of tumor growth. Moreover, Applicants have shown for the first time control of tumor growth by knocking out expression of complement component 3 (C3). Not being bound by a theory, expression of C3 in the tumor microenvironment may be in response to immune infiltration of a tumor and suppress an immune response. Inhibition of C3 may result in an enhanced immune response.

Use of Signature Genes

As used herein a signature may encompass any gene or genes, protein or proteins, or epigenetic element(s) whose expression profile or whose occurrence is associated with a specific cell type, subtype, or cell state of a specific cell type or subtype within a population of cells. Increased or decreased expression or activity or prevalence may be compared between different cells in order to characterize or identify for instance specific cell (sub)populations. A gene signature as used herein, may thus refer to any set of up- and down-regulated genes between different cells or cell (sub) populations derived from a gene-expression profile. For example, a gene signature may comprise a list of genes differentially expressed in a distinction of interest. It is to be understood that also when referring to proteins (e.g. differentially expressed proteins), such may fall within the definition of "gene" signature.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. blood samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of cancer cells that are linked to particular pathological condition (e.g. cancer grade), or linked to a particular outcome or progression of the disease, or linked to a particular response to treatment of the disease.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular tumor cell or tumor cell (sub)population if it is upregulated or only present, detected or detectable in that particular tumor cell or tumor cell (sub)population, or alternatively is downregulated or only absent, or undetectable in that particular tumor cell or tumor cell (sub)population. In this context, a signature consists of one or more differentially expressed genes/proteins or differential epigenetic elements when comparing different cells or cell (sub)populations, including comparing different tumor cells or tumor cell (sub)populations, as well as comparing tumor cells or tumor cell (sub)populations with non-tumor cells or non-tumor cell (sub)populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of tumor cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein and/or epigenetic element of the signature, such as for instance at least to, at least three, at least four, at least five, at least six, or all genes/proteins and/or epigenetic elements of the signature.

Signatures may be functionally validated as being uniquely associated with a particular immune responder phenotype. Induction or suppression of a particular signature may consequentially associated with or causally drive a particular immune responder phenotype.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

In further aspects, the invention relates to gene signatures, protein signature, and/or other genetic or epigenetic signature of particular tumor cell subpopulations, as defined herein elsewhere. The invention hereto also further relates to particular tumor cell subpopulations, which may be identified based on the methods according to the invention as discussed herein; as well as methods to obtain such cell (sub)populations and screening methods to identify agents capable of inducing or suppressing particular tumor cell (sub)populations.

The invention further relates to various uses of the gene signatures, protein signature, and/or other genetic or epigenetic signature as defined herein, as well as various uses of the tumor cells or tumor cell (sub)populations as defined herein. Particular advantageous uses include methods for identifying agents capable of inducing or suppressing particular tumor cell (sub)populations based on the gene signatures, protein signature, and/or other genetic or epigenetic signature as defined herein. The invention further relates to agents capable of inducing or suppressing particular tumor cell (sub)populations based on the gene signatures, protein signature, and/or other genetic or epigenetic signature as defined herein., as well as their use for modulating, such as inducing or repressing, a particular a particular gene signature, protein signature, and/or other genetic or epigenetic signature. In one embodiment, genes in one population of cells may be activated or suppressed in order to affect the cells of another population. In related aspects, modulating, such as inducing or repressing, a particular a particular gene signature, protein signature, and/or other genetic or epigenetic signature may modify overall tumor composition, such as tumor cell composition, such as tumor cell subpopulation composition or distribution, or functionality.

As used herein the term "signature gene" means any gene or genes whose expression profile is associated with a specific cell type, subtype, or cell state of a specific cell type or subtype within a population of cells. The signature gene can be used to indicate the presence of a cell type, a subtype of the cell type, the state of the microenvironment of a population of cells, and/or the overall status of the entire cell population. Furthermore, the signature genes may be indicative of cells within a population of cells in vivo. The signature genes of the present invention were discovered by analysis of expression profiles of single-cells within a population of cells from freshly isolated tumors, thus allowing the discovery of novel cell subtypes that were previously invisible in a population of cells within a tumor. The presence of subtypes may be determined by subtype specific signature genes. The presence of these specific cell types may be determined by applying the signature genes to bulk sequencing data in a patient tumor. Not being bound by a theory, a tumor is a conglomeration of many cells that make up a tumor microenvironment, whereby the cells communicate and affect each other in specific ways. As such, specific cell types within this microenvironment may express signature genes specific for this microenvironment. Not being bound by a theory the signature genes of the present invention may be microenvironment specific, such as their expression in a tumor. Not being bound by a theory, signature genes determined in single cells that originated in a tumor are specific to other tumors. Not being bound by a theory, a combination of cell subtypes in a tumor may indicate an outcome. Not being bound by a theory, the signature genes can be used to deconvolute the network of cells present in a tumor based on comparing them to data from bulk analysis of a tumor sample. Not being bound by a theory the presence of specific cells and cell subtypes are indicative of tumor growth and resistance to treatment. The signature gene may indicate the presence of one particular cell type. In one embodiment, the signature genes may indicate that tumor infiltrating T-cells are present. The presence of cell types within a tumor may indicate that the tumor will be resistant to a treatment. In one embodiment the signature genes of the present invention are applied to bulk sequencing data from a tumor sample to transform the data into information relating to disease outcome and personalized treatments. In one embodiment, the novel signature genes are used to detect multiple cell states that occur in a subpopulation of tumor cells that are linked to resistance to targeted therapies and progressive tumor growth.

In one embodiment, the signature genes are detected by immunofluorescence, by mass cytometry (CyTOF), drop-seq, single cell qPCR, MERFISH (multiplex (in situ) RNA FISH) and/or by in situ hybridization. Other methods including absorbance assays and colorimetric assays are known in the art and may be used herein.

In one embodiment, tumor cells are stained for cell subtype specific signature genes. In one embodiment, the cells are fixed. In another embodiment, the cells are formalin fixed and paraffin embedded. Not being bound by a theory, the presence of the cell subtypes in a tumor indicate outcome and personalized treatments. Not being bound by a theory, the cell subtypes may be quantitated in a section of a tumor and the number of cells indicates an outcome and personalized treatment.

It will be understood by the skilled person that treating as referred to herein encompasses enhancing treatment, or improving treatment efficacy. Treatment may include tumor regression as well as inhibition of tumor growth or tumor cell proliferation, or inhibition or reduction of otherwise deleterious effects associated with the tumor.

Figure 4A:
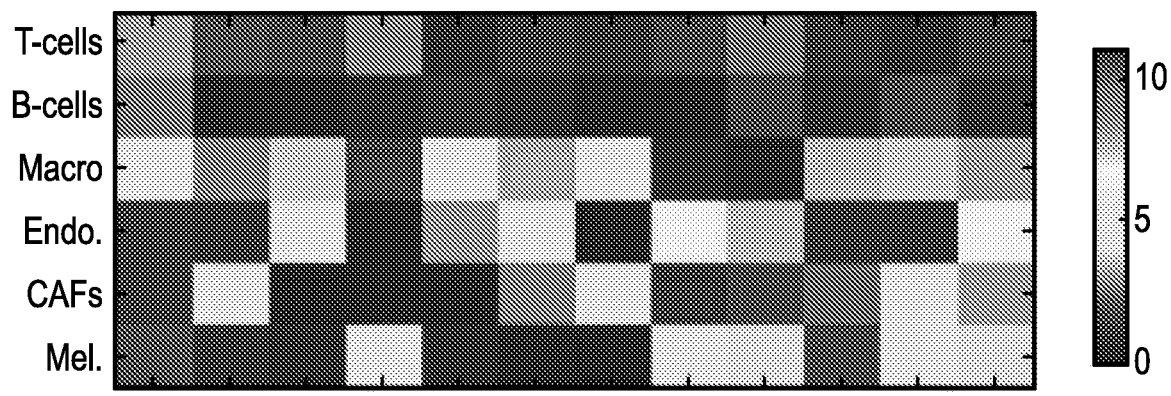
FIG. 4A-B depicts immune modulators preferentially expressed by in-vivo CAFs. Panel A shows average expression levels of a set of immune modulators, including those shown in FIG. 1, in the five non-malignant cell types as defined by single cell analysis in melanoma tumors. Panel B shows a correlation of the set of immune modulators shown in (A) with inferred abundances of non-malignant cell type across TGA melanoma tumors.
Figure 4B:
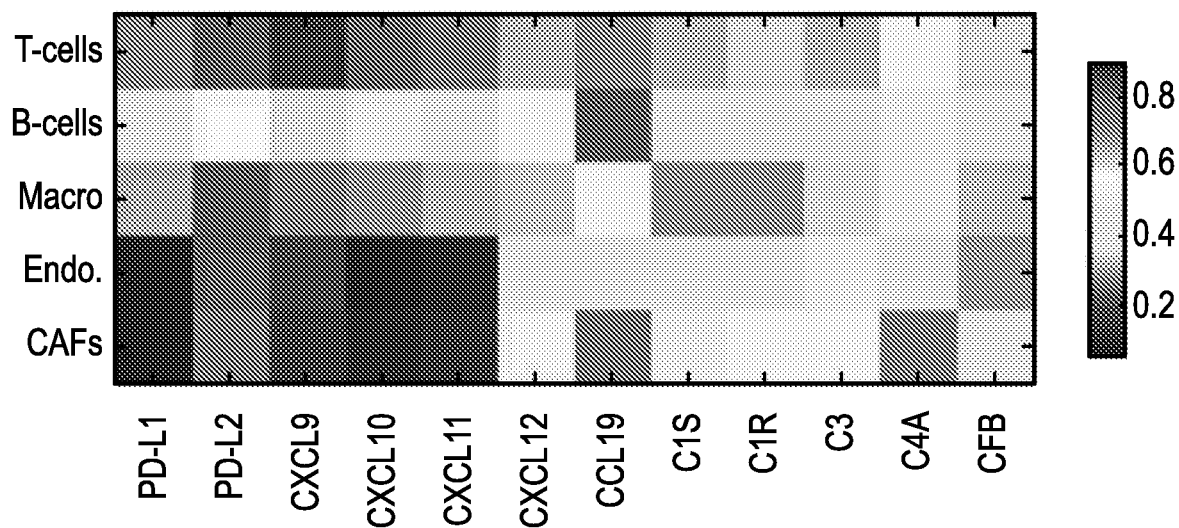

Immune checkpoints are inhibitory pathways that slow down or stop immune reactions and prevent excessive tissue damage from uncontrolled activity of immune cells. By "checkpoint inhibitor" is meant to refer to any small molecule chemical compound, antibody, nucleic acid molecule, or polypeptide, or fragments thereof, which inhibits the inhibitory pathways, allowing more extensive immune activity. In certain embodiments, the checkpoint inhibitor is an inhibitor of the programmed death-1 (PD-1) pathway, for example an anti-PD1 antibody, such as, but not limited to Nivolumab. In other embodiments, the checkpoint inhibitor is an anti-cytotoxic T-lymphocyte-associated antigen (CTLA-4) antibody. In additional embodiments, the checkpoint inhibitor is targeted at another member of the CD28CTLA4 Ig superfamily such as BTLA, LAG3, ICOS, PDL1 or KIR Page et al., Annual Review of Medicine 65:27 (2014)). In further additional embodiments, the checkpoint inhibitor is targeted at a member of the TNFR superfamily such as CD40, OX40, CD137, GITR, CD27 or TIM-3. In certain embodiments targeting a checkpoint inhibitor is accomplished with an inhibitory antibody or similar molecule. In other cases, it is accomplished with an agonist for the target; examples of this class include the stimulatory targets OX40 and GITR. In some cases it is accomplished with modulators targeting one or more of, e.g., chemotactic (CXCL12, CCL19) and immune modulating genes (PD-L2), and/or complement molecules provided in FIG. 4B.

The term "depth (coverage)" as used herein refers to the number of times a nucleotide is read during the sequencing process. Depth can be calculated from the length of the original genome (G), the number of reads(N), and the average read length(L) as N×l/G. For example, a hypothetical genome with 2,000 base pairs reconstructed from 8 reads with an average length of 500 nucleotides will have 2× redundancy. This parameter also enables one to estimate other quantities, such as the percentage of the genome covered by reads (sometimes also called coverage). A high coverage in shotgun sequencing is desired because it can overcome errors in base calling and assembly. The subject of DNA sequencing theory addresses the relationships of such quantities. Even though the sequencing accuracy for each individual nucleotide is very high, the very large number of nucleotides in the genome means that if an individual genome is only sequenced once, there will be a significant number of sequencing errors. Furthermore, rare single-nucleotide polymorphisms (SNPs) are common. Hence to distinguish between sequencing errors and true SNPs, it is necessary to increase the sequencing accuracy even further by sequencing individual genomes a large number of times.

The term "deep sequencing" as used herein indicates that the total number of reads is many times larger than the length of the sequence under study. The term "deep" as used herein refers to a wide range of depths greater than or equal to 1× up to 100×.

The terms "complement," "complement system" and "complement components" as used herein refer to proteins and protein fragments, including serum proteins, serosal proteins, and cell membrane receptors that are part of any of the classical complement pathway, the alternative complement pathway, and the lectin pathway. The terms "complement," "complement system" and "complement components" also includes the defense molecules (protection molecules) CD46, CD55 and CD59.

The classical pathway is triggered by activation of the C1-complex. The C1-complex is composed of 1 molecule of C1q, 2 molecules of C1r and 2 molecules of C1s, or C1qr2s2. This occurs when C1q binds to IgM or IgG complexed with antigens. A single pentameric IgM can initiate the pathway, while several, ideally six, IgGs are needed. This also occurs when C1q binds directly to the surface of the pathogen. Such binding leads to conformational changes in the C1q molecule, which leads to the activation of two C1r molecules. C1r is a serine protease. They then cleave Cis (another serine protease). The C1r2s2 component now splits C4 and then C2, producing C4a, C4b, C2a, and C2b. C4b and C2a bind to form the classical pathway C3-convertase (C4b2a complex), which promotes cleavage of C3 into C3a and C3b; C3b later joins with C4b2a (the C3 convertase) to make C5 convertase (C4b2a3b complex). The inhibition of C1r and C1s is controlled by C1-inhibitor (SERPING1).

The alternative pathway is continuously activated at a low level as a result of spontaneous C3 hydrolysis due to the breakdown of the internal thioester bond. The alternative pathway does not rely on pathogen-binding antibodies like the other pathways. C3b that is generated from C3 by a C3 convertase enzyme complex in the fluid phase is rapidly inactivated by factor H and factor I, as is the C3b-like C3 that is the product of spontaneous cleavage of the internal thioester. In contrast, when the internal thioester of C3 reacts with a hydroxyl or amino group of a molecule on the surface of a cell or pathogen, the C3b that is now covalently bound to the surface is protected from factor H-mediated inactivation. The surface-bound C3b may now bind factor B to form C3bB. This complex in the presence of factor D will be cleaved into Ba and Bb. Bb will remain associated with C3b to form C3bBb, which is the alternative pathway C3 convertase.

The C3bBb complex is stabilized by binding oligomers of factor P (Properdin). The stabilized C3 convertase, C3bBbP, then acts enzymatically to cleave much more C3, some of which becomes covalently attached to the same surface as C3b. This newly bound C3b recruits more B, D and P activity and greatly amplifies the complement activation. When complement is activated on a cell surface, the activation is limited by endogenous complement regulatory proteins, which include CD35, CD46, CD55 and CD59, depending on the cell. Pathogens, in general, don't have complement regulatory proteins. Thus, the alternative complement pathway is able to distinguish self from non-self on the basis of the surface expression of complement regulatory proteins. Host cells don't accumulate cell surface C3b (and the proteolytic fragment of C3b called iC3b) because this is prevented by the complement regulatory proteins, while foreign cells, pathogens and abnormal surfaces may be heavily decorated with C3b and iC3b. Accordingly, the alternative complement pathway is one element of innate immunity.

Once the alternative C3 convertase enzyme is formed on a pathogen or cell surface, it may bind covalently another C3b, to form C3bBbC3bP, the C5 convertase. This enzyme then cleaves C5 to C5a, a potent anaphylatoxin, and C5b. The C5b then recruits and assembles C6, C7, C8 and multiple C9 molecules to assemble the membrane attack complex. This creates a hole or pore in the membrane that can kill or damage the pathogen or cell.

The lectin pathway is homologous to the classical pathway, but with the opsonin, mannose-binding lectin (MBL), and ficolins, instead of C1q. This pathway is activated by binding of MBL to mannose residues on the pathogen surface, which activates the MBL-associated serine proteases, MASP-1, and MASP-2 (very similar to C1r and C1s, respectively), which can then split C4 into C4a and C4b and C2 into C2a and C2b. C4b and C2a then bind together to form the classical C3-convertase, as in the classical pathway. Ficolins are homologous to MBL and function via MASP in a similar way. Several single-nucleotide polymorphisms have been described in M-ficolin in humans, with effect on ligand-binding ability and serum levels. Historically, the larger fragment of C2 was named C2a, but it is now referred as C2b. In invertebrates without an adaptive immune system, ficolins are expanded and their binding specificities diversified to compensate for the lack of pathogen-specific recognition molecules.

The term "MDSC" (myeloid-derived suppressor cells) refers to a heterogenous group of immune cells from the myeloid lineage (a family of cells that originate from bone marrow stem cells), to which dendritic cells, macrophages and neutrophils also belong. MDSCs strongly expand in pathological situations such as chronic infections and cancer, as a result of an altered hematopoiesis. Thus, it is yet unclear whether MDSCs represent a group of immature myeloid cell types that have stopped their differentiation towards DCs, macrophages or granulocytes, or if they represent a myeloid lineage apart. MDSCs are however discriminated from other myeloid cell types in which they possess strong immunosuppressive activities rather than immunostimulatory properties. Similarly, to other myeloid cells, MDSCs interact with other immune cell types including T cells (the effector immune cells that kill pathogens, infected and cancer cells), dendritic cells, macrophages and NK cells to regulate their functions. Their mechanisms of action are beginning to be understood although they are still under heated debate and close examination by the scientific community. Nevertheless, clinical and experimental evidence has shown that cancer tissues with high infiltration of MDSC are associated with poor patient prognosis and resistance to therapies.

These signatures are useful in methods of monitoring a cancer in a subject by detecting a level of expression, activity and/or function of one or more signature genes or one or more products of one or more signature genes at a first time point, detecting a level of expression, activity and/or function of one or more signature genes or one or more products of one or more signature genes at a second time point, and comparing the first detected level of expression, activity and/or function with the second detected level of expression, activity and/or function, wherein a change in the first and second detected levels indicates a change in the cancer in the subject.

One unique aspect of the invention is the ability to relate expression of one gene or a gene signature in one cell type to that of another gene or signature in another cell type in the same tumor. In one embodiment, the methods and signatures of the invention are useful in patients with complex cancers, heterogeneous cancers or more than one cancer.

In an embodiment of the invention, these signatures are useful in monitoring subjects undergoing treatments and therapies for cancer to determine efficaciousness of the treatment or therapy. In an embodiment of the invention, these signatures are useful in monitoring subjects undergoing treatments and therapies for cancer to determine whether the patient is responsive to the treatment or therapy. In an embodiment of the invention, these signatures are also useful for selecting or modifying therapies and treatments that would be efficacious in treating, delaying the progression of or otherwise ameliorating a symptom of cancer. In an embodiment of the invention, the signatures provided herein are used for selecting a group of patients at a specific state of a disease with accuracy that facilitates selection of treatments.

The present invention also comprises a kit with a detection reagent that binds to one or more signature nucleic acids. Also provided by the invention is an array of detection reagents, e.g., oligonucleotides that can bind to one or more signature nucleic acids. Suitable detection reagents include nucleic acids that specifically identify one or more signature nucleic acids by having homologous nucleic acid sequences, such as oligonucleotide sequences, complementary to a portion of the signature nucleic acids packaged together in the form of a kit. The oligonucleotides can be fragments of the signature genes. For example the oligonucleotides can be 200, 150, 100, 50, 25, 10 or fewer nucleotides in length. The kit may contain in separate container or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a Northern hybridization or DNA chips or a sandwich ELISA or any other method as known in the art. Alternatively, the kit contains a nucleic acid substrate array comprising one or more nucleic acid sequences.

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include a T cell modulating agent, targeted therapies and checkpoint inhibitors, are used to treat or alleviate a symptom associated with a cancer. The present invention also provides methods of treating or alleviating a symptom associated with cancer. A therapeutic regimen is carried out by identifying a subject, e.g., a human patient suffering from cancer, using standard methods.

Efficaciousness of treatment is determined in association with any known method for diagnosing or treating the particular cancer. The invention comprehends a treatment method or Drug Discovery method or method of formulating or preparing a treatment comprising any one of the methods or uses herein discussed.

The phrase "therapeutically effective amount" as used herein refers to a nontoxic but sufficient amount of a drug, agent, or compound to provide a desired therapeutic effect.

As used herein "patient" refers to any human being receiving or who may receive medical treatment.

A "polymorphic site" refers to a polynucleotide that differs from another polynucleotide by one or more single nucleotide changes.

A "somatic mutation" refers to a change in the genetic structure that is not inherited from a parent, and also not passed to offspring.

Therapy or treatment according to the invention may be performed alone or in conjunction with another therapy, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, the stage of the cancer, and how the patient responds to the treatment. Additionally, a person having a greater risk of developing a cancer (e.g., a person who is genetically predisposed) may receive prophylactic treatment to inhibit or delay symptoms of the disease.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for oral, rectal, intravenous, intramuscular, subcutaneous, inhalation, nasal, topical or transdermal, vaginal, or ophthalmic administration. Thus, the medicament may be in form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, or aerosols.

In order to determine the genotype of a patient according to the methods of the present invention, it may be necessary to obtain a sample of genomic DNA from that patient. That sample of genomic DNA may be obtained from a sample of tissue or cells taken from that patient.

The tissue sample may comprise but is not limited to hair (including roots), skin, buccal swabs, blood, or saliva. The tissue sample may be marked with an identifying number or other indicia that relates the sample to the individual patient from which the sample was taken. The identity of the sample advantageously remains constant throughout the methods of the invention thereby guaranteeing the integrity and continuity of the sample during extraction and analysis. Alternatively, the indicia may be changed in a regular fashion that ensures that the data, and any other associated data, can be related back to the patient from whom the data was obtained. The amount/size of sample required is known to those skilled in the art.

Generally, the tissue sample may be placed in a container that is labeled using a numbering system bearing a code corresponding to the patient. Accordingly, the genotype of a particular patient is easily traceable.

In one embodiment of the invention, a sampling device and/or container may be supplied to the physician. The sampling device advantageously takes a consistent and reproducible sample from individual patients while simultaneously avoiding any cross-contamination of tissue. Accordingly, the size and volume of sample tissues derived from individual patients would be consistent.

According to the present invention, a sample of DNA is obtained from the tissue sample of the patient of interest. Whatever source of cells or tissue is used, a sufficient amount of cells must be obtained to provide a sufficient amount of DNA for analysis. This amount will be known or readily determinable by those skilled in the art.

DNA is isolated from the tissue/cells by techniques known to those skilled in the art (see, e.g., U.S. Pat. Nos. 6,548,256 and 5,989,431, Hirota et al., Jinrui Idengaku Zasshi. September 1989; 34(3):217-23 and John et al., Nucleic Acids Res. Jan. 25, 1991; 19(2):408; the disclosures of which are incorporated by reference in their entireties). For example, high molecular weight DNA may be purified from cells or tissue using proteinase K extraction and ethanol precipitation. DNA may be extracted from a patient specimen using any other suitable methods known in the art.

In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. Jan;12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October;14(10):955-958; and International patent application number PCT/US2016/059239, published as WO2017164936 on Sep. 28, 2017, which are herein incorporated by reference in their entirety.

Genetic Modifying Agents

In certain embodiments, the one or more modulating agents may be a genetic modifying agent. The genetic modifying agent may comprise a CRISPR system, a zinc finger nuclease system, a TALEN, or a meganuclease.

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOT: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters-especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

Guide Molecules

The methods described herein may be used to screen inhibition of CRISPR systems employing different types of guide molecules. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17,18, 19, 20, 21, 22, 23, 24, 25, 26, 27, 28, 29, 30, 31, 32, 33, 34, 35, 36, 37, 38, 3940, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15-30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such deamination of nucleotides is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and P A Carr and G M Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromouridine, pseudouridine, inosine, 7-methylguanosine. Examples of guide RNA chemical modifications include, without limitation, incorporation of 2'-O-methyl (M), 2'-O-methyl 3' phosphorothioate (MS), S-constrained ethyl(cEt), or 2'-O-methyl 3' thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., MedChemComm., 2014, 5:1454-1471; Hendel et al., Nat. Biotechnol. (2015) 33(9): 985-989; Li et al., Nature Biomedical Eigineering, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl(cEt), or 2'-O-methyl 3' thioPACE (MSP). Such modification can enhance genome editing efficiency (see Hendel et al., Nat. Biotechnol. (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemicially modified with 2'-O-Me, 2'-F or S-constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., eLife, 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (me1Ψ), 5-methoxyuridine(5moU), inosine, 7-methylguanosine, 2'-O-methyl 3'phosphorothioate (MS), S-constrained ethyl(cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU.

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sufonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of the guide sequence is approximately within the first 10 nucleotides of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire guide molecule is preserved. In one aspect, the loop that connects the stem made of X:Y basepairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

In particular embodiments the natural hairpin or stemloop structure of the guide molecule is extended or replaced by an extended stemloop. It has been demonstrated that extension of the stem can enhance the assembly of the guide molecule with the CRISPR-Cas proten (Chen et al. Cell. (2013); 155(7): 1479-1491). In particular embodiments the stem of the stemloop is extended by at least 1, 2, 3, 4, 5 or more complementary basepairs (i.e. corresponding to the addition of 2,4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a basepair flip.

In a particular embodiment, the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the complementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561):481-5. doi: 10.1038/nature14592. As further detailed herein, the skilled person will understand that Cas13 proteins may be modified analogously.

In particular embodiment, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green flourescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends an guide molecule that responds to normal or pathological physiological conditions, including without limitation pH, hypoxia, $O_2$ concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 mW/cm$^2$. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans;4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAT based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogren receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 µs and 500 milliseconds, preferably between 1 µs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100.mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between IV/cm and 20V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other Therapeutic applications, higher intensities of ultrasound may be employed, for example, Hifu at 100 w/cm up to 1 kw/cm2 (or even higher) for short periods of time. The term "ultrasound" as used in this specification is intended to encompass diagnostic, therapeutic and Focused ultrasound.

Focused ultrasound (fus) allows thermal energy to be delivered without an Invasive probe (see morocz et al 1998 journal of magnetic resonance imaging vol.8, no. 1, Pp. 136-142. Another form of focused ultrasound is high intensity focused ultrasound (hifu) Which is reviewed by moussatov et al in ultrasonics (1998) vol.36, no.8, pp. 893-900 and Tranhuuhue et al in acustica (1997) vol.83, no.6, pp.1103-1106.

Preferably, a combination of diagnostic ultrasound and a therapeutic ultrasound is Employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm−2.

Even more preferably, the exposure to an ultrasound energy source is at a power density of from about 1 to about 15 Wcm−2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm−2 to about 10 Wcm−2 with a frequency ranging from about 0.015 to about 10 MHz (see WO 98/52609). However, alternatives are also possible, for example, exposure to an ultrasound energy source at an acoustic power density of above 100 Wcm−2, but for reduced periods of time, for example, 1000 Wcm−2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm−2 or 1.25 Wcm−2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched basepairs at the 3' end. In particular embodiments of the invention, additional sequences comprising an extended length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

CRISPR RNA-Targeting Effector Proteins

In one example embodiment, the CRISPR system effector protein is an RNA-targeting effector protein. In certain embodiments, the CRISPR system effector protein is a Type VI CRISPR system targeting RNA (e.g., Cas13a, Cas13b, Cas13c or Cas13d). Example RNA-targeting effector proteins include Cas13b and C2c2 (now known as Cas13a). It will be understood that the term "C2c2" herein is used interchangeably with "Cas13a". "C2c2" is now referred to as "Cas13a", and the terms are used interchangeably herein unless indicated otherwise. As used herein, the term "Cas13" refers to any Type VI CRISPR system targeting RNA (e.g., Cas13a, Cas13b, Cas13c or Cas13d). When the CRISPR protein is a C2c2 protein, a tracrRNA is not required. C2c2 has been described in Abudayyeh et al. (2016) "C2c2 is a single-component programmable RNA-guided RNA-targeting CRISPR effector"; Science; DOI: 10.1126/science.aaf5573; and Shmakov et al. (2015) "Discovery and Functional Characterization of Diverse Class 2 CRISPR-Cas Systems", Molecular Cell, DOI: dx.doi.org/10.1016/j.molcel.2015.10.008; which are incorporated herein in their entirety by reference. Cas13b has been described in Smargon et al. (2017) "Cas13b Is a Type VI-B CRISPR-Associated RNA-Guided RNases Differentially Regulated by Accessory Proteins Csx27 and Csx28," Molecular Cell. 65, 1-13; dx.doi.org/10.1016/j.molcel.2016.12.023., which is incorporated herein in its entirety by reference.

In some embodiments, one or more elements of a nucleic acid-targeting system is derived from a particular organism comprising an endogenous CRISPR RNA-targeting system. In certain example embodiments, the effector protein CRISPR RNA-targeting system comprises at least one HEPN domain, including but not limited to the HEPN domains described herein, HEPN domains known in the art, and domains recognized to be HEPN domains by comparison to consensus sequence motifs. Several such domains are provided herein. In one non-limiting example, a consensus sequence can be derived from the sequences of C2c2 or Cas13b orthologs provided herein. In certain example embodiments, the effector protein comprises a single HEPN domain. In certain other example embodiments, the effector protein comprises two HEPN domains.

In one example embodiment, the effector protein comprise one or more HEPN domains comprising a RxxxxH motif sequence. The RxxxxH motif sequence can be, without limitation, from a HEPN domain described herein or a HEPN domain known in the art. RxxxxH motif sequences further include motif sequences created by combining portions of two or more HEPN domains. As noted, consensus sequences can be derived from the sequences of the orthologs disclosed in U.S. Provisional Patent Application 62/432,240 entitled "Novel CRISPR Enzymes and Systems," U.S. Provisional Patent Application 62/471,710 entitled "Novel Type VI CRISPR Orthologs and Systems" filed on Mar. 15, 2017, and U.S. Provisional Patent Application entitled "Novel Type VI CRISPR Orthologs and Systems," filed on Apr. 12, 2017.

In certain other example embodiments, the CRISPR system effector protein is a C2c2 nuclease. The activity of C2c2 may depend on the presence of two HEPN domains. These have been shown to be RNase domains, i.e. nuclease (in particular an endonuclease) cutting RNA. C2c2 HEPN may also target DNA, or potentially DNA and/or RNA. On the basis that the HEPN domains of C2c2 are at least capable of binding to and, in their wild-type form, cutting RNA, then it is preferred that the C2c2 effector protein has RNase function. Regarding C2c2 CRISPR systems, reference is made to U.S. Provisional 62/351,662 filed on Jun. 17, 2016 and U.S. Provisional 62/376,377 filed on Aug. 17, 2016. Reference is also made to U.S. Provisional 62/351,803 filed on Jun. 17, 2016. Reference is also made to U.S. Provisional entitled "Novel Crispr Enzymes and Systems" filed Dec. 8, 2016 bearing Broad Institute No. 10035.PA4. Reference is further made to East-Seletsky et al. "Two distinct RNase activities of CRISPR-C2c2 enable guide-RNA processing and RNA detection" Nature doi:10/1038/nature19802 and Abudayyeh et al. "C2c2 is a single-component programmable RNA-guided RNA targeting CRISPR effector" bioRxiv doi:10.1101/054742.

In certain embodiments, the C2c2 effector protein is from an organism of a genus selected from the group consisting of: Leptotrichia, *Listeria*, Corynebacter, Sutterella, *Legionella*, *Treponema*, *Filifactor*, *Eubacterium*, *Streptococcus*, *Lactobacillus*, *Mycoplasma*, *Bacteroides*, *Flavivirus*, *Flavobacterium*, Sphaerochaeta, Azospirillum, *Gluconacetobacter*, *Neisseria*, *Roseburia*, *Parvibaculum*, *Staphylococcus*, *Nitratifractor*, *Mycoplasma*, *Campylobacter*, and *Lachnospira*, or the C2c2 effector protein is an organism selected from the group consisting of: Leptotrichia shahii, Leptotrichia *wadei*, *Listeria seeligeri*, *Clostridium aminophilum*, *Carnobacterium gallinarum*, *Paludibacter propionicigenes*, *Listeria* weihenstephanensis, or the C2c2 effector protein is a *L. wadei* F0279 or *L. wadei* F0279 (Lw2) C2C2 effector protein. In another embodiment, the one or more guide RNAs are designed to detect a single nucleotide polymorphism, splice variant of a transcript, or a frameshift mutation in a target RNA or DNA.

In certain example embodiments, the RNA-targeting effector protein is a Type VI-B effector protein, such as Cas13b and Group 29 or Group 30 proteins. In certain example embodiments, the RNA-targeting effector protein comprises one or more HEPN domains. In certain example embodiments, the RNA-targeting effector protein comprises a C-terminal HEPN domain, a N-terminal HEPN domain, or both. Regarding example Type VI-B effector proteins that may be used in the context of this invention, reference is made to U.S. application Ser. No. 15/331,792 entitled "Novel CRISPR Enzymes and Systems" and filed Oct. 21, 2016, International Patent Application No. PCT/US2016/058302 entitled "Novel CRISPR Enzymes and Systems", and filed Oct. 21, 2016, and Smargon et al. "Cas13b is a Type VI-B CRISPR-associated RNA-Guided RNase differentially regulated by accessory proteins Csx27 and Csx28" Molecular Cell, 65, 1-13 (2017); dx.doi.org/10.1016/j.molcel.2016.12.023, and U.S. Provisional Application No. to be assigned, entitled "Novel Cas13b Orthologues CRISPR Enzymes and System" filed Mar. 15, 2017. In particular embodiments, the Cas13b enzyme is derived from *Bergeyella zoohelcum*.

In certain example embodiments, the RNA-targeting effector protein is a Cas13c effector protein as disclosed in U.S. Provisional Patent Application No. 62/525,165 filed Jun. 26, 2017, and PCT Application No. US 2017/047193 filed Aug. 16, 2017.

In some embodiments, one or more elements of a nucleic acid-targeting system is derived from a particular organism comprising an endogenous CRISPR RNA-targeting system. In certain embodiments, the CRISPR RNA-targeting system is found in *Eubacterium* and Ruminococcus. In certain embodiments, the effector protein comprises targeted and collateral ssRNA cleavage activity. In certain embodiments, the effector protein comprises dual HEPN domains. In certain embodiments, the effector protein lacks a counterpart to the Helical-1 domain of Cas13a. In certain embodiments, the effector protein is smaller than previously characterized class 2 CRISPR effectors, with a median size of 928 aa. This median size is 190 aa (17%) less than that of Cas13c, more than 200 aa (18%) less than that of Cas13b, and more than 300 aa (26%) less than that of Cas13a. In certain embodiments, the effector protein has no requirement for a flanking sequence (e.g., PFS, PAM).

In certain embodiments, the effector protein locus structures include a WYL domain containing accessory protein (so denoted after three amino acids that were conserved in the originally identified group of these domains; see, e.g., WYL domain IPR026881). In certain embodiments, the WYL domain accessory protein comprises at least one helix-turn-helix (HTH) or ribbon-helix-helix (RHH) DNA-binding domain. In certain embodiments, the WYL domain containing accessory protein increases both the targeted and the collateral ssRNA cleavage activity of the RNA-targeting effector protein. In certain embodiments, the WYL domain containing accessory protein comprises an N-terminal RHH domain, as well as a pattern of primarily hydrophobic conserved residues, including an invariant tyrosine-leucine doublet corresponding to the original WYL motif. In certain embodiments, the WYL domain containing accessory protein is WYL1. WYL1 is a single WYL-domain protein associated primarily with Ruminococcus.

In other example embodiments, the Type VI RNA-targeting Cas enzyme is Cas13d. In certain embodiments, Cas13d is *Eubacterium siraeum* DSM 15702 (EsCas13d) or Ruminococcus sp. N15.MGS-57 (RspCas13d) (see, e.g., Yan et al., Cas13d Is a Compact RNA-Targeting Type VI CRISPR Effector Positively Modulated by a WYL-Domain-Containing Accessory Protein, Molecular Cell (2018), doi.org/10.1016/j.molcel.2018.02.028). RspCas13d and EsCas13d have no flanking sequence requirements (e.g., PFS, PAM).

Cas13 RNA Editing

In one aspect, the invention provides a method of modifying or editing a target transcript in a eukaryotic cell. In some embodiments, the method comprises allowing a CRISPR-Cas effector module complex to bind to the target polynucleotide to effect RNA base editing, wherein the CRISPR-Cas effector module complex comprises a Cas effector module complexed with a guide sequence hybridized to a target sequence within said target polynucleotide, wherein said guide sequence is linked to a direct repeat sequence. In some embodiments, the Cas effector module comprises a catalytically inactive CRISPR-Cas protein. In some embodiments, the guide sequence is designed to introduce one or more mismatches to the RNA/RNA duplex formed between the target sequence and the guide sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

The present application relates to modifying a target RNA sequence of interest (see, e.g, Cox et al., Science. 2017 Nov. 24; 358(6366):1019-1027). Using RNA-targeting rather than DNA targeting offers several advantages relevant for therapeutic development. First, there are substantial safety benefits to targeting RNA: there will be fewer off-target events because the available sequence space in the transcriptome is significantly smaller than the genome, and if an off-target event does occur, it will be transient and less likely to induce negative side effects. Second, RNA-targeting therapeutics will be more efficient because they are cell-type independent and not have to enter the nucleus, making them easier to deliver.

A further aspect of the invention relates to the method and composition as envisaged herein for use in prophylactic or therapeutic treatment, preferably wherein said target locus of interest is within a human or animal and to methods of modifying an Adenine or Cytidine in a target RNA sequence of interest, comprising delivering to said target RNA, the composition as described herein. In particular embodiments, the CRISPR system and the adenonsine deaminase, or catalytic domain thereof, are delivered as one or more polynucleotide molecules, as a ribonucleoprotein complex, optionally via particles, vesicles, or one or more viral vectors. In particular embodiments, the invention thus comprises compositions for use in therapy. This implies that the methods can be performed in vivo, ex vivo or in vitro. In particular embodiments, when the target is a human or animal target, the method is carried out ex vivo or in vitro.

A further aspect of the invention relates to the method as envisaged herein for use in prophylactic or therapeutic treatment, preferably wherein said target of interest is within a human or animal and to methods of modifying an Adenine or Cytidine in a target RNA sequence of interest, comprising delivering to said target RNA, the composition as described herein. In particular embodiments, the CRISPR system and the adenonsine deaminase, or catalytic domain thereof, are delivered as one or more polynucleotide molecules, as a ribonucleoprotein complex, optionally via particles, vesicles, or one or more viral vectors.

In one aspect, the invention provides a method of generating a eukaryotic cell comprising a modified or edited gene. In some embodiments, the method comprises (a) introducing one or more vectors into a eukaryotic cell, wherein the one or more vectors drive expression of one or more of: Cas effector module, and a guide sequence linked to a direct repeat sequence, wherein the Cas effector module associate one or more effector domains that mediate base editing, and (b) allowing a CRISPR-Cas effector module complex to bind to a target polynucleotide to effect base editing of the target polynucleotide within said disease gene, wherein the CRISPR-Cas effector module complex comprises a Cas effector module complexed with the guide sequence that is hybridized to the target sequence within the target polynucleotide, wherein the guide sequence may be designed to introduce one or more mismatches between the RNA/RNA duplex formed between the guide sequence and the target sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

A further aspect relates to an isolated cell obtained or obtainable from the methods described herein comprising the composition described herein or progeny of said modified cell, preferably wherein said cell comprises a hypoxanthine or a guanine in replace of said Adenine in said target RNA of interest compared to a corresponding cell not subjected to the method. In particular embodiments, the cell is a eukaryotic cell, preferably a human or non-human animal cell, optionally a therapeutic T cell or an antibody-producing B-cell.

In some embodiments, the modified cell is a therapeutic T cell, such as a T cell suitable for adoptive cell transfer therapies (e.g., CAR-T therapies). The modification may result in one or more desirable traits in the therapeutic T cell, as described further herein.

The invention further relates to a method for cell therapy, comprising administering to a patient in need thereof the modified cell described herein, wherein the presence of the modified cell remedies a disease in the patient.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems.
Cong, L., Ran, F. A., Cox, D., Lin, S., Barretto, R., Habib, N., Hsu, P. D., Wu, X., Jiang, W., Marraffini, L. A., & Zhang, F. Science Feb 15; 339(6121):819-23 (2013);

RNA-guided editing of bacterial genomes using CRISPR-Cas systems. Jiang W., Bikard D., Cox D., Zhang F, Marraffini L A. Nat Biotechnol Mar;31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. Aug 22;500(7463):472-6. doi: 10.1038/Nature12466. Epub 2013 Aug 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell Aug 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols Nov;8(11):2281-308 (2013-B);

Genome-Scale CRISPR-Cas9 Knockout Screening in Human Cells. Shalem, O., Sanjana, NE., Hartenian, E., Shi, X., Scott, D A., Mikkelson, T., Heckl, D., Ebert, B L., Root, D E., Doench, J G., Zhang, F. Science Dec 12. (2013);

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell Feb 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. Apr 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. Jun 5;157(6):1262-78 (2014).

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. Dec;32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. Jan;33 (1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. Jan 29;517(7536):583-8 (2015).

A split-Cas9 architecture for inducible genome editing and transcription modulation, Zetsche B, Volz S E, Zhang F., (published online 2 Feb. 2015) Nat Biotechnol. Feb;33 (2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. Apr 9;520(7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR-Cas9 cleavage of viral DNA efficiently suppresses hepatitis B virus," Scientific Reports 5:10833. doi: 10.1038/srep10833 (Jun. 2, 2015).

Nishimasu et al., Crystal Structure of *Staphylococcus aureus* Cas9," Cell 162, 1113-1126 (Aug. 27, 2015).

BCL11A enhancer dissection by Cas9-mediated in situ saturating mutagenesis, Canver et al., Nature 527(7577): 192-7 (Nov. 12, 2015) doi: 10.1038/nature15521. Epub 2015 Sep. 16.

Cpf1 Is a Single RNA-Guided Endonuclease of a Class 2 CRISPR-Cas System, Zetsche et al., Cell 163, 759-71 (Sep. 25, 2015).

Discovery and Functional Characterization of Diverse Class 2 CRISPR-Cas Systems, Shmakov et al., Molecular Cell, 60(3), 385-397 doi: 10.1016/j.molcel.2015.10.008 Epub Oct. 22, 2015.

Rationally engineered Cas9 nucleases with improved specificity, Slaymaker et al., Science 2016 Jan 1 351(6268): 84-88 doi: 10.1126/science.aad5227. Epub 2015 Dec 1.

Gao et al, "Engineered Cpf1 Enzymes with Altered PAM Specificities," bioRxiv 091611; doi: http://dx.doi.org/10.1101/091611 (Dec. 4, 2016).

Cox et al., "RNA editing with CRISPR-Cas13," Science. 2017 Nov. 24; 358(6366):1019-1027. doi: 10.1126/science.aaq0180. Epub 2017 Oct 25.

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E coli,* 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas el al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver el al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Cox et al., (2017) reported the use of catalytically inactive Cas13 (dCas13) to direct adenosine-to-inosine deaminase activity by ADAR2 (adenosine deaminase acting on RNA type 2) to transcripts in mammalian cells. The system, referred to as RNA Editing for Programmable A to I Replacement (REPAIR), has no strict sequence constraints and can be used to edit full-length transcripts. The authors further engineered the system to create a high-specificity variant and minimized the system to facilitate viral delivery.

The methods and tools provided herein are may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayeh et al. 2016, Science, 5;353 (6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokT Nucleases that recognize extended sequences and can edit endogenous genes with high efficiencies in human cells.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105, 031), US 2014-0287938 A1 (U.S. application Ser. No. 14/213,991), US 2014-0273234 A1 (U.S. application Ser. No. 14/293,674), US 2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256, 912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. application 62/180,709, 17 Jun. 2015, PROTECTED GUIDE RNAS (PGRNAS); U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. applications 62/091,462, 12 Dec. 14, 62/096,324, 23 Dec. 2014, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 2014 and 62/180,692, 17 Jun. 2015, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, 62/181,641, 18 Jun. 2015, and 62/181,667, 18 Jun. 2015, RNA-TARGETING SYSTEM; U.S. application 62/096,656, 24 Dec. 2014 and 62/181,151, 17 Jun. 2015, CRISPR HAVING OR ASSOCIATED WITH DESTABILIZATION DOMAINS; U.S. application 62/096,697, 24-Dec-14, CRISPR HAVING OR ASSOCIATED WITH AAV; U.S. application 62/098,158,30-Dec-14, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12-F EB-14, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COM- PETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24 Sep. 2014 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. application 62/205,733, 16 Aug. 2015, U.S. application 62/201,542, 5-Aug-2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appin cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

In particular embodiments, pre-complexed guide RNA and CRISPR effector protein, (optionally, adenosine deaminase fused to a CRISPR protein or an adaptor) are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9;153 (4):910-8).

In particular embodiments, the ribonucleoprotein is delivered by way of a polypeptide-based shuttle agent as described in WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly these polypeptides can be used for the delivery of CRISPR-effector based RNPs in eukaryotic cells.

Tale Systems

As disclosed herein editing can be made by way of the transcription activator-like effector nucleases (TALENs) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011;39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

In advantageous embodiments of the invention, the methods provided herein use isolated, non-naturally occurring, recombinant or engineered DNA binding proteins that comprise TALE monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The TALE polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, polypeptide monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the TALE polypeptides will bind. As used herein the polypeptide monomers and at least one or more half polypeptide monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and TALE polypeptides may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8), which is included in the term "TALE monomer". Therefore, it follows that the length of the nucleic acid or DNA being targeted is equal to the number of full polypeptide monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

(SEQ. I.D. No. 1)
M D P I R S R T P S P A R E L L S G P Q P D G V Q

P T A D R G V S P P A G G P L D G L P A R R T M S

R T R L P S P P A P S P A F S A D S F S D L L R Q

F D P S L F N T S L F D S L P P F G A H H T E A A

T G E W D E V Q S G L R A A D A P P P T M R V A V

T A A R P P R A K P A P R R R A A Q P S D A S P A

A Q V D L R T L G Y S Q Q Q Q E K I K P K V R S T

V A Q H H E A L V G H G F T H A H I V A L S Q H P

A A L G T V A V K Y Q D M I A A L P E A T H E A I

V G V G K Q W S G A R A L E A L L T V A G E L R G

P P L Q L D T G Q L L K I A K R G G V T A V E A V

H A W R N A L T G A P L N

An exemplary amino acid sequence of a C-terminal capping region is:

(SEQ. I.D. No. 2)
R P A L E S I V A Q L S R P D P A L A A L T N D H

L V A L A C L G G R P A L D A V K K G L P H A P A

L I K R T N R R I P E R T S H R V A D H A Q V V R

V L G F F Q C H S H P A Q A F D D A M T Q F G M S

```
RHGLLQLFRRVGVTELEARSGTLPP

ASQRWDRILQASGMKRAKPSPTSTQ

TPDQASLHAFADSLERDLDAPSPMH

EGDQTRAS
```

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an m Sin interaction domain (SID). SID4X domain or a Krüppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

ZN-Finger Nucleases

Other preferred tools for genome editing for use in the context of this invention include zinc finger systems and TALE systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type 11S restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

Meganucleases

As disclosed herein editing can be made by way of meganucleases, which are endodeoxyribonucleases characterized by a large recognition site (double-stranded DNA sequences of 12 to 40 base pairs). Exemplary method for using meganucleases can be found in U.S. Pat. Nos. 8,163,514; 8,133,697; 8,021,867; 8,119,361; 8,119,381; 8,124,369; and 8,129,134, which are specifically incorporated by reference.

Adoptive Cell Transfer

In certain embodiments, a C3 inhibitor is administered in combination with adoptive cell therapy. Not being bound by a theory, C3 may inhibit tumor infiltrating immune cells and may suppress adoptively transferred immune cells. Thus, in one embodiment, a C3 inhibitor is administered before, after or during adoptive cell transfer to enhance the immune response. In certain embodiments, adoptively transferred immune cells are modified to decrease activity or expression of a C3 receptor. In certain embodiments, transferred immune cells are modified to completely abolish expression of a C3 receptor. As described herein, immune cells express complement receptors and CAFs express C3. Thus, CAFs may express C3 in response to tumor infiltration by lymphocytes and inactivate the TILs. TILs that do not express complement receptors may be protected from C3 activity by CAFs.

As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells (see, e.g., Mettananda et al., Editing an α-globin enhancer in primary human hematopoietic stem cells as a treatment for β-thalassemia, Nat Commun. 2017 Sep. 4; 8(1):424). As used herein, the term "engraft" or "engraftment" refers to the process of cell incorporation into a tissue of interest in vivo through contact with existing cells of the tissue. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogenic cells allows for cells to be obtained from healthy donors and prepared for use in patients as opposed to preparing autologous cells from a patient after diagnosis.

Aspects of the invention involve the adoptive transfer of immune system cells, such as T cells, specific for selected antigens, such as tumor associated antigens or tumor specific neoantigens (see, e.g., Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17; 124(3):453-62).

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: B cell maturation antigen (BCMA) (see, e.g., Friedman et al., Effective Targeting of Multiple BCMA-Expressing Hematological Malignancies by Anti-BCMA CAR T Cells, Hum Gene Ther. 2018 Mar. 8; Berdeja J G, et al. Durable clinical responses in heavily pretreated patients with relapsed/refractory multiple myeloma: updated results from a multicenter study of bb2121 anti-Bcma CAR T cell therapy. Blood. 2017; 130:740; and Mouhieddine and Ghobrial, Immunotherapy in Multiple Myeloma: The Era of CAR T Cell Therapy, Hematologist, May-June 2018, Volume 15, issue 3); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2 (Her2/neu)); Prostase; Prostatic acid phosphatase (PAP); elongation factor 2 mutant (ELF2M); Insulin-like growth factor 1 receptor (IGF-1R); gp1OO; BCR-ABL (breakpoint cluster region-Abelson); tyrosinase; New York esophageal squamous cell carcinoma 1 (NY-ESO-1); κ-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; prostein; survivin; PCTAI (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGE1); Renal ubiquitous 1, 2 (RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac (2-8)aNeu5Ac(2-3)bDGalp(1-4)bDGlcp(1-1)Cer); Tn antigen (Tn Ag); Fms-Like Tyrosine Kinase 3 (FLT3); CD38; CD138; CD44v6; B7H3 (CD276); KIT (CD117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis(Y) antigen; CD24; Platelet-derived growth factor receptor beta (PDGFR-beta); stage-specific embryonic antigen-4 (SSEA-4); Mucin 1, cell surface associated (MUC1); mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GM1; sialyl Lewis adhesion molecule (sLe); ganglioside GM3 (aNeu5Ac(2-3)bDGalp(1-4)bDGlcp(1-1) Cer); TGS5; high molecular weight-melanoma-associated antigen (HMWMAA); o-acetyl-GD2 ganglioside (OAcGD2); Folate receptor alpha; Folate receptor beta; tumor endothelial marker I (TEM1/CD248); tumor endothelial marker 7-related (TEM7R); claudin 6 (CLDN6); G protein-coupled receptor class C group 5, member D (GPRC5D); chromosome X open reading frame 61 (CXORF61); CD97; CD179a; anaplastic lymphoma kinase (ALK); Polysialic acid; placenta-specific I (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; p53; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyltransferase V (NA17); paired box protein Pax-3 (PAX3); Androgen receptor; Cyclin B1; Cyclin D1; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint-1, -2, -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); mouse double minute 2 homolog (MDM2); livin; alphafetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated); CAMEL (CTL-recognized antigen on melanoma); CAP1 (carcinoembryonic antigen peptide 1); CASP-8 (caspase-8); CDC27m (cell-division cycle 27 mutated); CDK4/m (cycline-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog-2, -3, 4); FBP (folate binding protein); fAchR (Fetal acetylcholine receptor); G250 (glycoprotein 250); GAGE (G antigen); GnT-V (N-acetylglucosaminyltransferase V); HAGE (helicase antigen); ULA-A (human leukocyte antigen-A); HST2 (human signet ring tumor 2); KTAA0205; KDR (kinase insert domain receptor); LDLR/FUT (low density lipid receptor/GDP L-fucose: b-D-galactosidase 2-a-L fucosyltransferase); L1CAM (L1 cell adhesion molecule); MC1R (melanocortin 1 receptor); Myosin/m (myosin mutated); MUM-1, -2, -3 (melanoma ubiquitous mutated 1, 2, 3); NA88-A (NA cDNA clone of patient M88); KG2D (Natural killer group 2, member D) ligands; oncofetal antigen (h5T4); p190 minor bcr-abl (protein of 190KD bcr-abl); Pml/RARa (promyelocytic leukaemia/retinoic acid receptor a); PRAME (preferentially expressed antigen of melanoma); SAGE (sarcoma antigen); TEL/AML1 (translocation Ets-family leukemia/acute myeloid leukemia 1); TPI/m (triosephosphate isomerase mutated); CD70; and any combination thereof.

In certain embodiments, an antigen to be targeted in adoptive cell therapy (such as particularly CAR or TCR T-cell therapy) of a disease (such as particularly of tumor or cancer) is a tumor-specific antigen (TSA).

In certain embodiments, an antigen to be targeted in adoptive cell therapy (such as particularly CAR or TCR T-cell therapy) of a disease (such as particularly of tumor or cancer) is a neoantigen.

In certain embodiments, an antigen to be targeted in adoptive cell therapy (such as particularly CAR or TCR T-cell therapy) of a disease (such as particularly of tumor or cancer) is a tumor-associated antigen (TAA).

In certain embodiments, an antigen to be targeted in adoptive cell therapy (such as particularly CAR or TCR T-cell therapy) of a disease (such as particularly of tumor or cancer) is a universal tumor antigen. In certain preferred embodiments, the universal tumor antigen is selected from the group consisting of: a human telomerase reverse transcriptase (hTERT), survivin, mouse double minute 2 homolog (MDM2), cytochrome P450 1B 1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (Dl), and any combinations thereof.

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: CD19, BCMA, CD70, CLL-1, MAGE A3, MAGE A6, HPV E6, HPV E7, WT1, CD22, CD171, ROR1, MUC16, and SSX2. In certain preferred embodiments, the antigen may be CD19. For example, CD19 may be targeted in hematologic malignancies, such as in lymphomas, more particularly in B-cell lymphomas, such as without limitation in diffuse large B-cell lymphoma, primary mediastinal b-cell lymphoma, transformed follicular lymphoma, marginal zone lymphoma, mantle cell lymphoma, acute lymphoblastic leukemia including adult and pediatric ALL, non-Hodgkin lymphoma, indolent non-Hodgkin lymphoma, or chronic lymphocytic leukemia. For example, BCMA may be targeted in multiple myeloma or plasma cell leukemia (see, e.g., 2018 American Association for Cancer Research (AACR) Annual meeting Poster: Allogeneic Chimeric Antigen Receptor T Cells Targeting B Cell Maturation Antigen). For example, CLL1 may be targeted in acute myeloid leukemia. For example, MAGE A3, MAGE A6, SSX2, and/or KRAS may be targeted in solid tumors. For example, HPV E6 and/or HPV E7 may be targeted in cervical cancer or head and neck cancer. For example, WT1 may be targeted in acute myeloid leukemia (AML), myelodysplastic syndromes (MDS), chronic myeloid leukemia (CML), non-small cell lung cancer, breast, pancreatic, ovarian or colorectal cancers, or mesothelioma. For example, CD22 may be targeted in B cell malignancies, including non-Hodgkin lymphoma, diffuse large B-cell lymphoma, or acute lymphoblastic leukemia. For example, CD171 may be targeted in neuroblastoma, glioblastoma, or lung, pancreatic, or ovarian cancers. For example, ROR1 may be targeted in ROR1+ malignancies, including non-small cell lung cancer, triple negative breast cancer, pancreatic cancer, prostate cancer, ALL, chronic lymphocytic leukemia, or mantle cell lymphoma. For example, MUC16 may be targeted in MUC16ecto+ epithelial ovarian, fallopian tube or primary peritoneal cancer. For example, CD70 may be targeted in both hematologic malignancies as well as in solid cancers such as renal cell carcinoma (RCC), gliomas (e.g., GBM), and head and neck cancers (HNSCC). CD70 is expressed in both hematologic malignancies as well as in solid cancers, while its expression in normal tissues is restricted to a subset of lymphoid cell types (see, e.g., 2018 American Association for Cancer Research (AACR) Annual meeting Poster: Allogeneic CRISPR Engineered Anti-CD70 CAR-T Cells Demonstrate Potent Preclinical Activity Against Both Solid and Hematological Cancer Cells).

Various strategies may for example be employed to genetically modify T cells by altering the specificity of the T cell receptor (TCR) for example by introducing new TCR a and P chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; U.S. Pat. No. 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3-chain, CD97, GDI 1a-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon R1b), CD79a, CD79b, Fc gamma RIIa, DAP10, and DAP12. In certain preferred embodiments, the primary signaling domain comprises a functional signaling domain of CD3ζ or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3ζ chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190; these can include the following portion of CD28 as set forth in Genbank identifier NM_006139 (sequence version 1, 2 or 3):

(SEQ ID NO: 3)
IEVMYPPPYLDNEKSNGTIIHVKGKHLCPSPLFPGPSKPFWVLVVVGGV

LACYSLLVTVAFIIFWVRSKRSRLLHSDYMNMTPRRPGPTRKHYQPYAP

PRDFAAYRS).

Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190). Hence, certain embodiments employ a CAR comprising (a) a zeta chain portion comprising the intracellular domain of human CD3ζ chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, costimulation may be orchestrated by expressing CARs in antigen-T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ζ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ζ molecule. The exact sequence of the CD28 molecule included in the FMC63-28Z CAR corresponded to Genbank identifier NM_006139; the sequence included all amino acids starting with the amino acid sequence IEVMYPPPY (SEQ ID NO: 4) and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated into a second XhoI and NotI-digested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-ζ molecule (as in Maher et al., 2002) Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3ζ chain, and a costimulatory signaling region comprising a signaling domain of CD28. Preferably, the CD28 amino acid sequence is as set forth in Genbank identifier NM_006139 (sequence version 1, 2 or 3) starting with the amino acid sequence IEVMYPPPY (SEQ ID NO: 4) and continuing all the way to the carboxy-terminus of the protein. The sequence is reproduced herein:

(SEQ ID NO: 3)
IEVMYPPPYLDNEKSNGTIIHVKGKHLCPSPLFPGPSKPFWVLVVVGGVL

ACYSLLVTVAFIIFWVRSKRSRLLHSDYMNMTPRRPGPTRKHYQPYAPPR

DFAAYRS.

Preferably, the antigen is CD19, more preferably the antigen-binding element is an anti-CD19 scFv, even more preferably the anti-CD19 scFv as described by Kochenderfer et al. (supra).

Additional anti-CD19 CARs are further described in WO2015187528. More particularly Example 1 and Table 1 of WO2015187528, incorporated by reference herein, demonstrate the generation of anti-CD19 CARs based on a fully human anti-CD19 monoclonal antibody (47G4, as described in US20100104509) and murine anti-CD19 monoclonal antibody (as described in Nicholson et al. and explained above). Various combinations of a signal sequence (human CD8-alpha or GM-CSF receptor), extracellular and transmembrane regions (human CD8-alpha) and intracellular T-cell signalling domains (CD28-CD3ζ; 4-1BB-CD3ζ; CD27-CD3ζ; CD28-CD27-CD3ζ; 4-1BB-CD27-CD3ζ; CD27-4-1BB-CD3ζ; CD28-CD27-FcεRI gamma chain; or CD28-FcεRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T-cell signalling domain as set forth in Table 1 of WO2015187528. Preferably, the antigen is CD19, more preferably the antigen-binding element is an anti-CD19 scFv, even more preferably the mouse or human anti-CD19 scFv as described in Example 1 of WO2015187528. In certain embodiments, the CAR comprises, consists essentially of or consists of an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 as set forth in Table 1 of WO2015187528.

By means of an example and without limitation, chimeric antigen receptor that recognizes the CD70 antigen is described in WO2012058460A2 (see also, Park et al., CD70 as a target for chimeric antigen receptor T cells in head and neck squamous cell carcinoma, Oral Oncol. 2018 March; 78:145-150; and Jin et al., CD70, a novel target of CAR T-cell therapy for gliomas, Neuro Oncol. 2018 Jan. 10; 20(1):55-65). CD70 is expressed by diffuse large B-cell and follicular lymphoma and also by the malignant cells of Hodgkins lymphoma, Waldenstrom's macroglobulinemia and multiple myeloma, and by HTLV-1- and EBV-associated malignancies. (Agathanggelou et al. Am.J.Pathol. 1995; 147: 1152-1160; Hunter et al., Blood 2004; 104:4881. 26; Lens et al., J Immunol. 2005; 174:6212-6219; Baba et al., J Virol. 2008; 82:3843-3852.) In addition, CD70 is expressed by non-hematological malignancies such as renal cell carcinoma and glioblastoma. (Junker et al., J Urol. 2005; 173:2150-2153; Chahlavi et al., Cancer Res 2005; 65:5428-5438) Physiologically, CD70 expression is transient and restricted to a subset of highly activated T, B, and dendritic cells.

By means of an example and without limitation, chimeric antigen receptor that recognizes BCMA has been described (see, e.g., US20160046724A1; WO2016014789A2; WO2017211900A1; WO2015158671A1; US20180085444A1; WO2018028647A1; US20170283504A1; and WO2013154760A1).

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T-cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T-cell response. Some CARs may also comprise a "suicide switch" to induce cell death of the CAR T-cells following treatment (Buddee et al., PLoS One, 2013) or to downregulate expression of the CAR following binding to the target antigen (WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

In certain embodiments, ACT includes co-transferring CD4+ Th1 cells and CD8+ CTLs to induce a synergistic antitumour response (see, e.g., Li et al., Adoptive cell therapy with CD4+ T helper 1 cells and CD8+ cytotoxic T cells enhances complete rejection of an established tumour, leading to generation of endogenous memory responses to non-targeted tumour epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787-98). Those studies involved an adoptive T cell transfer (ACT) therapy approach, which takes advantage of CD4+ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In Vivo, Cell Stem Cell 22, 1-13, 2018, doi.org/10.1016/j.stem.2018.01.016).

Unlike T-cell receptors (TCRs) that are MHC restricted, CARs can potentially bind any cell surface-expressed antigen and can thus be more universally used to treat patients (see Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267). In certain embodiments, in the absence of endogenous T-cell infiltrate (e.g., due to aberrant antigen processing and presentation), which precludes the use of TIL therapy and immune checkpoint blockade, the transfer of CAR T-cells may be used to treat patients (see, e.g., Hinrichs C S, Rosenberg S A. Exploiting the curative potential of adoptive T-cell therapy for cancer. Immunol Rev (2014) 257(1):56-71. doi:10.1111/imr.12132).

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In certain embodiments, the treatment can be administered after lymphodepleting pretreatment in the form of chemotherapy (typically a combination of cyclophosphamide and fludarabine) or radiation therapy. Initial studies in ACT had short lived responses and the transferred cells did not persist in vivo for very long (Houot et al., T-cell-based immunotherapy: adoptive cell transfer and checkpoint inhibition. Cancer Immunol Res (2015) 3(10):1115-22; and Kamta et al., Advancing Cancer Therapy with Present and Emerging Immuno-Oncology Approaches. Front. Oncol. (2017) 7:64). Immune suppressor cells like Tregs and MDSCs may attenuate the activity of transferred cells by outcompeting them for the necessary cytokines. Not being bound by a theory lymphodepleting pretreatment may eliminate the suppressor cells allowing the TILs to persist.

In one embodiment, the treatment can be administrated into patients undergoing an immunosuppressive treatment (e.g., glucocorticoid treatment). The cells or population of cells, may be made resistant to at least one immunosuppressive agent due to the inactivation of a gene encoding a receptor for such immunosuppressive agent. In certain embodiments, the immunosuppressive treatment provides for the selection and expansion of the immunoresponsive T cells within the patient.

In certain embodiments, the treatment can be administered before primary treatment (e.g., surgery or radiation therapy) to shrink a tumor before the primary treatment. In another embodiment, the treatment can be administered after primary treatment to remove any remaining cancer cells.

In certain embodiments, immunometabolic barriers can be targeted therapeutically prior to and/or during ACT to enhance responses to ACT or CAR T-cell therapy and to support endogenous immunity (see, e.g., Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267).

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administered parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853; Ren et al., 2017, Multiplex genome editing to generate universal CAR T cells resistant to PD1 inhibition, Clin Cancer Res. 2017 May 1;23(9):2255-2266. doi: 10.1158/1078-0432.CCR-16-1300. Epub 2016 Nov 4; Qasim et al., 2017, Molecular remission of infant B-ALL after infusion of universal TALEN gene-edited CAR T cells, Sci Transl Med. 2017 Jan. 25; 9(374); Legut, et al., 2018, CRISPR-mediated TCR replacement generates superior anticancer transgenic T cells. Blood, 131(3), 311-322; and Georgiadis et al., Long Terminal Repeat CRISPR-CAR-Coupled "Universal" T Cells Mediate Potent Anti-leukemic Effects, Molecular Therapy, In Press, Corrected Proof, Available online 6 Mar. 2018). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed for example to insert or knock-in an exogenous gene, such as an exogenous gene encoding a CAR or a TCR, at a preselected locus in a cell (e.g. TRAC locus); to eliminate potential alloreactive T-cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more MHC constituent proteins in a cell; to activate a T cell; to modulate cells such that the cells are resistant to exhaustion or dysfunction; and/or increase the differentiation and/or proliferation of functionally exhausted or dysfunctional CD8+ T-cells (see PCT Patent Publications: WO2013176915, WO2014059173, WO2014172606, WO2014184744, and WO2014191128).

In certain embodiments, editing may result in inactivation of a gene. By inactivating a gene, it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art. In certain embodiments, homology directed repair (HDR) is used to concurrently inactivate a gene (e.g., TRAC) and insert an endogenous TCR or CAR into the inactivated locus.

Hence, in certain embodiments, editing of cells (such as by CRISPR/Cas), particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1. Homology-directed repair (HDR) strategies are known and described elsewhere in this specification allowing to insert transgenes into desired loci (e.g., TRAC locus).

Further suitable loci for insertion of transgenes, in particular CAR or exogenous TCR transgenes, include without limitation loci comprising genes coding for constituents of endogenous T-cell receptor, such as T-cell receptor alpha locus (TRA) or T-cell receptor beta locus (TRB), for example T-cell receptor alpha constant (TRAC) locus, T-cell receptor beta constant 1 (TRBC1) locus or T-cell receptor beta constant 2 (TRBC1) locus. Advantageously, insertion of a transgene into such locus can simultaneously achieve expression of the transgene, potentially controlled by the endogenous promoter, and knock-out expression of the endogenous TCR. This approach has been exemplified in Eyquem et al., (2017) Nature 543: 113-117, wherein the authors used CRISPR/Cas9 gene editing to knock-in a DNA molecule encoding a CD19-specific CAR into the TRAC locus downstream of the endogenous promoter; the CAR-T cells obtained by CRISPR were significantly superior in terms of reduced tonic CAR signaling and exhaustion.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Hence, in certain embodiments, editing of cells (such as by CRISPR/Cas), particularly cells intended for adoptive cell therapies, more particularly immunoresponsive cells such as T cells, may be performed to knock-out or knock-down expression of an endogenous TCR in a cell. For example, NHEJ-based or HDR-based gene editing approaches can be employed to disrupt the endogenous TCR alpha and/or beta chain genes. For example, gene editing system or systems, such as CRISPR/Cas system or systems, can be designed to target a sequence found within the TCR beta chain conserved between the beta 1 and beta 2 constant region genes (TRBC1 and TRBC2) and/or to target the constant region of the TCR alpha chain (TRAC) gene.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1;112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells (such as by CRISPR/Cas), particularly cells intended for adoptive cell therapies, more particularly immunoresponsive cells such as T cells, may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT2 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1, TIM-3, CEACAM-1, CEACAM-3, or CEACAM-5. In preferred embodiments, the gene locus involved in the expression of PD-1 or CTLA-4 genes is targeted. In other preferred embodiments, combinations of genes are targeted, such as but not limited to PD-1 and TIGIT.

By means of an example and without limitation, WO2016196388 concerns an engineered T cell comprising (a) a genetically engineered antigen receptor that specifically binds to an antigen, which receptor may be a CAR, and (b) a disrupted gene encoding a PD-L1, an agent for disruption of a gene encoding a PD-L1, and/or disruption of a gene encoding PD-L1, wherein the disruption of the gene may be mediated by a gene editing nuclease, a zinc finger nuclease (ZFN), CRISPR/Cas9 and/or TALEN. WO2015142675 relates to immune effector cells comprising a CAR in combination with an agent (such as CRISPR, TALEN or ZFN) that increases the efficacy of the immune effector cells in the treatment of cancer, wherein the agent may inhibit an immune inhibitory molecule, such as PD1, PD-L1, CTLA-4, TIM-3, LAG-3, VISTA, BTLA, TIGIT, LAIR1, CD160, 2B4, TGFR beta, CEACAM-1, CEACAM-3, or CEACAM-5. Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CAR T cells deficient of TCR, HLA class I molecule and PD1.

In certain embodiments, cells may be engineered to express a CAR, wherein expression and/or function of methylcytosine dioxygenase genes (TET1, TET2 and/or TET3) in the cells has been reduced or eliminated, such as by CRISPR, ZNF or TALEN (for example, as described in WO201704916).

In certain embodiments, editing of cells (such as by CRISPR/Cas), particularly cells intended for adoptive cell therapies, more particularly immunoresponsive cells such as T cells, may be performed to knock-out or knock-down expression of an endogenous gene in a cell, said endogenous gene encoding an antigen targeted by an exogenous CAR or TCR, thereby reducing the likelihood of targeting of the engineered cells. In certain embodiments, the targeted antigen may be one or more antigen selected from the group consisting of CD38, CD138, CS-1, CD33, CD26, CD30, CD53, CD92, CD100, CD148, CD150, CD200, CD261, CD262, CD362, human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), B cell maturation antigen (BCMA), transmembrane activator and CAML Interactor (TACI), and B-cell activating factor receptor (BAFF-R) (for example, as described in WO2016011210 and WO2017011804).

In certain embodiments, editing of cells (such as by CRISPR/Cas), particularly cells intended for adoptive cell therapies, more particularly immunoresponsive cells such as T cells, may be performed to knock-out or knock-down expression of one or more MHC constituent proteins, such as one or more HLA proteins and/or beta-2 microglobulin (B2M), in a cell, whereby rejection of non-autologous (e.g., allogeneic) cells by the recipient's immune system can be reduced or avoided. In preferred embodiments, one or more HLA class I proteins, such as HLA-A, B and/or C, and/or B2M may be knocked-out or knocked-down. Preferably, B2M may be knocked-out or knocked-down. By means of an example, Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CAR T cells deficient of TCR, HLA class I molecule and PD1. In certain embodiments, a receptor for C3 is disrupted by editing in T cells in combination with editing of any of the genes listed herein.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ, B2M and TCRα, B2M and TCRβ.

In certain embodiments, a cell may be multiply edited (multiplex genome editing) as taught herein to (1) knock-out or knock-down expression of an endogenous TCR (for example, TRBC1, TRBC2 and/or TRAC), (2) knock-out or knock-down expression of an immune checkpoint protein or receptor (for example PD1, PD-L1 and/or CTLA4); and (3) knock-out or knock-down expression of one or more MHC constituent proteins (for example, HLA-A, B and/or C, and/or B2M, preferably B2M).

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment, allogenic T cells may be obtained from healthy subjects. In one embodiment T cells that have infiltrated a tumor are isolated. T cells may be removed during surgery. T cells may be isolated after removal of tumor tissue by biopsy. T cells may be isolated by any means known in the art. In one embodiment, T cells are obtained by apheresis. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells, bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and by depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments, the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5\times10^6$/ ml. In other embodiments, the concentration used can be from about $1\times10^5$/ml to $1\times10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to $-80°$ C. at a rate of 1° per minute and stored in the vapor phase of a liquid nitrogen storage tank. Other methods of controlled freezing may be used as well as uncontrolled freezing immediately at $-20°$ C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment, neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. No. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment, the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin ($2m) into MHC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one embodiment, T cells are isolated by contacting with T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In certain embodiments, T cells comprising a CAR or an exogenous TCR, may be manufactured as described in WO2015120096, by a method comprising: enriching a population of lymphocytes obtained from a donor subject; stimulating the population of lymphocytes with one or more T-cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO2015120096, by a method comprising: obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in WO2017070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

In certain embodiments, a patient in need of a T cell therapy may be conditioned by a method as described in WO2016191756 comprising administering to the patient a dose of cyclophosphamide between 200 mg/m2/day and 2000 mg/m2/day and a dose of fludarabine between 20 mg/m2/day and 900 mg/m$^2$/day.

Therapeutic Agents

As used herein, an "agent" can refer to a protein-binding agent that permits modulation of activity of proteins or disrupts interactions of proteins and other biomolecules, such as but not limited to disrupting protein-protein interaction, ligand-receptor interaction, or protein-nucleic acid interaction. Agents can also refer to DNA targeting or RNA targeting agents. Agents may include a fragment, derivative and analog of an active agent. The terms "fragment," "derivative" and "analog" when referring to polypeptides as used herein refers to polypeptides which either retain substantially the same biological function or activity as such polypeptides. An analog includes a proprotein which can be activated by cleavage of the proprotein portion to produce an active mature polypeptide. Such agents include, but are not limited to, antibodies ("antibodies" includes antigen-binding portions of antibodies such as epitope- or antigen-binding peptides, paratopes, functional CDRs; recombinant antibodies; chimeric antibodies; humanized antibodies; nanobodies; tribodies; midibodies; or antigen-binding derivatives, analogs, variants, portions, or fragments thereof), protein-binding agents, nucleic acid molecules, small molecules, recombinant protein, peptides, aptamers, avimers and protein-binding derivatives, portions or fragments thereof. An "agent" as used herein, may also refer to an agent that inhibits expression of a gene, such as but not limited to a DNA targeting agent (e.g., CRISPR system, TALE, Zinc finger protein) or RNA targeting agent (e.g., inhibitory nucleic acid molecules such as RNAi, miRNA, ribozyme).

In one embodiment of the present invention, any combination of therapeutic, not limited to a small molecule, compound, mixture, nucleic acid, vector, or protein, is administered to a subject in order to increase or decrease the activity of the complement system. Exemplary embodiments for activation of complement are natural products such as snake venom and caterpillar bristles (PLoS Negl Trop Dis. 2013 Oct. 31; 7(10):e2519; and PLoS One. 2015 Mar. 11; 10(3):e0118615). Other molecules capable of activating complement have been described, such as C-reactive protein (CRP). Pharmaceutical grade CRP has been described previously (Circulation Research. 2014; 114: 672-676). Additionally, therapeutic antibodies may be used to activate or inhibit complement. In one embodiment, antibody drug conjugates may be used. In other embodiments, dual dual targeting compounds and/or antibodies may be used. Not being bound by a theory, a dual antibody may bind complement in one aspect and, for example, a tumor in another aspect, so as to localize the complement to a tumor. An antibody of the present invention may be an antibody fragment. The antibody fragment may be a nanobody, Fab, Fab', (Fab')2, Fv, ScFv, diabody, triabody, tetrabody, Bis-scFv, minibody, Fab2, or Fab3 fragment.

Inhibitors of the complement system are well known in the art and are useful for the practice of the present invention (see, e.g., Ricklin et al., Progress and trends in complement therapeutics. Adv Exp Med Biol. 2013; 735:1-22.; Ricklin et al., Complement-targeted therapeutics. Nat Biotechnol. 2007 November; 25(11): 1265-1275; and Reis et al., Applying complement therapeutics to rare diseases. Clin Immunol. 2015 December; 161(2):225-40, herein incorporated by reference in their entirety).

A "complement inhibitor" is a molecule that prevents or reduces activation and/or propagation of the complement cascade that results in the formation of C3a or signaling through the C3a receptor, or C5a or signaling through the C5a receptor. A complement inhibitor can operate on one or more of the complement pathways, i.e., classical, alternative or lectin pathway. A "C3 inhibitor" is a molecule or substance that prevents or reduces the cleavage of C3 into C3a and C3b. A "C5a inhibitor" is a molecule or substance that prevents or reduces the activity of C5a. A "C5aR inhibitor" is a molecule or substance that prevents or reduces the binding of C5a to the C5a receptor. A "C3aR inhibitor" is a molecule or substance that prevents or reduces binding of C3a to the C3a receptor. A "factor D inhibitor" is a molecule or substance that prevents or reduces the activity of Factor D. A "factor B inhibitor" is a molecule or substance that prevents or reduces the activity of factor B. A "C4 inhibitor" is a molecule or substance that prevents or reduces the cleavage of C4 into C4b and C4a. A "C1q inhibitor" is a molecule or substance that prevents or reduces C1q binding to antibody-antigen complexes, virions, infected cells, or other molecules to which C1q binds to initiate complement activation. Any of the complement inhibitors described herein may comprise antibodies or antibody fragments, as would be understood by the person of skill in the art.

Antibodies useful in the present invention, such as antibodies that specifically bind to either C4, C3 or C5 and prevent cleavage, or antibodies that specifically bind to factor D, factor B, C1q, or the C3a or C5a receptor, can be made by the skilled artisan using methods known in the art. Anti-C3 and anti-C5 antibodies are also commercially available.

The term "antibody" is used interchangeably with the term "immunoglobulin" herein, and includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc, Fd, dAb, VHH and scFv and/or Fv fragments.

As used herein, a preparation of antibody protein having less than about 50% of non-antibody protein (also referred to herein as a "contaminating protein"), or of chemical precursors, is considered to be "substantially free." 40%, 30%, 20%, 10% and more preferably 5% (by dry weight), of non-antibody protein, or of chemical precursors is considered to be substantially free. When the antibody protein or biologically active portion thereof is recombinantly produced, it is also preferably substantially free of culture medium, i.e., culture medium represents less than about 30%, preferably less than about 20%, more preferably less than about 10%, and most preferably less than about 5% of the volume or mass of the protein preparation.

The term "antigen-binding fragment" refers to a polypeptide fragment of an immunoglobulin or antibody that binds antigen or competes with intact antibody (i.e., with the intact antibody from which they were derived) for antigen binding (i.e., specific binding). As such these antibodies or fragments thereof are included in the scope of the invention, provided that the antibody or fragment binds specifically to a target molecule.

It is intended that the term "antibody" encompass any Ig class or any Ig subclass (e.g. the IgG1, IgG2, IgG3, and IgG4 subclassess of IgG) obtained from any source (e.g., humans and non-human primates, and in rodents, lagomorphs, caprines, bovines, equines, ovines, etc.).

The term "Ig class" or "immunoglobulin class", as used herein, refers to the five classes of immunoglobulin that have been identified in humans and higher mammals, IgG, IgM, IgA, igD, and IgE. The term "Ig subclass" refers to the two subclasses of IgM (H and L), three subclasses of IgA (IgA1, IgA2, and secretory IgA), and four subclasses of IgG (IgG1, IgG2, IgG3, and IgG4) that have been identified in humans and higher mammals. The antibodies can exist in monomeric or polymeric form; for example, IgM antibodies exist in pentameric form, and IgA antibodies exist in monomeric, dimeric or multimeric form.

The term "IgG subclass" refers to the four subclasses of immunoglobulin class IgG-IgG1, IgG2, IgG3, and IgG4 that have been identified in humans and higher mammals by the heavy chains of the immunoglobulins, V1-γ4, respectively. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The "variable" domains of an antibody heavy chain are referred to interchangeably as "heavy chain constant regions", "heavy chain constant domains", "VH" regions or "VH" domains).

The term "region" can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10 Fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins-harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

"Specific binding" of an antibody means that the antibody exhibits appreciable affinity for a particular antigen or epitope and, generally, does not exhibit significant cross reactivity. "Appreciable" binding includes binding with an affinity of at least 25 μM. Antibodies with affinities greater than $1\times10^7$ M−1 (or a dissociation coefficient of 1 μM or less or a dissociation coefficient of 1 nm or less) typically bind with correspondingly greater specificity. Values intermediate of those set forth herein are also intended to be within the scope of the present invention and antibodies of the invention bind with a range of affinities, for example, 100 nM or less, 75 nM or less, 50 nM or less, 25 nM or less, for example 10 nM or less, 5 nM or less, 1 nM or less, or in embodiments 500 μM or less, 100 μM or less, 50 μM or less or 25 μM or less. An antibody that "does not exhibit significant cross-reactivity" is one that will not appreciably bind to an entity other than its target (e.g., a different epitope or a different molecule). For example, an antibody that specifically binds to a target molecule will appreciably bind the target molecule but will not significantly react with non-target molecules or peptides. An antibody specific for a particular epitope will, for example, not significantly cross-react with remote epitopes on the same protein or peptide. Specific binding can be determined according to any art-recognized means for determining such binding. Preferably, specific binding is determined according to Scatchard analysis and/or competitive binding assays.

As used herein, the term "affinity" refers to the strength of the binding of a single antigen-combining site with an antigenic determinant. Affinity depends on the closeness of stereochemical fit between antibody combining sites and antigen determinants, on the size of the area of contact between them, on the distribution of charged and hydrophobic groups, etc. Antibody affinity can be measured by equilibrium dialysis or by the kinetic BIACORE™ method. The dissociation constant, Kd, and the association constant, Ka, are quantitative measures of affinity.

As used herein, the term "monoclonal antibody" refers to an antibody derived from a clonal population of antibody-producing cells (e.g., B lymphocytes or B cells) which is homogeneous in structure and antigen specificity. The term "polyclonal antibody" refers to a plurality of antibodies originating from different clonal populations of antibody-producing cells which are heterogeneous in their structure and epitope specificity but which recognize a common antigen. Monoclonal and polyclonal antibodies may exist within bodily fluids, as crude preparations, or may be purified, as described herein.

The term "binding portion" of an antibody (or "antibody portion") includes one or more complete domains, e.g., a pair of complete domains, as well as fragments of an antibody that retain the ability to specifically bind to a target molecule. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab')2, Fabc, Fd, dAb, Fv, single chains, single-chain antibodies, e.g., scFv, and single domain antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Examples of portions of antibodies or epitope-binding proteins encompassed by the present definition include: (i) the Fab fragment, having VL, CL, VH and CH1 domains; (ii) the Fab' fragment, which is a Fab fragment having one or more cysteine residues at the C-terminus of the CHI domain; (iii) the Fd fragment having VH and CHI domains; (iv) the Fd' fragment having VH and CHI domains and one or more cysteine residues at the C-terminus of the CHI domain; (v) the Fv fragment having the VL and VH domains of a single arm of an antibody; (vi) the dAb fragment (Ward et al., 341 Nature 544 (1989)) which consists of a VH domain or a VL domain that binds antigen; (vii) isolated CDR regions or isolated CDR regions presented in a functional framework; (viii) F(ab')2 fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen binding sites, comprising a heavy chain variable domain (VH) connected to a light chain variable domain (VL) in the same polypeptide chain (see, e.g., EP 404,097; WO 93/11161; Hollinger et al., 90 PNAS 6444 (1993)); (xi) "linear antibodies" comprising a pair of tandem Fd segments (VH-Ch1-VH-Ch1) which, together with complementary light chain polypeptides, form a pair of antigen binding regions (Zapata et al., Protein Eng. 8(10):1057-62 (1995); and U.S. Pat. No. 5,641,870).

As used herein, a "blocking" antibody or an antibody "antagonist" is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt complement interactions either partially or fully.

The dose of antibody required in humans to be effective in the treatment cancer differs with the type and severity of the cancer to be treated, the age and condition of the patient, etc. Typical doses of antibody to be administered are in the range of 1 µg to 1 g, preferably 1-1000 µg, more preferably 2-500, even more preferably 5-50, most preferably 10-20 µg per unit dosage form. In certain embodiments, infusion of antibodies of the present invention may range from 10-500 mg/m2.

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10Fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type ITT domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins-harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

A "complement activator" is a molecule that activates or increases activation and/or propagation of the complement cascade that results in the formation of C3a or signaling through the C3a receptor, or C5a or signaling through the C5a receptor. A complement activator can operate on one or more of the complement pathways, i.e., classical, alternative or lectin pathway.

Inhibitors or activators of the complement system may be administered by any known means in the art and by any means described herein. The inhibitors or activators may be targeted to a specific site of disease, such as, but not limited to a tumor. Monitoring by any means described herein may be used to determine if the therapy is effective. Such combination of a therapeutic targeting complement and monitoring provides advantages over any methods known in the art. Not being bound by a theory, the infiltration of cell populations, such as CAFs, T cells, macrophages, B cells may be monitored during treatment with an agent that activates or inhibits a component of the complement system. Not being bound by a theory a gene signature within a specific cell population as described herein may be monitored during treatment with an agent that activates or inhibits a component of the complement system. Not being bound by a theory, the present invention is provided by the Applicants discovery of cell specific gene expression signatures of cells within different cancers correlating to immune status, tumor status, and immune cell abundance. Moreover, applicants discovery of the correlation of complement gene expression in specific cell types to immune cell abundance allows for activating or inhibiting complement in order to modulate the microenvironment, including an immune response, for treatment of a disease. As illustrated by the examples, Applicants show that the expression of complement in relation to an immune response, and specifically, immune cell abundance is not limited to a specific cancer. Applicants provide data showing consistent gene expression patterns of complement components in single cells for melanoma, head and neck cancer, glioma, metastases to the brain, and across the TCGA tumors (see Examples). Not being bound by a theory, immune cell abundance is and gene expression signatures in single cells part of the microenvironment is a general phenomenon that provides for activating and inhibiting complement in relation to many diseases and conditions, preferably cancer.

These and other technologies may be employed in or as to the practice of the instant invention.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1—Non-Malignant Cells and their Interactions within the Tumor Microenvironment Various non-malignant cells comprise the tumor microenvironment. The composition of the microenvironment has an important impact on tumorigenesis and in the modulation of treatment responses. Tumor infiltration with T cells, for example, was found to be predictive for the response to immune checkpoint inhibitors in various cancer types (34).

Applicants leveraged single-cell RNA-seq to characterize 4,645 malignant and non-malignant cells of the tumor microenvironment from 19 patient-derived melanomas. The analysis uncovered intra- and inter-individual, spatial, functional and genomic heterogeneity in melanoma cells and associated tumor components that shape the microenvironment, including immune cells, CAFs, and endothelial cells.

To resolve the composition of the melanoma microenvironment, Applicants first used the single-cell RNA-seq profiles to define unique expression signatures for each of five distinct non-malignant cell types: T cells, B cells, macrophages, endothelial cells, and CAFs. Because the signatures were derived from single cell profiles, Applicants could ensure that they are based on distinct genes for each cells type, avoiding confounders. Next, Applicants used these signatures to infer the relative abundance of those cell types in a larger compendium of tumors published recently by the TCGA consortium (Methods, FIG. 1A, FIG. 2). Supporting the strategy, Applicants found a strong correlation (R~0.8) between the estimated tumor purity and that predicted from DNA analysis (35) (FIG. 1A, first lane below the heatmap).

Figure 2:
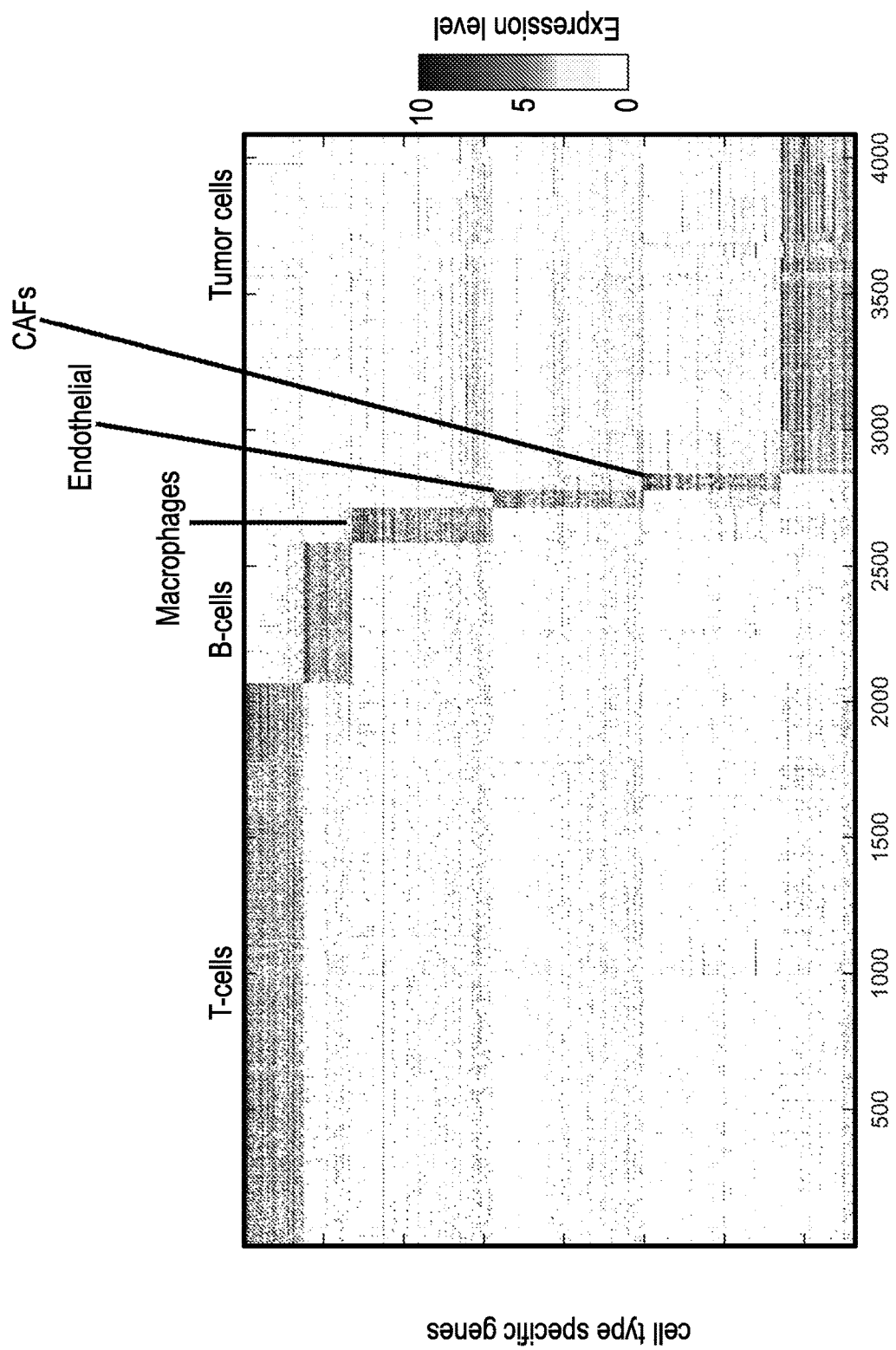
FIG. 2 depicts the identification of cell-type specific genes in melanoma tumors. Shown are the cell-type specific genes (rows) as chosen from single cell profiles (Methods), sorted by their associated cells cell type, and their expression levels (log 2(TPM/10+1)) across non-malignant and malignant tumor cells, also sorted by type (columns).
Figures 3A, 3B:
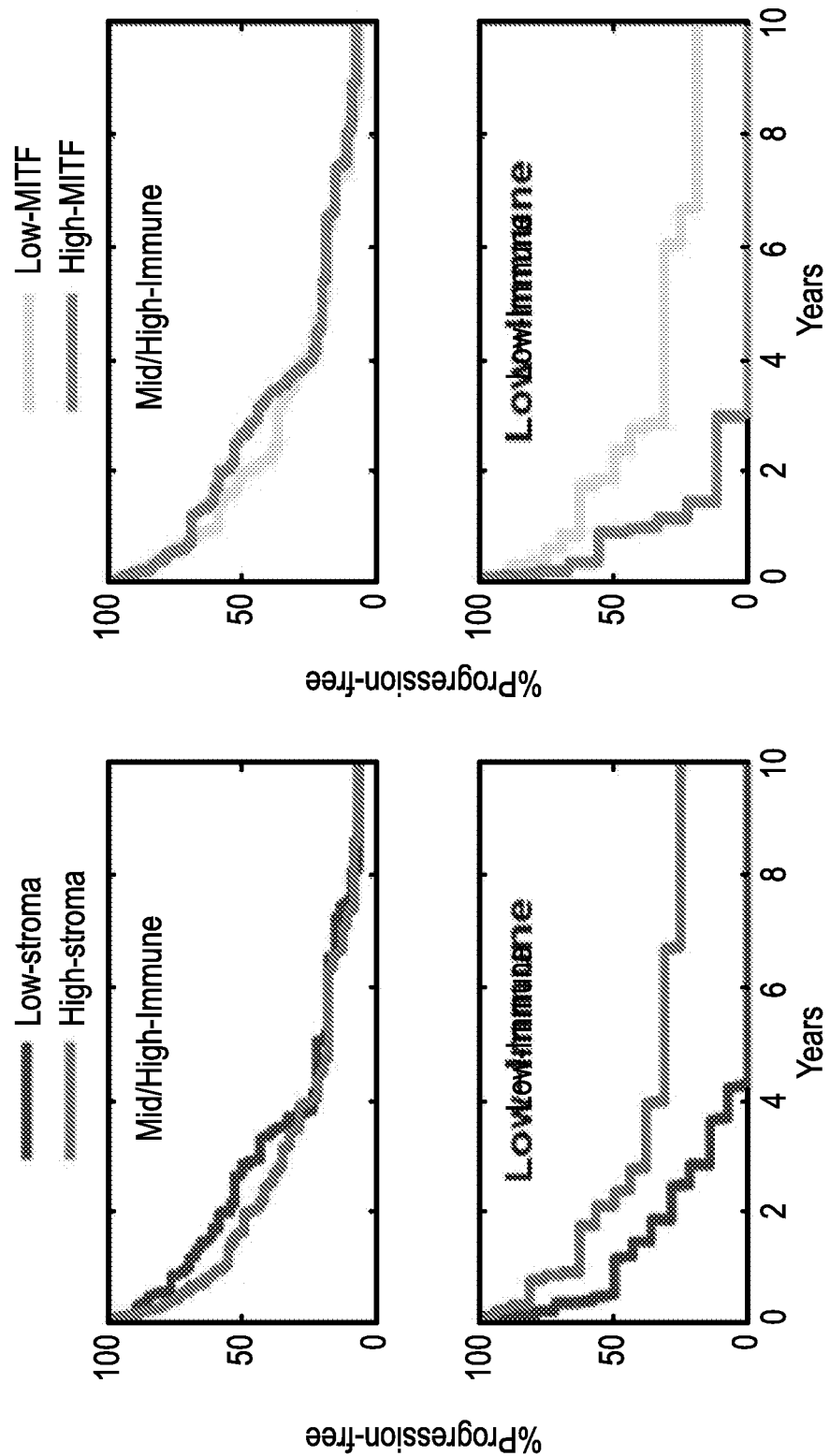
FIG. 3A-3B depicts the association of immune and stroma abundance in melanoma with progression-free survival.

Using this approach, Applicants partitioned 495 TCGA tumors into 10 distinct microenvironment clusters based on their inferred cell type composition (FIG. 1A). For example, Cluster 9 consisted of tumors with a particularly high inferred content of B cells, whereas Cluster 4 had a relatively high inferred proportion of endothelial cells and CAFs. Clusters were mostly independent of the site of metastasis (FIG. 1A, second lane), with some notable exceptions (e.g., Clusters 8 and 9).

Next, Applicants examined how these different microenvironments may relate to the phenotype of the malignant cells. In particular, CAF abundance is predictive of the AXL-MITF distinction, such that CAF-rich tumors strongly expressed the AXL-high signature (FIG. 1A, bottom lane). Interestingly, an "AXL-high" program was expressed both by melanoma cells and by CAFs. However, using the single cell RNA-seq data, Applicants distinguished AXL-high genes that are preferentially expressed by melanoma cells ("melanoma-derived AXL program") and those that are preferentially expressed by CAFs ("CAF derived AXL program"). Both sets of genes were correlated with the inferred CAF abundance in TCGA tumors (36). Furthermore, the MITF-high program, which is specific to melanoma cells, was negatively correlated with inferred CAF abundance. Taken together, these results suggest that CAF abundance may be linked to preferential expression of the AXL-high over the MITF-high program within the melanoma cells. The findings raised the possibility that specific tumor-CAF interactions may shape the melanoma cell transcriptome.

Figure 5A:
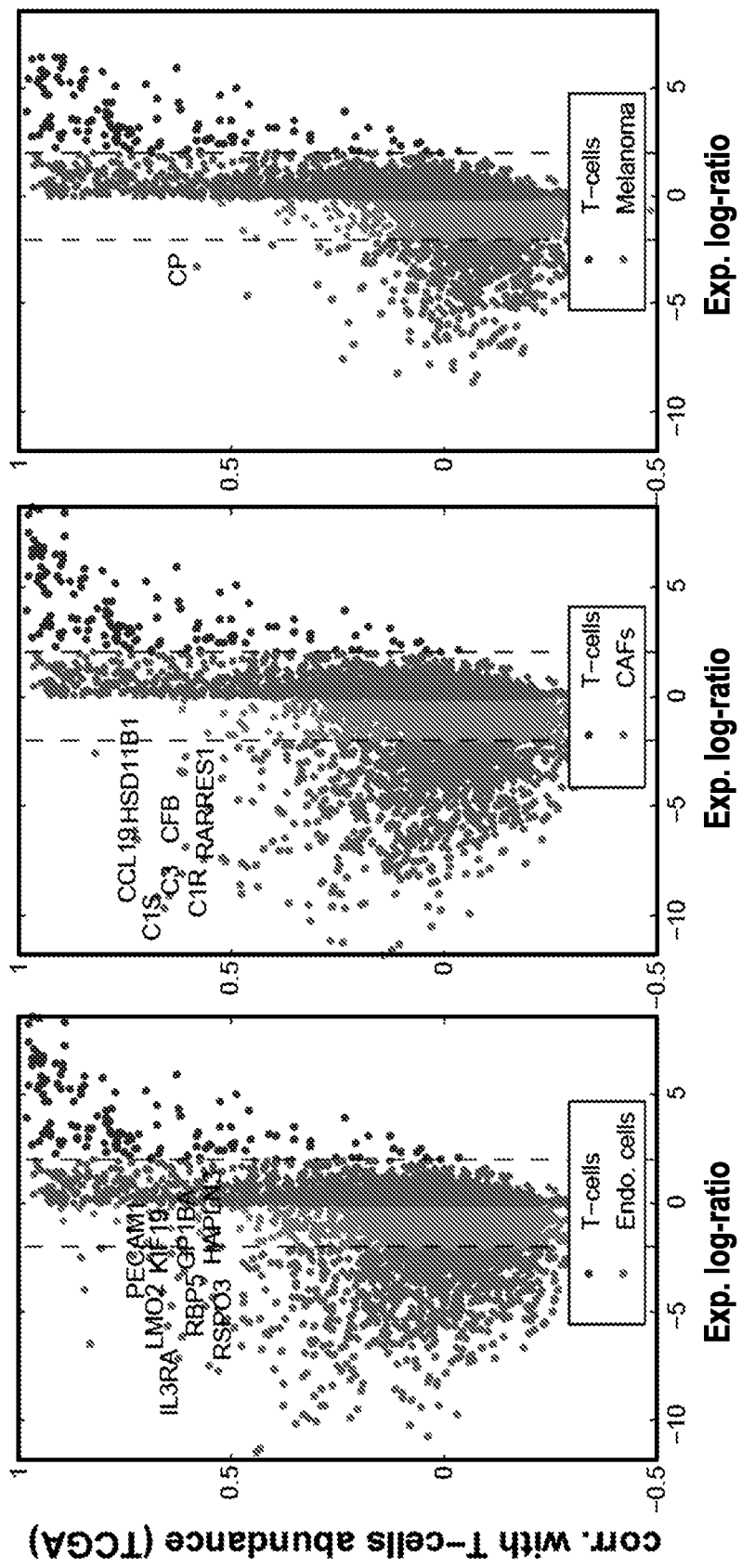
FIG. 5A-5C depicts the identification of putative genes underlying cell-to-cell interactions from analysis of single cell profiles and TCGA samples. Applicants searched for genes that underlie potential cell-to-cell interactions, defined as those that are primarily expressed by cell type M (as defined by the single cell data) but correlate with the inferred relative frequency of cell type N (as defined from correlations across TCGA samples). For each pair of cell types (M and N), Applicants restricted the analysis to genes that are at least four-fold higher in cell type M than in cell type N and in any of the other four cell types. Applicants then calculated the Pearson correlation coefficient (R) between the expression of each of these genes in TCGA samples and the relative frequency of cell type N in those samples, and converted these into Z-scores. The set of genes with Z>3 and a correlation above 0.5 was defined as potential candidates that mediate an interaction between cell type M and cell type N. (A) Of all the pairwise comparisons Applicants identified interactions only between immune cells (B, T, macrophages) and non-immune cells (CAFs, endothelial cells, malignant melanoma) cells, such that the expression of genes from non-immune cells correlated with the relative frequency of immune cell types. Each plot shows a single pairwise comparison (M vs. N), including interactions of non-immune cell types (endothelial cells: left; CAFs: middle; malignant melanoma: right) with each of T-cells (A), B-cells (B) and macrophages (C). Each plot compares for each gene (dot) the relative expression of genes in the two cell types being compared (M-N) and the correlations of these genes' expression with the inferred frequency of cell type N across bulk TCGA tumors. Dashed lines denote the four-fold threshold. Genes that may underlie potential interactions, as defined above, are highlighted.
Figure 5B:
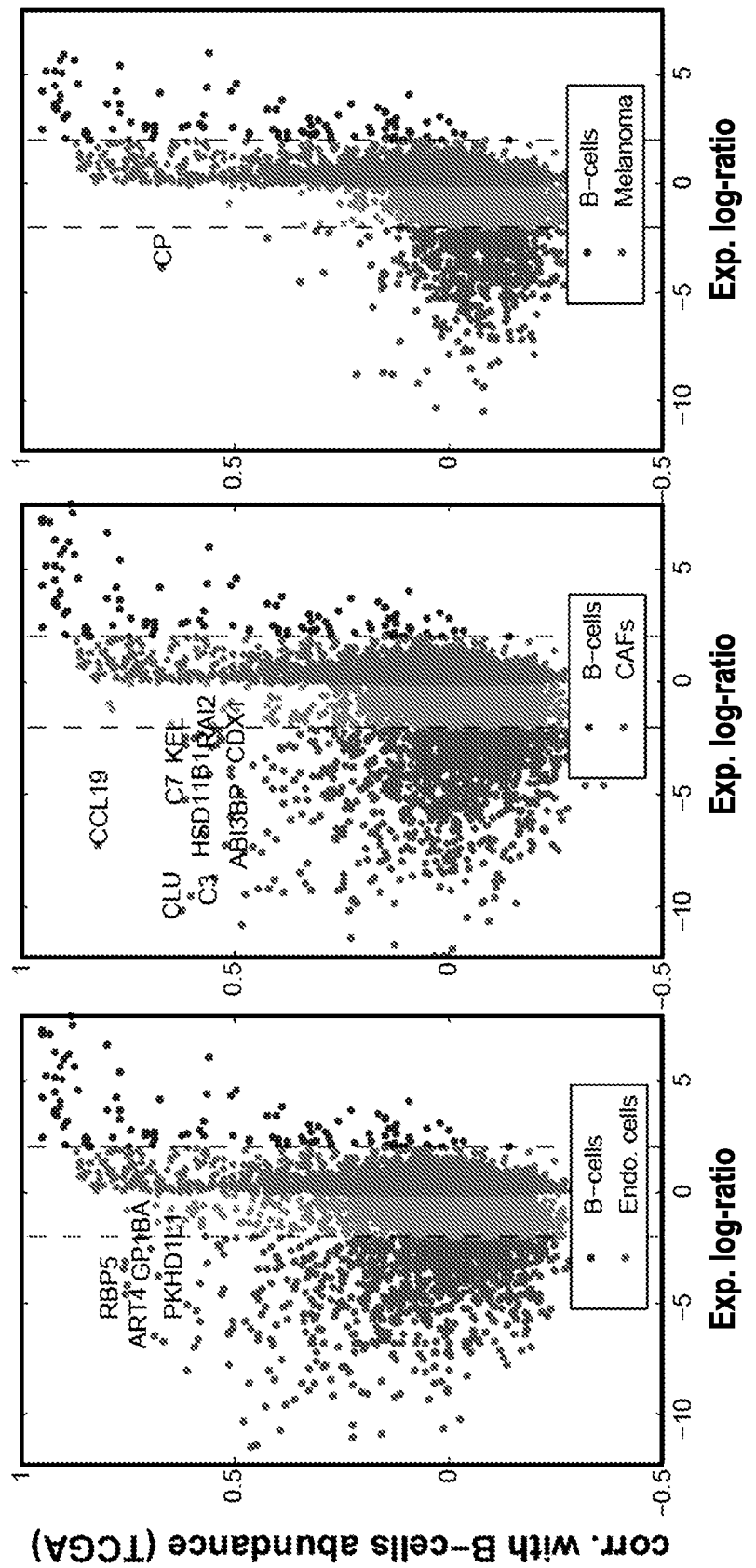
Figure 5C:
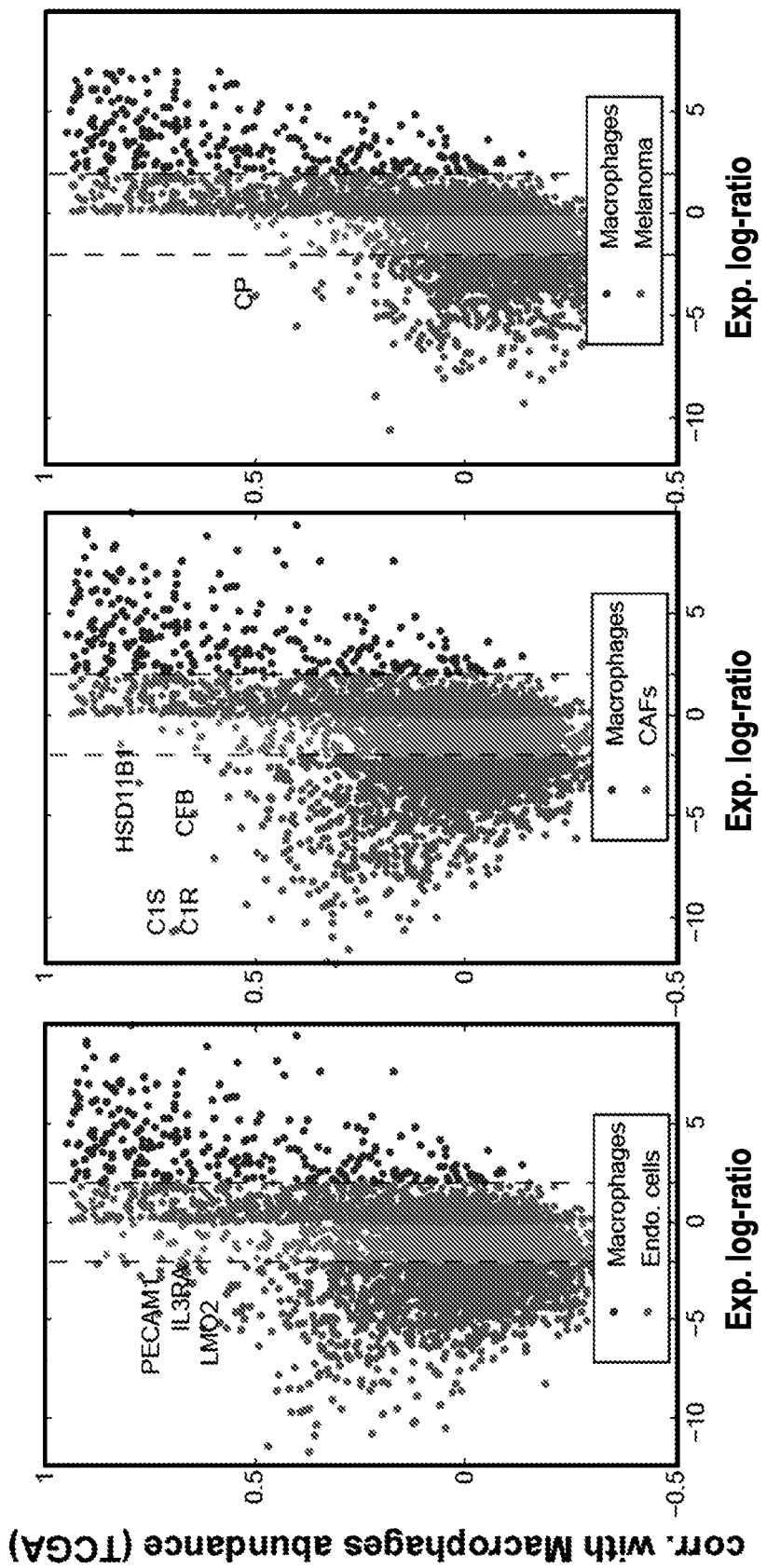
Figure 6A:
FIG. 6A-6C depicts immune modulators expressed by CAFs and macrophages. (A) Pearson correlation coefficient (color bar) across TCGA melanoma tumors between the expression level of each of the immune modulators shown in FIG. 1B and additional complement factors with significant expression levels. (B) Correlations across TCGA melanoma tumors between the expression level of the genes shown in (A) and the average expression levels of T cell marker genes. (C) Average expression level (log 2(TPM+1), color bar) of the genes shown in (A) in the single cell data, for cells classified into each of the major cell types Applicants identified. These results show that most complement factors are correlated with one another and with the abundance of T cells, even though some are primarily expressed by CAFs (including C3) and others by macrophages. In contrast, two complement factors (CFI, C5) and the complement regulatory genes (CD46 and CD55) show a different expression pattern.
Figure 6B:
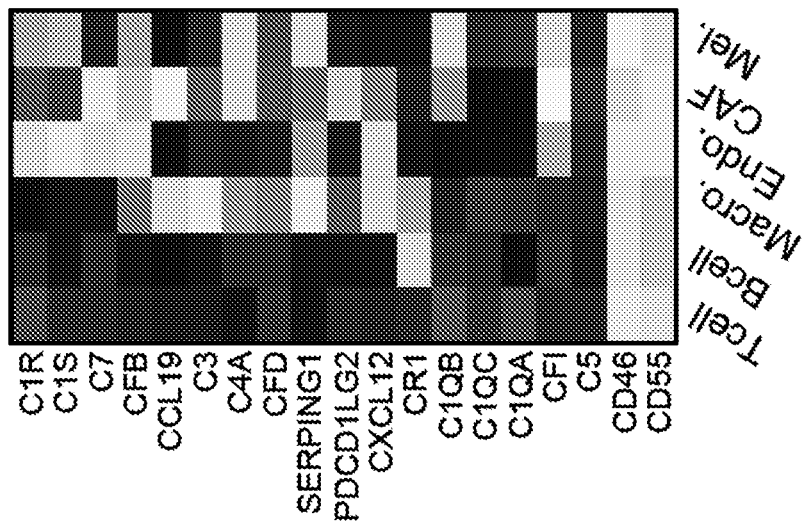
Figure 6C:
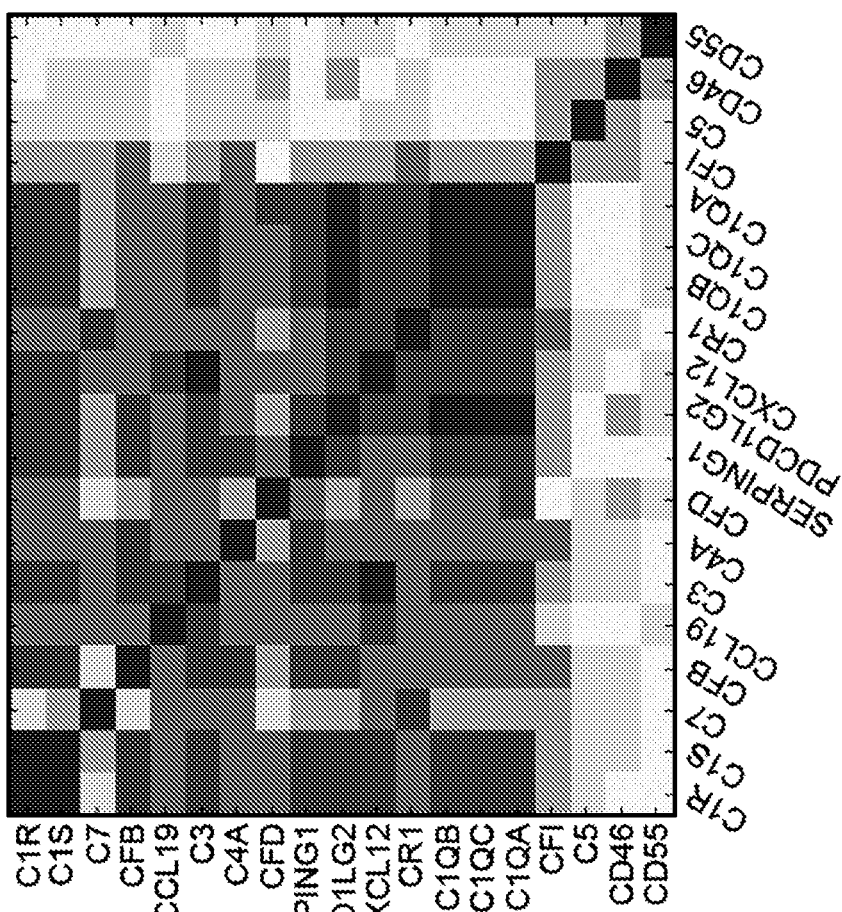
Figure 7A:
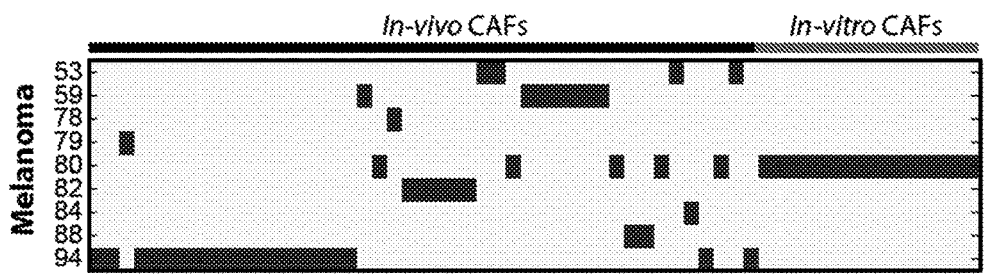
FIG. 7A-7C depicts unique expression profiles of in vivo CAFs. (A-B) Distinct expression profiles in in vivo and in vitro CAFs. Shown are Pearson correlation coefficient between individual CAFs isolated in vivo from seven melanoma tumors, and CAFs cultured from one tumor (melanoma 80). Hierarchical clustering shows two clusters, one consisting of all in vivo CAFs, regardless of their tumor-of-origin (marked in (A)), and another of the in vitro CAFs. (C) Unique markers of in vivo CAFs include putative cell-cell interaction candidates. Left: Heatmap shows the expression level (log 2(TPM+1)) of CAF markers (bottom) and the top 14 genes with higher expression in in-vivo compared to in-vitro CAFs (t-test). Right: average (bulk) expression of the genes in the in-vivo CAFs, in-vitro CAFs, and primary foreskin fibroblasts from the Roadmap Epigenome project. Potential interacting genes from FIG. 1B are highlighted in bold red.
Figure 7B:
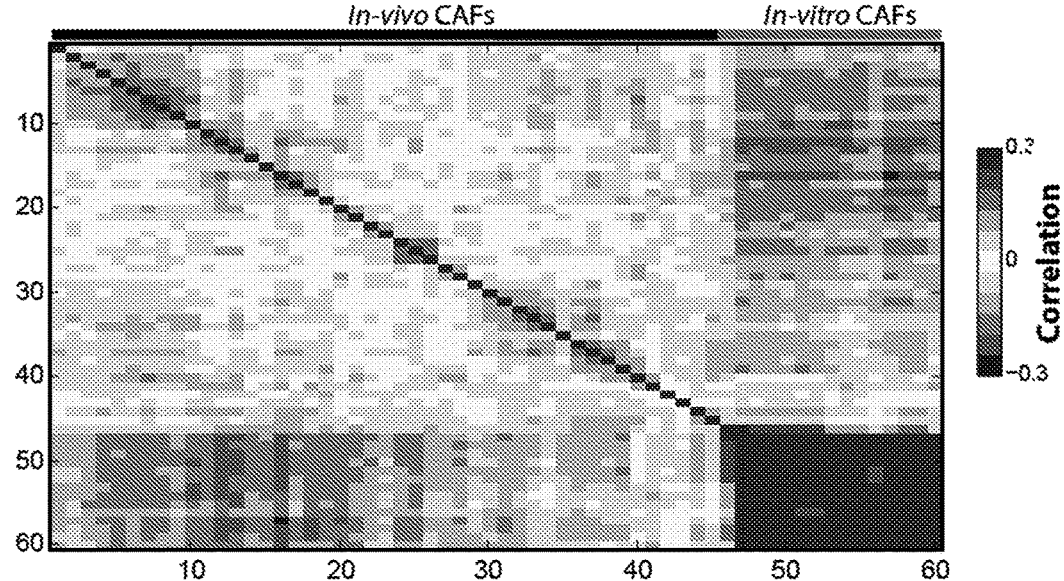
Figure 7C:
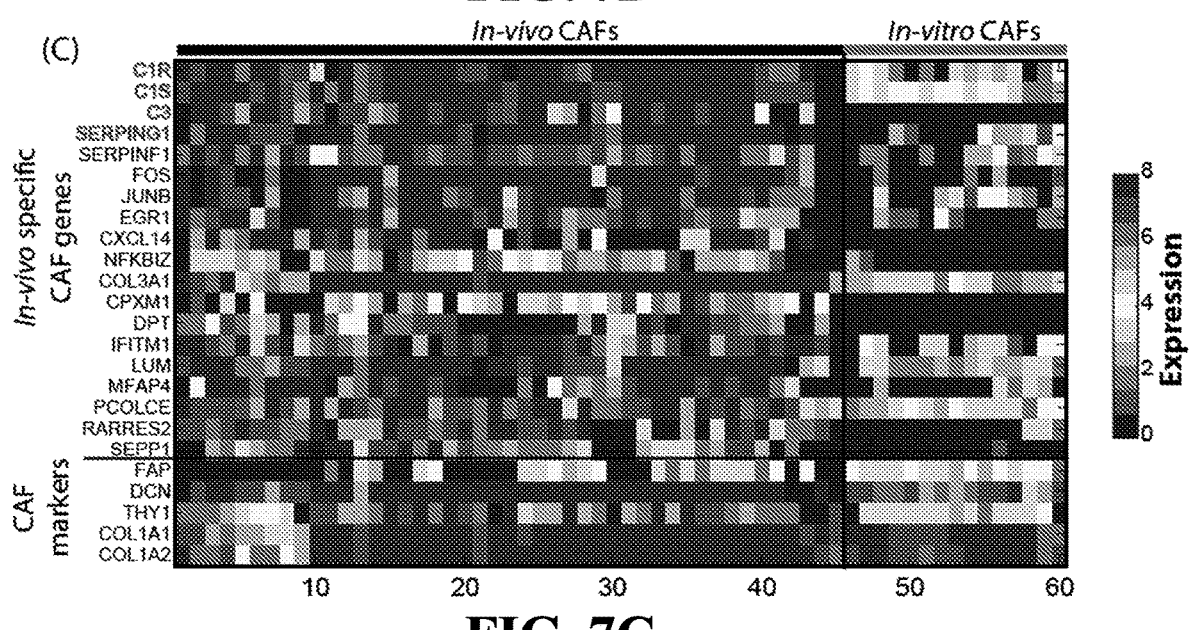

Interactions between cells play crucial roles in the tumor microenvironment. To assess systematically how cell-cell interactions may influence tumor composition, Applicants searched for genes expressed by cells of one type that may influence the proportion of cells of a different type in the tumor (FIG. 5). For example, Applicants searched for genes expressed primarily by CAFs (but not T cells) in single cell data that correlated with T cell abundance (as inferred by T cell specific genes) in bulk tumor tissue from the TCGA data set (37). Applicants identified a set of CAF-expressed genes that correlated strongly with T cell infiltration (FIG. 1B, red circles). These included known chemotactic (CXCL12, CCL19) and immune modulating (PD-L2) genes, which are significantly expressed by both CAFs and macrophages (FIG. 6). A separate set of genes exclusively expressed by CAFs that correlated with T cell infiltration (FIG. 6) included multiple complement factors (C1S, C1R, C3, C4A, CFB and C1NH [SERPING1]). Notably, these complement genes were specifically expressed by freshly isolated CAFs but not by cultured CAFs (FIG. 7) or macrophages (FIG. 6). These findings were intriguing in light of several studies that have implicated complement activity in the recruitment and modulation of T cell mediated anti-tumor immune responses (in addition to the established role of complement in innate immunity (38)).

Applicants validated a high correlation (R>0.8) between complement factor 3 (C3) levels (one of the CAF expressed complement genes) and infiltration of CD8+ T cells. To this end, Applicants performed dual IF staining and quantitative slide analysis of two tissue microarrays (TMAs) with a total of 308 core biopsies, including primary tumors, metastatic lesions, normal skin with adjacent tumor and healthy skin controls (FIG. 1C; FIG. 8). To test the generalizability of the association between CAF derived complement factors with T cell infiltration, Applicants expanded the analysis to bulk RNA-seq datasets across all TCGA cancer types (FIG. 1D). Consistent with the results in melanoma, complement factors correlated with inferred T cell abundance in many cancer types, and more highly than in normal tissues (e.g., R>0.4 for 65% of cancer types but only for 14% of normal tissue types). Although correlation analysis cannot determine causality, this indicated a potential in vivo role for cell-to-cell interactions. Overall, this analysis suggests stroma-derived and immune-derived mechanisms that may regulate the recruitment or proliferation of immune cells.

By leveraging single cell profiles from a few tumors to deconvolve a large collection of bulk profiles from TCGA, Applicants discovered different microenvironments that are associated with distinct malignant cell profiles, and a subset of genes expressed by one cell type (e.g., CAFs) that may influence the proportion of cells present of another cell type (e.g., T cells), suggesting the importance of intercellular communication for tumor phenotype. Applicants validated putative interactions between stromal-derived factors and the immune-cell abundance in a large independent set of melanoma core biopsies. These observations suggest that new diagnostic and therapeutic strategies that consider tumor cell composition rather than bulk expression may prove advantageous in the future.

Example 2—Decoupling Genetic, Developmental and Micro-Environmental Programs in IDH-Mutant Gliomas Through Single-Cell RNA-Seq In adults, diffuse gliomas are classified into three main categories based on integrated genetic and histologic criteria: IDH-wildtype glioblastoma (GBM) is the most prevalent and aggressive form of the disease, while mutations in IDH1/2 define two major classes of gliomas: astrocytoma (IDH-A) and oligodendroglioma (IDH-O) (98). IDH-A and IDH-O are two distinct tumor types that differ in their genetics, histopathology and prognosis. Genetically, IDH-A are characterized by TP53 and ATRX mutations, while IDH-O are characterized by mutations in TERT promoter and loss of chromosome arms 1p and 19q, defining a robust genetic separation into two disease entities (112). In histopathology, IDH-A and IDH-O are distinct and thought to predominantly recapitulate astrocytic and oligodendrocytic lineage differentiation, respectively. The notion that lineages differ between astrocytoma and oligodendroglioma, as implied by their names, originates from distinct morphology and tissue staining. However, expression of both oligodendroglial (e.g., OLIG2) and astrocytic (e.g., GFAP) markers can be readily identified in both diseases (98), mixtures of cells with histological features of neoplastic astrocytic and oligodendroglial cells are frequently observed within individual tumors, and cellular morphologies are only partially reminiscent of distinct glial cells, thus questioning the hypothesis of distinct lineages. Two models may explain morphological differences in IDH-mutant gliomas: in one model, distinct glial cells or glial progenitor cells give rise to different types of gliomas; in another model, all IDH-mutant gliomas originate from the same progenitors, but distinct signature genetic events give rise to two different classes of tumors of different morphology (127).

Applicants reasoned that scRNA-seq of a limited number of representative tumors (10 IDH-A and 6 IDH-O tumors) could be combined with existing bulk data from large cohorts to decouple these distinct effects, and sought to apply this approach to understand the differences between two types of diffuse gliomas.

Figure 9A:
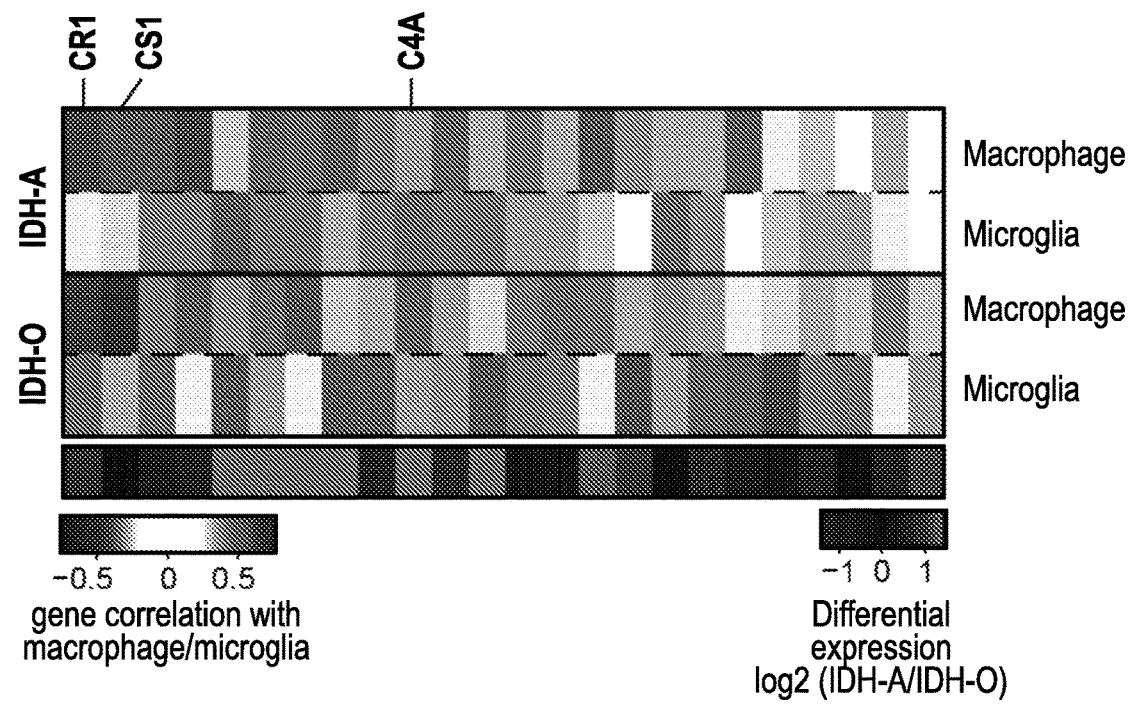
FIG. 9A-9B. Diversity and frequency of microglia and macrophages across IDH-mutant glioma and factors associated with immune infiltration. (A) Top: correlation of the expression of each gene (column) with microglia or macrophage (row) scores across IDH-A (top two rows) and across IDH-O (bottom two rows) bulk tumors, for the 24 genes that are not expressed by microglia/macrophages but correlate significantly (P<0.05) with both microglia and macrophage scores. Bottom: differential expression of the same genes between IDH-A and IDH-O bulk tumors. Three genes from the complement system are marked. (B) Immune scores (X-axis: macrophage, left; microglia, right) correlate with the average expression of the 24 non-immune genes from (A) (Y-axis) across bulk IDH-A (purple) and IDH-O (blue) TCGA tumors.
Figure 9B:
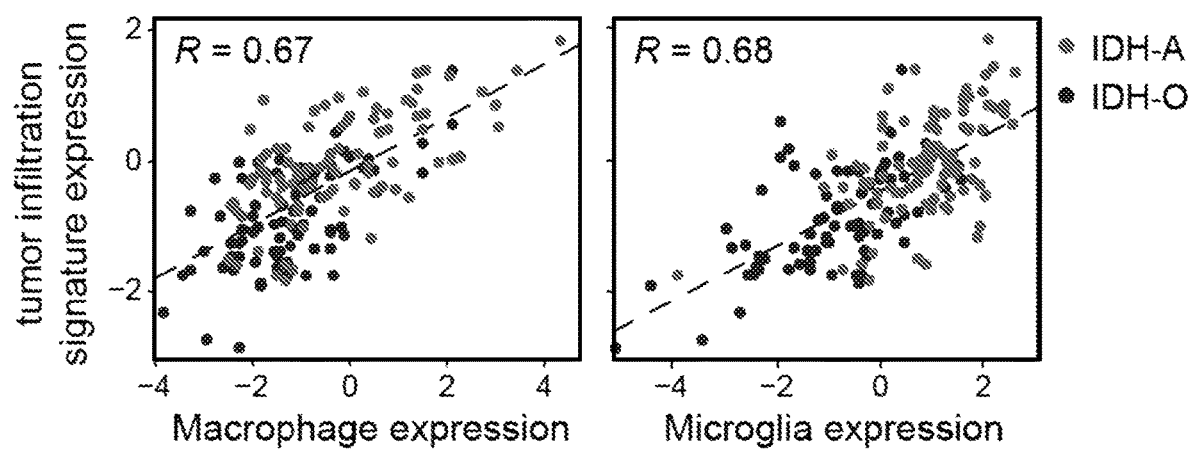

Applicants determined genes that are not expressed by macrophage/microglia, but are correlated with the inferred abundance of macrophage/microglia cells across bulk tumor samples. Applicants found 24 genes which are correlated both with microglia and with macrophage expression across IDH-A tumors, and separately, across IDH-O tumors (FIG. 9A, left). Although these analyses were performed within a tumor type and thus were not directly influenced by differences between IDH-A and IDH-O, these genes were preferentially expressed in IDH-A (FIG. 9A, right), consistent with the increased macrophage/microglia signatures in IDH-A. Applicants could not determine if these association are causal (i.e., Applicants cannot distinguish whether these genes influence, or are influenced by, immune infiltration, or whether both are affected by a third hidden factor). The ability of this expression program to predict the extent of macrophage/microglia infiltration across tumors and tumor types (FIG. 9B) suggested interactions between immune infiltration and other cells in the tumor. Interestingly, three of those genes were components of the complement system, as Applicants recently observed in melanoma (126) and described herein.

Example 3—Cell Interactions within Breast Cancer

Figure 10:
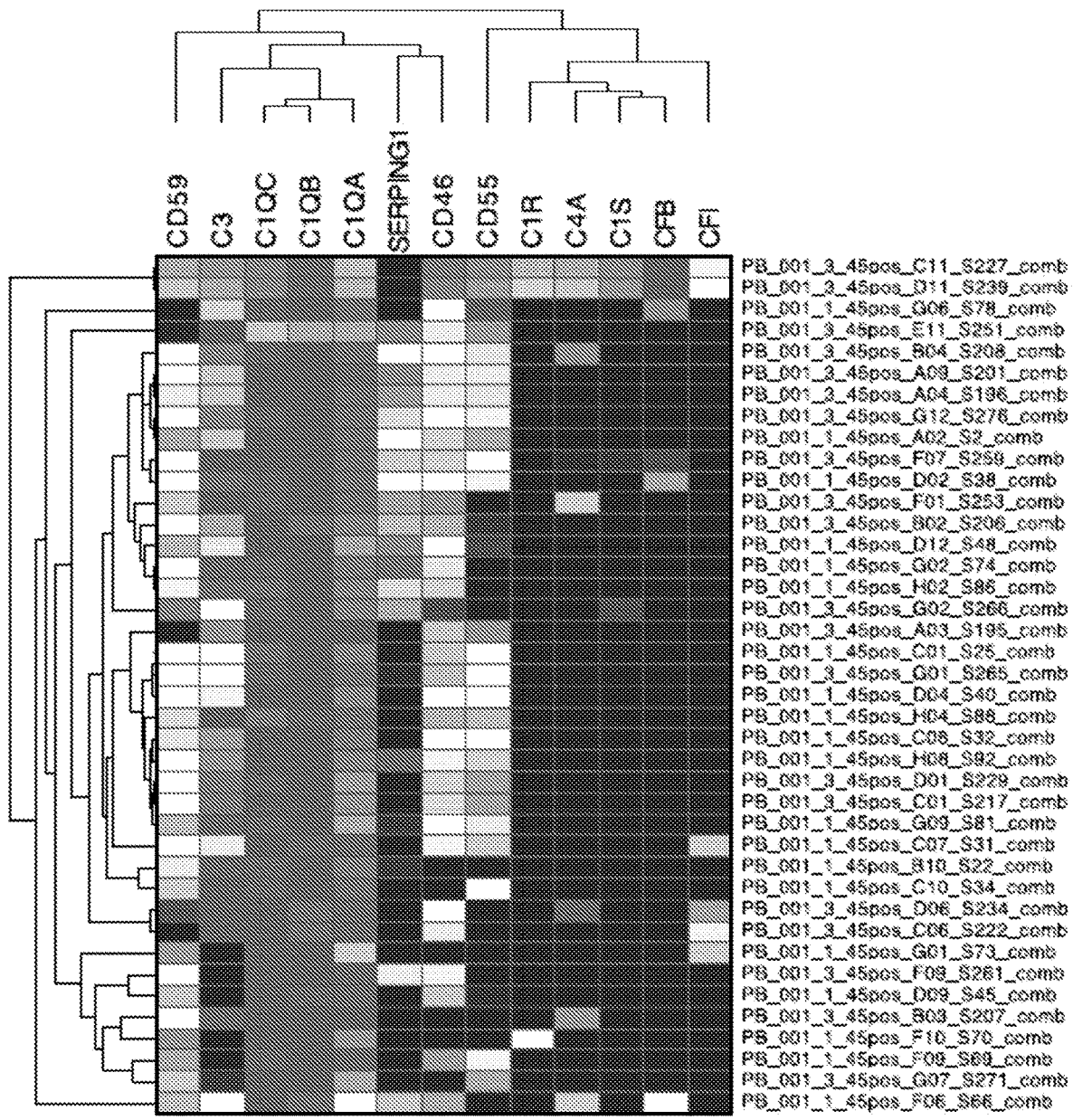
FIG. 10 depicts expression of complement genes in microglia cells in breast metastases in the brain. Heatmap shows the expression level of indicated genes (x-axis) in single microglia cells (y-axis).

Applicants performed downstream analyses of human patient-derived single-cell RNA seq data from malignant tissue of a human patient with breast cancer metastasis in the brain. Applicants discovered correlations with complement gene signatures by analyzing the expression of CD59, C3, C1QC, C1QB, CiQA, SERPING1, CD46, CD55, C1R, C4A, CIS, CFB and CFI in microglia, T-cell, and tumor cell populations in breast metastases in the brain. Microglia strongly upregulate expression of C1q genes (FIG. 10). This is consistent with the activity of macrophage-like species to develop C1q downstream of the classical complement pathway. In particular, the genes of the C1 subunits (e.g. C1QB, C1QC, and C1R) are upregulated. Interestingly, CIS is not produced by microglia (see tumors). Microglia strongly downregulate CFB and CFI. CFI is a deregulator of the classical complement pathway by downstream enzymatic cleavage of C3b. CFB activates the alternative pathway, by association with C3b to form C3 convertase. This suggests that microglia in this patient are upregulating the classical vs. the alternative pathway to signal an IgG-based antibody response, leading to T cell density. Moreover, the expression pattern could suggest the possibility of activating the alternative pathway depending on the T-cell response.

Figure 11:
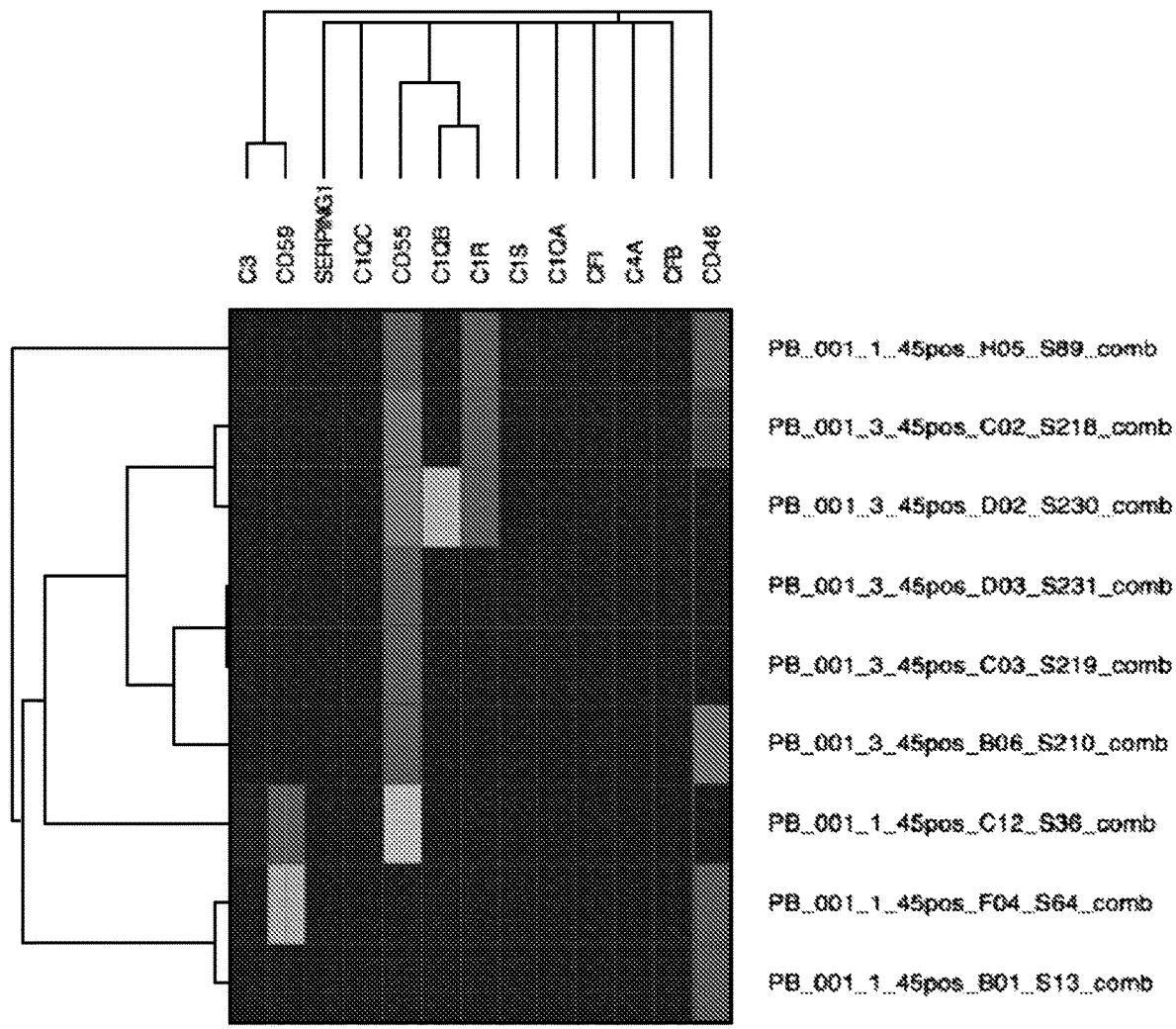
FIG. 11 depicts expression of complement genes in T cells in breast metastases in the brain. Heatmap shows the expression level of indicated genes (x-axis) in single T cells (y-axis).

Based on the discovery that microglia may be activating the classical complement pathway, Applicants looked at the T-cell population in this patient's brain metastases (FIG. 11). In the event of metastases, it has been reported that the blood-brain barrier is compromised, allowing external cells to intravasate into the brain region of the tumor. As expected, T-cells were discovered in the CD45+ population in the resected brain metastases. Applicants confirmed T-cell identity by observing differential markers and unsupervised reduction analyses. Applicants investigated these cells with respect to the complement pathway. Approximately 9 CD45+ cells have CD8+ T-cell-specific expression. T-cells demonstrate expression of complement regulatory genes CD55, CD59, and CD46. The majority of cells express CD55, and those that do not, express CD46 or CD59. CD55 directly inhibits the formation of complement convertases, and thereby directly inhibits the formation of the attack complex (which is the primary, resultant effector of the complement pathway). This strongly suggests that T-cells infiltrating the metastases have an inhibitory role in complement activation, and could be a potential source of regulation subject to modulation, specifically in metastases.

Figure 12:
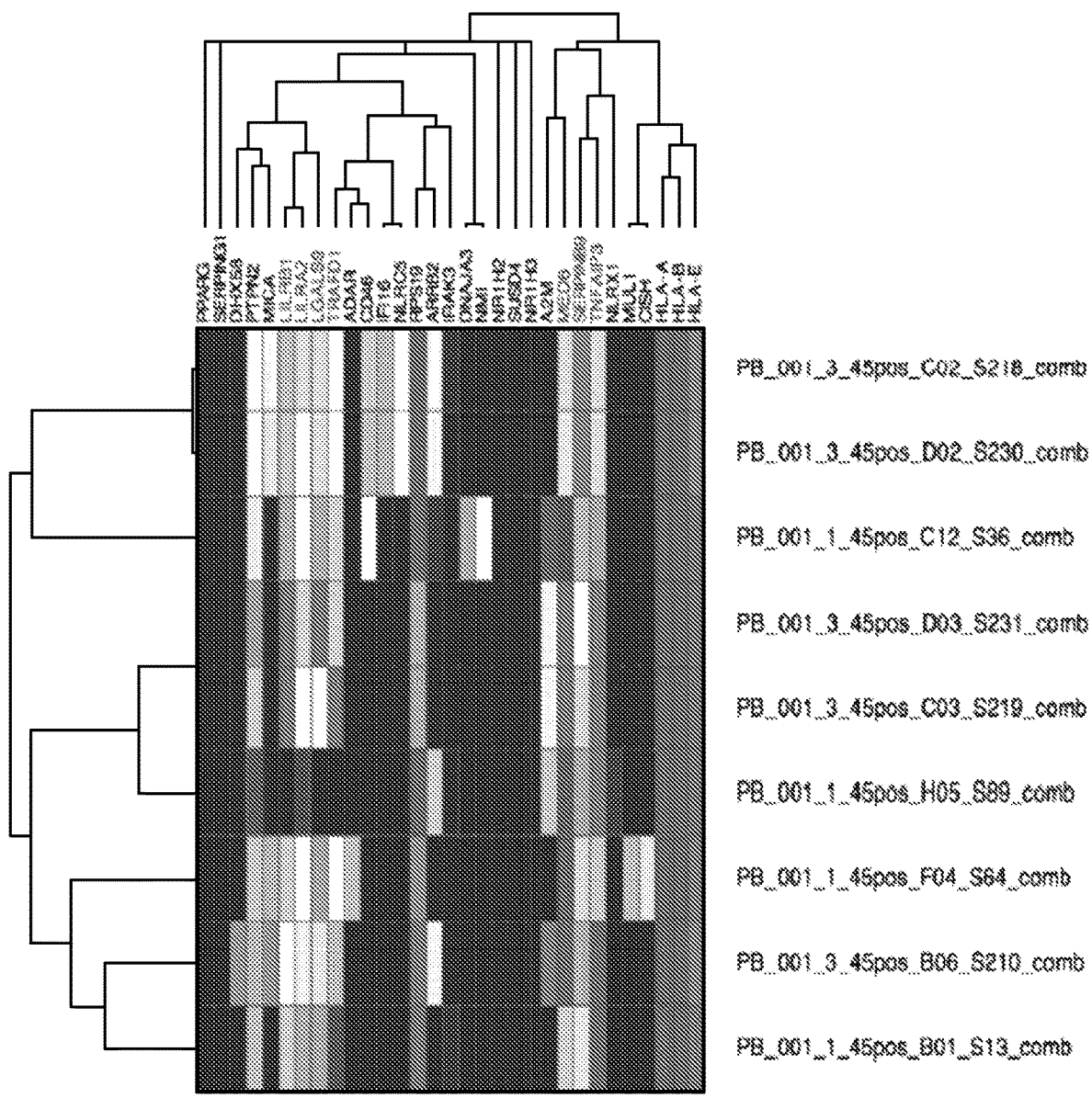
FIG. 12 depicts expression of immune regulatory genes in T cells in breast metastases in the brain. Heatmap shows the expression level of indicated genes (x-axis) in single T cells (y-axis).

Applicants also analyzed these cells according to their expression of known immune regulatory genes (GO: 0050777) (FIG. 12). The Results showed concomitant expression of MED6, SERPINB6, and TNFAIP3 which downregulate cytotoxicity in CD8+ T-cells and NK cells against tumors. Additionally, several cells (7/9) express TRAFD1 and LGALS9 which are negative feedback regulators of immune response. Finally, LILRB1/LILRA2 are expressed in a subset, which downregulate innate response and antigen binding. The data suggests that infiltrating T-cells are inhibitory to complement activation and suggests regulatory source of modulation.

Figure 13:
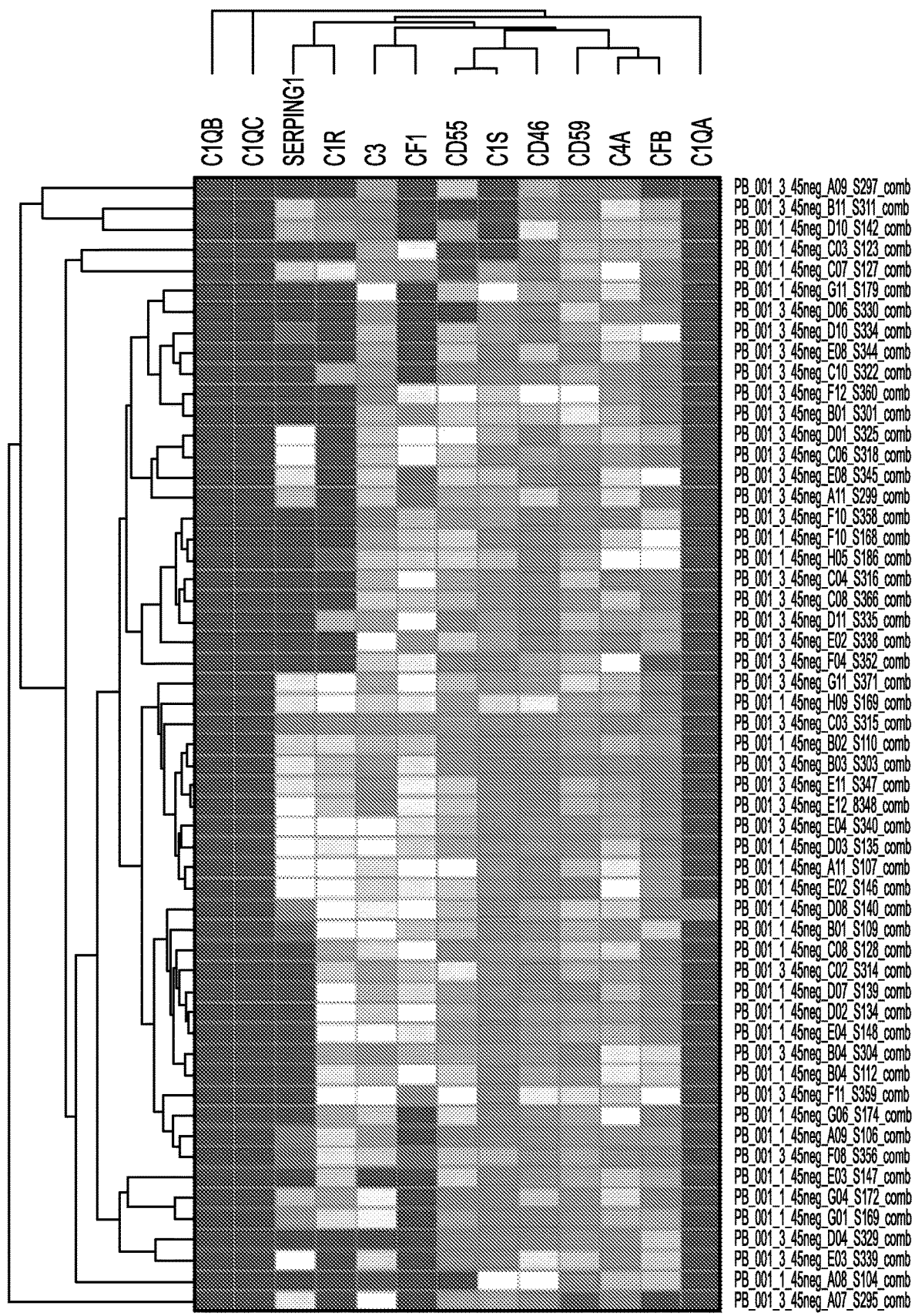
FIG. 13 depicts expression of complement genes in tumor cells in breast metastases in the brain. Heatmap shows the expression level of indicated genes (x-axis) in single tumor cells (y-axis).

Finally, Applicants analyzed this subset of complement genes in CD45− cells confirmed through variable expression analysis to qualify as tumor-derived single cells (FIG. 13). Constituent expression of CD55/CD59/CD46 was observed. The complement "defense" genes (CD46, CD55 and CD59) are expressed quite uniformly across all six cell types previously analyzed herein and this is consistent with data in other tumor types analyzed. All of the tumor cells (55/55) express CD59. CD59 prevents C9 polymerization and thereby prevents attack complex formation. C1S is co-expressed with CD59 (microglia do not express C1S). C1S is required for activation of the classical pathway. There also exists a prominent subpopulation of tumor cells that express SERPING1, which inhibits C1S production. Genes differentially expressed in SERPING1(−) cells are enriched for upregulated genes in MCF7 cells (breast cancer cell line) during estradiol treatment for the primary tumor. The patient described herein was receiving hormone treatment therapy. This suggests that SERPING1 downregulation is a consequence of estradiol. SERPING1 is a C1 inhibitor. Not being bound by a theory, if SERPING1 is downregulated, it provides an explanation for C1S upregulation in these cells and provides an upstream target for deregulation of the complement system in these tumors.

Applicants also observed that the defense genes, CD46, CD55 and CD59, are correlated with a specific pattern of cell cycle. This pattern seems to be linked to a global pattern of whether malignant tumor cells express a "chromatin" or a "mitochondria" signature. Some tumors have higher levels of a large set of chromatin-related proteins, while the other tumors have lower chromatin-related gene expression and higher expression of oxidative phosphorylation and mitochondrial genes. This is a strong effect that exists within all tumor types. The link to the complement regulatory genes is that CD46 (and to a lower extent CD55) is highly correlated with the "chromatin" arm, which would suggest that despite their membrane-based function they are also linked to the chromatin, or to cell biology of the tumor.

Applicants also analyzed genes enriched in the complement pathway according to Gene Set Enrichment Analysis (GSEA) (Table 1). In certain embodiments, these genes may be used as biomarkers for activation of complement. In certain embodiments, genes expressed on the cell surface may be used as biomarkers for determining an immune state of a tumor. The cell surface biomarkers may be used to stain tissue from a patient.

TABLE 1

Genes correlated with complement pathway in each subset (Microglia, Tumor, and T cell)

| Microglia | Tumor | T cell |
|---|---|---|
| 1 LGALS9 | 1 SLC9A3R1 | 1 UQCRC1 |
| 2 TNXB | 2 CA5B | 2 TCP1 |
| 3 DBNL | 3 POR | 3 USP15 |
| 4 PRDX1 | 4 TMED10 | 4 MED21 |
| 5 SNX2 | 5 MCFD2 | 5 CHURC1 |
| 6 SPCS1 | 6 SLC7A11 | 6 ZNF267 |
| 7 EZR | 7 PCED1B-AS1 | 7 ERO1L |
| 8 SAR1A | 8 FAM73A | 8 CARD16 |
| 9 PPP1CA | 9 DCXR | 9 PIGB |
| 10 ATP5O | 10 PTP4A1 | 10 RAB18 |
| 11 PTPN3 | 11 KPNA6 | 11 CPSF3L |
| 12 RHOG | | 12 CDK6 |
| 13 SYNJ2 | | 13 GLUD1 |
| 14 COPE | | 14 DPP3 |
| 15 MTCH2 | | 15 PPP2R1A |
| 16 PRDX6 | | 16 FKBP3 |
| 17 SLC25A3 | | 17 PPP6R3 |
| 18 PDIA6 | | 18 ERP29 |
| 19 CYP4B1 | | 19 SNRPA1 |
| 20 TPD52L2 | | 20 ARL6IP6 |
| 21 CCT2 | | 21 CCNK |
| 22 EDF1 | | 22 ATP6V1E1 |
| 23 H2AFZ | | 23 SENP1 |
| 24 STXBP2 | | 24 OAS3 |
| 25 EIF4A1 | | 25 NXF1 |
| 26 MOB1A | | 26 GID8 |
| | | 27 NSA2 |
| | | 28 SLC9A8 |
| | | 29 BRCA1 |
| | | 30 NADSYN1 |
| | | 31 METTL23 |
| | | 32 PLP2 |
| | | 33 ZDHHC4 |
| | | 34 ZFR |
| | | 35 FAM96B |
| | | 36 LAMTOR2 |
| | | 37 EIF3A |
| | | 38 XRCC5 |
| | | 39 MGST3 |
| | | 40 SKIV2L |
| | | 41 NBEAL2 |
| | | 42 PRDX4 |
| | | 43 DNAJC1 |
| | | 44 FAM105B |
| | | 45 MLLT3 |
| | | 46 GPN1 |
| | | 47 IFI35 |
| | | 48 ELOVL5 |
| | | 49 STIP1 |
| | | 50 GAPDH |
| | | 51 EIF4G1 |

Genes are selected by having correlation of 0.5+ in at least:
50% of complement genes in microglia
50% of complement genes in tumor cells
80% of complement genes in T-cells Example 4—Cell Interactions within Head and Neck Squamous Cell Carcinoma (HNSCC)

Figure 14:
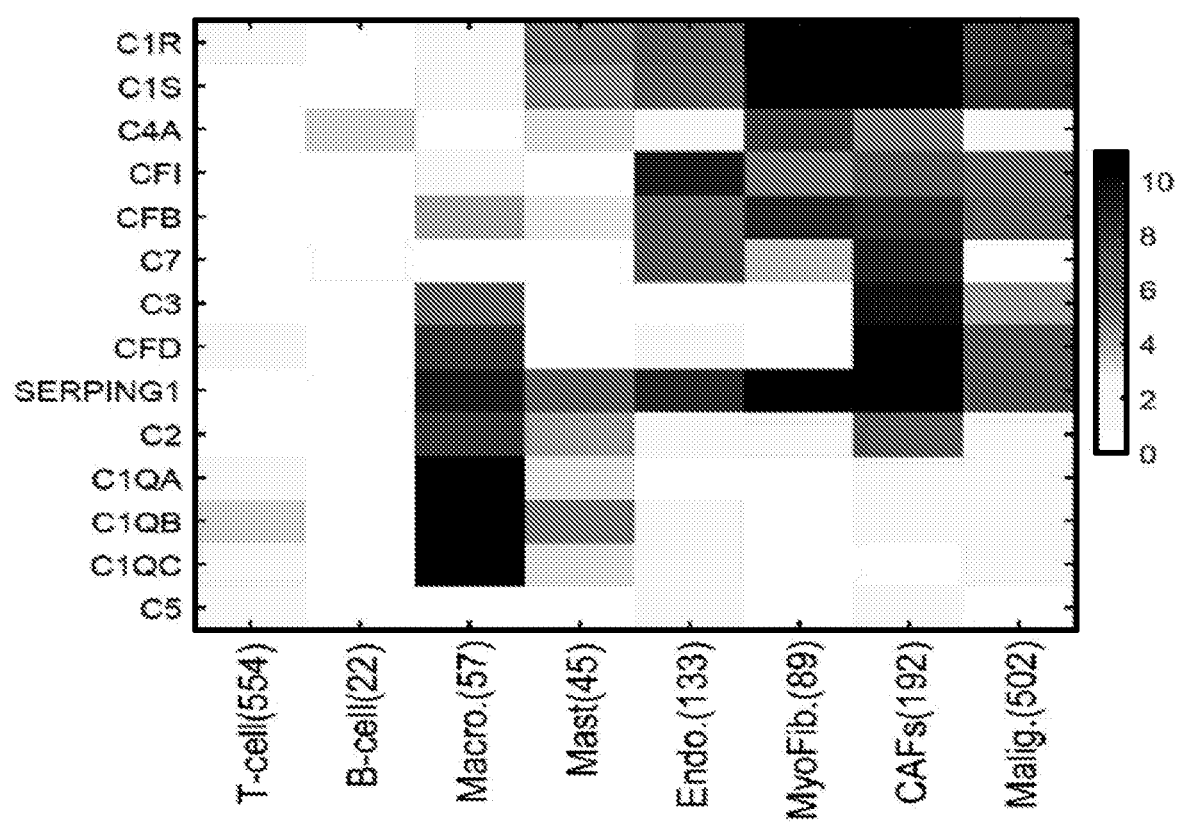
FIG. 14 depicts the expression of complement genes by CAFs and macrophages in head and neck squamous cell carcinoma (HNSCC). 2150 single cells from 10 HNSCC tumors were profiled by single cell RNA-seq and were classified into 8 cells types based on tSNE analysis, as described herein for melanoma tumors. Shown are the average expression levels (log 2(TPM+1), color coded) of complement genes (Y-axis) in cells from each of the 8 cell types, demonstrating high expression of most complement genes by fibroblasts or macrophages, consistent with the patterns found in melanoma analysis. The predicted cell types (X-axis) are T-cells, B-cells, macrophages, mast cells, endothelial cells, myofibroblasts, CAFs, and malignant HNSCC cells; the number of cells classified to each cell type is indicated in parenthesis (X-axis).

Applicants analyzed expression of complement genes by CAFs and macrophages in head and neck squamous cell carcinoma (HNSCC) (FIG. 14) (see also, Puram et al., Single-Cell Transcriptomic Analysis of Primary and Metastatic Tumor Ecosystems in Head and Neck Cancer, Cell. 2017 Dec. 14; 171(7):1611-1624.e24. doi: 10.1016/j.cell.2017.10.044. Epub 2017 Nov 30). 2150 single cells from 10 HNSCC tumors were profiled by single cell RNA-seq and were classified into 8 cells types based on tSNE analysis, as described herein for melanoma tumors. Shown are the average expression levels (log 2(TPM+1), of complement genes (Y-axis) in cells from each of the 8 cell types, demonstrating high expression of most complement genes by fibroblasts or macrophages. This observation is consistent with the patterns found in melanoma analysis. The predicted cell types (X-axis) are T-cells, B-cells, macrophages, mast cells, endothelial cells, myofibroblasts, CAFs, and malignant HNSCC cells; the number of cells classified to each cell type is indicated in parenthesis (X-axis). Consistent with the data from melanoma C1QA, B and C are highly expressed in macrophages. The analysis shows that expression signatures of complement genes is maintained across cancers. Not being bound by a theory, complement genes are a universal target for treating cancer. This result was previously not appreciated and unexpected because these signatures would not be detectable by sequencing of bulk tumors. Not being bound by a theory, analysis of tumors by single cell RNA-seq for the first time advantageously provides new targets for treating not only cancer, but any disease requiring a shift in an immune response.

Example 5—Role of Complement 3 (C3) in Cancer

Based on the associations discovered between tumors and complement pathways, Applicants sought to understand the role of complement in cancer, specifically C3. Not being bound by a theory, therapeutic strategies to treat cancer by targeting C3 can be developed by understanding the role played by C3 in tumors. Applicants tested the role of C3 expression in wildtype mice and C3 KO mice.

Figure 15:
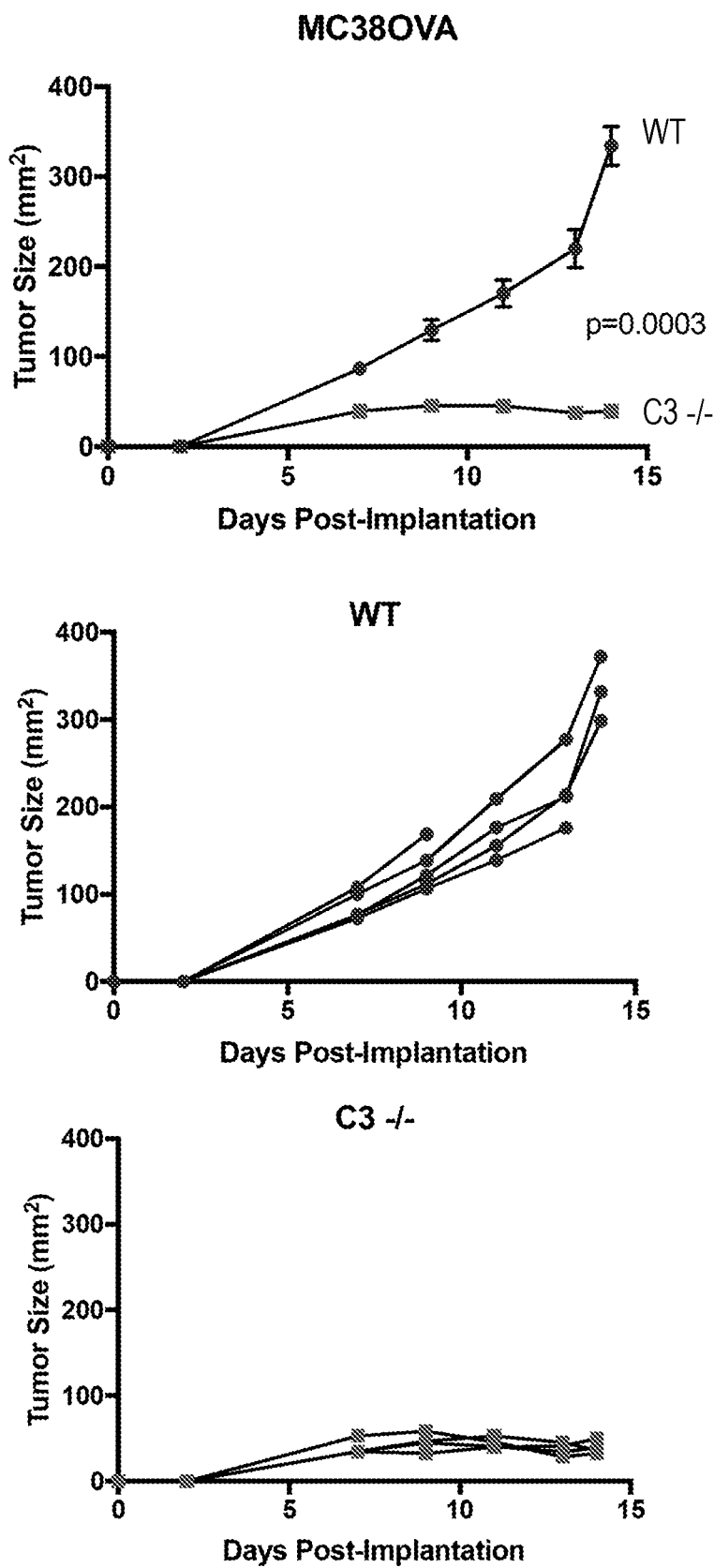
FIG. 15 illustrates tumor growth in C3 knockout (KO) and wildtype mice. C3 KO mice bearing MC38 tumors that express Ova (MCA38-Ova) shows increased tumor growth control as compared to wildtype mice.

MC380VA were injected ($5 \times 10^5$ in 100 uL volume) into five WT B6 females and four C3 −/− females (all 7-8 weeks old). Two WT mice were euthanized on Days 9 and 13 because of large ulcerations. All other tumors were harvested on Day 14 (FIG. 15). Tumor size was decreased in C3 −/− mice.

Figure 21:
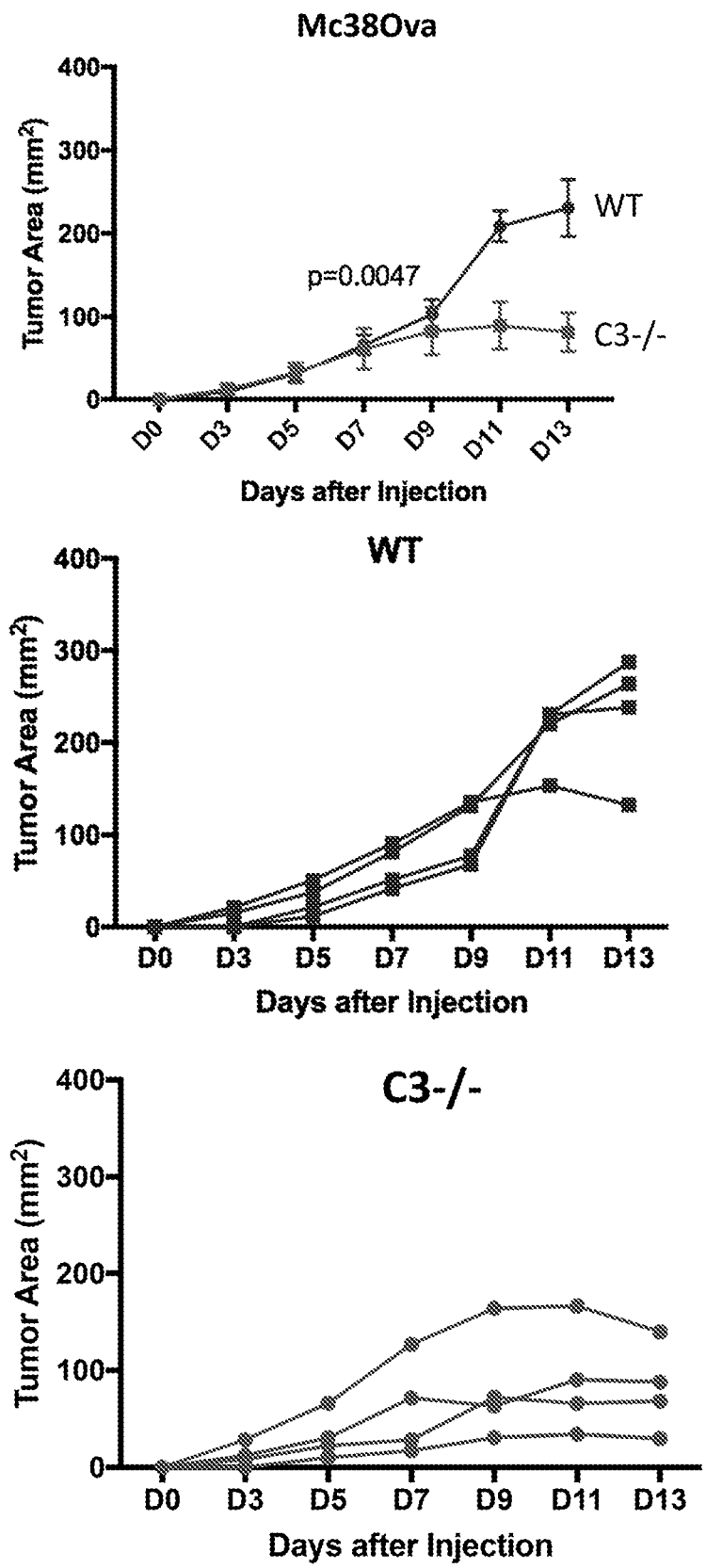
FIG. 21 illustrates tumor growth in C3 knockout (KO) and wildtype mice using littermate controls. C3 KO mice bearing MC38 tumors that express Ova (MCA38-Ova) shows increased tumor growth control as compared to wildtype mice.

The results were reproduced in C3 knockout (KO) and wildtype mice using littermate controls. C3 KO mice bearing MC38 tumors that express Ova (MCA38-Ova) shows increased tumor growth control as compared to wildtype mice (FIG. 21). MC380VA were injected ($5 \times 10^5$ in 100 uL volume) into four WT B6 females, four C3 −/−, and 2 heterozygous females (all 7-8 weeks old). All tumors were harvested on Day 14.

Figure 18:
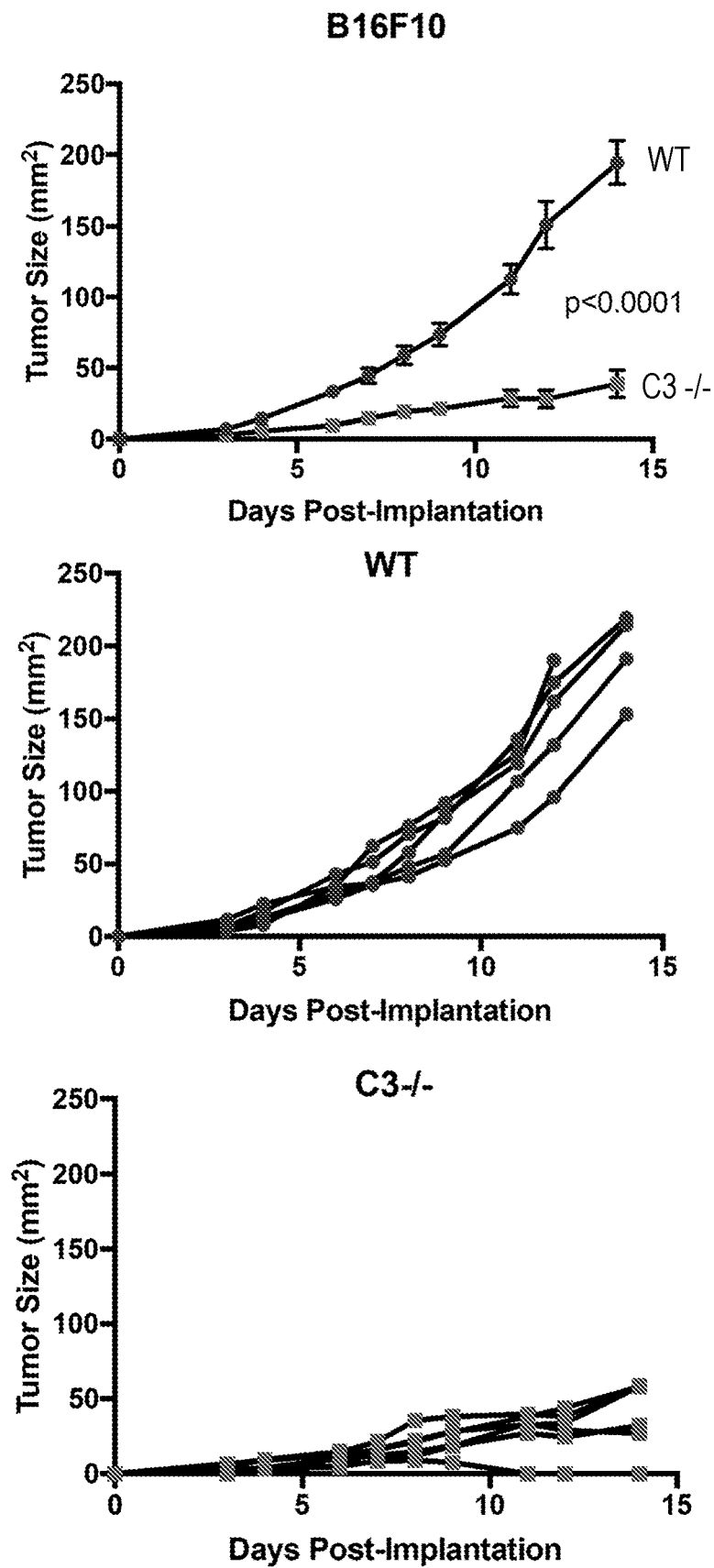
FIG. 18 illustrates tumor growth in C3 knockout (KO) and wildtype mice. C3 KO mice bearing B16F10 tumors shows increased tumor growth control as compared to wildtype mice.

Applicants also tested the role of C3 expression in wildtype mice and C3 KO mice using a B16F10 model and showed that tumor size was decreased in C3 −/− mice (FIG. 18). B16F10 were injected ($5 \times 10^5$ in 100 uL volume) into five WT B6 females and six C3 −/− females Tumors were harvested on Day 14.

Unexpectedly, C3 KO resulted in strong inhibition of tumor growth in the different cancer models. Thus, Applicants hypothesized that C3 may suppress a tumor immune response.

Figure 16:
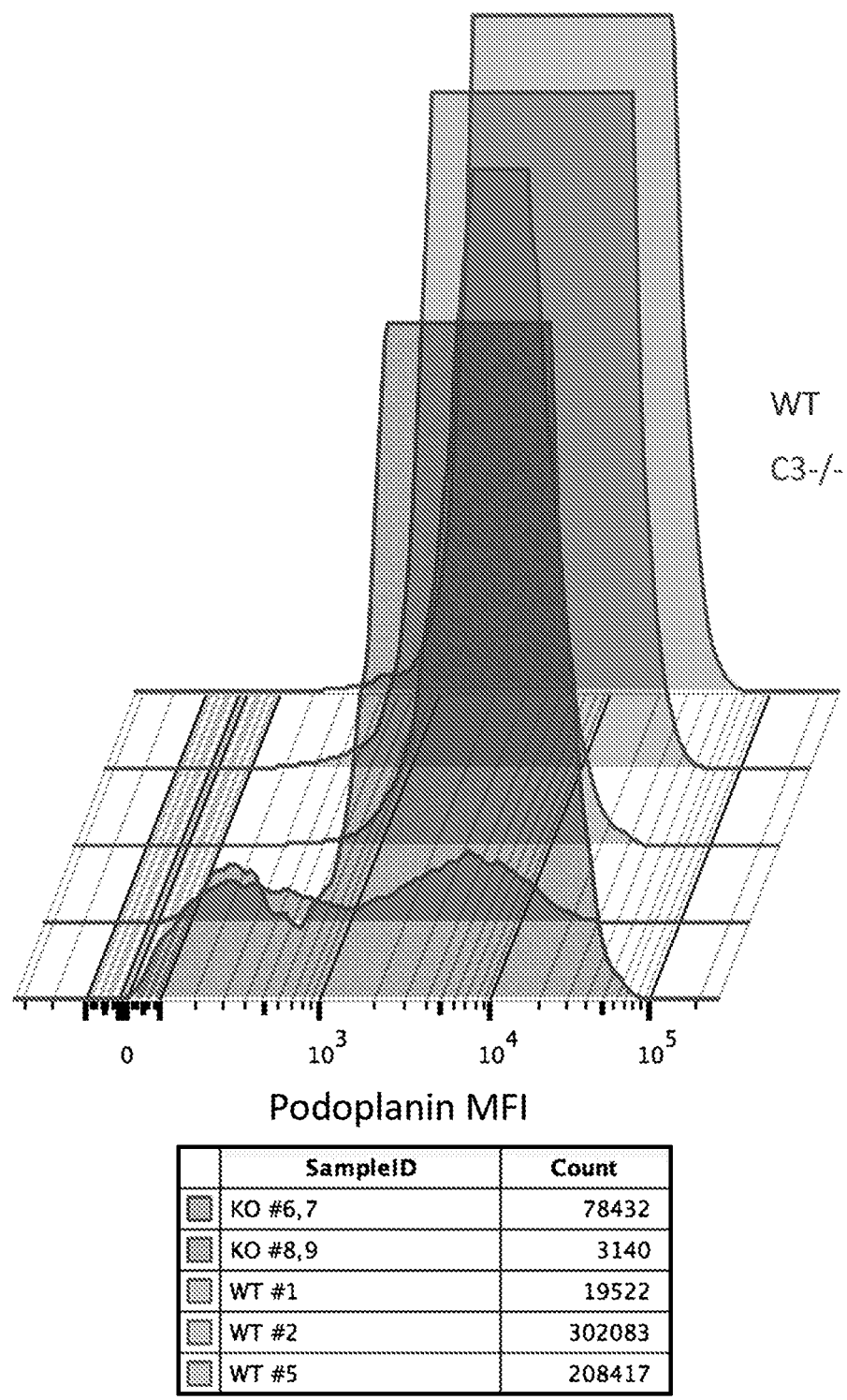
FIG. 16 illustrates decreased expression of Podoplanin (Pdpn) in CAF's in Mc38Ova C3−/− mice.
Figure 25:
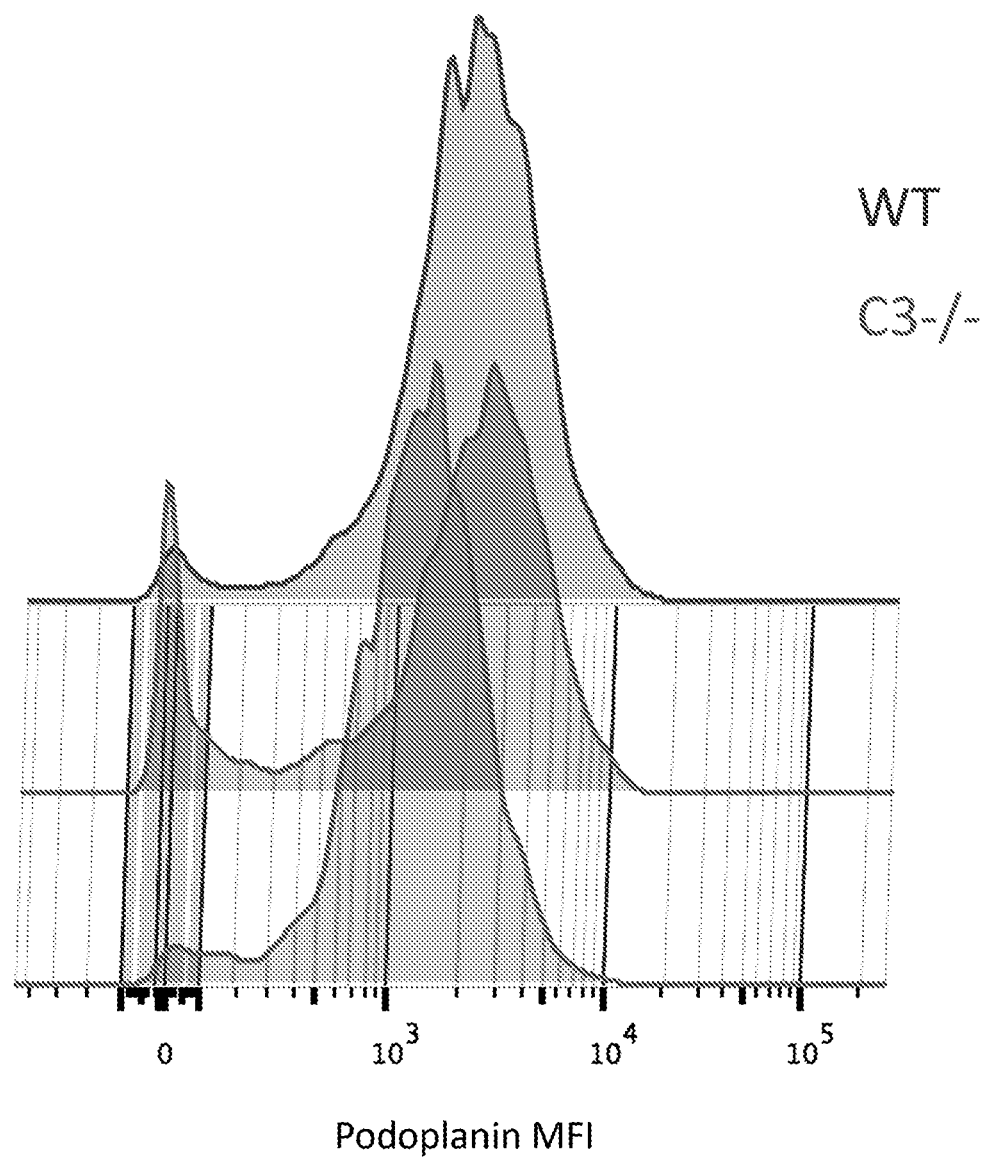
FIG. 25 illustrates reduced CAF expression of Podoplanin in Mc38Ova C3−/− mice.

PDPN has been studied extensively in the cancer field. It is a specific lymphatic vessel marker, and since lymphangiogenesis levels are correlated with poor prognosis in cancer patients, it can be used as a diagnostic marker (Astarita, J L, et al., (2012). "Podoplanin: emerging functions in development, the immune system, and cancer". Frontiers in Immunology. 3: 283). It is often upregulated in certain types of cancer, including several types of squamous cell carcinomas, malignant mesothelioma and brain tumors (Astarita, et al., 2012). Moreover, it can be upregulated by cancer-associated fibroblasts (CAFs) in the tumor stroma, (Astarita, et al., 2012; and Kitano, H; et al., (2010). "Podoplanin expression in cancerous stroma induces lymphangiogenesis and predicts lymphatic spread and patient survival". Archives of pathology & laboratory medicine. 134 (10): 1520-7) where it has been associated with poor prognosis (Chuang, W Y, et al., (2014). "Concordant podoplanin expression in cancer-associated fibroblasts and tumor cells is an adverse prognostic factor in esophageal squamous cell carcinoma". International Journal of Clinical and Experimental Pathology. 7 (8): 4847-56). In squamous cell carcinomas, PDPN is believed to play a role in the cancer cell invasiveness by controlling invadopodia, and thus mediating efficient ECM degradation (Martin-Villar, E, et al., (2015). "Podoplanin mediates ECM degradation by squamous carcinoma cells through control of invadopodia stability". Oncogene. 34 (34): 4531-44). Applicants determined Pdpn expression in WT and C3 −/− mice. In WT mice all CAFs express Pdpn and in C3−/− mice a small percentage does not (FIG. 16). CAFs were defined as CD45− PDGFRa+CD31− cells coming from TIL isolation. A similar experiment performed in littermate control mice also showed reduced CAF expression of Podoplanin in C3−/− mice (FIG. 25). Thus, there is decreased expression of podoplanin in CAF's in C3−/− mice.

Figure 17:
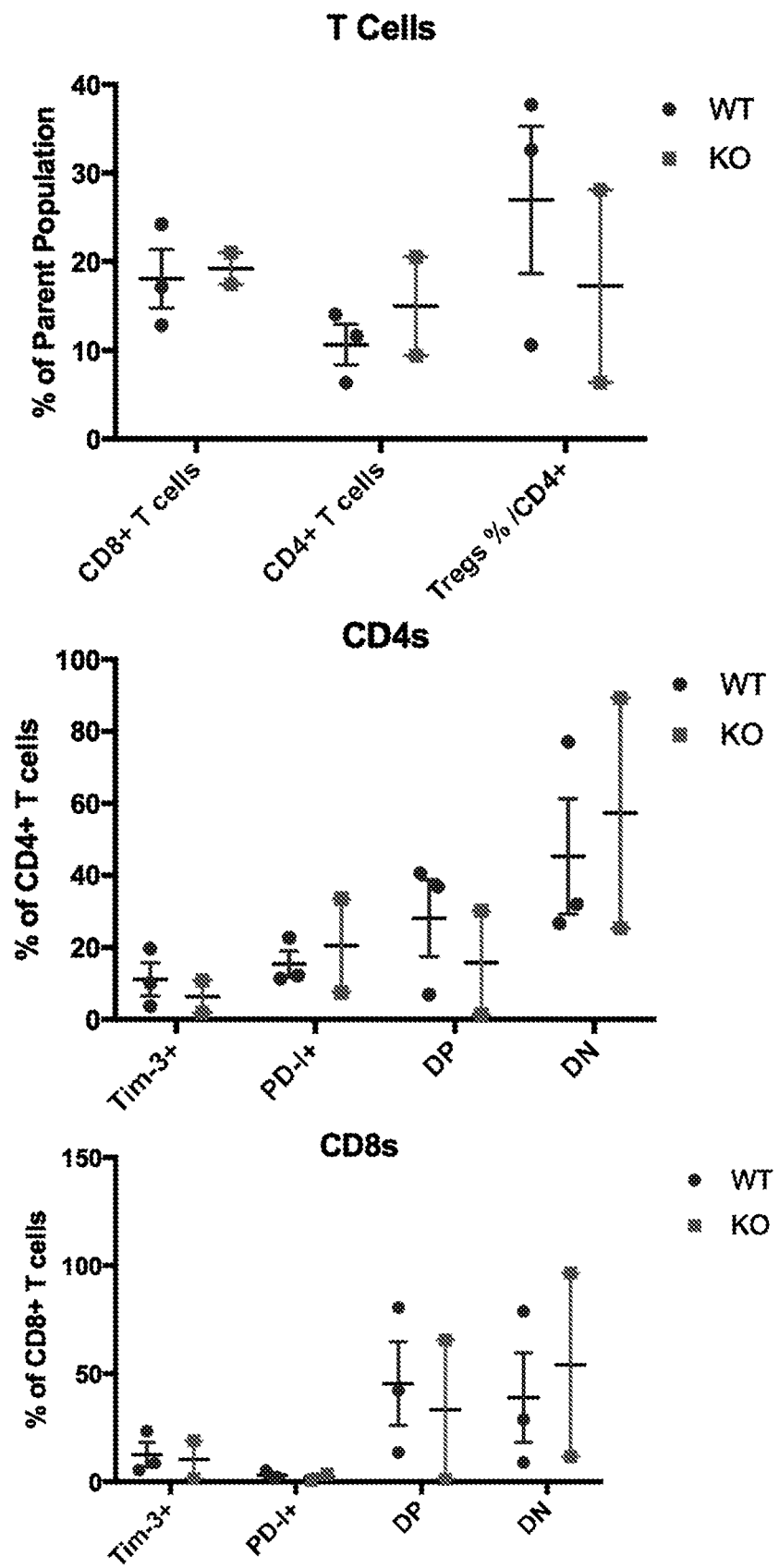
FIG. 17 illustrates the analysis of T cells in Mc38Ova WT and C3−/− mice.
Figure 19:
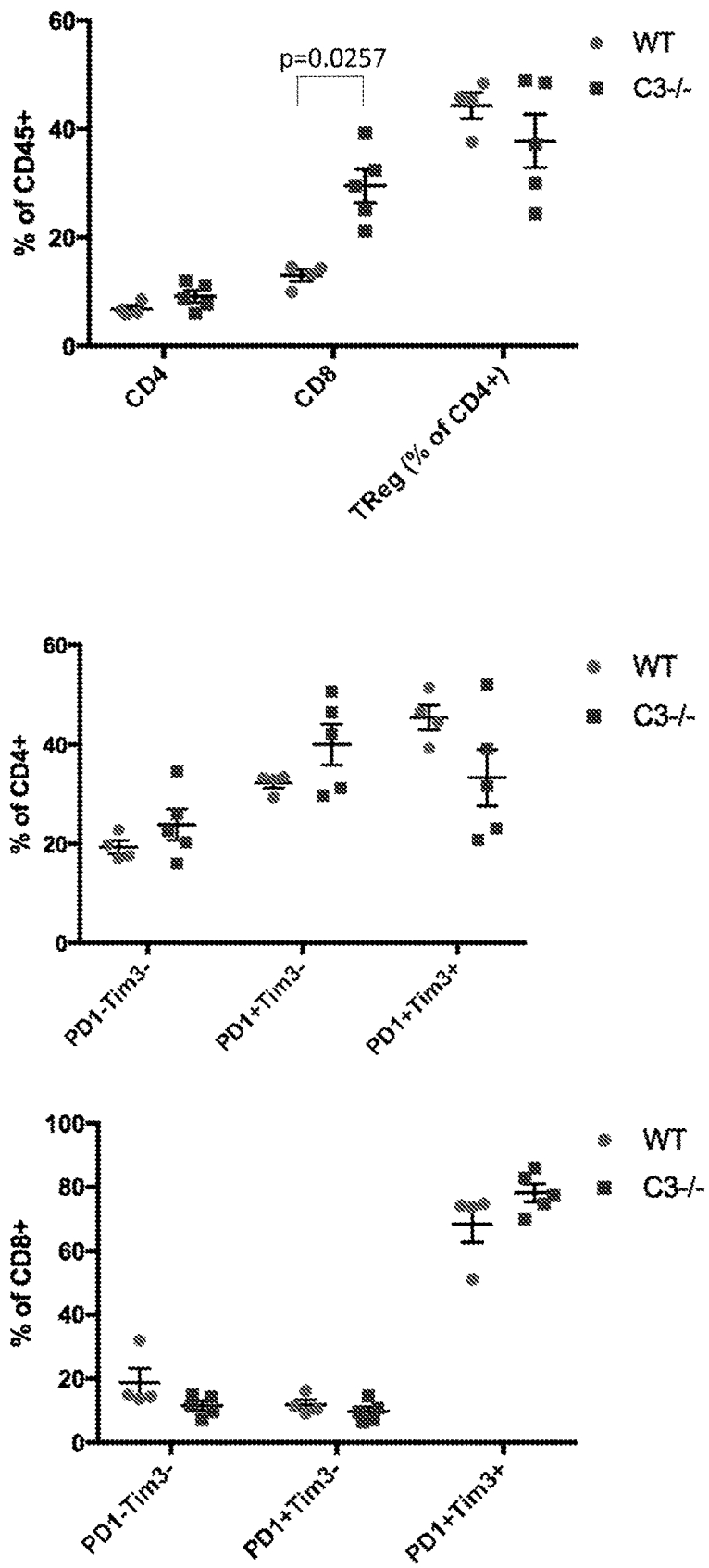
FIG. 19 illustrates the analysis of T cells in B16F10 WT and C3−/− mice.
Figure 20:
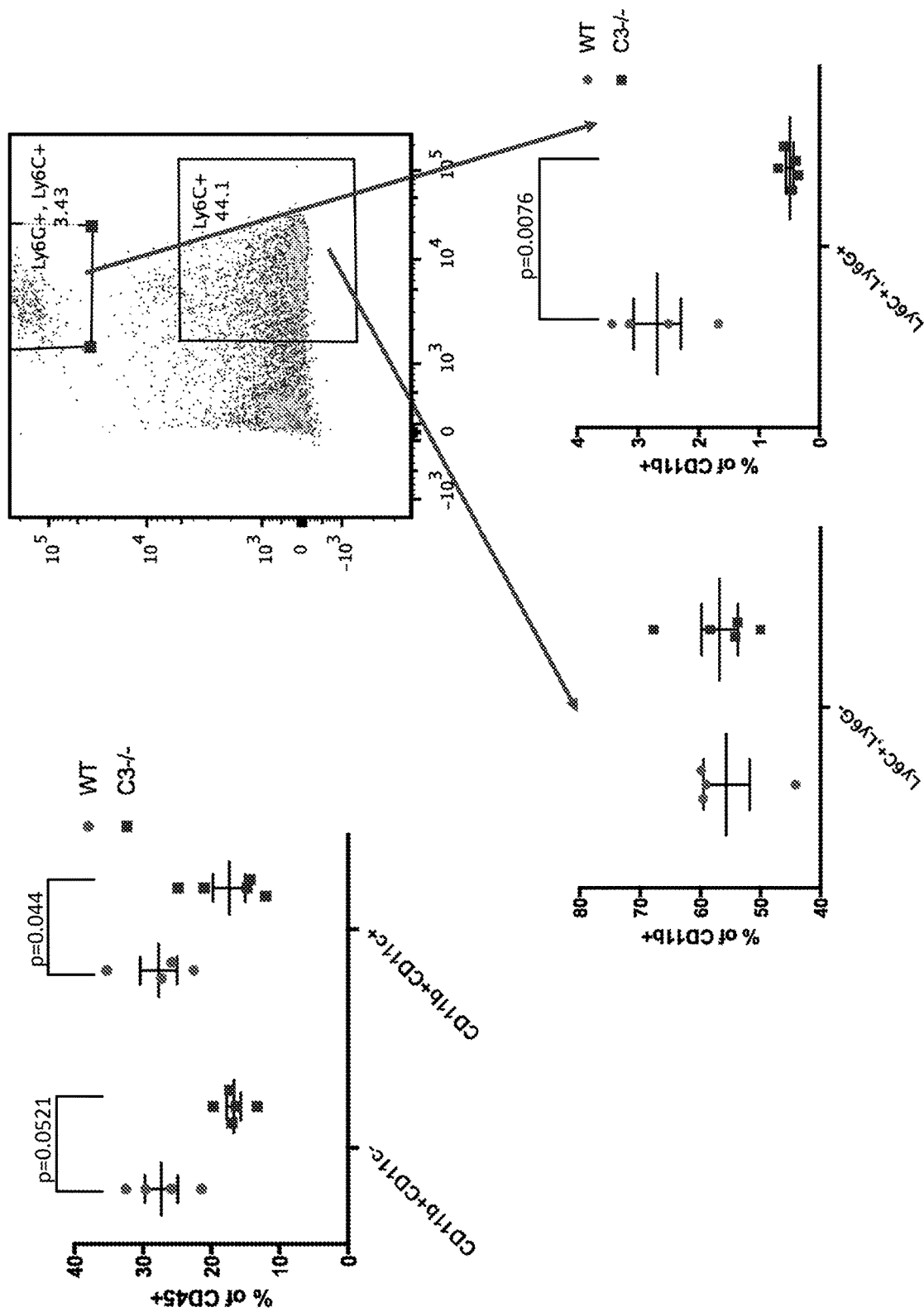
FIG. 20 illustrates the analysis of myeloid cells in B16F10 WT and C3−/− mice.
Figure 22:
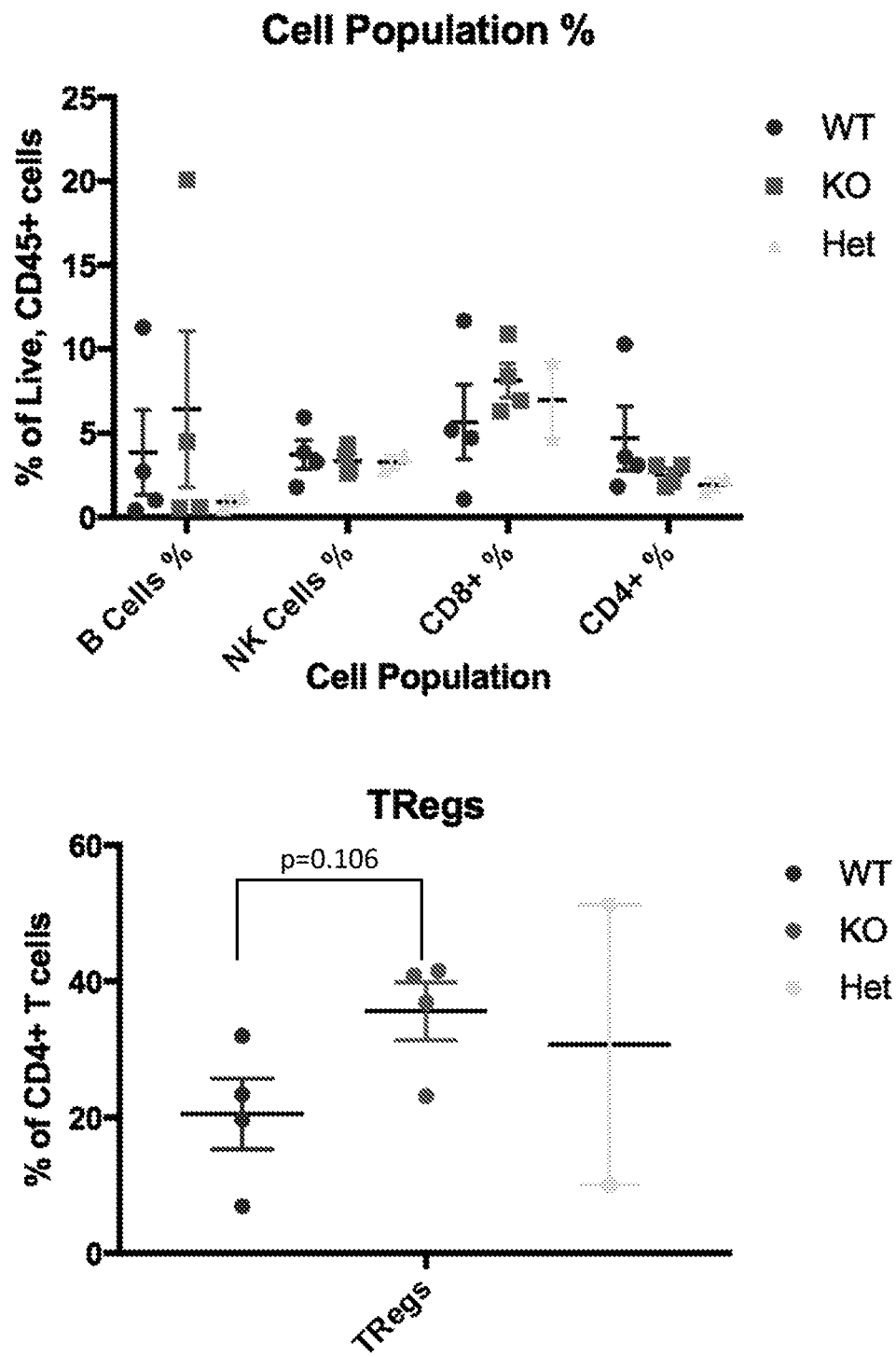
FIG. 22 illustrates the analysis of immune cells in Mc38Ova WT, C3−/− and heterozygote mice.

Applicants, next determined percentage of cell types in WT and C3−/− mice (FIGS. 17, 19, 20 and 22). FIG. 17 illustrates an experiment analyzing T cells in Mc38Ova WT and C3−/− mice. FIG. 19 illustrates an experiment analyzing T cells in B16F10 WT and C3−/− mice. The results show that there is more CD8+ T cell infiltration in C3−/− tumors. FIG. 20 illustrates an experiment analyzing myeloid cells in B16F10 WT and C3−/− mice. The results show that there are decreased myeloid cells in TME in C3−/− tumors. FIG. 22 illustrates an experiment further analyzing B cells, NK cells, CD8+ cells, CD4+ cells and CD4+ Tregs in Mc38Ova WT, C3−/− and heterozygote mice. The results show that there are increased Tregs in in Mc38Ova C3−/− mice.

Figure 23:
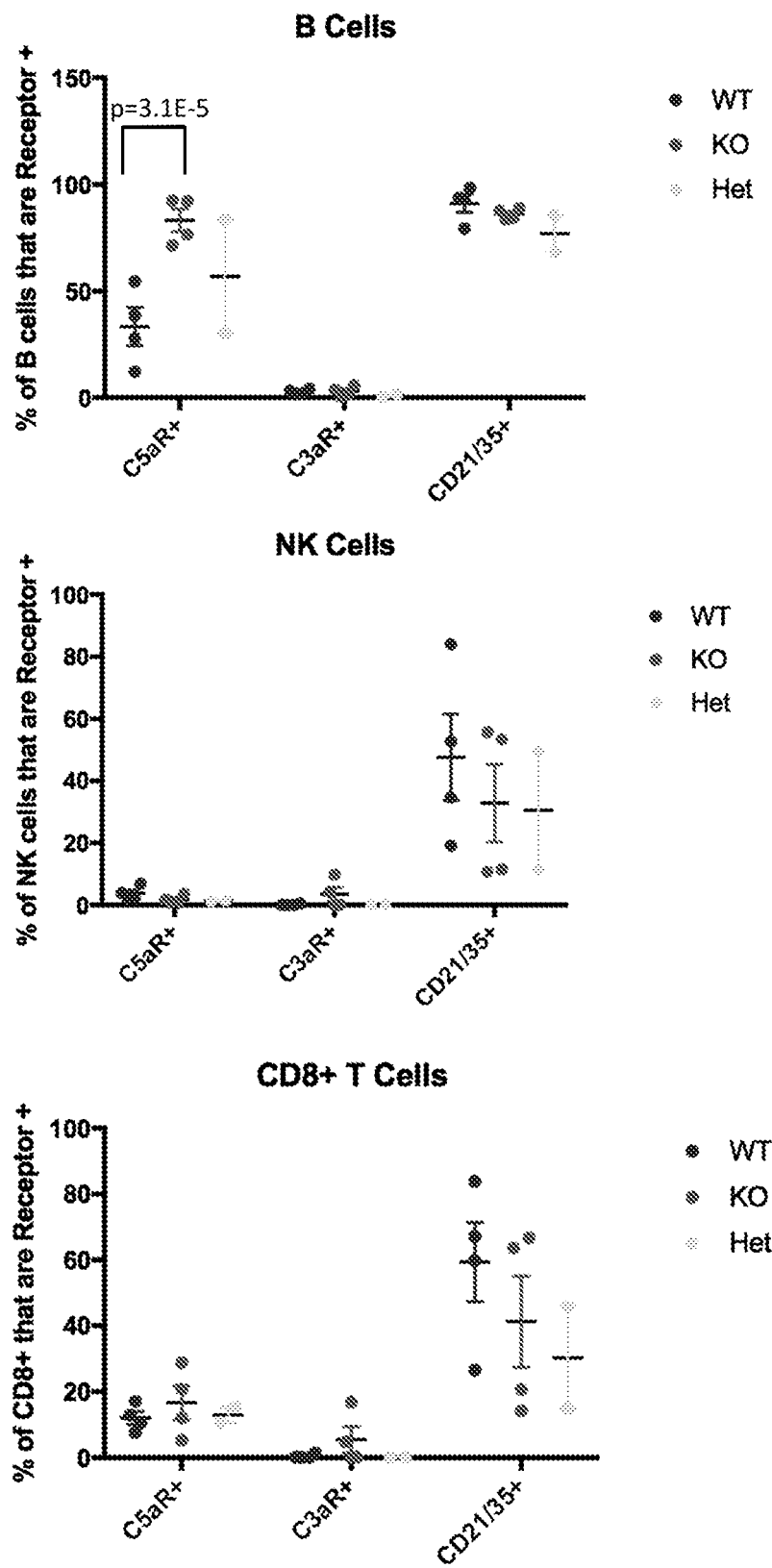
FIG. 23 illustrates complement receptor expression in Mc38Ova WT, C3−/− and heterozygote mice.
Figure 24:
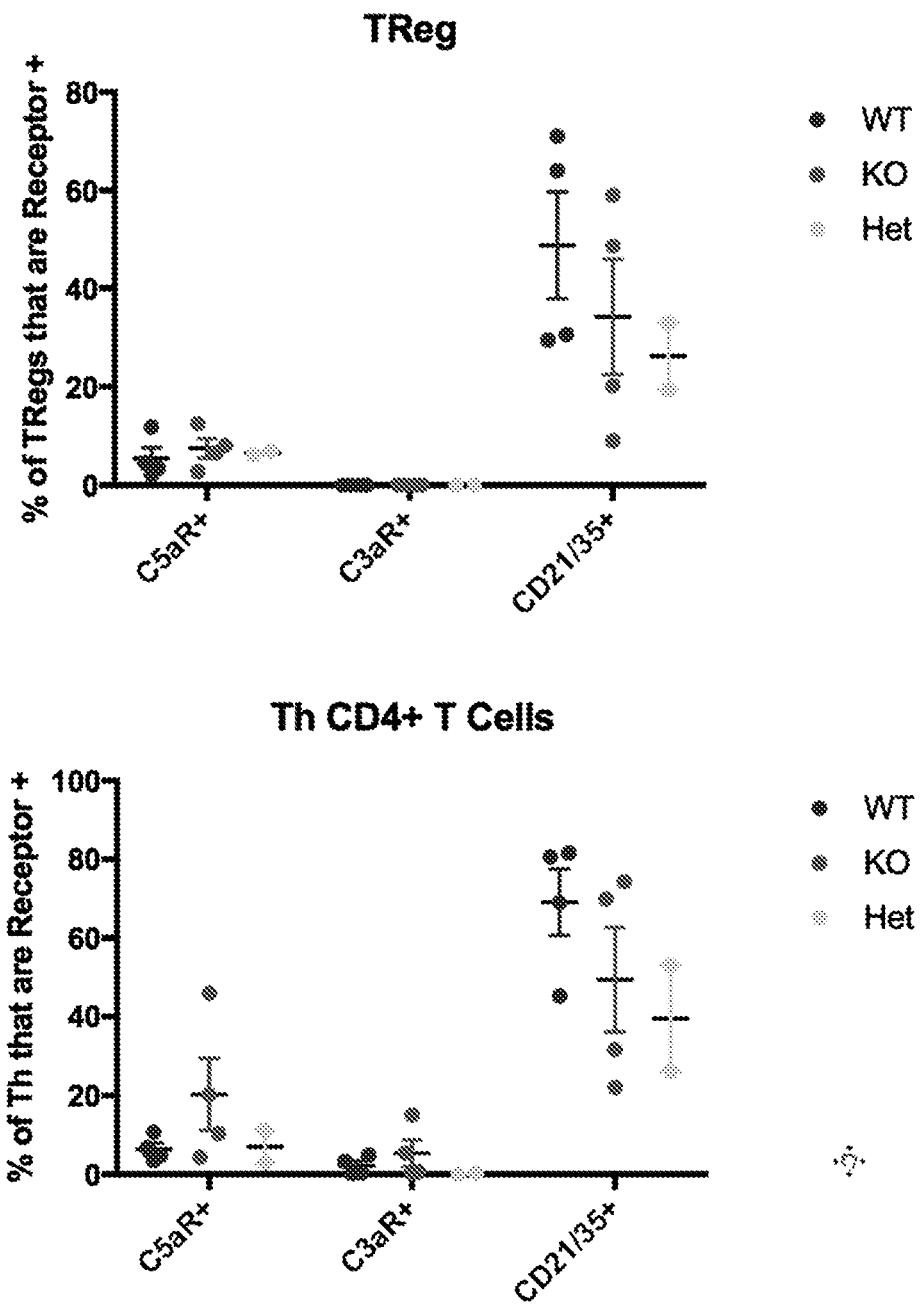
FIG. 24 illustrates complement receptor expression in TRegs and Th CD4+ T cells from Mc38Ova WT, C3−/− and heterozygote mice.
Figure 26:
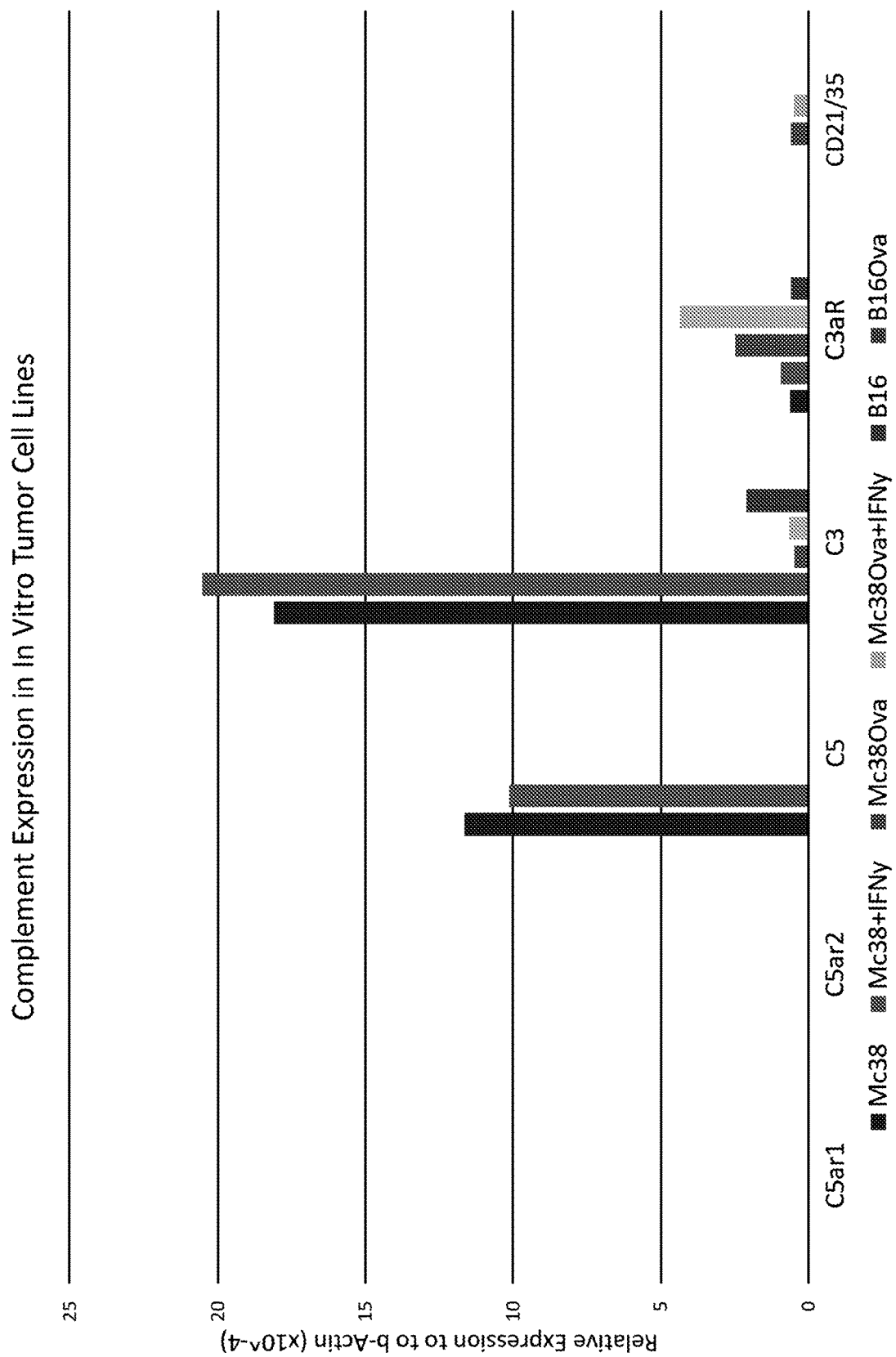
FIG. 26 illustrates that tumor cell lines express complement components in vitro.

Applicants, next determined complement receptor expression in immune cells (B cells, NK cells, CD8+ T cells, Th CD4+ T cells and TRegs) using Mc38Ova WT, C3−/− and heterozygote mice (FIGS. 23 and 24). CD35/CD21 was expressed by all cell types. C5aR was differentially on B cells between wt and C3−/− mice. Furthermore, it has been shown that either upon binding, the complement receptor is internalized, or there are intracellular complement receptors. Thus, internal complement may be responsible for the tumor control phenotype seen in C3 −/− mice. Consistant with the examples above, previous human studies showed that intracellular complement activation is not T cell specific and observed intracellular activated C3 in fibroblasts (see, e.g., Liszewski et al., intracellular complement activation sustains T cell homeostasis and mediates effector differentiation, Immunity. 2013 Dec. 12; 39(6):1143-57. doi: 10.1016/j.immuni.2013.10.018. Epub 2013 Dec 5). Additionally, Applicants show that tumor cell lines express complement components in vitro (FIG. 26).

Applicants performed single cell RNA sequencing analysis on cells obtained from the B16 melanoma model in wild type (WT) and C3 knockout (KO) mice. Single cell RNA-seq was performed using the 10× system (10× Genomics, Inc., Pleasanton, CA).

Applicants observed 14 cell subsets on all pooled cells, 10 subsets on CD45+ sorted cells and 8 subsets on melanoma cells.

Figure 27:
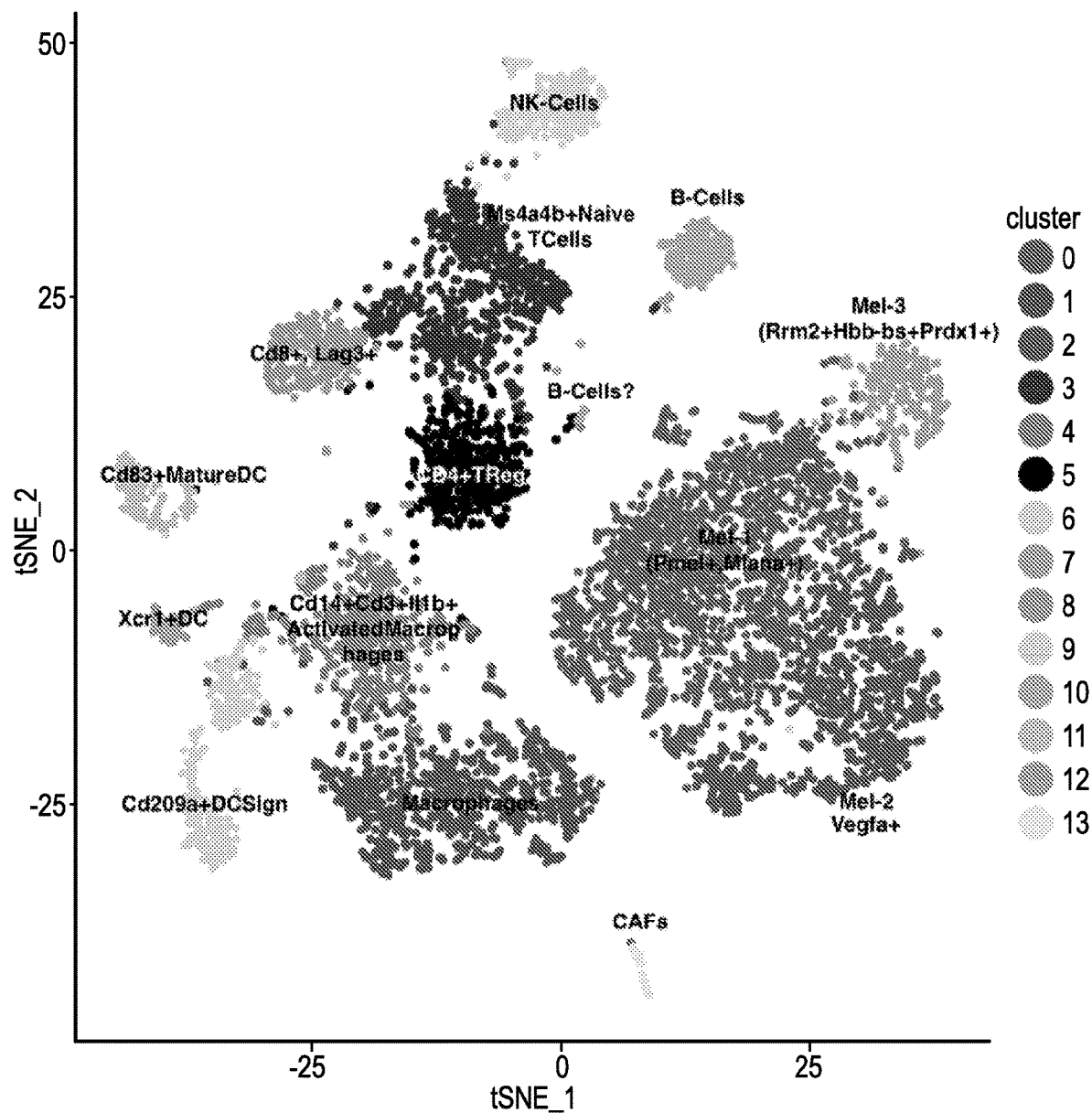
FIG. 27 illustrates tSNE analysis of sorted and unsorted combined cells from B16 melanoma mice.
Figure 28:
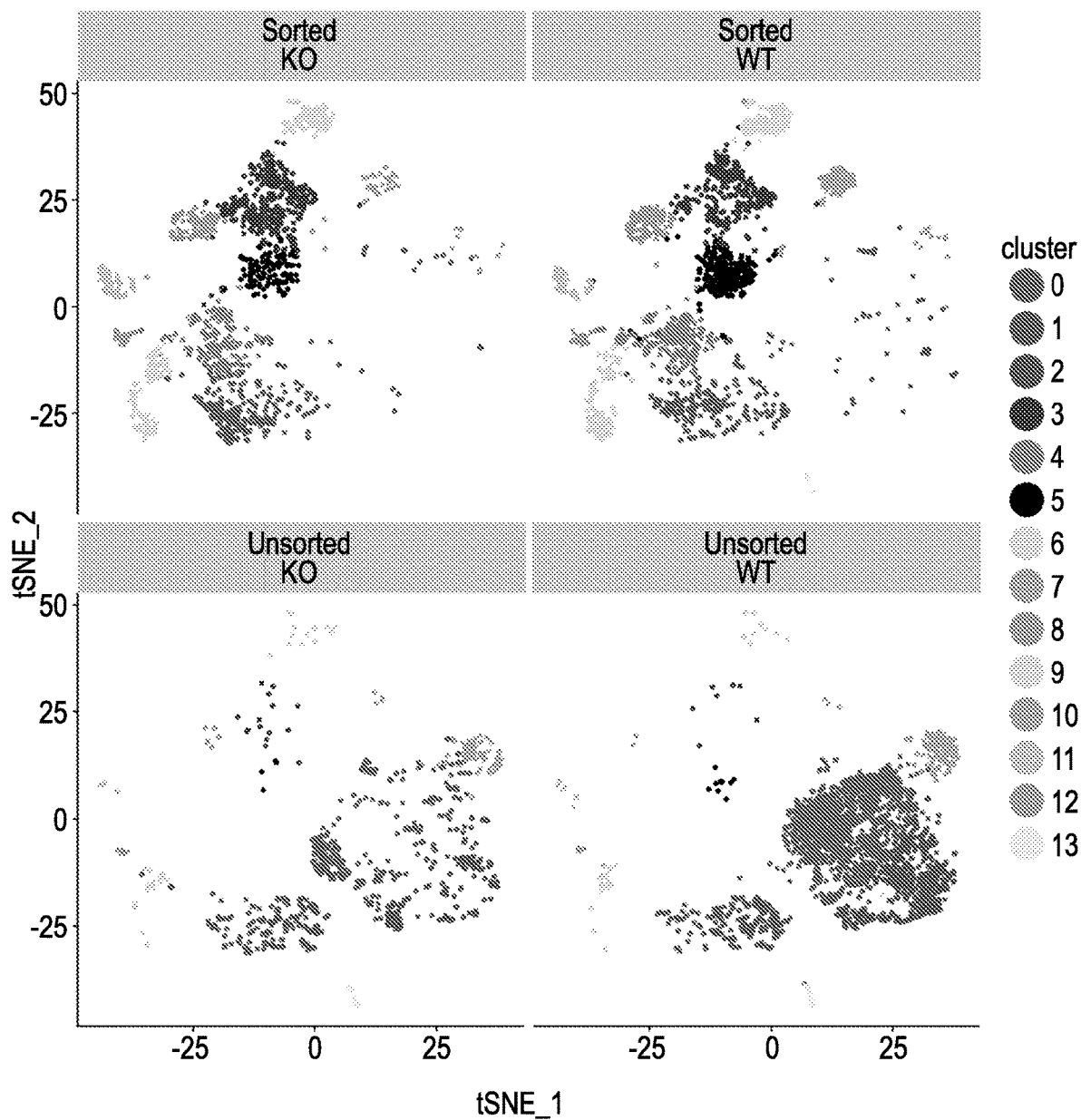
FIG. 28 illustrates tSNE analysis of sorted and unsorted cells from B16 melanoma in wild type and C3 KO mice.
Figure 29:
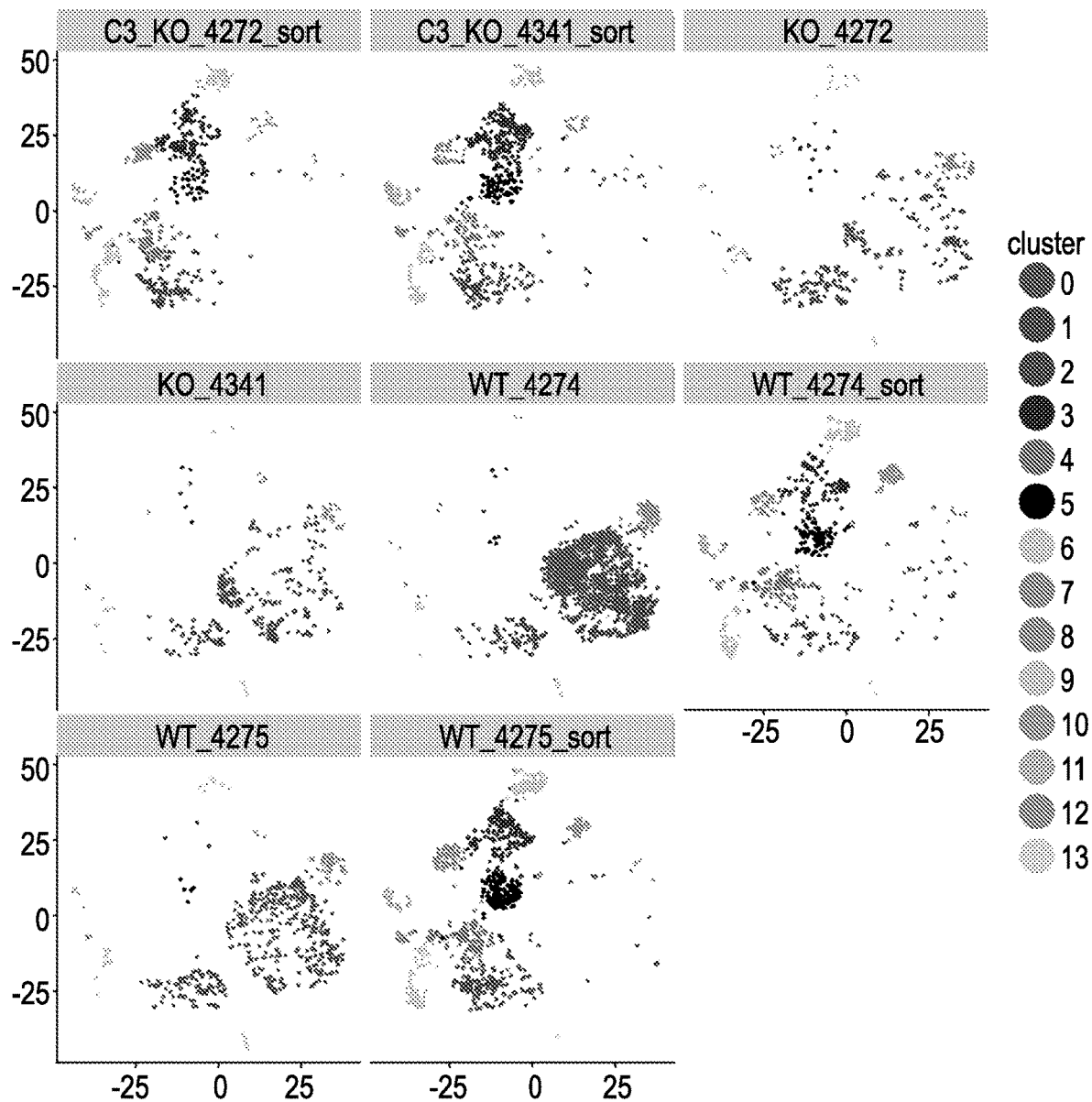
FIG. 29 illustrates tSNE analysis of sorted and unsorted cells from B16 melanoma in wild type and C3 KO mice.

Applicants observed that CAFs comprised only 1.74% of unsorted cells (n=60) (FIG. 27). Applicants observed that there were more tumor cells in WT mice as compared to C3 KO mice (FIGS. 28 and 29).

Figure 30:
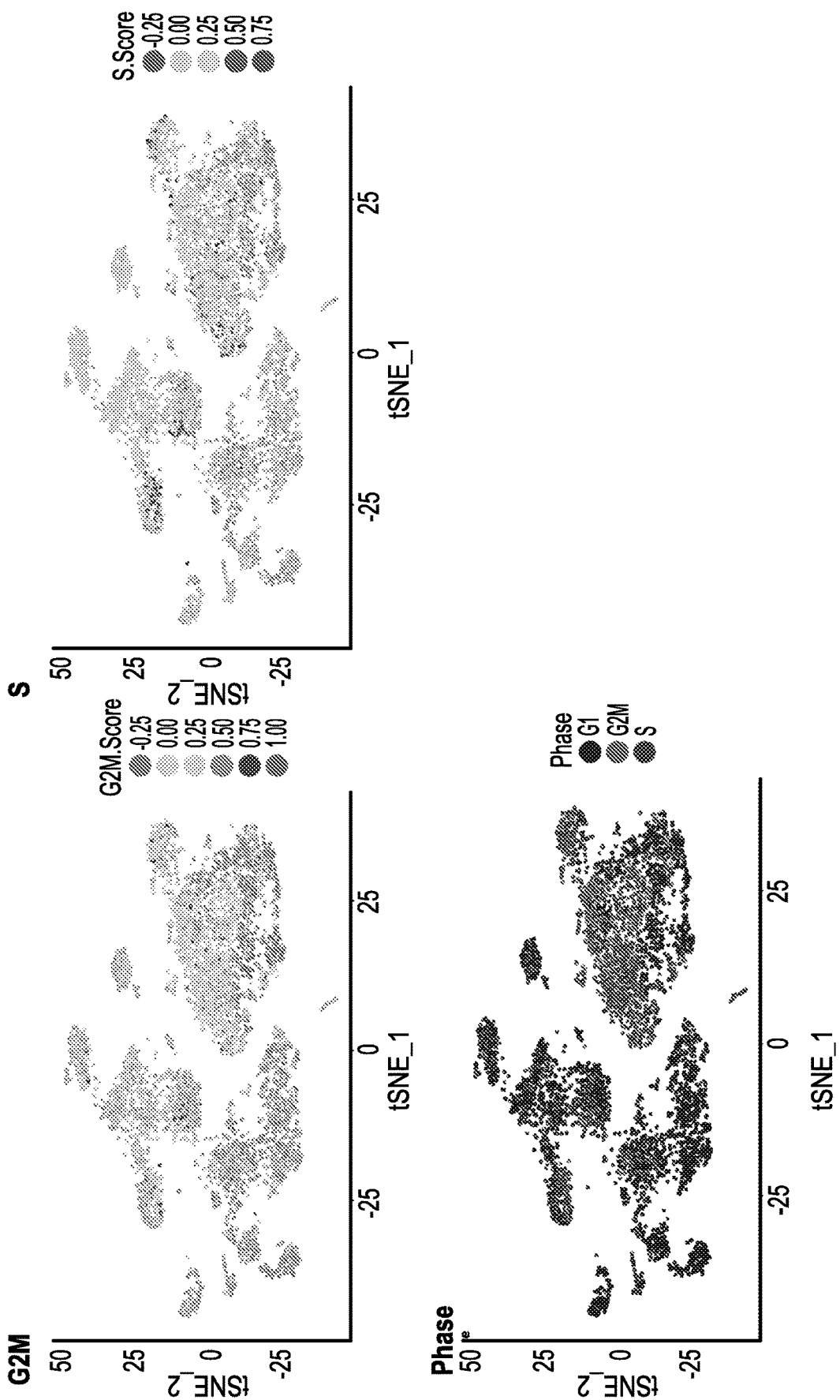
FIG. 30 illustrates expression of cell-cycle signatures on the tSNE analysis in FIG. 27.
Figure 35:
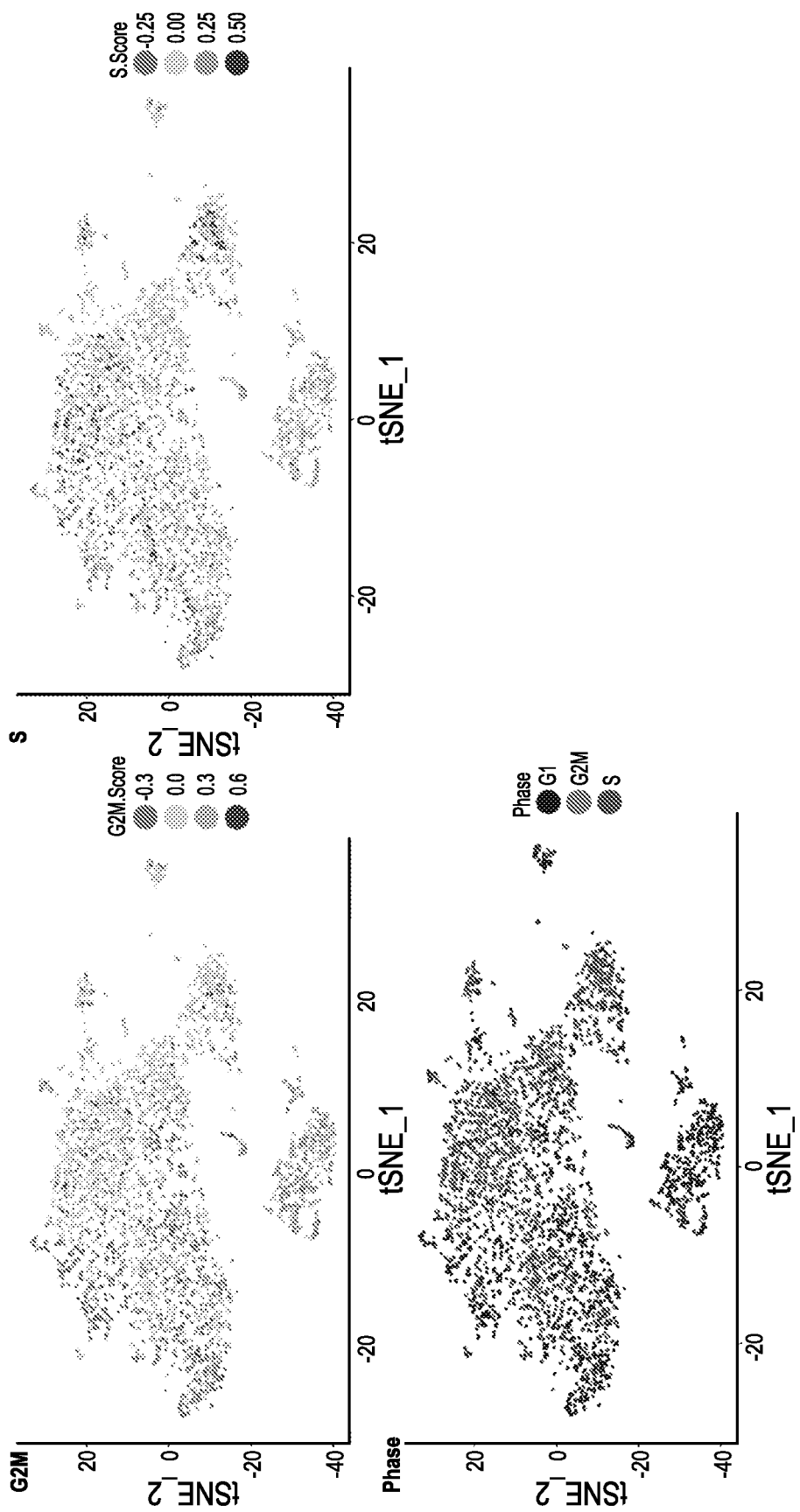
FIG. 35 illustrates expression of cell-cycle signatures on the tSNE analysis in FIG. 33.
Figure 38:
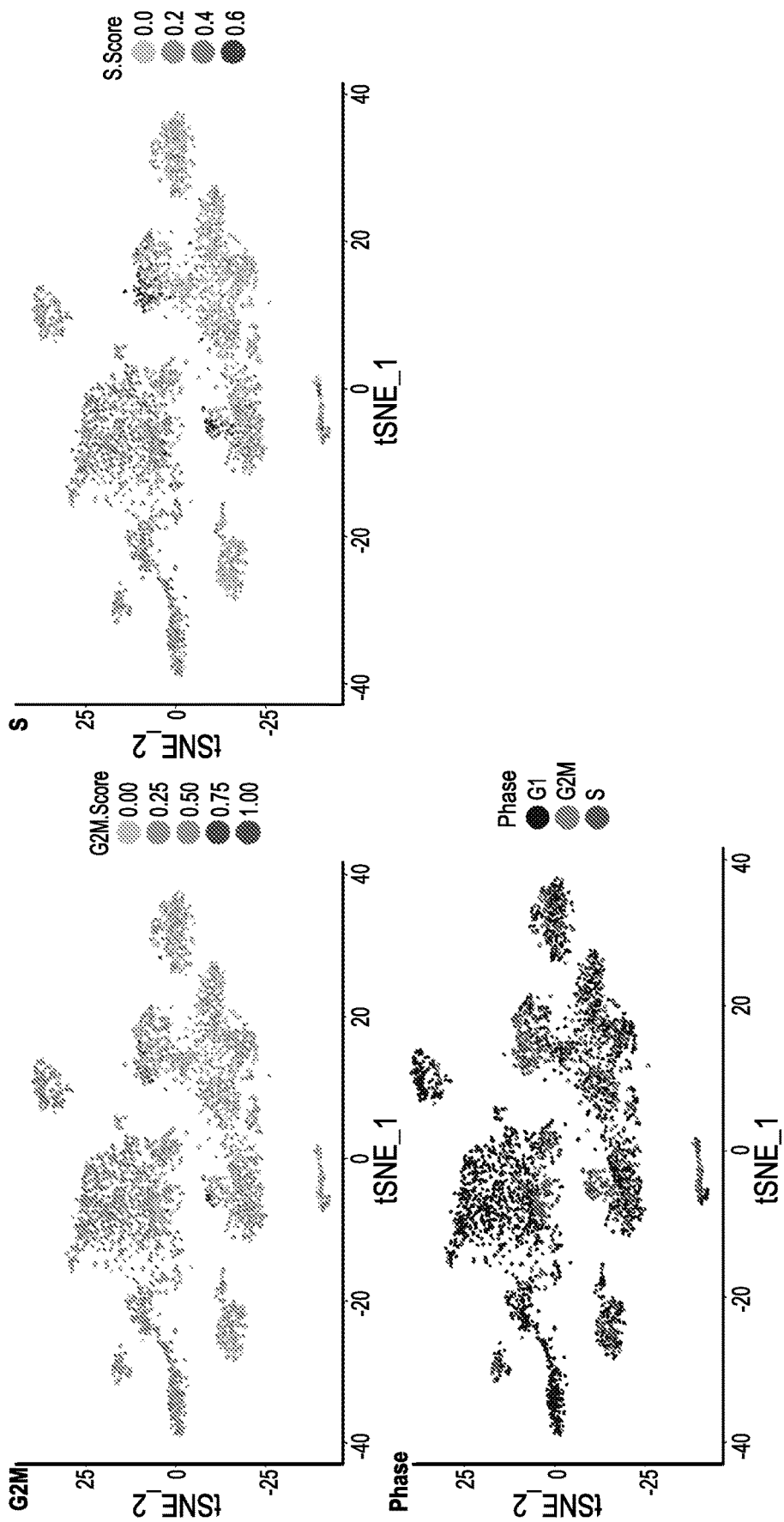
FIG. 38 illustrates expression of cell-cycle signatures on the tSNE analysis in FIG. 37.

Applicants also observed that melanoma cells are cycling in both conditions (WT and C3 KO) (FIGS. 30, 35 and 38).

Figure 31:
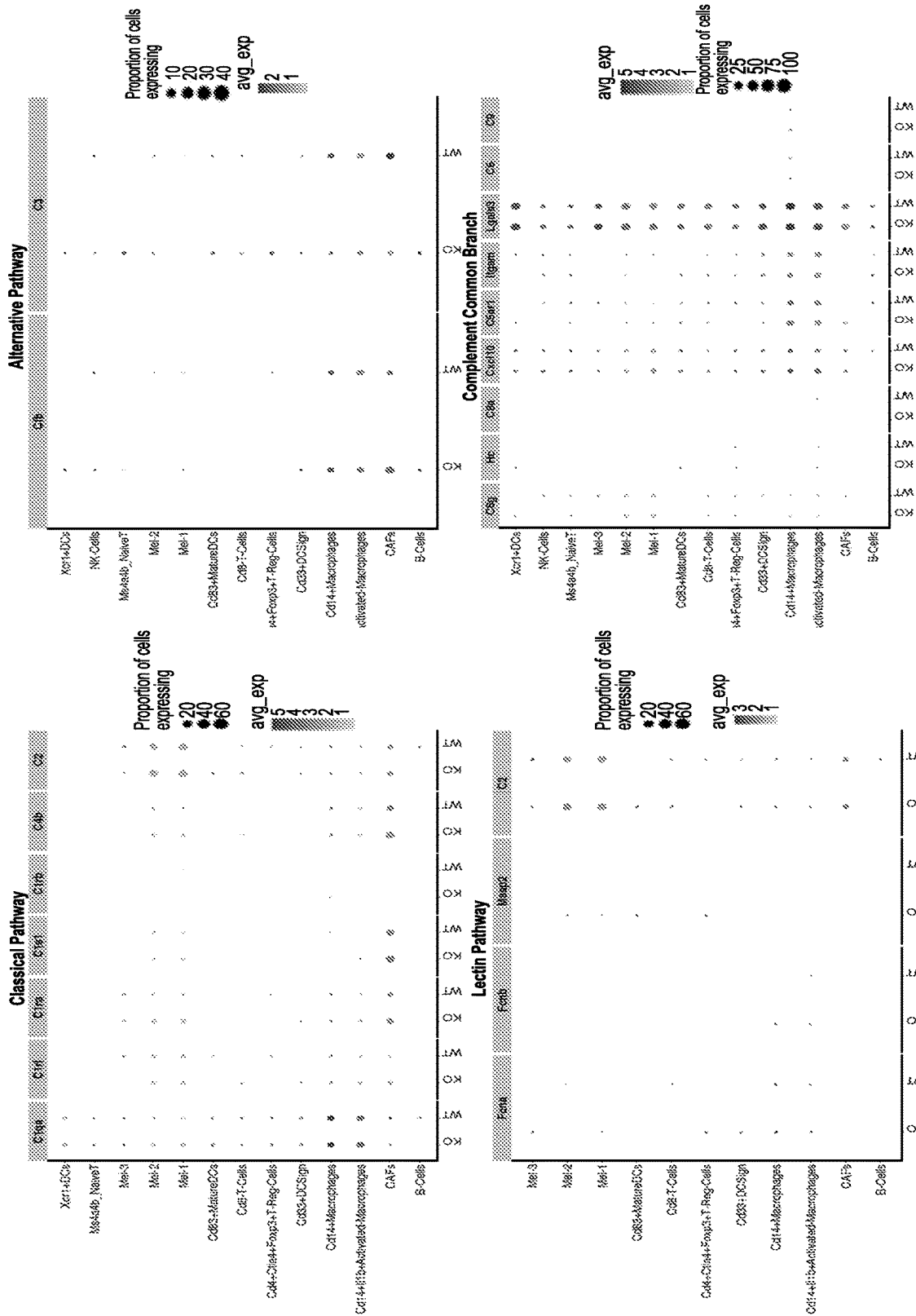
FIG. 31 illustrates complement pathway expression on the combined data.
Figure 32:
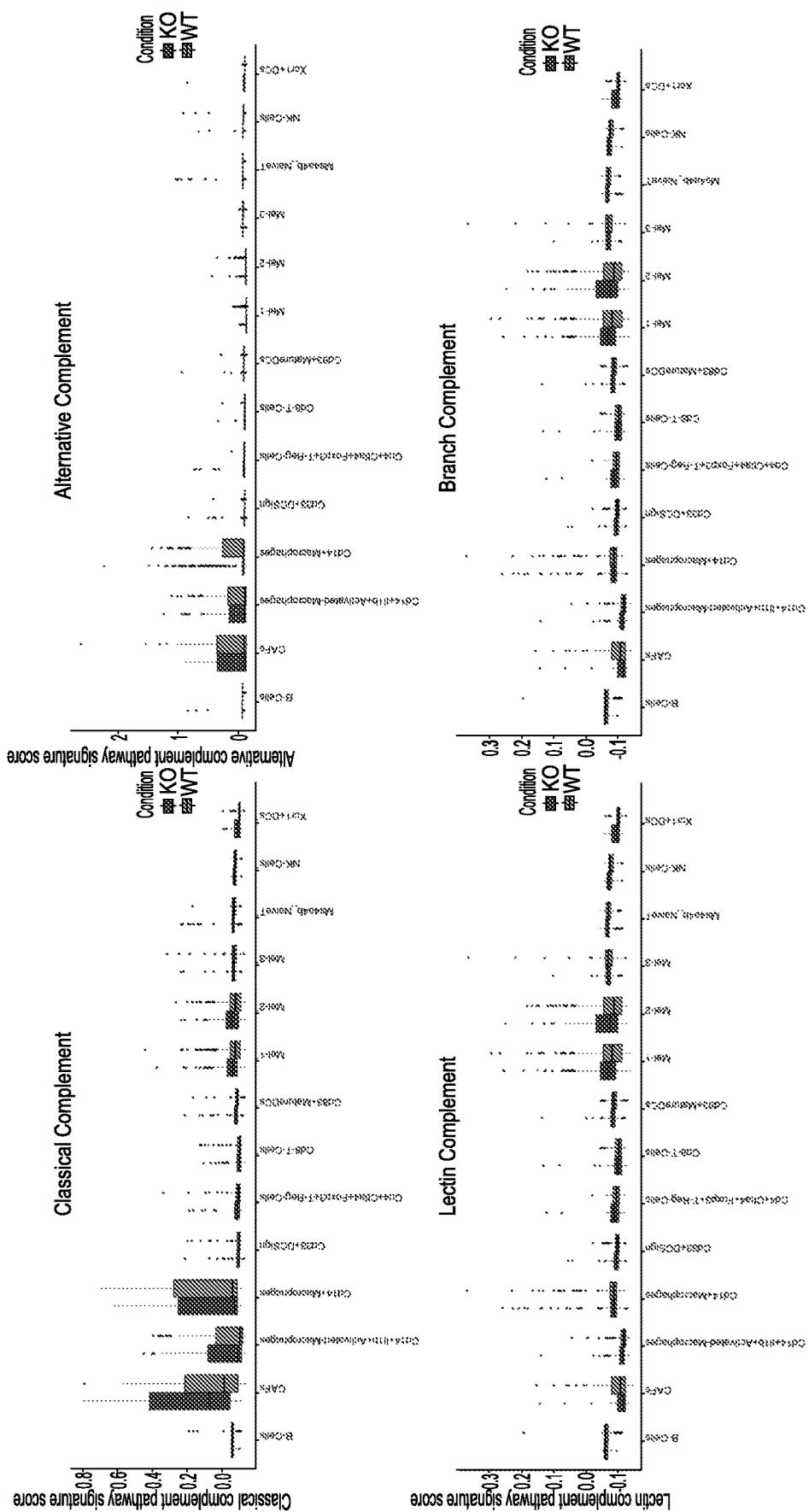
FIG. 32 illustrates complement pathway signatures on the combined data.

Applicants observed changes in complement component ON/OFF patterns in WT versus C3 KO mice on the combined data (FIGS. 31 and 32).

Figure 33:
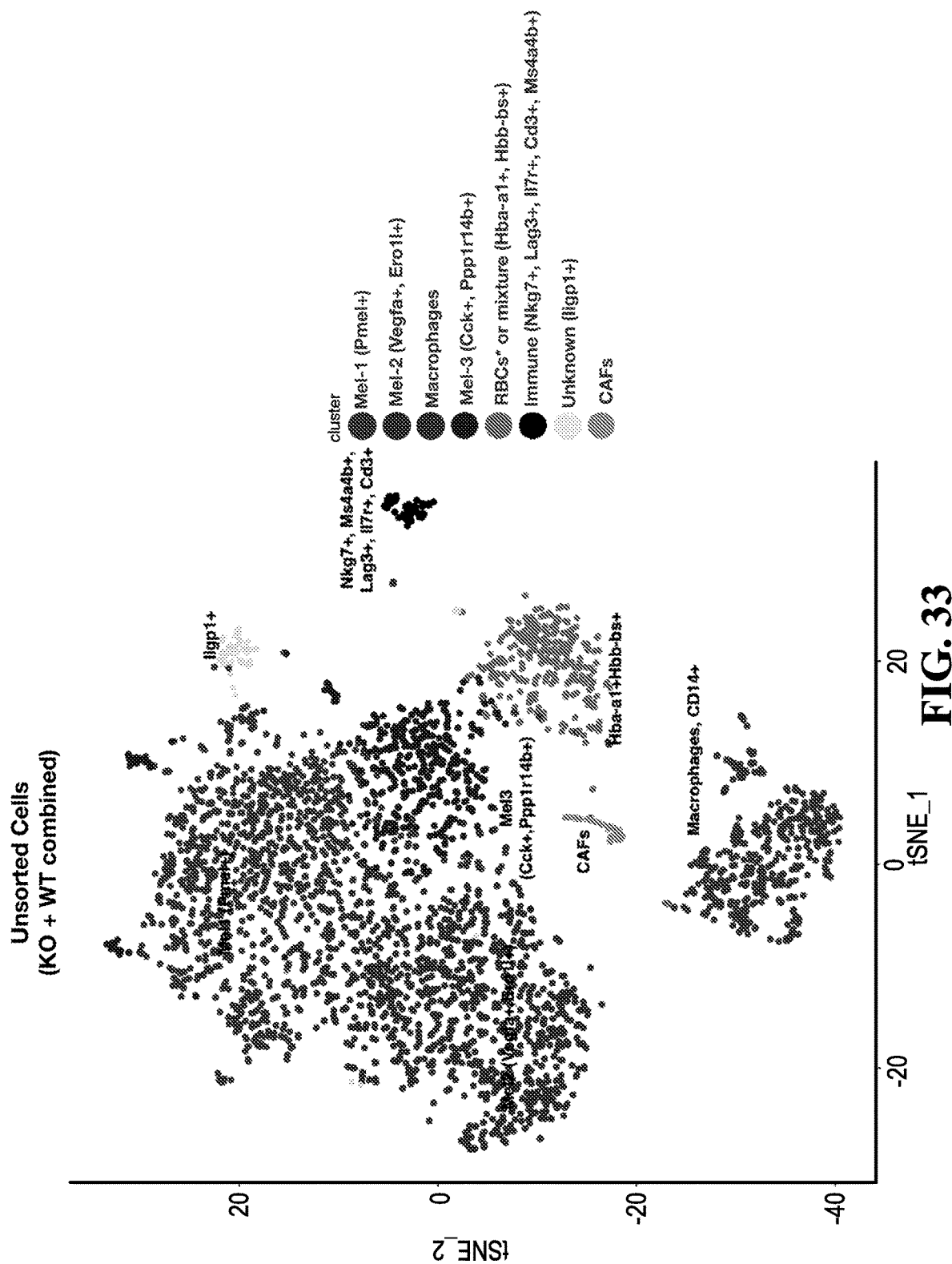
FIG. 33 illustrates tSNE analysis on unsorted only cells from B16 melanoma mice (KO+WT combined).

Classical pathway:
C1r1 ON in WT Mel-3
C1qa higher expression in WT CAFs
C2 only expressed in WT B-cells
Alternative pathway:
Cfb, C3 only expressed in KO B-cells, Cfb only expressed in KO CD33+DC,
KO Xcr1DCC3 only expressed in KO B-cells,
Naive TC3 highly expressed in WT CAFs
Lectin Pathway:
C2 higher expression in WT Mel3
Masp2 only expressed in T-regs
Branch:
Cxcl10 higher expression in WT Xcr1+DCs,
Cxcl10, C5ar1 ON in WT B-cells Applicants also observed that there is a VEGFA+ tumor cluster (FIG. 33).

Figure 34:
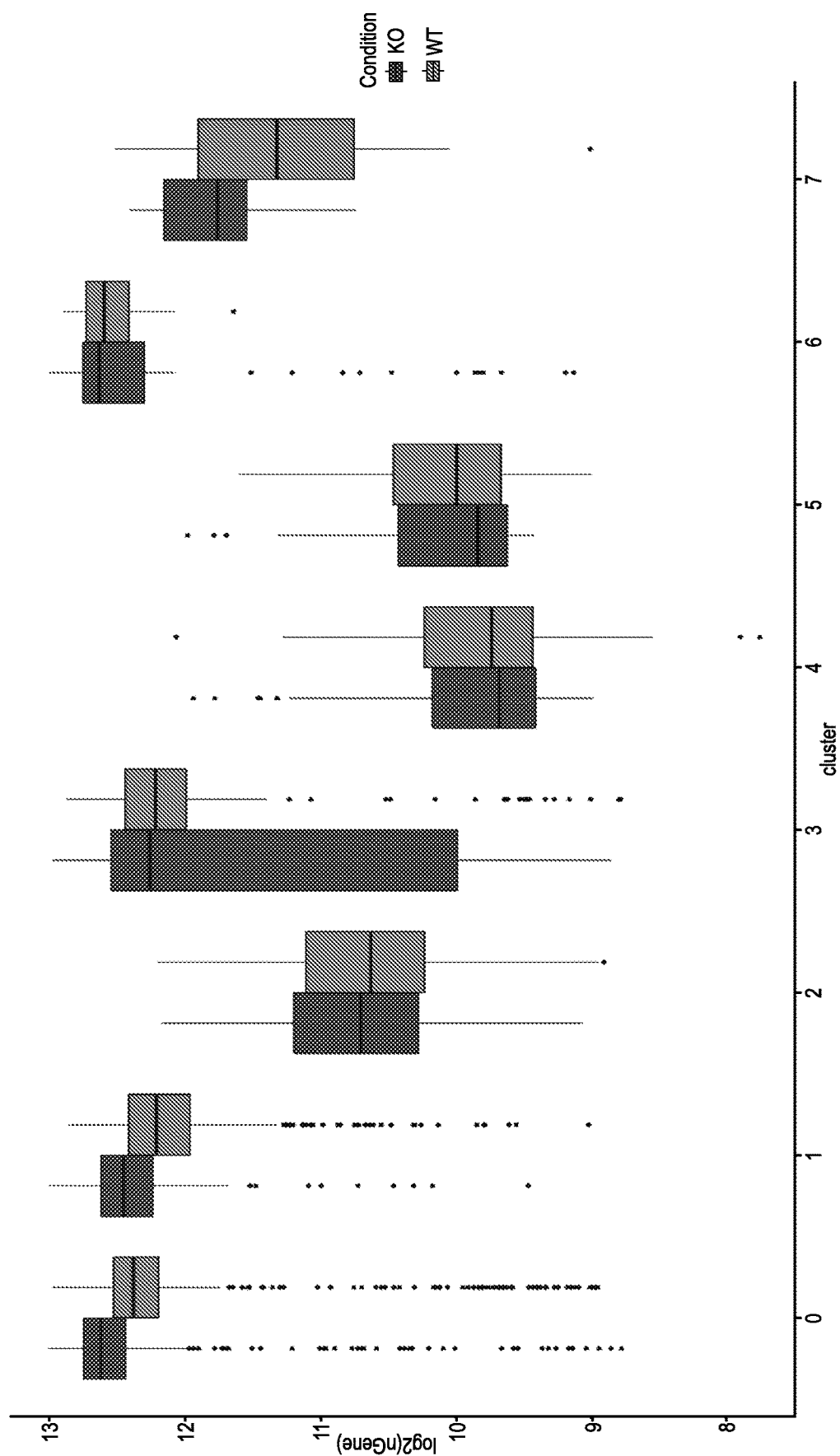
FIG. 34 illustrates the number of expressed genes in the clusters from tSNE analysis on unsorted only cells from B16 melanoma mice.
Figure 36:
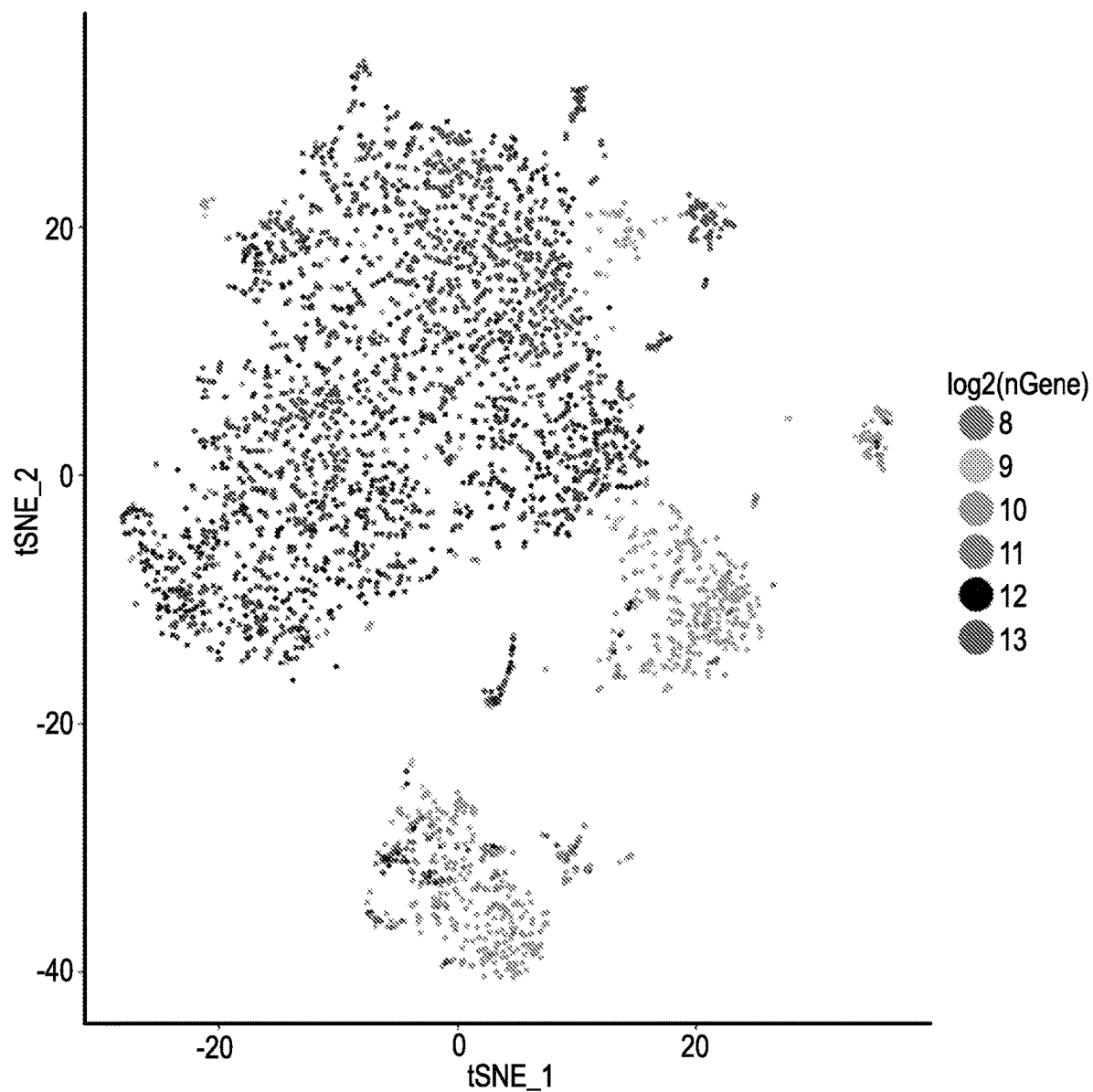
FIG. 36 illustrates the number of expressed genes on the tSNE analysis in FIG. 33.
Figure 37:
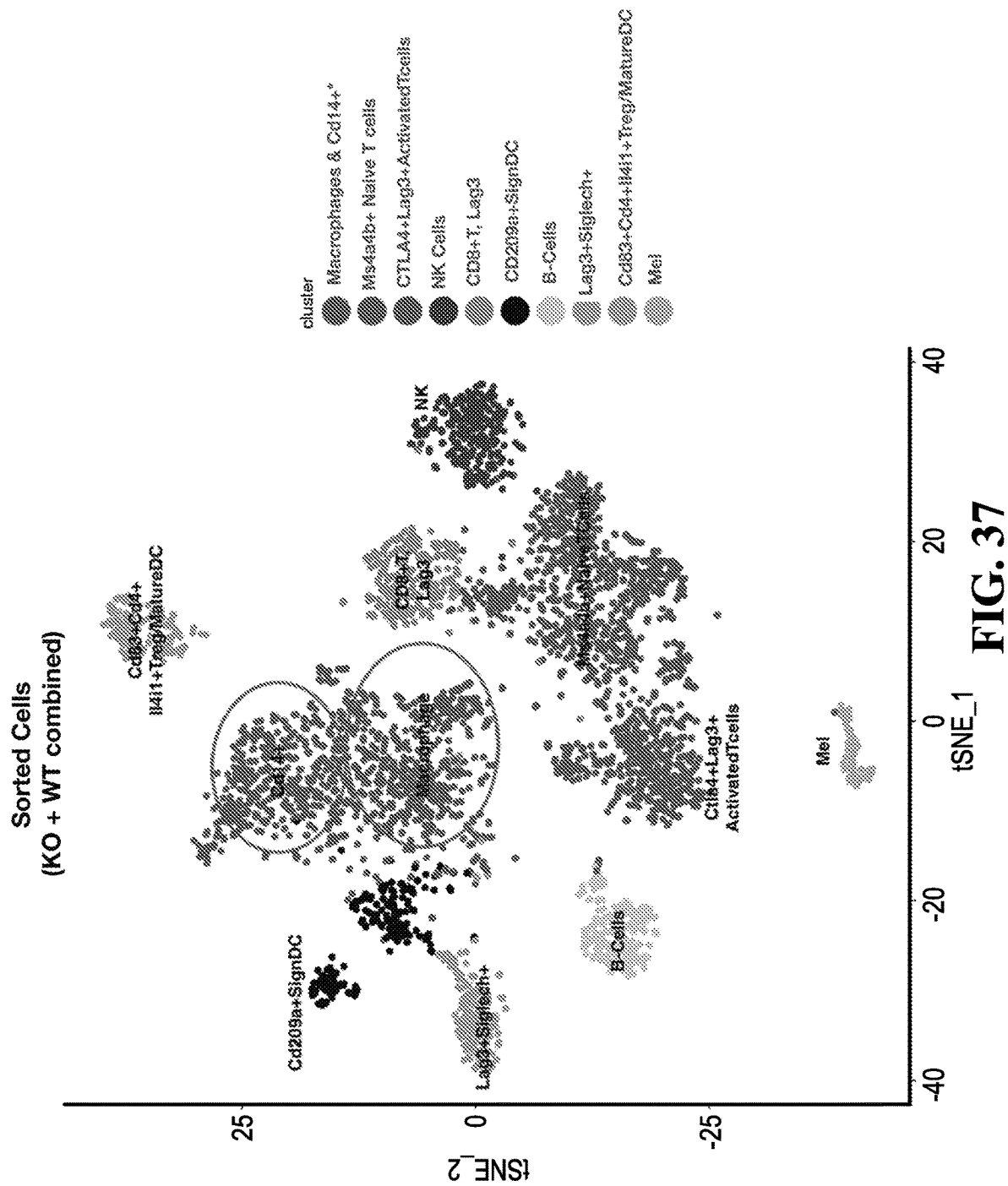
FIG. 37 illustrates tSNE analysis on sorted only cells from B16 melanoma mice (KO+WT combined).

CAFs appeared to be activated in the C3 KO as there was an increase in the numbers of expressed genes (cluster 7) (FIGS. 34 and 36). Applicants identified a list of 774 genes which are expressed in KO CAFs but not in WT (Table 2). In certain embodiments, these genes may be activated or targeted in CAFs to enhance tumor control. In certain embodiments, activated CAFs are used in adoptive cell transfer. In certain embodiments, an agent that enhances the gene signature may be administered to enhance tumor control.

TABLE 2

| Gene | Normalized_Expression (log2TPX) | percent_KO | percent_WT | Absolute_Normalized_Expression |
|---|---|---|---|---|
| Tcf24 | 0.027497498 | 0.05 | 0 | 0.027497498 |
| Slco5a1 | 0.121330181 | 0.15 | 0 | 0.121330181 |
| 6720483E21Rik | 0.046887496 | 0.05 | 0 | 0.046887496 |
| Gm29107 | 0.050322311 | 0.05 | 0 | 0.050322311 |
| Npas2 | 0.050322311 | 0.05 | 0 | 0.050322311 |
| 4930558J18Rik | 0.027497498 | 0.05 | 0 | 0.027497498 |
| Ino80dos | 0.06031708 | 0.05 | 0 | 0.06031708 |
| Tmem169 | 0.021191554 | 0.05 | 0 | 0.021191554 |
| Catip | 0.019980585 | 0.05 | 0 | 0.019980585 |
| Plcd4 | 0.021191554 | 0.05 | 0 | 0.021191554 |
| Sphkap | 0.082907736 | 0.05 | 0 | 0.082907736 |
| Fbxo36 | 0.080645506 | 0.05 | 0 | 0.080645506 |
| Glrp1 | 0.027497498 | 0.05 | 0 | 0.027497498 |
| Gm19589 | 0.021191554 | 0.05 | 0 | 0.021191554 |
| Agxt | 0.078473584 | 0.05 | 0 | 0.078473584 |
| Rnf152 | 0.082686567 | 0.15 | 0 | 0.082686567 |
| Serpinb5 | 0.039770285 | 0.05 | 0 | 0.039770285 |
| Gli2 | 0.143433759 | 0.1 | 0 | 0.143433759 |
| 2900009J06Rik | 0.046887496 | 0.05 | 0 | 0.046887496 |
| Mfsd4 | 0.073667987 | 0.15 | 0 | 0.073667987 |
| Klhdc8a | 0.156828592 | 0.1 | 0 | 0.156828592 |
| Lgr6 | 0.079484936 | 0.1 | 0 | 0.079484936 |
| Kcnt2 | 0.064027859 | 0.05 | 0 | 0.064027859 |
| Pdc | 0.019980585 | 0.05 | 0 | 0.019980585 |
| Serpinc1 | 0.070361859 | 0.05 | 0 | 0.070361859 |
| Dars2 | 0.039770285 | 0.05 | 0 | 0.039770285 |
| Xcl1 | 0.021191554 | 0.05 | 0 | 0.021191554 |
| Cd247 | 0.06031708 | 0.05 | 0 | 0.06031708 |
| Gm16701 | 0.036749186 | 0.05 | 0 | 0.036749186 |
| Lmx1a | 0.039770285 | 0.05 | 0 | 0.039770285 |
| Fcgr4 | 0.030059739 | 0.05 | 0 | 0.030059739 |
| Gm20045 | 0.079612773 | 0.05 | 0 | 0.079612773 |
| B930036N10Rik | 0.133874953 | 0.1 | 0 | 0.133874953 |
| Igsf9 | 0.036749186 | 0.05 | 0 | 0.036749186 |
| Olfr433 | 0.039770285 | 0.05 | 0 | 0.039770285 |
| Opn3 | 0.112201724 | 0.1 | 0 | 0.112201724 |
| Chml | 0.030059739 | 0.05 | 0 | 0.030059739 |
| Kif26b | 0.095019408 | 0.1 | 0 | 0.095019408 |
| 1700056E22Rik | 0.039770285 | 0.05 | 0 | 0.039770285 |
| Gm34342 | 0.074834738 | 0.15 | 0 | 0.074834738 |
| 4930532G15Rik | 0.019980585 | 0.05 | 0 | 0.019980585 |
| Kcnk2 | 0.122717326 | 0.05 | 0 | 0.122717326 |
| Proser2 | 0.072585481 | 0.05 | 0 | 0.072585481 |
| Gata3 | 0.021191554 | 0.05 | 0 | 0.021191554 |
| 4930426L09Rik | 0.021191554 | 0.05 | 0 | 0.021191554 |
| Thnsl1 | 0.096877296 | 0.15 | 0 | 0.096877296 |
| 1700084E18Rik | 0.036749186 | 0.05 | 0 | 0.036749186 |
| 1700001O22Rik | 0.072585481 | 0.05 | 0 | 0.072585481 |
| Cfap157 | 0.082907736 | 0.05 | 0 | 0.082907736 |
| Zbtb43 | 0.127864238 | 0.1 | 0 | 0.127864238 |
| Lmx1b | 0.030059739 | 0.05 | 0 | 0.030059739 |
| Phf19 | 0.039770285 | 0.05 | 0 | 0.039770285 |

TABLE 2-continued

| Gene | Normalized_Expression (log2TPX) | percent_KO | percent_WT | Absolute_Normalized_Expression |
|---|---|---|---|---|
| Crb2 | 0.021191554 | 0.05 | 0 | 0.021191554 |
| Wdr38 | 0.034683507 | 0.05 | 0 | 0.034683507 |
| Lypd6 | 0.030059739 | 0.05 | 0 | 0.030059739 |
| Scn2a1 | 0.034683507 | 0.05 | 0 | 0.034683507 |
| Mettl5os | 0.019980585 | 0.05 | 0 | 0.019980585 |
| 2600014E21Rik | 0.056077601 | 0.05 | 0 | 0.056077601 |
| Rbm45 | 0.050322311 | 0.05 | 0 | 0.050322311 |
| Zfp385b | 0.021191554 | 0.05 | 0 | 0.021191554 |
| Gm13715 | 0.054422171 | 0.1 | 0 | 0.054422171 |
| C1qtnf4 | 0.036749186 | 0.05 | 0 | 0.036749186 |
| Spi1 | 0.056077601 | 0.05 | 0 | 0.056077601 |
| Ambra1 | 0.034683507 | 0.05 | 0 | 0.034683507 |
| Abtb2 | 0.039770285 | 0.05 | 0 | 0.039770285 |
| Tcp11l1 | 0.085835693 | 0.1 | 0 | 0.085835693 |
| Mettl15 | 0.034683507 | 0.05 | 0 | 0.034683507 |
| Gm26899 | 0.019980585 | 0.05 | 0 | 0.019980585 |
| Catsper2 | 0.031826382 | 0.05 | 0 | 0.031826382 |
| Bloc1s6os | 0.027437878 | 0.05 | 0 | 0.027437878 |
| 1810024B03Rik | 0.056077601 | 0.05 | 0 | 0.056077601 |
| Gm14029 | 0.027497498 | 0.05 | 0 | 0.027497498 |
| AV099323 | 0.027497498 | 0.05 | 0 | 0.027497498 |
| Mcm8 | 0.177211524 | 0.2 | 0 | 0.177211524 |
| Ism1 | 0.039688224 | 0.05 | 0 | 0.039688224 |
| Slc52a3 | 0.074777044 | 0.1 | 0 | 0.074777044 |
| Defb25 | 0.039770285 | 0.05 | 0 | 0.039770285 |
| Mylk2 | 0.019980585 | 0.05 | 0 | 0.019980585 |
| Rbm12 | 0.309762751 | 0.3 | 0 | 0.309762751 |
| Gm14286 | 0.082907736 | 0.05 | 0 | 0.082907736 |
| Fam209 | 0.064027859 | 0.05 | 0 | 0.064027859 |
| Gm20721 | 0.174193274 | 0.15 | 0 | 0.174193274 |
| Gm14325 | 0.021191554 | 0.05 | 0 | 0.021191554 |
| Gm14327 | 0.036749186 | 0.05 | 0 | 0.036749186 |
| Phactr3 | 0.034683507 | 0.05 | 0 | 0.034683507 |
| Tcfl5 | 0.263120847 | 0.15 | 0 | 0.263120847 |
| Nkain4 | 0.039770285 | 0.05 | 0 | 0.039770285 |
| Col20a1 | 0.021191554 | 0.05 | 0 | 0.021191554 |
| Nudt10 | 0.036749186 | 0.05 | 0 | 0.036749186 |
| Rpgr | 0.080645506 | 0.05 | 0 | 0.080645506 |
| Gm26652 | 0.059211238 | 0.1 | 0 | 0.059211238 |
| Jade3 | 0.046887496 | 0.05 | 0 | 0.046887496 |
| Usp11 | 0.082907736 | 0.05 | 0 | 0.082907736 |
| Cfp | 0.019980585 | 0.05 | 0 | 0.019980585 |
| 2310010G23Rik | 0.027497498 | 0.05 | 0 | 0.027497498 |
| Smim10l2a | 0.066446459 | 0.1 | 0 | 0.066446459 |
| Xlr3a | 0.036749186 | 0.05 | 0 | 0.036749186 |
| Xlr3c | 0.056077601 | 0.05 | 0 | 0.056077601 |
| Pdzd4 | 0.089397596 | 0.1 | 0 | 0.089397596 |
| Tab3 | 0.108826966 | 0.1 | 0 | 0.108826966 |
| Gm14798 | 0.019980585 | 0.05 | 0 | 0.019980585 |
| Spin4 | 0.123818949 | 0.1 | 0 | 0.123818949 |
| Eda2r | 0.054480686 | 0.05 | 0 | 0.054480686 |
| Dlg3 | 0.056927414 | 0.05 | 0 | 0.056927414 |
| Ercc6l | 0.079024092 | 0.15 | 0 | 0.079024092 |
| C77370 | 0.046887496 | 0.05 | 0 | 0.046887496 |
| Uprt | 0.030059739 | 0.05 | 0 | 0.030059739 |
| Mum1l1 | 0.064036418 | 0.1 | 0 | 0.064036418 |
| Pfkfb1 | 0.039770285 | 0.05 | 0 | 0.039770285 |
| Nhs | 0.031826382 | 0.05 | 0 | 0.031826382 |
| Ofd1 | 0.145075053 | 0.15 | 0 | 0.145075053 |
| Prps2 | 0.150039991 | 0.15 | 0 | 0.150039991 |
| Il7 | 0.052558867 | 0.1 | 0 | 0.052558867 |
| Zbtb10 | 0.156002785 | 0.15 | 0 | 0.156002785 |
| C030034L19Rik | 0.080645506 | 0.05 | 0 | 0.080645506 |
| Naaladl2 | 0.021191554 | 0.05 | 0 | 0.021191554 |
| Lrrc34 | 0.080645506 | 0.05 | 0 | 0.080645506 |
| Usp13 | 0.056230619 | 0.1 | 0 | 0.056230619 |
| Gm15952 | 0.052558867 | 0.1 | 0 | 0.052558867 |
| D3Ertd254e | 0.192210496 | 0.2 | 0 | 0.192210496 |
| 1810062G17Rik | 0.048233073 | 0.1 | 0 | 0.048233073 |
| Fgf2os | 0.021191554 | 0.05 | 0 | 0.021191554 |
| D3Ertd751e | 0.031826382 | 0.05 | 0 | 0.031826382 |
| Gm30074 | 0.034683507 | 0.05 | 0 | 0.034683507 |
| Ccdc169 | 0.036749186 | 0.05 | 0 | 0.036749186 |
| P2ry1 | 0.031826382 | 0.05 | 0 | 0.031826382 |
| Gm6634 | 0.127869616 | 0.15 | 0 | 0.127869616 |
| Map9 | 0.108263688 | 0.1 | 0 | 0.108263688 |
| Rbm46 | 0.019980585 | 0.05 | 0 | 0.019980585 |
| Crabp2 | 0.021191554 | 0.05 | 0 | 0.021191554 |

TABLE 2-continued

| Gene | Normalized_Expression (log2TPX) | percent_KO | percent_WT | Absolute_Normalized_Expression |
|---|---|---|---|---|
| Gm3764 | 0.031826382 | 0.05 | 0 | 0.031826382 |
| Gm16069 | 0.021191554 | 0.05 | 0 | 0.021191554 |
| Muc1 | 0.021191554 | 0.05 | 0 | 0.021191554 |
| S100a14 | 0.034683507 | 0.05 | 0 | 0.034683507 |
| S100a3 | 0.203434102 | 0.1 | 0 | 0.203434102 |
| S100a7a | 0.137451082 | 0.05 | 0 | 0.137451082 |
| Tchh | 0.06031708 | 0.05 | 0 | 0.06031708 |
| Ctss | 0.088747285 | 0.1 | 0 | 0.088747285 |
| Ciart | 0.036749186 | 0.05 | 0 | 0.036749186 |
| Hist2h3c2 | 0.027437878 | 0.05 | 0 | 0.027437878 |
| Hist2h2aa1 | 0.067783653 | 0.1 | 0 | 0.067783653 |
| Zfp697 | 0.039770285 | 0.05 | 0 | 0.039770285 |
| Dennd2c | 0.031826382 | 0.05 | 0 | 0.031826382 |
| Ptpn22 | 0.030059739 | 0.05 | 0 | 0.030059739 |
| Atxn7l2 | 0.031826382 | 0.05 | 0 | 0.031826382 |
| Dpyd | 0.056927414 | 0.05 | 0 | 0.056927414 |
| A530020G20Rik | 0.056077601 | 0.05 | 0 | 0.056077601 |
| Prss12 | 0.073513757 | 0.1 | 0 | 0.073513757 |
| Gm43254 | 0.027437878 | 0.05 | 0 | 0.027437878 |
| Lpar3 | 0.059505921 | 0.05 | 0 | 0.059505921 |
| Spata1 | 0.031826382 | 0.05 | 0 | 0.031826382 |
| Gdf6 | 0.050322311 | 0.05 | 0 | 0.050322311 |
| Rad54b | 0.021191554 | 0.05 | 0 | 0.021191554 |
| Rragd | 0.056927414 | 0.05 | 0 | 0.056927414 |
| Tmem215 | 0.082907736 | 0.05 | 0 | 0.082907736 |
| Kif24 | 0.064027859 | 0.05 | 0 | 0.064027859 |
| AI464131 | 0.056077601 | 0.05 | 0 | 0.056077601 |
| Ccl19 | 0.149084077 | 0.1 | 0 | 0.149084077 |
| Gm26881 | 0.114957082 | 0.1 | 0 | 0.114957082 |
| Zbtb5 | 0.064027859 | 0.05 | 0 | 0.064027859 |
| Palm2 | 0.031826382 | 0.05 | 0 | 0.031826382 |
| Akap2 | 0.114287765 | 0.15 | 0 | 0.114287765 |
| Tnfsf15 | 0.039688224 | 0.05 | 0 | 0.039688224 |
| Ptprd | 0.021191554 | 0.05 | 0 | 0.021191554 |
| Cdkn2a | 0.087893625 | 0.1 | 0 | 0.087893625 |
| E130102H24Rik | 0.027497498 | 0.05 | 0 | 0.027497498 |
| Pars2 | 0.056927414 | 0.05 | 0 | 0.056927414 |
| Echdc2 | 0.080646994 | 0.1 | 0 | 0.080646994 |
| Dmrta2 | 0.019980585 | 0.05 | 0 | 0.019980585 |
| Bend5 | 0.072585481 | 0.05 | 0 | 0.072585481 |
| Stil | 0.070361859 | 0.05 | 0 | 0.070361859 |
| Faah | 0.027497498 | 0.05 | 0 | 0.027497498 |
| Tmem69 | 0.034683507 | 0.05 | 0 | 0.034683507 |
| Hpdl | 0.064027859 | 0.05 | 0 | 0.064027859 |
| Col8a2 | 0.108934836 | 0.1 | 0 | 0.108934836 |
| Gm12942 | 0.027437878 | 0.05 | 0 | 0.027437878 |
| Gjb5 | 0.266462217 | 0.15 | 0 | 0.266462217 |
| Tmem54 | 0.021191554 | 0.05 | 0 | 0.021191554 |
| Gm12976 | 0.046887496 | 0.05 | 0 | 0.046887496 |
| Serinc2 | 0.054480686 | 0.05 | 0 | 0.054480686 |
| Cd52 | 0.056927414 | 0.05 | 0 | 0.056927414 |
| Ubxn11 | 0.070361859 | 0.05 | 0 | 0.070361859 |
| Runx3 | 0.057411552 | 0.1 | 0 | 0.057411552 |
| 6030445D17Rik | 0.027497498 | 0.05 | 0 | 0.027497498 |
| C1qa | 0.056077601 | 0.05 | 0 | 0.056077601 |
| Wnt4 | 0.021191554 | 0.05 | 0 | 0.021191554 |
| Tmco4 | 0.088009355 | 0.15 | 0 | 0.088009355 |
| 4921514A10Rik | 0.030059739 | 0.05 | 0 | 0.030059739 |
| Gm29367 | 0.027497498 | 0.05 | 0 | 0.027497498 |
| Gm20707 | 0.030059739 | 0.05 | 0 | 0.030059739 |
| Casz1 | 0.027437878 | 0.05 | 0 | 0.027437878 |
| Gpr157 | 0.030059739 | 0.05 | 0 | 0.030059739 |
| Nol9 | 0.223516403 | 0.2 | 0 | 0.223516403 |
| Kcnab2 | 0.167024966 | 0.1 | 0 | 0.167024966 |
| Megf6 | 0.056077601 | 0.05 | 0 | 0.056077601 |
| B930041F14Rik | 0.101779727 | 0.1 | 0 | 0.101779727 |
| Tmem240 | 0.027497498 | 0.05 | 0 | 0.027497498 |
| Gm16008 | 0.050322311 | 0.05 | 0 | 0.050322311 |
| Tnfrsf18 | 0.019980585 | 0.05 | 0 | 0.019980585 |
| 9430015G10Rik | 0.021191554 | 0.05 | 0 | 0.021191554 |
| Sema3a | 0.027437878 | 0.05 | 0 | 0.027437878 |
| Fbxl13 | 0.080646994 | 0.1 | 0 | 0.080646994 |
| Napepld | 0.019980585 | 0.05 | 0 | 0.019980585 |
| Crygn | 0.064027859 | 0.05 | 0 | 0.064027859 |
| Gm7361 | 0.06031708 | 0.05 | 0 | 0.06031708 |
| Drc1 | 0.050322311 | 0.05 | 0 | 0.050322311 |
| Fam184b | 0.027437878 | 0.05 | 0 | 0.027437878 |
| Sell13 | 0.039770285 | 0.05 | 0 | 0.039770285 |

TABLE 2-continued

| Gene | Normalized_Expression (log2TPX) | percent_KO | percent_WT | Absolute_Normalized_Expression |
|---|---|---|---|---|
| Wdr19 | 0.196850069 | 0.1 | 0 | 0.196850069 |
| Limch1 | 0.079612773 | 0.05 | 0 | 0.079612773 |
| Rasl11b | 0.12938134 | 0.15 | 0 | 0.12938134 |
| C530008M17Rik | 0.030059739 | 0.05 | 0 | 0.030059739 |
| Spink2 | 0.115313029 | 0.15 | 0 | 0.115313029 |
| Gm9958 | 0.080645506 | 0.05 | 0 | 0.080645506 |
| Cdkl2 | 0.094351605 | 0.1 | 0 | 0.094351605 |
| Nup54 | 0.197081334 | 0.25 | 0 | 0.197081334 |
| 2010109A12Rik | 0.031826382 | 0.05 | 0 | 0.031826382 |
| Fgf5 | 0.030059739 | 0.05 | 0 | 0.030059739 |
| 1700010H22Rik | 0.079612773 | 0.05 | 0 | 0.079612773 |
| Agpat9 | 0.06031708 | 0.05 | 0 | 0.06031708 |
| Gm29707 | 0.021191554 | 0.05 | 0 | 0.021191554 |
| Klhl8 | 0.089397596 | 0.1 | 0 | 0.089397596 |
| Gm42749 | 0.064027859 | 0.05 | 0 | 0.064027859 |
| Gm28050 | 0.050322311 | 0.05 | 0 | 0.050322311 |
| A830010M20Rik | 0.101779727 | 0.1 | 0 | 0.101779727 |
| Ccdc18 | 0.084305915 | 0.1 | 0 | 0.084305915 |
| E130006D01Rik | 0.031826382 | 0.05 | 0 | 0.031826382 |
| Myo1h | 0.036749186 | 0.05 | 0 | 0.036749186 |
| Trpv4 | 0.049631101 | 0.1 | 0 | 0.049631101 |
| Gm10399 | 0.027437878 | 0.05 | 0 | 0.027437878 |
| Rnft2 | 0.070361859 | 0.05 | 0 | 0.070361859 |
| Tbx3 | 0.036749186 | 0.05 | 0 | 0.036749186 |
| Iqcd | 0.056077601 | 0.05 | 0 | 0.056077601 |
| Gm42918 | 0.027497498 | 0.05 | 0 | 0.027497498 |
| 4932422M17Rik | 0.108883316 | 0.1 | 0 | 0.108883316 |
| Kntc1 | 0.030059739 | 0.05 | 0 | 0.030059739 |
| Gm10369 | 0.118146289 | 0.15 | 0 | 0.118146289 |
| Pilrb1 | 0.027497498 | 0.05 | 0 | 0.027497498 |
| 6330418K02Rik | 0.092281452 | 0.15 | 0 | 0.092281452 |
| Rbak | 0.039770285 | 0.05 | 0 | 0.039770285 |
| Zfp316 | 0.021191554 | 0.05 | 0 | 0.021191554 |
| Gm20635 | 0.031826382 | 0.05 | 0 | 0.031826382 |
| Alox5ap | 0.060389735 | 0.1 | 0 | 0.060389735 |
| Gm19719 | 0.046887496 | 0.05 | 0 | 0.046887496 |
| D730045B01Rik | 0.021191554 | 0.05 | 0 | 0.021191554 |
| D830026I12Rik | 0.027437878 | 0.05 | 0 | 0.027437878 |
| Kcp | 0.173985946 | 0.15 | 0 | 0.173985946 |
| Tspan33 | 0.036749186 | 0.05 | 0 | 0.036749186 |
| Klf14 | 0.042076328 | 0.05 | 0 | 0.042076328 |
| D630045J12Rik | 0.031826382 | 0.05 | 0 | 0.031826382 |
| 4930599N23Rik | 0.069622533 | 0.1 | 0 | 0.069622533 |
| Clcn1 | 0.027497498 | 0.05 | 0 | 0.027497498 |
| 1600015I10Rik | 0.064027859 | 0.05 | 0 | 0.064027859 |
| Gm16499 | 0.031826382 | 0.05 | 0 | 0.031826382 |
| Ndnf | 0.021191554 | 0.05 | 0 | 0.021191554 |
| Reep1 | 0.107553141 | 0.05 | 0 | 0.107553141 |
| Atoh8 | 0.042076328 | 0.05 | 0 | 0.042076328 |
| M1ap | 0.087602028 | 0.15 | 0 | 0.087602028 |
| Wdr54 | 0.137105214 | 0.1 | 0 | 0.137105214 |
| Cml3 | 0.039770285 | 0.05 | 0 | 0.039770285 |
| Add2 | 0.106922233 | 0.1 | 0 | 0.106922233 |
| Gm44089 | 0.027497498 | 0.05 | 0 | 0.027497498 |
| Rab43 | 0.021191554 | 0.05 | 0 | 0.021191554 |
| Hdac11 | 0.082907736 | 0.05 | 0 | 0.082907736 |
| Srgap3 | 0.036749186 | 0.05 | 0 | 0.036749186 |
| Fancd2 | 0.031826382 | 0.05 | 0 | 0.031826382 |
| Fxyd4 | 0.056077601 | 0.05 | 0 | 0.056077601 |
| 4930540M05Rik | 0.082907736 | 0.05 | 0 | 0.082907736 |
| Gm26826 | 0.034683507 | 0.05 | 0 | 0.034683507 |
| C1rl | 0.176405493 | 0.15 | 0 | 0.176405493 |
| Ptpn6 | 0.027437878 | 0.05 | 0 | 0.027437878 |
| Kcna1 | 0.036749186 | 0.05 | 0 | 0.036749186 |
| Gm10010 | 0.06031708 | 0.05 | 0 | 0.06031708 |
| Klrb1a | 0.027497498 | 0.05 | 0 | 0.027497498 |
| Klrk1 | 0.056077601 | 0.05 | 0 | 0.056077601 |
| Pbp2 | 0.031826382 | 0.05 | 0 | 0.031826382 |
| Rerg | 0.064027859 | 0.05 | 0 | 0.064027859 |
| Gm15704 | 0.056927414 | 0.05 | 0 | 0.056927414 |
| Pthlh | 0.115735938 | 0.1 | 0 | 0.115735938 |
| Far2os1 | 0.019980585 | 0.05 | 0 | 0.019980585 |
| Mettl20 | 0.079484936 | 0.1 | 0 | 0.079484936 |
| Tarm1 | 0.019980585 | 0.05 | 0 | 0.019980585 |
| Gm15510 | 0.036749186 | 0.05 | 0 | 0.036749186 |
| Zfp583 | 0.102501087 | 0.15 | 0 | 0.102501087 |
| Zim1 | 0.021191554 | 0.05 | 0 | 0.021191554 |
| Zfp772 | 0.140792393 | 0.15 | 0 | 0.140792393 |

TABLE 2-continued

| Gene | Normalized_Expression (log2TPX) | percent_KO | percent_WT | Absolute_Normalized_Expression |
|---|---|---|---|---|
| Dhx34 | 0.056927414 | 0.05 | 0 | 0.056927414 |
| C5ar1 | 0.079612773 | 0.05 | 0 | 0.079612773 |
| Pnmal2 | 0.076466924 | 0.1 | 0 | 0.076466924 |
| Zfp94 | 0.027437878 | 0.05 | 0 | 0.027437878 |
| Tmem91 | 0.034683507 | 0.05 | 0 | 0.034683507 |
| Rab4b | 0.054422171 | 0.1 | 0 | 0.054422171 |
| Itpkc | 0.142084329 | 0.05 | 0 | 0.142084329 |
| Zfp607 | 0.050322311 | 0.05 | 0 | 0.050322311 |
| Zfp568 | 0.054422171 | 0.1 | 0 | 0.054422171 |
| Zfp382 | 0.030059739 | 0.05 | 0 | 0.030059739 |
| Gm26810 | 0.082907736 | 0.05 | 0 | 0.082907736 |
| Krtdap | 0.099004835 | 0.1 | 0 | 0.099004835 |
| Lsr | 0.036749186 | 0.05 | 0 | 0.036749186 |
| Zfp536 | 0.036749186 | 0.05 | 0 | 0.036749186 |
| Vsig10l | 0.019980585 | 0.05 | 0 | 0.019980585 |
| Ctu1 | 0.046887496 | 0.05 | 0 | 0.046887496 |
| Lrrc4b | 0.030059739 | 0.05 | 0 | 0.030059739 |
| Napsa | 0.021191554 | 0.05 | 0 | 0.021191554 |
| Lmtk3 | 0.034683507 | 0.05 | 0 | 0.034683507 |
| Uevld | 0.101779727 | 0.1 | 0 | 0.101779727 |
| Fancf | 0.056927414 | 0.05 | 0 | 0.056927414 |
| Nipa1 | 0.080645506 | 0.05 | 0 | 0.080645506 |
| Mkrn3 | 0.064027859 | 0.05 | 0 | 0.064027859 |
| Lysmd4 | 0.092739539 | 0.15 | 0 | 0.092739539 |
| Ticrr | 0.105069062 | 0.2 | 0 | 0.105069062 |
| Homer2 | 0.030059739 | 0.05 | 0 | 0.030059739 |
| Sh3gl3 | 0.070361859 | 0.05 | 0 | 0.070361859 |
| Arnt2 | 0.021191554 | 0.05 | 0 | 0.021191554 |
| RP24-118K20.1 | 0.042076328 | 0.05 | 0 | 0.042076328 |
| Rab30 | 0.091754524 | 0.1 | 0 | 0.091754524 |
| Tenm4 | 0.072585481 | 0.05 | 0 | 0.072585481 |
| Kctd21 | 0.115051672 | 0.1 | 0 | 0.115051672 |
| Wnt11 | 0.056927414 | 0.05 | 0 | 0.056927414 |
| Dgat2 | 0.034683507 | 0.05 | 0 | 0.034683507 |
| C2cd3 | 0.149074592 | 0.15 | 0 | 0.149074592 |
| RP23-299D2.2 | 0.034683507 | 0.05 | 0 | 0.034683507 |
| Folr2 | 0.080645506 | 0.05 | 0 | 0.080645506 |
| Hbb-bt | 0.027437878 | 0.05 | 0 | 0.027437878 |
| Gm15133 | 0.031826382 | 0.05 | 0 | 0.031826382 |
| Ppfibp2 | 0.142084329 | 0.05 | 0 | 0.142084329 |
| Pdzd9 | 0.079612773 | 0.05 | 0 | 0.079612773 |
| 4933440M02Rik | 0.036749186 | 0.05 | 0 | 0.036749186 |
| Coro1a | 0.031826382 | 0.05 | 0 | 0.031826382 |
| Gdpd3 | 0.031826382 | 0.05 | 0 | 0.031826382 |
| Pagr1a | 0.046887496 | 0.05 | 0 | 0.046887496 |
| Mylpf | 0.166970843 | 0.1 | 0 | 0.166970843 |
| Zfp668 | 0.205015001 | 0.3 | 0 | 0.205015001 |
| 9130023H24Rik | 0.057411552 | 0.1 | 0 | 0.057411552 |
| Ifitm5 | 0.136116049 | 0.1 | 0 | 0.136116049 |
| Sct | 0.064036418 | 0.1 | 0 | 0.064036418 |
| Eps8l2 | 0.06031708 | 0.05 | 0 | 0.06031708 |
| Syt8 | 0.021191554 | 0.05 | 0 | 0.021191554 |
| Tnni2 | 0.039770285 | 0.05 | 0 | 0.039770285 |
| Gm21781 | 0.039770285 | 0.05 | 0 | 0.039770285 |
| Rgs17 | 0.056077601 | 0.05 | 0 | 0.056077601 |
| Adat2 | 0.058729476 | 0.1 | 0 | 0.058729476 |
| Heca | 0.082478942 | 0.1 | 0 | 0.082478942 |
| Map7 | 0.070570516 | 0.1 | 0 | 0.070570516 |
| Eya4 | 0.056077601 | 0.05 | 0 | 0.056077601 |
| Slc18b1 | 0.084305915 | 0.1 | 0 | 0.084305915 |
| Fam26f | 0.031826382 | 0.05 | 0 | 0.031826382 |
| Tube1 | 0.085835693 | 0.1 | 0 | 0.085835693 |
| Slc16a10 | 0.056927414 | 0.05 | 0 | 0.056927414 |
| 9030612E09Rik | 0.021191554 | 0.05 | 0 | 0.021191554 |
| Bend3 | 0.06031708 | 0.05 | 0 | 0.06031708 |
| Fam184a | 0.030059739 | 0.05 | 0 | 0.030059739 |
| Sh3rf3 | 0.021191554 | 0.05 | 0 | 0.021191554 |
| Gm5424 | 0.031826382 | 0.05 | 0 | 0.031826382 |
| 1700120B22Rik | 0.064027859 | 0.05 | 0 | 0.064027859 |
| Dnajc12 | 0.031826382 | 0.05 | 0 | 0.031826382 |
| Lrrc3 | 0.021191554 | 0.05 | 0 | 0.021191554 |
| Gm10146 | 0.082907736 | 0.05 | 0 | 0.082907736 |
| Slc1a6 | 0.046887496 | 0.05 | 0 | 0.046887496 |
| Hcn2 | 0.039770285 | 0.05 | 0 | 0.039770285 |
| Plppr3 | 0.058729476 | 0.1 | 0 | 0.058729476 |
| Hmha1 | 0.132734395 | 0.1 | 0 | 0.132734395 |
| Mex3d | 0.27491498 | 0.3 | 0 | 0.27491498 |
| Celf5 | 0.030059739 | 0.05 | 0 | 0.030059739 |

TABLE 2-continued

| Gene | Normalized_Expression (log2TPX) | percent_KO | percent_WT | Absolute_Normalized_Expression |
|---|---|---|---|---|
| Tle6 | 0.039770285 | 0.05 | 0 | 0.039770285 |
| Zfp873 | 0.027497498 | 0.05 | 0 | 0.027497498 |
| Gm4924 | 0.071829391 | 0.15 | 0 | 0.071829391 |
| Glt8d2 | 0.112201724 | 0.1 | 0 | 0.112201724 |
| Gm15990 | 0.027437878 | 0.05 | 0 | 0.027437878 |
| Anks1b | 0.027497498 | 0.05 | 0 | 0.027497498 |
| Nts | 0.046887496 | 0.05 | 0 | 0.046887496 |
| Bbs10 | 0.034683507 | 0.05 | 0 | 0.034683507 |
| Glipr1 | 0.054480686 | 0.05 | 0 | 0.054480686 |
| Lgr5 | 0.021191554 | 0.05 | 0 | 0.021191554 |
| Fam19a2 | 0.126107528 | 0.1 | 0 | 0.126107528 |
| Lrig3 | 0.034683507 | 0.05 | 0 | 0.034683507 |
| F420014N23Rik | 0.056077601 | 0.05 | 0 | 0.056077601 |
| Gli1 | 0.042076328 | 0.05 | 0 | 0.042076328 |
| Stac3 | 0.027497498 | 0.05 | 0 | 0.027497498 |
| Gls2 | 0.027497498 | 0.05 | 0 | 0.027497498 |
| A430046D13Rik | 0.046887496 | 0.05 | 0 | 0.046887496 |
| Camsap3 | 0.030059739 | 0.05 | 0 | 0.030059739 |
| Lrrc8e | 0.019980585 | 0.05 | 0 | 0.019980585 |
| RP23-216D14.4 | 0.039770285 | 0.05 | 0 | 0.039770285 |
| RP23-156J8.1 | 0.027437878 | 0.05 | 0 | 0.027437878 |
| RP23-366O14.5 | 0.079612773 | 0.05 | 0 | 0.079612773 |
| 3930402G23Rik | 0.019980585 | 0.05 | 0 | 0.019980585 |
| Myom2 | 0.06031708 | 0.05 | 0 | 0.06031708 |
| Xkr5 | 0.030059739 | 0.05 | 0 | 0.030059739 |
| Nek3 | 0.021191554 | 0.05 | 0 | 0.021191554 |
| Gm26909 | 0.027497498 | 0.05 | 0 | 0.027497498 |
| Thap1 | 0.019980585 | 0.05 | 0 | 0.019980585 |
| Tex15 | 0.039688224 | 0.05 | 0 | 0.039688224 |
| 6430573F11Rik | 0.064027859 | 0.05 | 0 | 0.064027859 |
| AI429214 | 0.021191554 | 0.05 | 0 | 0.021191554 |
| Msr1 | 0.030059739 | 0.05 | 0 | 0.030059739 |
| 1700029J07Rik | 0.108911283 | 0.1 | 0 | 0.108911283 |
| Acsl1 | 0.069020924 | 0.1 | 0 | 0.069020924 |
| Asb5 | 0.021191554 | 0.05 | 0 | 0.021191554 |
| Sh2d4a | 0.068552733 | 0.05 | 0 | 0.068552733 |
| Zfp963 | 0.056077601 | 0.05 | 0 | 0.056077601 |
| 1700030K09Rik | 0.06031708 | 0.05 | 0 | 0.06031708 |
| Tmem38a | 0.061533867 | 0.1 | 0 | 0.061533867 |
| Ccdc130 | 0.027497498 | 0.05 | 0 | 0.027497498 |
| Cks1brt | 0.149935198 | 0.15 | 0 | 0.149935198 |
| Neto2 | 0.066060523 | 0.1 | 0 | 0.066060523 |
| 9330175E14Rik | 0.070792559 | 0.1 | 0 | 0.070792559 |
| Gm3830 | 0.042076328 | 0.05 | 0 | 0.042076328 |
| Nol3 | 0.06296579 | 0.05 | 0 | 0.06296579 |
| Rltpr | 0.027497498 | 0.05 | 0 | 0.027497498 |
| Ddx28 | 0.118115222 | 0.15 | 0 | 0.118115222 |
| Pdpr | 0.070361859 | 0.05 | 0 | 0.070361859 |
| Spata2l | 0.119382205 | 0.15 | 0 | 0.119382205 |
| 2810455O05Rik | 0.021191554 | 0.05 | 0 | 0.021191554 |
| Kcnk1 | 0.06031708 | 0.05 | 0 | 0.06031708 |
| 6230400D17Rik | 0.021191554 | 0.05 | 0 | 0.021191554 |
| Plau | 0.027497498 | 0.05 | 0 | 0.027497498 |
| Dnah12 | 0.027437878 | 0.05 | 0 | 0.027437878 |
| Tnnc1 | 0.072585481 | 0.05 | 0 | 0.072585481 |
| Ncoa4 | 0.019980585 | 0.05 | 0 | 0.019980585 |
| Lrrc18 | 0.056077601 | 0.05 | 0 | 0.056077601 |
| Gdf10 | 0.06031708 | 0.05 | 0 | 0.06031708 |
| A630023A22Rik | 0.039770285 | 0.05 | 0 | 0.039770285 |
| 2610528A11Rik | 0.036749186 | 0.05 | 0 | 0.036749186 |
| Pnp2 | 0.197047254 | 0.15 | 0 | 0.197047254 |
| Slc39a2 | 0.034683507 | 0.05 | 0 | 0.034683507 |
| Tgm1 | 0.039770285 | 0.05 | 0 | 0.039770285 |
| Phf11a | 0.178170763 | 0.1 | 0 | 0.178170763 |
| Phf11c | 0.019980585 | 0.05 | 0 | 0.019980585 |
| Setdb2 | 0.081069245 | 0.1 | 0 | 0.081069245 |
| Gm27010 | 0.027437878 | 0.05 | 0 | 0.027437878 |
| Wdfy2 | 0.019980585 | 0.05 | 0 | 0.019980585 |
| Neil2 | 0.06031708 | 0.05 | 0 | 0.06031708 |
| Blk | 0.027497498 | 0.05 | 0 | 0.027497498 |
| Fam167a | 0.108074465 | 0.1 | 0 | 0.108074465 |
| Ptk2b | 0.114618872 | 0.15 | 0 | 0.114618872 |
| Cdca2 | 0.265143775 | 0.2 | 0 | 0.265143775 |
| Nefm | 0.034683507 | 0.05 | 0 | 0.034683507 |
| Nefl | 0.205871639 | 0.15 | 0 | 0.205871639 |
| Gm27222 | 0.070361859 | 0.05 | 0 | 0.070361859 |
| Gm16867 | 0.027437878 | 0.05 | 0 | 0.027437878 |
| Hr | 0.070361859 | 0.05 | 0 | 0.070361859 |

TABLE 2-continued

| Gene | Normalized_Expression (log2TPX) | percent_KO | percent_WT | Absolute_Normalized_Expression |
|---|---|---|---|---|
| Dmtn | 0.083830586 | 0.1 | 0 | 0.083830586 |
| Cysltr2 | 0.031826382 | 0.05 | 0 | 0.031826382 |
| Tnfsf11 | 0.019980585 | 0.05 | 0 | 0.019980585 |
| Pcdh9 | 0.133540244 | 0.1 | 0 | 0.133540244 |
| Tpm3-rs7 | 0.056937079 | 0.1 | 0 | 0.056937079 |
| Ggact | 0.034683507 | 0.05 | 0 | 0.034683507 |
| Trpc6 | 0.125334459 | 0.05 | 0 | 0.125334459 |
| Vstm5 | 0.061475638 | 0.1 | 0 | 0.061475638 |
| Gm7808 | 0.027437878 | 0.05 | 0 | 0.027437878 |
| Swsap1 | 0.054192665 | 0.1 | 0 | 0.054192665 |
| Rgl3 | 0.036749186 | 0.05 | 0 | 0.036749186 |
| Zfp653 | 0.021191554 | 0.05 | 0 | 0.021191554 |
| Gm16845 | 0.064027859 | 0.05 | 0 | 0.064027859 |
| Cnn1 | 0.031826382 | 0.05 | 0 | 0.031826382 |
| Tbx20 | 0.046887496 | 0.05 | 0 | 0.046887496 |
| Tmem136 | 0.036749186 | 0.05 | 0 | 0.036749186 |
| Nlrx1 | 0.039770285 | 0.05 | 0 | 0.039770285 |
| Hinfp | 0.027437878 | 0.05 | 0 | 0.027437878 |
| Ube4a | 0.088009355 | 0.15 | 0 | 0.088009355 |
| Plet1 | 0.036749186 | 0.05 | 0 | 0.036749186 |
| 2310030G06Rik | 0.072585481 | 0.05 | 0 | 0.072585481 |
| Gm7293 | 0.067783653 | 0.1 | 0 | 0.067783653 |
| Elmod1 | 0.12727749 | 0.1 | 0 | 0.12727749 |
| Lingo1 | 0.027497498 | 0.05 | 0 | 0.027497498 |
| Rec114 | 0.115676094 | 0.1 | 0 | 0.115676094 |
| Zwilch | 0.101059874 | 0.1 | 0 | 0.101059874 |
| Snx22 | 0.031826382 | 0.05 | 0 | 0.031826382 |
| Car12 | 0.127232648 | 0.1 | 0 | 0.127232648 |
| Fam81a | 0.046887496 | 0.05 | 0 | 0.046887496 |
| 4933433G15Rik | 0.034683507 | 0.05 | 0 | 0.034683507 |
| A130057D12Rik | 0.06031708 | 0.05 | 0 | 0.06031708 |
| Lca5 | 0.059211238 | 0.1 | 0 | 0.059211238 |
| Elovl4 | 0.021191554 | 0.05 | 0 | 0.021191554 |
| 9430037G07Rik | 0.143478938 | 0.15 | 0 | 0.143478938 |
| Adamts7 | 0.027437878 | 0.05 | 0 | 0.027437878 |
| 4933400C23Rik | 0.039770285 | 0.05 | 0 | 0.039770285 |
| Slc9a9 | 0.034683507 | 0.05 | 0 | 0.034683507 |
| Nphp3 | 0.031826382 | 0.05 | 0 | 0.031826382 |
| Col6a5 | 0.069020924 | 0.1 | 0 | 0.069020924 |
| Glyctk | 0.142084329 | 0.05 | 0 | 0.142084329 |
| Mst1r | 0.146282937 | 0.1 | 0 | 0.146282937 |
| Traip | 0.073521686 | 0.1 | 0 | 0.073521686 |
| Col7a1 | 0.083258675 | 0.1 | 0 | 0.083258675 |
| Als2c1 | 0.027437878 | 0.05 | 0 | 0.027437878 |
| Gm2415 | 0.152448425 | 0.15 | 0 | 0.152448425 |
| Acaa1b | 0.031826382 | 0.05 | 0 | 0.031826382 |
| Acvr2b | 0.027437878 | 0.05 | 0 | 0.027437878 |
| Ulk4 | 0.056077601 | 0.05 | 0 | 0.056077601 |
| Cck | 0.021191554 | 0.05 | 0 | 0.021191554 |
| Lyzl4 | 0.027497498 | 0.05 | 0 | 0.027497498 |
| Ccr5 | 0.070361859 | 0.05 | 0 | 0.070361859 |
| Lif | 0.17385255 | 0.1 | 0 | 0.17385255 |
| Rasl10a | 0.030059739 | 0.05 | 0 | 0.030059739 |
| Nacad | 0.036749186 | 0.05 | 0 | 0.036749186 |
| Gm12056 | 0.034683507 | 0.05 | 0 | 0.034683507 |
| Zrsr1 | 0.034683507 | 0.05 | 0 | 0.034683507 |
| Papolg | 0.021191554 | 0.05 | 0 | 0.021191554 |
| Adra1b | 0.046887496 | 0.05 | 0 | 0.046887496 |
| Trim7 | 0.036749186 | 0.05 | 0 | 0.036749186 |
| Col23a1 | 0.056077601 | 0.05 | 0 | 0.056077601 |
| Jade2 | 0.07614006 | 0.1 | 0 | 0.07614006 |
| Cdkl3 | 0.056077601 | 0.05 | 0 | 0.056077601 |
| Fam183b | 0.050322311 | 0.05 | 0 | 0.050322311 |
| 2810021J22Rik | 0.034683507 | 0.05 | 0 | 0.034683507 |
| Gjc2 | 0.076466924 | 0.1 | 0 | 0.076466924 |
| Jmjd4 | 0.181135885 | 0.2 | 0 | 0.181135885 |
| Zkscan6 | 0.034683507 | 0.05 | 0 | 0.034683507 |
| Usp43 | 0.054363654 | 0.05 | 0 | 0.054363654 |
| 9130213A22Rik | 0.036749186 | 0.05 | 0 | 0.036749186 |
| Kcnab3 | 0.064027859 | 0.05 | 0 | 0.064027859 |
| Efnb3 | 0.054363654 | 0.05 | 0 | 0.054363654 |
| Cd68 | 0.103413163 | 0.1 | 0 | 0.103413163 |
| Zmynd15 | 0.056077601 | 0.05 | 0 | 0.056077601 |
| 4933427D14Rik | 0.083146802 | 0.1 | 0 | 0.083146802 |
| Rap1gap2 | 0.072997629 | 0.1 | 0 | 0.072997629 |
| Rph3al | 0.070361859 | 0.05 | 0 | 0.070361859 |
| Gemin4 | 0.019980585 | 0.05 | 0 | 0.019980585 |
| Dbil5 | 0.021191554 | 0.05 | 0 | 0.021191554 |

TABLE 2-continued

| Gene | Normalized_Expression (log2TPX) | percent_KO | percent_WT | Absolute_Normalized_Expression |
|---|---|---|---|---|
| Atad5 | 0.056995491 | 0.1 | 0 | 0.056995491 |
| Adap2 | 0.064027859 | 0.05 | 0 | 0.064027859 |
| Rhbdl3 | 0.021191554 | 0.05 | 0 | 0.021191554 |
| Tmem132e | 0.056077601 | 0.05 | 0 | 0.056077601 |
| Gm11423 | 0.106437307 | 0.15 | 0 | 0.106437307 |
| Slfn9 | 0.021191554 | 0.05 | 0 | 0.021191554 |
| Slfn8 | 0.214006115 | 0.15 | 0 | 0.214006115 |
| Slfn1 | 0.027497498 | 0.05 | 0 | 0.027497498 |
| Slfn4 | 0.027437878 | 0.05 | 0 | 0.027437878 |
| Rasl10b | 0.050817446 | 0.1 | 0 | 0.050817446 |
| Ccl5 | 2.463086534 | 0.15 | 0 | 2.463086534 |
| Dusp14 | 0.118213262 | 0.05 | 0 | 0.118213262 |
| Myo19 | 0.070361859 | 0.05 | 0 | 0.070361859 |
| Car4 | 0.58794336 | 0.05 | 0 | 0.58794336 |
| Rad51c | 0.027497498 | 0.05 | 0 | 0.027497498 |
| Pctp | 0.046887496 | 0.05 | 0 | 0.046887496 |
| Cdc34b | 0.06031708 | 0.05 | 0 | 0.06031708 |
| Dlx3 | 0.034683507 | 0.05 | 0 | 0.034683507 |
| Dlx4 | 0.079612773 | 0.05 | 0 | 0.079612773 |
| Gm11520 | 0.034683507 | 0.05 | 0 | 0.034683507 |
| Fam117a | 0.039770285 | 0.05 | 0 | 0.039770285 |
| Skap1 | 0.027497498 | 0.05 | 0 | 0.027497498 |
| Cacnb1 | 0.139921944 | 0.1 | 0 | 0.139921944 |
| Rapgefl1 | 0.056077601 | 0.05 | 0 | 0.056077601 |
| Gm11940 | 0.034683507 | 0.05 | 0 | 0.034683507 |
| Krt36 | 0.056077601 | 0.05 | 0 | 0.056077601 |
| Hap1 | 0.034683507 | 0.05 | 0 | 0.034683507 |
| Wnk4 | 0.06031708 | 0.05 | 0 | 0.06031708 |
| Aarsd1 | 0.14971165 | 0.15 | 0 | 0.14971165 |
| Gm11551 | 0.042076328 | 0.05 | 0 | 0.042076328 |
| Nags | 0.141693282 | 0.05 | 0 | 0.141693282 |
| Gm11627 | 0.039688224 | 0.05 | 0 | 0.039688224 |
| 2810433D01Rik | 0.076885834 | 0.1 | 0 | 0.076885834 |
| 2410004I01Rik | 0.050322311 | 0.05 | 0 | 0.050322311 |
| Arhgap27os2 | 0.036749186 | 0.05 | 0 | 0.036749186 |
| Milr1 | 0.046887496 | 0.05 | 0 | 0.046887496 |
| Polg2 | 0.027497498 | 0.05 | 0 | 0.027497498 |
| Rgs9 | 0.050322311 | 0.05 | 0 | 0.050322311 |
| D11Wsu47e | 0.077304814 | 0.1 | 0 | 0.077304814 |
| Galr2 | 0.036749186 | 0.05 | 0 | 0.036749186 |
| Mgat5b | 0.039770285 | 0.05 | 0 | 0.039770285 |
| Tbc1d16 | 0.06031708 | 0.05 | 0 | 0.06031708 |
| Aatk | 0.027437878 | 0.05 | 0 | 0.027437878 |
| Sectm1a | 0.021191554 | 0.05 | 0 | 0.021191554 |
| B3gntl1 | 0.056927414 | 0.05 | 0 | 0.056927414 |
| Heatr1 | 0.050322311 | 0.05 | 0 | 0.050322311 |
| Ero1lb | 0.019980585 | 0.05 | 0 | 0.019980585 |
| Vdac3-ps1 | 0.056937079 | 0.1 | 0 | 0.056937079 |
| Gpr141 | 0.110056776 | 0.05 | 0 | 0.110056776 |
| Hist1h2bp | 0.056995491 | 0.1 | 0 | 0.056995491 |
| Hist1h2bk | 0.031826382 | 0.05 | 0 | 0.031826382 |
| Hist1h4h | 0.036749186 | 0.05 | 0 | 0.036749186 |
| Hist1h3d | 0.031826382 | 0.05 | 0 | 0.031826382 |
| Hist1h4c | 0.064027859 | 0.05 | 0 | 0.064027859 |
| Hist1h2ab | 0.021191554 | 0.05 | 0 | 0.021191554 |
| Hist1h3a | 0.034683507 | 0.05 | 0 | 0.034683507 |
| Lrrc16a | 0.073521686 | 0.1 | 0 | 0.073521686 |
| Gm26735 | 0.019980585 | 0.05 | 0 | 0.019980585 |
| Serpinb1b | 0.039770285 | 0.05 | 0 | 0.039770285 |
| Bmp6 | 0.079612773 | 0.05 | 0 | 0.079612773 |
| Sirt5 | 0.027437878 | 0.05 | 0 | 0.027437878 |
| Nhlrc1 | 0.056927414 | 0.05 | 0 | 0.056927414 |
| A830005F24Rik | 0.027437878 | 0.05 | 0 | 0.027437878 |
| Ptpdc1 | 0.050322311 | 0.05 | 0 | 0.050322311 |
| Ippk | 0.090284384 | 0.1 | 0 | 0.090284384 |
| Omd | 0.082907736 | 0.05 | 0 | 0.082907736 |
| Diras2 | 0.036749186 | 0.05 | 0 | 0.036749186 |
| Syk | 0.079361919 | 0.1 | 0 | 0.079361919 |
| Gm5449 | 0.021191554 | 0.05 | 0 | 0.021191554 |
| Unc5a | 0.056077601 | 0.05 | 0 | 0.056077601 |
| Fancc | 0.148127207 | 0.15 | 0 | 0.148127207 |
| Cdc14b | 0.070361859 | 0.05 | 0 | 0.070361859 |
| 1810034E14Rik | 0.086703412 | 0.1 | 0 | 0.086703412 |
| Gm37276 | 0.021191554 | 0.05 | 0 | 0.021191554 |
| Mtrr | 0.258469225 | 0.25 | 0 | 0.258469225 |
| Adamts16 | 0.098948343 | 0.05 | 0 | 0.098948343 |
| Cep72 | 0.068552733 | 0.05 | 0 | 0.068552733 |
| Gm17259 | 0.034683507 | 0.05 | 0 | 0.034683507 |

TABLE 2-continued

| Gene | Normalized_Expression (log2TPX) | percent_KO | percent_WT | Absolute_Normalized_Expression |
|---|---|---|---|---|
| Rasgrf2 | 0.046887496 | 0.05 | 0 | 0.046887496 |
| Msh3 | 0.058671133 | 0.1 | 0 | 0.058671133 |
| Mtx3 | 0.064027859 | 0.05 | 0 | 0.064027859 |
| Cmya5 | 0.142084329 | 0.05 | 0 | 0.142084329 |
| S100z | 0.027497498 | 0.05 | 0 | 0.027497498 |
| Gm6169 | 0.021191554 | 0.05 | 0 | 0.021191554 |
| Gm26619 | 0.056927414 | 0.05 | 0 | 0.056927414 |
| Gm9828 | 0.027437878 | 0.05 | 0 | 0.027437878 |
| Naip2 | 0.056077601 | 0.05 | 0 | 0.056077601 |
| Naip6 | 0.039770285 | 0.05 | 0 | 0.039770285 |
| Ppwd1 | 0.142084329 | 0.05 | 0 | 0.142084329 |
| Gm10735 | 0.019980585 | 0.05 | 0 | 0.019980585 |
| Hcn1 | 0.039770285 | 0.05 | 0 | 0.039770285 |
| Gm7120 | 0.019980585 | 0.05 | 0 | 0.019980585 |
| Gm26520 | 0.027497498 | 0.05 | 0 | 0.027497498 |
| Fam228b | 0.027437878 | 0.05 | 0 | 0.027437878 |
| Kcns3 | 0.021191554 | 0.05 | 0 | 0.021191554 |
| Greb1 | 0.027497498 | 0.05 | 0 | 0.027497498 |
| 5730507C01Rik | 0.027497498 | 0.05 | 0 | 0.027497498 |
| Gm3944 | 0.070361859 | 0.05 | 0 | 0.070361859 |
| Gm10479 | 0.027497498 | 0.05 | 0 | 0.027497498 |
| 2410018L13Rik | 0.056937079 | 0.1 | 0 | 0.056937079 |
| 9030624G23Rik | 0.050322311 | 0.05 | 0 | 0.050322311 |
| Taf1b | 0.027437878 | 0.05 | 0 | 0.027437878 |
| Dus4l | 0.067406193 | 0.1 | 0 | 0.067406193 |
| Ispd | 0.070361859 | 0.05 | 0 | 0.070361859 |
| Prps1l3 | 0.079612773 | 0.05 | 0 | 0.079612773 |
| Gpr135 | 0.019980585 | 0.05 | 0 | 0.019980585 |
| 4930447C04Rik | 0.034683507 | 0.05 | 0 | 0.034683507 |
| Tmem30b | 0.050322311 | 0.05 | 0 | 0.050322311 |
| Hspa2 | 0.095579746 | 0.1 | 0 | 0.095579746 |
| Exd2 | 0.039770285 | 0.05 | 0 | 0.039770285 |
| Zfyve1 | 0.019980585 | 0.05 | 0 | 0.019980585 |
| 2410016O06Rik | 0.039770285 | 0.05 | 0 | 0.039770285 |
| Acot4 | 0.021191554 | 0.05 | 0 | 0.021191554 |
| Dnal1 | 0.059211238 | 0.1 | 0 | 0.059211238 |
| Pnma1 | 0.06031708 | 0.05 | 0 | 0.06031708 |
| Lin52 | 0.096477356 | 0.15 | 0 | 0.096477356 |
| Gm16381 | 0.0470446 | 0.1 | 0 | 0.0470446 |
| Em15 | 0.031826382 | 0.05 | 0 | 0.031826382 |
| Serpina3f | 0.076466924 | 0.1 | 0 | 0.076466924 |
| Wdr25 | 0.019980585 | 0.05 | 0 | 0.019980585 |
| Tecpr2 | 0.021191554 | 0.05 | 0 | 0.021191554 |
| Amn | 0.031826382 | 0.05 | 0 | 0.031826382 |
| Gm266 | 0.021191554 | 0.05 | 0 | 0.021191554 |
| 2810029C07Rik | 0.040882771 | 0.1 | 0 | 0.040882771 |
| Ptger4 | 0.059505921 | 0.05 | 0 | 0.059505921 |
| Fyb | 0.021191554 | 0.05 | 0 | 0.021191554 |
| Slc1a3 | 0.096572099 | 0.1 | 0 | 0.096572099 |
| 4930556M19Rik | 0.027497498 | 0.05 | 0 | 0.027497498 |
| Fbxl7 | 0.021191554 | 0.05 | 0 | 0.021191554 |
| Nipal2 | 0.163293078 | 0.15 | 0 | 0.163293078 |
| Spag1 | 0.082907736 | 0.05 | 0 | 0.082907736 |
| Baalc | 0.036749186 | 0.05 | 0 | 0.036749186 |
| Lrp12 | 0.055375267 | 0.1 | 0 | 0.055375267 |
| Zfpm2 | 0.079612773 | 0.05 | 0 | 0.079612773 |
| Angpt1 | 0.089454 | 0.1 | 0 | 0.089454 |
| Has2 | 0.213937369 | 0.15 | 0 | 0.213937369 |
| Gm16006 | 0.082907736 | 0.05 | 0 | 0.082907736 |
| Gsdmc | 0.021191554 | 0.05 | 0 | 0.021191554 |
| Zfat | 0.059505921 | 0.05 | 0 | 0.059505921 |
| Ly6k | 0.199590791 | 0.1 | 0 | 0.199590791 |
| Gml | 0.070361859 | 0.05 | 0 | 0.070361859 |
| Mapk15 | 0.027437878 | 0.05 | 0 | 0.027437878 |
| Nrbp2 | 0.039770285 | 0.05 | 0 | 0.039770285 |
| Smpd5 | 0.064027859 | 0.05 | 0 | 0.064027859 |
| Kifc2 | 0.056077601 | 0.05 | 0 | 0.056077601 |
| Gpt | 0.021191554 | 0.05 | 0 | 0.021191554 |
| Zfp251 | 0.056077601 | 0.05 | 0 | 0.056077601 |
| Apol7a | 0.142084329 | 0.05 | 0 | 0.142084329 |
| Phf21b | 0.027437878 | 0.05 | 0 | 0.027437878 |
| Ppp6r2 | 0.102028857 | 0.1 | 0 | 0.102028857 |
| Alg10b | 0.036749186 | 0.05 | 0 | 0.036749186 |
| Prickle1 | 0.070111089 | 0.15 | 0 | 0.070111089 |
| A130051J06Rik | 0.030059739 | 0.05 | 0 | 0.030059739 |
| Slc4a8 | 0.079612773 | 0.05 | 0 | 0.079612773 |
| Krt7 | 0.031826382 | 0.05 | 0 | 0.031826382 |
| Soat2 | 0.036749186 | 0.05 | 0 | 0.036749186 |

TABLE 2-continued

| Gene | Normalized_Expression (log2TPX) | percent_KO | percent_WT | Absolute_Normalized_Expression |
|---|---|---|---|---|
| Gm26518 | 0.083830586 | 0.1 | 0 | 0.083830586 |
| Hoxc5 | 0.019980585 | 0.05 | 0 | 0.019980585 |
| D930007P13Rik | 0.036749186 | 0.05 | 0 | 0.036749186 |
| Slx4 | 0.188586332 | 0.1 | 0 | 0.188586332 |
| Srl | 0.030059739 | 0.05 | 0 | 0.030059739 |
| 2610020C07Rik | 0.077918297 | 0.15 | 0 | 0.077918297 |
| Snx29 | 0.027437878 | 0.05 | 0 | 0.027437878 |
| 3110001I22Rik | 0.050322311 | 0.05 | 0 | 0.050322311 |
| Pkp2 | 0.046887496 | 0.05 | 0 | 0.046887496 |
| Gm15648 | 0.019980585 | 0.05 | 0 | 0.019980585 |
| Rtn4r | 0.042076328 | 0.05 | 0 | 0.042076328 |
| Tbx1 | 0.034683507 | 0.05 | 0 | 0.034683507 |
| Clcn2 | 0.036749186 | 0.05 | 0 | 0.036749186 |
| Chrd | 0.161532628 | 0.15 | 0 | 0.161532628 |
| BC106179 | 0.027437878 | 0.05 | 0 | 0.027437878 |
| Cldn1 | 0.030059739 | 0.05 | 0 | 0.030059739 |
| Fgfl2 | 0.050322311 | 0.05 | 0 | 0.050322311 |
| Bdh1 | 0.021191554 | 0.05 | 0 | 0.021191554 |
| Ccdc14 | 0.046887496 | 0.05 | 0 | 0.046887496 |
| Zbtb11os1 | 0.141111611 | 0.15 | 0 | 0.141111611 |
| Eva1c | 0.080645506 | 0.05 | 0 | 0.080645506 |
| Dopey2 | 0.153971183 | 0.2 | 0 | 0.153971183 |
| Zfp97 | 0.079612773 | 0.05 | 0 | 0.079612773 |
| Gm7535 | 0.031826382 | 0.05 | 0 | 0.031826382 |
| Zfp944 | 0.149474551 | 0.15 | 0 | 0.149474551 |
| Kifc5b | 0.036749186 | 0.05 | 0 | 0.036749186 |
| Syngap1 | 0.021191554 | 0.05 | 0 | 0.021191554 |
| Ip6k3 | 0.031826382 | 0.05 | 0 | 0.031826382 |
| Gm26549 | 0.185914903 | 0.15 | 0 | 0.185914903 |
| Zfp811 | 0.083370704 | 0.1 | 0 | 0.083370704 |
| Zfp799 | 0.030059739 | 0.05 | 0 | 0.030059739 |
| Zfp870 | 0.115201526 | 0.15 | 0 | 0.115201526 |
| Zfp563 | 0.070361859 | 0.05 | 0 | 0.070361859 |
| Myo1f | 0.070361859 | 0.05 | 0 | 0.070361859 |
| H2-Ob | 0.079612773 | 0.05 | 0 | 0.079612773 |
| Aif1 | 0.056927414 | 0.05 | 0 | 0.056927414 |
| H2-Q1 | 0.072585481 | 0.05 | 0 | 0.072585481 |
| H2-Q2 | 0.107553141 | 0.05 | 0 | 0.107553141 |
| Pou5f1 | 0.019980585 | 0.05 | 0 | 0.019980585 |
| Gm20442 | 0.036749186 | 0.05 | 0 | 0.036749186 |
| Ppp1r18os | 0.056077601 | 0.05 | 0 | 0.056077601 |
| BC023719 | 0.036749186 | 0.05 | 0 | 0.036749186 |
| Gm8909 | 0.036749186 | 0.05 | 0 | 0.036749186 |
| Ankrd66 | 0.027497498 | 0.05 | 0 | 0.027497498 |
| Enpp5 | 0.089454 | 0.1 | 0 | 0.089454 |
| 1600014C23Rik | 0.019980585 | 0.05 | 0 | 0.019980585 |
| Rsph9 | 0.039770285 | 0.05 | 0 | 0.039770285 |
| Cul9 | 0.170204858 | 0.1 | 0 | 0.170204858 |
| Plcl2 | 0.142084329 | 0.05 | 0 | 0.142084329 |
| Prr22 | 0.039770285 | 0.05 | 0 | 0.039770285 |
| Vav1 | 0.082907736 | 0.05 | 0 | 0.082907736 |
| Cdkl4 | 0.072585481 | 0.05 | 0 | 0.072585481 |
| Thumpd2 | 0.052558867 | 0.1 | 0 | 0.052558867 |
| Kcnk12 | 0.048291839 | 0.1 | 0 | 0.048291839 |
| Gm6225 | 0.050322311 | 0.05 | 0 | 0.050322311 |
| Gm17430 | 0.019980585 | 0.05 | 0 | 0.019980585 |
| Dsc2 | 0.093596664 | 0.1 | 0 | 0.093596664 |
| Rprd1a | 0.06031708 | 0.05 | 0 | 0.06031708 |
| Gm3550 | 0.087602028 | 0.15 | 0 | 0.087602028 |
| Prob1 | 0.046887496 | 0.05 | 0 | 0.046887496 |
| Pcdhb17 | 0.019980585 | 0.05 | 0 | 0.019980585 |
| Gpr151 | 0.056077601 | 0.05 | 0 | 0.056077601 |
| Eif3j2 | 0.119460996 | 0.1 | 0 | 0.119460996 |
| Cdo1 | 0.079612773 | 0.05 | 0 | 0.079612773 |
| Eno1b | 0.082629185 | 0.15 | 0 | 0.082629185 |
| Dtwd2 | 0.030059739 | 0.05 | 0 | 0.030059739 |
| Gm4841 | 0.050322311 | 0.05 | 0 | 0.050322311 |
| Spink10 | 0.050322311 | 0.05 | 0 | 0.050322311 |
| Pmaip1 | 0.027437878 | 0.05 | 0 | 0.027437878 |
| Lipg | 0.034683507 | 0.05 | 0 | 0.034683507 |
| Katnal2 | 0.039770285 | 0.05 | 0 | 0.039770285 |
| 8030462N17Rik | 0.115256931 | 0.15 | 0 | 0.115256931 |
| Epg5 | 0.075532536 | 0.1 | 0 | 0.075532536 |
| Hsbp1l1 | 0.040882771 | 0.1 | 0 | 0.040882771 |
| Syt12 | 0.056927414 | 0.05 | 0 | 0.056927414 |
| Fosl1 | 0.299861459 | 0.25 | 0 | 0.299861459 |
| Ctsw | 0.080645506 | 0.05 | 0 | 0.080645506 |
| Ccdc88b | 0.039770285 | 0.05 | 0 | 0.039770285 |

TABLE 2-continued

| Gene | Normalized_Expression (log2TPX) | percent_KO | percent_WT | Absolute_Normalized_Expression |
|---|---|---|---|---|
| Macrod1 | 0.158369767 | 0.15 | 0 | 0.158369767 |
| Pcna-ps2 | 0.036749186 | 0.05 | 0 | 0.036749186 |
| Best1 | 0.135910371 | 0.1 | 0 | 0.135910371 |
| Ms4a6b | 0.064027859 | 0.05 | 0 | 0.064027859 |
| Mpeg1 | 0.110875389 | 0.1 | 0 | 0.110875389 |
| Vps13a | 0.076885834 | 0.1 | 0 | 0.076885834 |
| 2410080I02Rik | 0.110056776 | 0.05 | 0 | 0.110056776 |
| 4430402I18Rik | 0.06031708 | 0.05 | 0 | 0.06031708 |
| Cd274 | 0.056927414 | 0.05 | 0 | 0.056927414 |
| Ranbp6 | 0.021191554 | 0.05 | 0 | 0.021191554 |
| Rnls | 0.036749186 | 0.05 | 0 | 0.036749186 |
| Exoc6 | 0.106605047 | 0.1 | 0 | 0.106605047 |
| Sorbs1 | 0.050322311 | 0.05 | 0 | 0.050322311 |
| Tctn3 | 0.064027859 | 0.05 | 0 | 0.064027859 |
| Slit1 | 0.072585481 | 0.05 | 0 | 0.072585481 |
| Loxl4 | 0.021191554 | 0.05 | 0 | 0.021191554 |
| Neurl1a | 0.031826382 | 0.05 | 0 | 0.031826382 |
| Gpam | 0.031826382 | 0.05 | 0 | 0.031826382 |
| B230217O12Rik | 0.027437878 | 0.05 | 0 | 0.027437878 |
| Sfxn4 | 0.050322311 | 0.05 | 0 | 0.050322311 |

Figure 39:
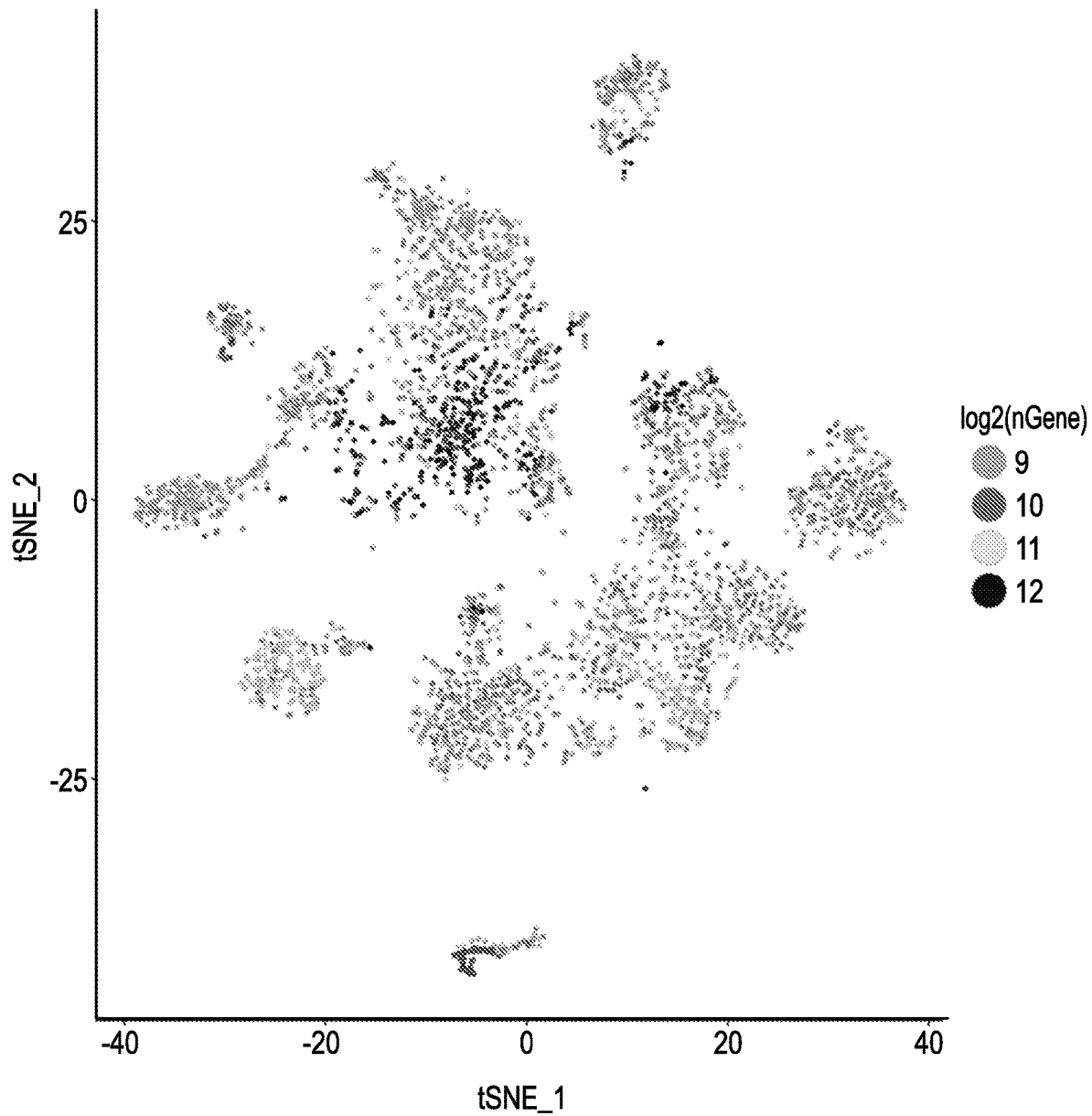
FIG. 39 illustrates the number of expressed genes on the tSNE analysis in FIG. 37.

Applicants also identified clusters with high numbers of genes expressed in sorted cells (WT+C3 KO combined) (FIG. 39).

CAFs are important for survival and response to treatment (see, e.g., Su et al., CD10+GPR77+ Cancer-Associated Fibroblasts Promote Cancer Formation and Chemoresistance by Sustaining Cancer Stemness, 2018, Cell 172, 1-16). Applicants have shown the importance of C3 in tumor control and CAF activation in the tumor microenvironment. C3 signaling in the tumor microenvironment may affect TILs, specifically the TIL states (e.g., activated vs exhausted) of T-cell subsets (Tregs vs Thelper vs CTLs etc). C3 is involved in immune surveillance and its absence has now been shown to be protective. Applicants observed an increase in complement in CAFs and this was associated with an increase in infiltration of lymphocytes. Not being bound by a theory CAFs can be inactivated by C3 in response to TIL infiltration. Not being bound by a theory C3 inhibition in CAFs causes the CAFs to be activated and this controls tumor growth in the tumor microenvironment, possibly through regulation of TILs.

Example 6—Methods

Cell type-specific signatures and deconvolution of bulk expression profiles. To identify genes that may mediate interactions between cell types Applicants examined the correlation between the expression of genes that are expressed primarily by one cell type, based on single cell profiles, and the relative frequency of another cell type, based on bulk TCGA profiles. Applicants focused on comparison of T cells and CAFs and identified a set of genes that although they have much higher expression in CAFs than in T cells (fold-change>4 across single cells), their expression in bulk tumors is highly correlated (R>0.5) with the estimated relative abundance of T cells (Table 3). The correlation between complement expression (the CAF signature) and T cell proportion (the T cell signature) is maintained in many cancer, and far less/non-existent in normal tissues in GTEX. A similar analysis was performed for all other pairs of cell-types (FIG. 5). These are candidates for therapeutic manipulation.

TABLE 3

CAF-expressed genes that correlate with the abundance of T-cells

| CAF-expressed, T/B-cell correlated genes | corr. With T | corr. With B | Exp(Stroma)-Exp(T) | Exp(Stroma)-Exp(B) |
|---|---|---|---|---|
| C1S | 0.6427 | 0.5602 | 8.5056 | 9.1346 |
| UBD | 0.8315 | 0.6448 | 7.4089 | 6.6673 |
| SERPING1 | 0.654 | 0.5038 | 7.8987 | 6.7935 |
| CCL19 | 0.6804 | 0.8174 | 7.3149 | 7.7101 |
| C3 | 0.6218 | 0.6592 | 7.376 | 7.9377 |
| TGM2 | 0.5066 | 0.4779 | 7.2166 | 7.4967 |
| CXCL9 | 0.8843 | 0.6474 | 6.05 | 5.0659 |
| CXCL12 | 0.6146 | 0.6264 | 6.8387 | 7.6955 |
| TMEM176A | 0.7123 | 0.6878 | 6.5212 | 6.1329 |
| TMEM176B | 0.7597 | 0.6944 | 6.3695 | 6.355 |
| STAB1 | 0.5043 | 0.5036 | 6.9587 | 7.123 |
| CCL2 | 0.5939 | 0.5702 | 6.6362 | 6.5794 |
| PLXDC2 | 0.5126 | 0.4198 | 6.4016 | 5.8247 |
| C1R | 0.5927 | 0.5121 | 6.0416 | 8.8604 |
| CLIC2 | 0.6149 | 0.5437 | 5.9547 | 5.2628 |
| ALDH2 | 0.5594 | 0.5011 | 6.0847 | 2.554 |
| IL3RA | 0.5823 | 0.6769 | 5.7522 | 5.7951 |
| FPR2 | 0.6515 | 0.4368 | 5.518 | 5.1341 |
| SERPINA1 | 0.7051 | 0.5423 | 5.2067 | 4.9607 |
| FCGR1A | 0.7911 | 0.558 | 4.9287 | 4.8433 |
| CYBB | 0.7772 | 0.6783 | 4.9267 | −0.6677 |
| FCER1G | 0.6571 | 0.5105 | 5.2772 | 5.6419 |
| CD33 | 0.6287 | 0.5308 | 5.3447 | 4.8667 |
| LMO2 | 0.6401 | 0.6525 | 5.2456 | 2.6269 |
| SLC7A7 | 0.7918 | 0.677 | 4.7193 | 1.2406 |
| CSF1R | 0.7088 | 0.6403 | 4.7985 | 4.1882 |
| C1orf54 | 0.6741 | 0.5969 | 4.8415 | 4.1724 |
| IL34 | 0.5268 | 0.5875 | 5.2006 | 4.9851 |
| C4A | 0.5342 | 0.5331 | 5.0867 | 3.6486 |
| LILRB2 | 0.8126 | 0.6318 | 4.2076 | 3.413 |
| CSF2RB | 0.8282 | 0.8371 | 4.086 | 3.2589 |
| FPR1 | 0.6026 | 0.4769 | 4.688 | 3.4311 |
| CARD9 | 0.702 | 0.607 | 4.2483 | 3.7544 |
| TNFAIP2 | 0.721 | 0.6305 | 4.1466 | 4.1593 |
| SLCO2B1 | 0.6674 | 0.6414 | 4.2601 | 4.1278 |
| PKHD1L1 | 0.5344 | 0.6724 | 4.6243 | 3.7536 |
| FCN1 | 0.6645 | 0.5696 | 4.1683 | 3.797 |
| GP1BA | 0.586 | 0.7698 | 4.4014 | 4.1461 |
| SIGLEC6 | 0.5803 | 0.7426 | 4.4152 | 1.6201 |
| CFB | 0.6177 | 0.4997 | 4.2981 | 4.5079 |
| P2RX1 | 0.7057 | 0.7816 | 4.0268 | 1.0778 |
| NR1H3 | 0.6209 | 0.5427 | 4.2767 | 3.0717 |
| GPBAR1 | 0.7153 | 0.5332 | 3.982 | 4.0663 |
| RGS18 | 0.7173 | 0.6346 | 3.9658 | 4.0236 |
| IL7 | 0.5684 | 0.5081 | 4.3512 | 2.1569 |
| IFI30 | 0.7563 | 0.6052 | 3.7497 | 0.7839 |

TABLE 3-continued

CAF-expressed genes that correlate with the abundance of T-cells

| CAF-expressed, T/B-cell correlated genes | corr. With T | corr. With B | Exp(Stroma)-Exp(T) | Exp(Stroma)-Exp(B) |
|---|---|---|---|---|
| CLEC12A | 0.7339 | 0.5695 | 3.7939 | 4.7004 |
| TYROBP | 0.7613 | 0.6212 | 3.704 | 3.6344 |
| HCK | 0.8049 | 0.7162 | 3.332 | 2.0961 |
| PIK3R6 | 0.7079 | 0.6681 | 3.6123 | 2.9298 |
| ADAP2 | 0.6982 | 0.5583 | 3.6361 | 1.7039 |
| CD14 | 0.65 | 0.5399 | 3.7675 | 5.0578 |
| GHRL | 0.6626 | 0.7863 | 3.6905 | 3.8084 |
| SIGLEC9 | 0.6999 | 0.5765 | 3.5768 | 4.1243 |
| TMEM37 | 0.5852 | 0.591 | 3.8859 | 3.3609 |
| LILRA1 | 0.7067 | 0.6562 | 3.501 | 2.7022 |
| DHRS9 | 0.6137 | 0.6338 | 3.7097 | 1.8531 |
| PECAM1 | 0.6303 | 0.6685 | 3.6566 | 4.0629 |
| SPI1 | 0.782 | 0.7028 | 3.1278 | 0.44 |
| IL15RA | 0.8483 | 0.7059 | 2.904 | 5.0966 |
| SLC8A1 | 0.6955 | 0.5858 | 3.336 | 3.4454 |
| RBP5 | 0.5908 | 0.7632 | 3.6363 | 4.2231 |
| FGL2 | 0.6938 | 0.58 | 3.3051 | 3.3252 |
| MNDA | 0.7768 | 0.649 | 3.041 | 1.6354 |
| VNN1 | 0.5805 | 0.5384 | 3.6243 | 3.4418 |
| FLT3 | 0.8024 | 0.8645 | 2.9555 | 2.7583 |
| SOD2 | 0.6537 | 0.483 | 3.3772 | 3.6145 |
| CXCL11 | 0.7862 | 0.5054 | 2.9284 | 1.7897 |
| CLEC10A | 0.7288 | 0.7206 | 3.075 | 1.5159 |
| KIF19 | 0.632 | 0.5924 | 3.3161 | 3.479 |
| HSD11B1 | 0.7324 | 0.6252 | 2.9007 | 5.061 |
| CXorf21 | 0.7986 | 0.7615 | 2.6654 | 1.0901 |
| KEL | 0.5108 | 0.6335 | 3.5054 | 3.4601 |
| RARRES1 | 0.5535 | 0.5304 | 3.294 | 4.2727 |
| CFP | 0.6405 | 0.7309 | 3.0086 | 5.3814 |
| TNFSF10 | 0.7397 | 0.6063 | 2.6883 | 3.7574 |
| LILRB4 | 0.8079 | 0.6724 | 2.4161 | 2.5607 |
| P2RY12 | 0.5291 | 0.4793 | 3.2508 | 0.6342 |
| RSPO3 | 0.6312 | 0.664 | 2.8586 | 3.3143 |
| FGR | 0.7674 | 0.7263 | 2.4379 | 2.5568 |
| DRAM1 | 0.6425 | 0.4365 | 2.7659 | 1.9578 |
| ANKRD22 | 0.8067 | 0.5523 | 2.2727 | 1.9429 |
| P2RY13 | 0.83 | 0.78 | 2.1731 | 1.0301 |
| CLEC4A | 0.755 | 0.6835 | 2.3837 | 0.6484 |
| HK3 | 0.7416 | 0.5854 | 2.4237 | 2.4947 |
| FBP1 | 0.652 | 0.551 | 2.6863 | 2.8232 |
| IL18BP | 0.8309 | 0.6479 | 2.0746 | 1.5386 |
| PILRA | 0.757 | 0.6081 | 2.2904 | 2.2428 |
| TFEC | 0.776 | 0.6433 | 2.1393 | 1.1232 |
| CXCL16 | 0.5645 | 0.4462 | 2.7645 | 1.5609 |
| FCGR3A | 0.7456 | 0.4996 | 2.185 | 6.9459 |
| WARS | 0.592 | 0.3048 | 2.6364 | 2.8448 |
| LAP3 | 0.646 | 0.4136 | 2.4573 | 3.1552 |
| LGMN | 0.5569 | 0.3972 | 2.6516 | 3.0199 |
| CMKLR1 | 0.7127 | 0.6338 | 2.1556 | 1.6946 |
| RBM47 | 0.6204 | 0.5302 | 2.4299 | 1.4025 |
| SLC43A2 | 0.5629 | 0.5127 | 2.5179 | 0.8269 |
| LRRC25 | 0.7206 | 0.6321 | 2.0053 | 1.3417 |
| CP | 0.573 | 0.6772 | 2.3796 | 3.0212 |
| SLC40A1 | 0.5064 | 0.5608 | 2.4482 | 5.2851 |
| MAFB | 0.5796 | 0.4531 | 2.2015 | 2.6236 |
| CD163 | 0.622 | 0.4865 | 2.0074 | 0.9562 |
| SH2D3C | 0.5986 | 0.7095 | 2.0363 | 1.6083 |
| ODF3B | 0.5278 | 0.4128 | 2.1018 | 2.2454 |
| TLR2 | 0.5331 | 0.3832 | 2.0839 | 1.1407 |

The first column include the names of genes with average expression higher in CAFs than in T-cells by at least 4-fold (based on single cell data) and with a correlation of at least 0.5 with the abundance of T-cells across TCGA tumors.
The second to fifth columns include the correlation with T and B cell abumdances, and the expression difference (log-ratio) between CAF and T or B cells.
Genes are sorted by the average of the fourth and fifth columns.

Additional methods used to study single cells in tumor samples are available (see e.g., International patent applications PCT/US2016/40015, filed Jun. 29, 2016 and PCT/US2017/014995, filed Jan. 25, 2017; Tirosh et al., Dissecting the multicellular ecosystem of metastatic melanoma by single-cell RNA-seq, Science. 2016 Apr. 8; 352(6282):189-96); Tirosh et al., Single-cell RNA-seq supports a developmental hierarchy in human oligodendroglioma, Nature. (2016), vol. 539, pp. 309-313; and Venteicher et al., Decoupling genetics, lineages, and microenvironment in IDH-mutant gliomas by single-cell RNA-seq, Science. (2017), Mar 31;355(6332)).

REFERENCES

1. D. Hanahan, R. A. Weinberg, Hallmarks of cancer: the next generation. Cell. 144, 646-674 (2011).
2. C. E. Meacham, S. J. Morrison, Tumour heterogeneity and cancer cell plasticity. Nature. 501, 328-337 (2013).
3. F. S. Hodi et al., Improved Survival with Ipilimumab in Patients with Metastatic Melanoma. N. Engl. J. Med 363, 711-723 (2010).
4. J. R. Brahmer et al., Phase I study of single-agent anti-programmed death-1 (MDX-1106) in refractory solid tumors: safety, clinical activity, pharmacodynamics, and immunologic correlates. J. Clin. Oncol. Off J. Am. Soc. Clin. Oncol. 28, 3167-3175 (2010).
5. J. R. Brahmer et al., Safety and Activity of Anti-PD-L1 Antibody in Patients with Advanced Cancer. N. Engl. J. Med. 366, 2455-2465 (2012).
6. S. L. Topalian et al., Safety, activity, and immune correlates of anti-PD-1 antibody in cancer. N. Engl. J. Med. 366, 2443-2454 (2012).
7. O. Hamid et al., Safety and tumor responses with lambrolizumab (anti-PD-1) in melanoma. N. Engl. J. Med. 369, 134-144 (2013).
8. J. S. Weber et al., Safety, efficacy, and biomarkers of nivolumab with vaccine in ipilimumabrefractory or -naive melanoma. J. Clin. Oncol. Off J. Am. Soc. Clin. Oncol. 31, 4311-4318 (2013).
9. K. M. Mahoney, M. B. Atkins, Prognostic and predictive markers for the new immunotherapies. Oncol. Williston Park N. 28 Suppl 3, 39-48 (2014).
10. J. Larkin et al., Combined Nivolumab and Ipilimumab or Monotherapy in Untreated Melanoma. N. Engl. J. Med. 373, 23-34 (2015).
11. A. Snyder et al., Genetic basis for clinical response to CTLA-4 blockade in melanoma. N. Engl. J. Med. 371, 2189-2199 (2014).
12. N. Wagle et al., Dissecting Therapeutic Resistance to RAF Inhibition in Melanoma by Tumor Genomic Profiling. J. Clin. Oncol. (2011), doi:10.1200/JCO.2010.33.2312.
13. E. M. Van Allen et al., The genetic landscape of clinical resistance to RAF inhibition in metastatic melanoma. Cancer Discov. 4, 94-109 (2014).
14. A. K. Shalek et al., Single-cell transcriptomics reveals bimodality in expression and splicing in immune cells. Nature. 498, 236-240 (2013).
15. A. P. Patel et al., Single-cell RNA-seq highlights intratumoral heterogeneity in primary glioblastoma. Science. 344, 1396-1401 (2014).
16. E. Z. Macosko et al., Highly Parallel Genome-wide Expression Profiling of Individual Cells Using Nanoliter Droplets. Cell. 161, 1202-1214 (2015).
17. L. van der Maaten, G. Hinton, Visualizing Data using t-SNE. 9, 2579-2605 (2008).
18. M. Ester, H. Kriegel, J. Sander, and X. Xu, "A density-based algorithm for discovering clusters in large spatial databases with noise," in Proc. 2nd Int. Conf. Knowledge Discovery and Data Mining (KDD'96), 1996, pp. 226-231.
19. M. L. Whitfield, L. K. George, G. D. Grant, C. M. Perou, Common markers of proliferation. Nat. Rev. Cancer. 6, 99-106 (2006).

20. A. Roesch et al., A temporarily distinct subpopulation of slow-cycling melanoma cells is required for continuous tumor growth. *Cell*. 141, 583-594 (2010).
21. A first-in-human phase I study of the CDK4/6 inhibitor, LY2835219, for patients with advanced cancer. *J. Clin. Oncol.* (available at meetinglibrary.asco.org/content/111069-132).
22. C. M. Johannessen et al., A melanocyte lineage program confers resistance to MAP kinase pathway inhibition. *Nature*. 504, 138-142 (2013).
23. D. J. Konieczkowski et al., A melanoma cell state distinction influences sensitivity to MAPK pathway inhibitors. *Cancer Discov.* 4, 816-827 (2014).
24. L. A. Garraway et al., Integrative genomic analyses identify MITF as a lineage survival oncogene amplified in malignant melanoma. *Nature*. 436, 117-122 (2005).
25. Z. Zhang et al., Activation of the AXL kinase causes resistance to EGFR-targeted therapy in lung cancer. *Nat. Genet.* 44, 852-860 (2012).
26. X. Wu et al., AXL kinase as a novel target for cancer therapy. *Oncotarget*. 5, 9546-9563 (2014).
27. A. D. Boiko et al., Human melanoma-initiating cells express neural crest nerve growth factor receptor CD271. *Nature*. 466, 133-137 (2010).
28. K. S. Hoek et al., In vivo Switching of Human Melanoma Cells between Proliferative and Invasive States. *Cancer Res.* 68, 650-656 (2008).
29. J. Möller et al., Low MITF/AXL ratio predicts early resistance to multiple targeted drugs in melanoma. *Nat. Commun.* 5, 5712 (2014).
30. F. Z. Li, A. S. Dhillon, R. L. Anderson, G. McArthur, P. T. Ferrao, Phenotype switching in melanoma: implications for progression and therapy. *Mol. Cell. Oncol.* 5, 31 (2015).
31. W. Hugo et al., Non-genomic and Immune Evolution of Melanoma Acquiring MAPKi Resistance. *Cell*. 162, 1271-1285 (2015).
32. R. Nazarian et al., Melanomas acquire resistance to B-RAF(V600E) inhibition by RTK or N-RAS upregulation. *Nature*. 468, 973-977 (2010).
33. J. Barretina et al., The Cancer Cell Line Encyclopedia enables predictive modelling of anticancer drug sensitivity. *Nature*. 483, 603-607 (2012).
34. W. H. Fridman, F. Pages, C. Sautés-Fridman, J. Galon, The immune contexture in human tumours: impact on clinical outcome. *Nat. Rev. Cancer.* 12, 298-306 (2012).
35. S. L. Carter et al., Absolute quantification of somatic DNA alterations in human cancer. *Nat. Biotechnol.* 30, 413-421 (2012).
36. Roadmap Epigenomics Consortium et al., Integrative analysis of 111 reference human epigenomes. *Nature*. 518, 317-330 (2015).
37. R. Akbani et al., Genomic Classification of Cutaneous Melanoma. *Cell*. 161, 1681-1696 (2015).
38. M. M. Markiewski et al., Modulation of the antitumor immune response by complement. *Nat. Immunol.* 9, 1225-1235 (2008).
39. E. J. Wherry, T cell exhaustion. *Nat. Immunol.* 12, 492-499 (2011).
40. L. Chen, D. B. Flies, Molecular mechanisms of T cell co-stimulation and co-inhibition. *Nat. Rev. Immunol.* 13, 227-242 (2013).
41. H. Borghaei et al., Nivolumab versus Docetaxel in Advanced Nonsquamous Non-Small-Cell Lung Cancer. *N. Engl. J. Med.* 373, 1627-1639 (2015).
42. R. J. Motzer et al., Nivolumab versus Everolimus in Advanced Renal-Cell Carcinoma. *N. Engl. J.Med.* 373, 1803-1813 (2015).
43. N. A. Rizvi et al., Cancer immunology. Mutational landscape determines sensitivity to PD-1 blockade in non-small cell lung cancer. *Science*. 348, 124-128 (2015).
44. E. M. Van Allen et al., Genomic correlates of response to CTLA-4 blockade in metastatic melanoma. *Science*. 350, 207-211 (2015).
45. E. J. Wherry et al., Molecular signature of CD8+ T cell exhaustion during chronic viral infection. *Immunity*. 27, 670-684 (2007).
46. L. Baitsch et al., Exhaustion of tumor-specific CD8+ T cells in metastases from melanoma patients. *J. Clin Invest.* 121, 2350-2360 (2011).
47. G. J. Martinez et al., The transcription factor NFAT promotes exhaustion of activated CD8+ T cells. *Immunity*. 42, 265-278 (2015).
48. S. D. Blackburn, H. Shin, G. J. Freeman, E. J. Wherry, Selective expansion of a subset of exhausted CD8 T cells by αPD-L1 blockade. *Proc. Natl. Acad. Sci. U.S.A* (2008) (available at agris.fao.org/agris-search/search.do?recordID=US201301547699).
49. L. Baitsch et al., Extended Co-Expression of Inhibitory Receptors by Human CD8 T-Cells Depending on Differentiation, Antigen-Specificity and Anatomical Localization. *PLoS ONE*. 7, e30852 (2012).
50. S. Picelli et al., Smart-seq2 for sensitive full-length transcriptome profiling in single cells. *Nat. Methods*. 10, 1096-1098 (2013).
51. J. J. Trombetta et al., Preparation of Single-Cell RNA-Seq Libraries for Next Generation Sequencing. *Curr. Protoc. Mol Biol. Ed. Frederick M Ausubel A1*. 107, 4.22.1-4.22.17 (2014).
52. H. Li, R. Durbin, Fast and accurate short read alignment with Burrows-Wheeler transform. *Bioinforma. Oxf. Engl.* 25, 1754-1760 (2009).
53. A. McKenna et al., The Genome Analysis Toolkit: a MapReduce framework for analyzing nextgeneration DNA sequencing data. *Genome Res.* 20, 1297-1303 (2010).
54. M. F. Berger et al., The genomic complexity of primary human prostate cancer. *Nature*. 470, 214-20 (2011).
55. K. Cibulskis et al., Sensitive detection of somatic point mutations in impure and heterogeneous cancer samples. *Nat. Biotechnol.* 31, 213-9 (2013).
56. C. T. Saunders et al., Strelka: accurate somatic small-variant calling from sequenced tumor normal sample pairs. *Bioinforma. Oxf Engl* 28, 1811-7 (2012).
57. A. H. Ramos et al., Oncotator: cancer variant annotation tool. *Hum. Mutat.* 36, E2423-9 (2015).
58. E. S. Venkatraman, A. B. Olshen, A faster circular binary segmentation algorithm for the analysis of array CGH data. *Bioinforma. Ox. Engl.* 23, 657-63 (2007).
59. B. Langmead, C. Trapnell, M. Pop, S. L. Salzberg, Ultrafast and memory-efficient alignment of short DNA sequences to the human genome. *Genome Biol.* 10, R25 (2009).
60. B. Li, C. N. Dewey, RSEM: accurate transcript quantification from RNA-Seq data with or without a reference genome. *BMC Bioinformatics*. 12, 323 (2011).
61. A. K. Shalek et al., Single-cell RNA-seq reveals dynamic paracrine control of cellular variation. *Nature*. 510, 363-369 (2014).
62. M. L. Whitfield et al., Identification of genes periodically expressed in the human cell cycle and their expression in tumors. *Mol. Biol. Cell.* 13, 1977-2000 (2002).

63. D. E. Campton el al., High-recovery visual identification and single-cell retrieval of circulating tumor cells for genomic analysis using a dual-technology platform integrated with automated immunofluorescence staining. *BMC Cancer.* 15, 360 (2015).

64. I. Skaland et al., Comparing subjective and digital image analysis HER2/neu expression scores with conventional and modified FISH scores in breast cancer. *J. Clin. Pathol.* 61, 68-71 (2008).

65. J. Konsti et al., Development and evaluation of a virtual microscopy application for automated assessment of Ki-67 expression in breast cancer. *BMC Clin. Pathol.* 11, 3 (2011).

66. W. Hugo et al., Non-genomic and Immune Evolution of Melanoma Acquiring MAPKi Resistance. *Cell.* 162, 1271-1285 (2015).

67. L. Baitsch et al., Extended Co-Expression of Inhibitory Receptors by Human CD8 T-Cells Depending on Differentiation, Antigen-Specificity and Anatomical Localization. *PLoS ONE.* 7, e30852 (2012).

68. E. J. Wherry et al., Molecular signature of CD8+ T cell exhaustion during chronic viral infection. *Immunity.* 27, 670-684 (2007).

69. G. J. Martinez et al., The transcription factor NFAT promotes exhaustion of activated CD8+ T cells. *Immunity.* 42, 265-278 (2015).

70. E. A. Eisenhauer et al., New response evaluation criteria in solid tumours: revised RECIST guideline (version 1.1). *Eur. J. Cancer Oxf Engl.* 1990. 45, 228-247 (2009).

71. J. Barretina et al., The Cancer Cell Line Encyclopedia enables predictive modelling of anticancer drug sensitivity. *Nature.* 483, 603-607 (2012).

72. Kreso, A. & Dick, J. E. Evolution of the cancer stem cell model. Cell stem cell 14, 275-291, (2014).

73. Baylin, S. B. & Jones, P. A. A decade of exploring the cancer epigenome-biological and translational implications. Nature reviews. Cancer 11, 726-734, (2011).

74. Suva, M. L., Riggi, N. & Bernstein, B. E. Epigenetic reprogramming in cancer. Science 339, 1567-1570, (2013).

75. Bao, S., Wu, Q., McLendon, R. E., Hao, Y., Shi, Q., Hjelmeland, A. B. et al. Glioma stem cells promote radioresistance by preferential activation of the DNA damage response. Nature 444, 756-760, (2006).

76. Chen, J., Li, Y., Yu, T. S., McKay, R. M., Burns, D. K., Kernie, S. G. et al. A restricted cell population propagates glioblastoma growth after chemotherapy. Nature 488, 522-526, (2012).

77. Ito, K., Bernardi, R., Morotti, A., Matsuoka, S., Saglio, G., Ikeda, Y. et al. PML targeting eradicates quiescent leukaemia-initiating cells. Nature 453, 1072-1078, (2008).

78. Lathia, J. D., Gallagher, J., Heddleston, J. M., Wang, J., Eyler, C. E., Macswords, J. et al. Integrin alpha 6 regulates glioblastoma stem cells. Cell stem cell 6, 421-432, (2010).

79. Piccirillo, S. G., Reynolds, B. A., Zanetti, N., Lamorte, G., Binda, E., Broggi, G. et al. Bone morphogenetic proteins inhibit the tumorigenic potential of human brain tumour-initiating cells. Nature 444, 761-765, (2006).

80. Singh, S. K., Hawkins, C., Clarke, I. D., Squire, J. A., Bayani, J., Hide, T. et al. Identification of human brain tumour initiating cells. Nature 432, 396-401, (2004).

81. Anido, J., Saez-Borderias, A., Gonzalez-Junca, A., Rodon, L., Folch, G., Carmona, M. A. et al. TGF-beta Receptor Inhibitors Target the CD44(high)/Id1(high) Glioma-Initiating Cell Population in Human Glioblastoma. Cancer cell 18, 655-668, (2010).

82. Son, M. J., Woolard, K., Nam, D. H., Lee, J. & Fine, H. A. SSEA-1 is an enrichment marker for tumor-initiating cells in human glioblastoma. Cell stem cell 4, 440-452, (2009).

83. Srikanth, M., Kim, J., Das, S. & Kessler, J. A. BMP signaling induces astrocytic differentiation of clinically derived oligodendroglioma propagating cells. Mol Cancer Res 12 283-294 (2014).

84. Friedmann-Morvinski, D., Bushong, E. A., Ke, E., Soda, Y., Marumoto, T., Singer, O. et al. Dedifferentiation of neurons and astrocytes by oncogenes can induce gliomas in mice. Science 338, 1080-1084, (2012).

85. Dalerba, P., Kalisky, T., Sahoo, D., Rajendran, P. S., Rothenberg, M. E., Leyrat, A. A. et al. Single-cell dissection of transcriptional heterogeneity in human colon tumors. Nature biotechnology 29 1120-1127 (2011).

86. Lawson, D. A., Bhakta, N. R., Kessenbrock, K., Prummel, K. D., Yu, Y., Takai, K. et al. Single-cell analysis reveals a stem-cell program in human metastatic breast cancer cells. Nature 526 131-135 (2015).

87. Jaitin, D. A., Kenigsberg, E., Keren-Shaul, H., Elefant, N., Paul, F., Zaretsky, I. et al. Massively parallel single-cell RNA-seq for marker-free decomposition of tissues into cell types. Science 343 776-779 (2014).

88. Pollen, A. A., Nowakowski, T. J., Shuga, J., Wang, X., Leyrat, A. A., Lui, J. H. et al. Low-coverage single-cell mRNA sequencing reveals cellular heterogeneity and activated signaling pathways in developing cerebral cortex. Nature biotechnology 32 1053-1058 (2014).

89. Treutlein, B., Brownfield, D. G., Wu, A. R., Neff, N. F., Mantalas, G. L., Espinoza, F. H. et al. Reconstructing lineage hierarchies of the distal lung epithelium using single-cell RNA-seq. Nature 509 371-375 (2014).

90. Zeisel, A., Munoz-Manchado, A. B., Codeluppi, S., Lonnerberg, P., La Manno, G., Jureus, A. et al. Brain structure. Cell types in the mouse cortex and hippocampus revealed by single-cell RNA-seq. Science 347 1138-1142 (2015).

91. Suva, M. L. & Louis, D. N. Next-generation molecular genetics of brain tumours. Current opinion in neurology 26, 681-687, (2013).

92. Louis, D. N., Perry, A., Burger, P., Ellison, D. W., Reifenberger, G., von Deimling, A. et al. International Society Of Neuropathology-Haarlem consensus guidelines for nervous system tumor classification and grading. Brain pathology 24, 429-435, (2014).

93. Picelli, S., Faridani, O. R., Bjorklund, A. K., Winberg, G., Sagasser, S. & Sandberg, R. Full-length RNA-seq from single cells using Smart-seq2. Nat Protoc 9 171-181 (2014).

94. Butovsky, O., Jedrychowski, M. P., Moore, C. S., Cialic, R., Lanser, A. J., Gabriely, G. et al. Identification of a unique TGF-beta-dependent molecular and functional signature in microglia. Nat Neurosci 17 131-143 (2014).

95. Rousseau, A., Nutt, C. L., Betensky, R. A., Iafrate, A. J., Han, M., Ligon, K. L. et al. Expression of oligodendroglial and astrocytic lineage markers in diffuse gliomas: use of YKL-96. ApoE, ASCL1, and NKX2-2. Journal of neuropathology and experimental neurology 65 1149-1156 (2006).

97. Zhang, Y., Chen, K., Sloan, S. A., Bennett, M. L., Scholze, A. R., O'Keeffe, S. et al. An RNA-sequencing transcriptome and splicing database of glia, neurons, and vascular cells of the cerebral cortex. J Neurosci 34 11929-11947 (2014).

98. Louis, D. N., Ohgaki, H., Wiestler, O. D., Cavenee, W. K., Burger, P. C., Jouvet, A. et al. The 2007 WHO classification of tumours of the central nervous system. Acta neuropathologica 114, 97-109, (2007).
99. Feng, W., Khan, M. A., Bellvis, P., Zhu, Z., Bernhardt, O., Herold-Mende, C. et al. The chromatin remodeler CHD7 regulates adult neurogenesis via activation of SoxC transcription factors. Cell stem cell 13, 62-72, (2013).
100. Ikushima, H., Todo, T., Ino, Y., Takahashi, M., Miyazawa, K. & Miyazono, K. Autocrine TGF-beta signaling maintains tumorigenicity of glioma-initiating cells through Sry-related HMG-box factors. Cell stem cell 5, 504-514, (2009).
101. Suva, M. L., Rheinbay, E., Gillespie, S. M., Patel, A. P., Wakimoto, H., Rabkin, S. D. et al. Reconstructing and reprogramming the tumor-propagating potential of glioblastoma stem-like cells. Cell 157, 580-594, (2014).
102. Mille, F., Tamayo-Orrego, L., Levesque, M., Remke, M., Korshunov, A., Cardin, J. et al. The Shh receptor Boc promotes progression of early medulloblastoma to advanced tumors. Developmental cell 31, 34-47, (2014).
103. Panchision, D. M., Chen, H. L., Pistollato, F., Papini, D., Ni, H. T. & Hawley, T. S. Optimized flow cytometric analysis of central nervous system tissue reveals novel functional relationships among cells expressing CD133, CD15, and CD24. Stem cells 25 1560-1570 (2007).
104. Rheinbay, E., Suva, M. L., Gillespie, S. M., Wakimoto, H., Patel, A. P., Shahid, M. et al. An Aberrant Transcription Factor Network Essential for Wnt Signaling and Stem Cell Maintenance in Glioblastoma. Cell reports 3, 1567-1579, (2013).
105. Miller, J. A., Ding, S. L., Sunkin, S. M., Smith, K. A., Ng, L., Szafer, A. et al. Transcriptional landscape of the prenatal human brain. Nature 508, 199-206, (2014).
106. Darmanis, S., Sloan, S. A., Zhang, Y., Enge, M., Caneda, C., Shuer, L. M. et al. A survey of human brain transcriptome diversity at the single cell level. Proceedings of the National Academy of Sciences of the United States of America, (2015).
107. Kelly, J. J., Blough, M. D., Stechishin, O. D., Chan, J. A., Beauchamp, D., Perizzolo, M. et al. Oligodendroglioma cell lines containing t(1;19)(q10;p10). Neuro-oncology 12 745-755 (2010).
108. Sugiarto, S., Persson, A. I., Munoz, E. G., Waldhuber, M., Lamagna, C., Andor, N. et al. Asymmetry-defective oligodendrocyte progenitors are glioma precursors. Cancer cell 20 328-340 (2011).
109. Aguirre, A., Dupree, J. L., Mangin, J. M. & Gallo, V. A functional role for EGFR signaling in myelination and remyelination. Nat Neurosci 10 990-1002 (2007).
110. Shah, N. M., Marchionni, M. A., Isaacs, I., Stroobant, P. & Anderson, D. J. Glial growth factor restricts mammalian neural crest stem cells to a glial fate. Cell 77 349-360 (1994).
111. Shin, J., Berg, D. A., Zhu, Y., Shin, J. Y., Song, J., Bonaguidi, M. A. et al. Single-Cell RNA-Seq with Waterfall Reveals Molecular Cascades underlying Adult Neurogenesis. Cell stem cell 17, 360-372, (2015).
112. Cancer Genome Atlas Research, N., Brat, D. J., Verhaak, R. G., Aldape, K. D., Yung, W. K., Salama, S. R. et al. Comprehensive, Integrative Genomic Analysis of Diffuse Lower-Grade Gliomas. The New England journal of medicine 372, 2481-2498, (2015).
113. Lange, C. & Calegari, F. Cdks and cyclins link G1 length and differentiation of embryonic, neural and hematopoietic stem cells. Cell Cycle 9 1893-1900 (2010).
114. Koyama-Nasu, R., Nasu-Nishimura, Y., Todo, T., Tno, Y., Saito, N., Aburatani, H. et al. The critical role of cyclin D2 in cell cycle progression and tumorigenicity of glioblastoma stem cells. Oncogene 32 3840-3845 (2013).
115. Bettegowda, C., Agrawal, N., Jiao, Y., Sausen, M., Wood, L. D., Hruban, R. H. et al. Mutations in CIC and FUBP1 contribute to human oligodendroglioma. Science 333 1453-1455 (2011).
116. Padul, V., Epari, S., Moiyadi, A., Shetty, P. & Shirsat, N. V. ETV/Pea3 family transcription factor-encoding genes are overexpressed in CIC-mutant oligodendrogliomas. Genes, chromosomes & cancer 54, 725-733, (2015).
117. Liu, C., Sage, J. C., Miller, M. R., Verhaak, R. G., Hippenmeyer, S., Vogel, H. et al. Mosaic analysis with double markers reveals tumor cell of origin in glioma. Cell 146 209-221 (2011).
118. Ducray, F. & Idbaih, A. Neuro-oncology: anaplastic oligodendrogliomas-value of early chemotherapy. Nat Rev Neurol 9 7-8 (2013).
119. Satija, R., Farrell, J. A., Gennert, D., Schier, A. F. & Regev, A. Spatial reconstruction of single-cell gene expression data. Nature biotechnology 33 495-502 (2015).
120. Mohapatra, G., Betensky, R. A., Miller, E. R., Carey, B., Gaumont, L. D., Engler, D. A. et al. Glioma test array for use with formalin-fixed, paraffin-embedded tissue: array comparative genomic hybridization correlates with loss of heterozygosity and fluorescence in situ hybridization. J Mol Diagn 8 268-276 (2006).
121. Cibulskis, K., McKenna, A., Fennell, T., Banks, E., DePristo, M. & Getz, G. ContEst: estimating cross-contamination of human samples in next-generation sequencing data. Bioinformatics 27 2601-2602 (2011).
122. Costello, M., Pugh, T. J., Fennell, T. J., Stewart, C., Lichtenstein, L., Meldrim, J. C. et al. Discovery and characterization of artifactual mutations in deep coverage targeted capture sequencing data due to oxidative DNA damage during sample preparation. Nucleic Acids Res 41 e67 (2013).
123. Zhang, Y., Sloan, S. A., Clarke, L. E., Caneda, C., Plaza, C. A., Blumenthal, P. D. et al. Purification and Characterization of Progenitor and Mature Human Astrocytes Reveals Transcriptional and Functional Differences with Mouse. Neuron 89, 37-53, (2016).
124. Kowalczyk, M. S., Tirosh, I., Heckl, D., Rao, T. N., Dixit, A., Haas, B. J. et al. Single-cell RNA-seq reveals changes in cell cycle and differentiation programs upon aging of hematopoietic stem cells. Genome Res 25; 1860-1872 (2015).
125. Lawrence M. S., Stojanov P., Mermel C. H., Robinson J. T., Garraway L. A., Golub T. R. et al. Discovery and saturation analysis of cancer genes across 21 tumour types. *Nature* 505, 495-501 (2014).
126. Tirosh I., Izar B., Prakadan S. M., Wadsworth M. H. 2nd, Treacy D., Trombetta J. J. et al. Dissecting the multicellular ecosystem of metastatic melanoma by single-cell RNA-seq. *Science,* 352, 189-96 (2016).
127. Filbin, M. G. and Suva, M. L. Gliomas Genomics and Epigenomics: Arriving at the Start and Knowing It for the First Time. *Annual review of pathology,* 11: 497-521 (2016).
128. Dai C, Celestino J C, Okada Y, Louis D N, Fuller G N, Holland E C, PDGF autocrine stimulation dedifferentiates cultured astrocytes and induces oligodendrogliomas and oligoastrocytomas from neural progenitors and astrocytes in vivo. *Genes & development* 15, 1913 (2001).

129. Bennett M. L., Bennett F. C., Liddelow S. A., Ajami B., Zamanian J. L., Fernhoff N. B. et al., New tools for studying microglia in the mouse and human CNS. *Proceedings of the National Academy of Sciences of the United States of America.* 113, E1738-46 (2016).
130. Lavin Y., Winter D., Blecher-Gonen R., David E., Keren-Shaul H., Merad M. et al., Tissue-resident macrophage enhancer landscapes are shaped by the local microenvironment. *Cell* 159, 1312 (2014).
131. H. Zong, L. F. Parada, S. J. Baker, Cell of origin for malignant gliomas and its implication in therapeutic development. *Cold Spring Harbor perspectives in biology* 7(5) (2015).
132. Sahm F., Reuss D., Koelsche C., Capper D., Schittenhelm J., Heim S. et al., Farewell to oligoastrocytoma: in situ molecular genetics favor classification as either oligodendroglioma or astrocytoma. *Acta neuropathologica* 128, 551 (2014).
133. Matcovitch-Natan O., Winter D R., Giladi A., Vargas Aguilar S., Spinrad A., Sarrazin S. et al. Microglia development follows a stepwise program to regulate brain homeostasis. *Science,* 19;353, 6301 (2016).
134. Wei C. L., Wu Q., Vega V. B., Chiu K. P., Ng P., Zhang T. et al., A global map of p53 transcription-factor binding sites in the human genome. *Cell.* 124, 207-19 (2006).
135. I. C. Macaulay et al., in *Nat Methods.* (United States, 2015), vol. 12, pp. 519-522.
136. I. C. Macaulay et al., in *Nat Protoc.* (England, 2016), vol. 11, pp. 2081-2103.
137. I. Tirosh et al., in *Nature.* (England, 2016), vol. 539, pp. 309-313.
138. L. Sequeira, C. W. Dubyk, T. A. Riesenberger, C. R. Cooper, K. L. van Golen, Rho GTPases in PC-3 prostate cancer cell morphology, invasion and tumor cell diapedesis. *Clin Exp Metastasis* 25, 569-579 (2008).
139. M. Tseliou et al., in *Cell Physiol Biochem.* (Switzerland, 2016), vol. 38, pp. 94-109.
140. T. Cooks, C. C. Harris, M. Oren, in *Carcinogenesis.* (England, 2014), vol. 35, pp. 1680-1690.
141. N. Cancer Genome Atlas Research, Genomic and epigenomic landscapes of adult de novo acute myeloid leukemia. *The New England journal of medicine* 368, 2059-2074 (2013).
142. P. Guilhamon et al., in *Nat Commun.* (England, 2013), vol. 4, pp. 2166.
143. M. J. Aryee et al., in *Bioinformatics.* (England, 2014), vol. 30, pp. 1363-1369. 144. J. Ihmels et al., in *Nature genetics.* (United States, 2002), vol. 31, pp. 370-377.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. An isolated CD8+ T cell genetically modified to decrease the expression of complement receptor CR1 (CD35) and/or CR2 (CD21) wherein the T cell is a tumor infiltrating lymphocyte (TIL) and/or expresses an endogenous T cell receptor (TCR) or a chimeric antigen receptor (CAR), wherein said TCR or CAR targets a tumor-specific or tumor-associated antigen.

2. A pharmaceutical composition comprising one or more cells according to claim 1.

3. A method of treating cancer in a subject in need thereof, comprising administering the pharmaceutical composition of claim 2 to the subject.

* * * * *

UNITED STATES PATENT AND TRADEMARK OFFICE
CERTIFICATE OF CORRECTION

| | |
|---|---|
| PATENT NO. | : 11,897,953 B2 |
| APPLICATION NO. | : 16/622636 |
| DATED | : February 13, 2024 |
| INVENTOR(S) | : Aviv Regev et al. |

It is certified that error appears in the above-identified patent and that said Letters Patent is hereby corrected as shown below:

On the Title Page

On the page 2, in Column 2, under "foreign patent documents", Line 4, delete "NO" and insert -- WO --.

In the Specification

In Column 6, Line 3, delete "CIS. C3. C4A." and insert -- C1S, C3, C4A, --.

In Column 6, Line 3, delete "ClNH" and insert -- C1NH --.

In Column 9, Line 63, delete "el" and insert -- et --.

In Column 15, Line 61, delete "N×I/G." and insert -- N×L/G. --.

In Column 15, Line 63, delete "2×" and insert -- 2x --.

In Column 16, Line 36, delete "Cis" and insert -- C1s --.

In Column 22, Line 16, delete "DOT:" and insert -- DOI: --.

In Column 25, Lines 54-55, delete "joumal/" and insert -- journal/ --.

In Column 27, Line 61, delete "3940," and insert -- 39, 40, --.

In Column 29, Line 11, delete "Eigineering," and insert -- Engineering, --.

In Column 34, Line 39, delete "GAT" and insert -- GAI --.

Signed and Sealed this
Twelfth Day of November, 2024

Katherine Kelly Vidal
*Director of the United States Patent and Trademark Office*

CERTIFICATE OF CORRECTION (continued)
U.S. Pat. No. 11,897,953 B2

In Column 36, Line 24, delete "IV/cm" and insert -- 1V/cm --.

In Column 36, Line 46, delete "Therapeutic" and insert -- therapeutic --.

In Column 36, Line 48, delete "Hifu" and insert -- HIFU --.

In Column 36, Line 51, delete "Focused" and insert -- focused --.

In Column 36, Line 52, delete "(fus)" and insert -- (FUS) --.

In Column 36, Line 53, delete "morocz" and insert -- Morocz --.

In Column 36, Line 56, delete "(hifu) Which" and insert -- (HIFU) which --.

In Column 36, Lines 56-57, delete "moussatov" and insert -- Moussatov --.

In Column 36, Line 57, delete "ultrasonics" and insert -- Ultrasonics --.

In Column 36, Line 58, delete "Tranhuuhue" and insert -- TranHuuHue --.

In Column 36, Line 58, delete "acustica" and insert -- Acustica --.

In Column 36, Line 61, delete "Employed." and insert -- employed. --.

In Column 45, Line 29, delete "E" and insert -- E. --.

In Column 47, Line 64, delete "el" and insert -- et --.

In Column 48, Line 23, delete "el" and insert -- et --.

In Column 49, Line 16, delete "FokT" and insert -- FokI --.

In Column 51, Line 64, delete "("appin" and insert -- ("appln --.

In Column 56, Line 30, delete "m Sin" and insert -- mSin --.

In Column 56, Line 67, delete "11S" and insert -- IIS --.

In Column 58, Line 61, delete "PCTAI" and insert -- PCTA1 --.

In Column 59, Line 27, delete "I" and insert -- 1 --.

In Column 59, Line 32, delete "I" and insert -- 1 --.

In Column 59, Line 55, delete "(CYPIB1);" and insert -- (CYP1B1); --.

CERTIFICATE OF CORRECTION (continued)
U.S. Pat. No. 11,897,953 B2

In Column 60, Line 23, delete "KTAA0205;" and insert -- KIAA0205; --.

In Column 62, Line 57, delete "1a" and insert -- Ia --.

In Column 63, Line 59, delete "antigen-T" and insert -- antigen-specific T --.

In Column 73, Line 39, delete "CAR," and insert -- CAR; --.

In Column 77, Line 38, delete "5×10$^6$/ ml." and insert -- 5×10$^6$/ml. --.

In Column 78, Line 24, delete "($2m)" and insert -- (β2m) --.

In Column 82, Line 29, delete "igD," and insert -- IgD, --.

In Column 83, Line 55, delete "(10 Fn3)," and insert -- (10Fn3), --.

In Column 84, Line 25, delete "500 μM or less, 100 μM or less, 50 μM" and insert -- 500 pM or less, 100 pM or less, 50 pM --.

In Column 84, Line 26, delete "25 μM" and insert -- 25 pM --.

In Column 85, Line 31, delete "CHI" and insert -- CH1 --.

In Column 85, Line 32, delete "CHI" and insert -- CH1 --.

In Column 85, Line 33, delete "CHI" and insert -- CH1 --.

In Column 86, Line 44, delete "ITT" and insert -- III --.

In Column 90, Line 47, delete "CIS," and insert -- C1S, --.

In Column 91, Line 41, delete "CIS" and insert -- C1S --.

In Column 91, Line 42, delete "CIS). CIS" and insert -- C1S). C1S --.

In Column 91, Line 45, delete "CIS" and insert -- C1S --.

In Column 93, Line 39, delete "MC380VA" and insert -- MC38OVA --.

In Column 93, Line 49, delete "MC380VA" and insert -- MC38OVA --.

In Column 94, Line 57, delete "intracellular" and insert -- Intracellular --.

In Column 94, Line 66, delete "10× system (10×" and insert -- 10x system (10x --.

In Column 95, Line 14, delete "C1r1" and insert -- C1rl --.

CERTIFICATE OF CORRECTION (continued)
U.S. Pat. No. 11,897,953 B2

In Column 119, Line 29, delete "Möller" and insert -- Müller --.

In Column 120, Line 33, delete "A1." and insert -- Al. --.

In Column 120, Line 54, delete "Ox." and insert -- Oxf. --.

In Column 121, Line 1, delete "el" and insert -- et --.

In Column 121, Line 67, delete "1d1" and insert -- Id1 --.

In Column 124, Line 1, delete "Tno," and insert -- Ino, --.